(12) United States Patent  
Mori et al.

(10) Patent No.: US 7,230,023 B2  
(45) Date of Patent: Jun. 12, 2007

(54) WATER-SOLUBLE TRIAZOLE FUNGICIDE

(75) Inventors: Makoto Mori, Tokyo (JP); Yoshiko Kagoshima, Tokyo (JP); Takuya Uchida, Tokyo (JP); Toshiyuki Konosu, Tokyo (JP); Takahiro Shibayama, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 585 days.

(21) Appl. No.: 10/647,023

(22) Filed: Aug. 20, 2003

(65) Prior Publication Data

US 2004/0198790 A1   Oct. 7, 2004

Related U.S. Application Data

(63) Continuation-in-part of application No. PCT/JP02/01500, filed on Feb. 20, 2002.

(30) Foreign Application Priority Data

Feb. 22, 2001   (JP) ............................... 2001-046890

(51) Int. Cl.  
*A61K 31/4196* (2006.01)  
*C07D 249/08* (2006.01)

(52) U.S. Cl. .................... 514/383; 548/266.2; 514/383

(58) Field of Classification Search ............. 548/266.2; 514/383  
See application file for complete search history.

(56) References Cited

U.S. PATENT DOCUMENTS

| 4,404,216 A |   | 9/1983  | Richardson |
|---|---|---|---|
| 4,663,463 A | * | 5/1987  | Kunz et al. ............. 548/268.6 |
| 5,622,944 A |   | 4/1997  | Hale et al. |
| 6,083,968 A |   | 7/2000  | Takeda et al. |
| 6,653,330 B2 |  | 11/2003 | Uchida et al. |

FOREIGN PATENT DOCUMENTS

| EP | 0 510 700 A2 | 10/1992 |
|---|---|---|
| EP | 0 841 327 A1 | 5/1998 |
| EP | 1 284 267 A1 | 2/2003 |
| JP | 62-12766 A | 1/1987 |
| JP | 62-14766 A | 1/1987 |
| JP | 2625584 B2 | 8/1992 |
| JP | 3050982 B2 | 6/1993 |
| JP | 5-345768 A | 12/1993 |
| JP | 8-53426 A | 2/1996 |
| JP | 9-183769 A | 7/1997 |
| JP | 10-279567 A | 10/1998 |
| JP | 11-80135 A | 3/1999 |
| JP | 11-240871 A | 9/1999 |
| JP | 2001-342187 A | 12/2001 |
| WO | WO 95/25107 A1 | 9/1995 |
| WO | WO 97/05130 A1 | 2/1997 |
| WO | WO 98/31675 A1 | 7/1998 |
| WO | WO 99/45008 A1 | 9/1999 |
| WO | WO 99/61017 A1 | 12/1999 |
| WO | WO 00/27852 A1 | 5/2000 |
| WO | WO 00/30655 A1 | 6/2000 |
| WO | WO 01/05819 A1 | 1/2001 |
| WO | WO 01/52852 A1 | 7/2001 |
| WO | WO 01/66551 A2 | 9/2001 |
| WO | WO 01/79196 A2 | 10/2001 |

* cited by examiner

*Primary Examiner*—Kamal A. Saeed  
*Assistant Examiner*—Janet L. Coppins  
(74) *Attorney, Agent, or Firm*—Frishauf, Holtz, Goodman & Chick, P.C.

(57) ABSTRACT

A triazole compound of the formula (I) or a pharmacologically salt thereof:

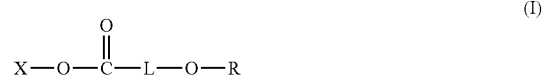

wherein X represents a group of formula X—OH which has antifungal activity, L represents an -(adjacently substituted $C_6$-$C_{10}$ aryl)-$CH_2$ group and R represents a —P(=O)(OH)$_2$ group.

63 Claims, 1 Drawing Sheet

WATER-SOLUBLE TRIAZOLE FUNGICIDE

CROSS-REFERENCE TO RELATED APPLICATION

This application is a continuation-in-part application of International application PCT/JP02/01500 filed Feb. 20, 2002, the entire contents of which are hereby incorporated by reference herein.

BACKGROUND OF THE INVENTION

1. Technical Field

The present invention relates to triazole compounds and pharmacologically acceptable salts thereof, which have excellent characteristics in terms of pharmacokinetics and antifungal activity, as medicaments (compositions which include carriers) (especially for injection), and to medicaments (especially antifungals) containing said compounds or salts thereof as an active ingredient. The present invention also concerns methods of treating or preventing fungal infections in warm-blooded animals by administering to such animals the triazole compound.

2. Background Art

Various types of triazole compounds have so far been reported as agents for the treatment of fungal infections. For example, triazole compounds having a tertiary hydroxy group are described in Japanese Patent Application Publication No. Hei 8-333350, Japanese Patent Application Publication No. Hei 11-80135, Japanese Patent Application Publication No. Hei 10-279567, and Japanese Patent Application Publication No. 2001-342187. In Japanese Patent Application Publication No. Sho 62-12766, 2-(2,4-difluorophenyl)-1,3bis(1H-1,2,4-triazol-1-yl)-2-propanol (fluconazole) is described. In Japanese Patent Application Publication No. Hei 8-53426, 3-[4-(4-cyanophenyl)thiazol-2-yl]-2-(2,4-difluorophenyl)-1(1H-1,2,4-triazol-1-yl)-2butanol (ravuconazole) is described. In WO 99/45008, 2-(2,5-difluorophenyl)-3-[4-(4-cyanophenyl)thiazol-2-yl]-1-(1H-1,2,4-triazol-1-yl)-2-butanol (R00094815) is described. In Japanese Patent No. 2625584, 2-(2,4-difluorophenyl)-3-(5-fluoro-4-pyrimidinyl)-1-(1H-1,2,4-triazol-1-yl)-2-butanol (voriconazole) is described. In Japanese Patent Application Publication No. Hei 9-183769, 1-[(1R,2R)-2-(2,4difluorophenyl)-2-hydroxy-1-methyl-3-(1H-1,2,4-triazol-1-yl)propyl]-3-[4-(1H-1-tetrazolyl)phenyl]-2-imidazolidinone (TAK-456) is described. In Japanese Patent Application Publication No. Hei 11-240871, 2-(2,4-difluorophenyl)-1-(ethylsulfonyl)-1,1-difluoro-3-(1H-1,2,4-triazol-1-yl)-2-propanol (SS750) is described. In WO 98/31675, (2R,3R)-2-(2,4-difluorophenyl)-3-[4-[4-[3-oxo-2-(4-trifluoromethoxybenzyl)-2H-1,2,4-triazol-4-yl]phenyl]-1-piperazinyl]-1-(1H-1,2,4-triazol-1-yl)-2-butanol (Syn-2869) is described. In WO97/05130, 7-chloro-3-[(1R,2R)-2-(2,4-difluorophenyl)-2-hydroxy-1-methyl-3-(1H-1,2,4-triazol-1-yl)propyl]quinazolin-4(3H)-one (UR-9825) is described. Analogous triazole compounds are also described in Japanese Patent No. 3050982, WO 95/25107, WO 00/27852, WO 01/66551, and WO 01/79196.

Further, ester compounds interrupted by a methylenedioxy group for improving the water solubility of agents for the treatment of fungal infections are described in WO 00/30655, WO 99/61017 and WO 01/52852.

The administration form of agents for treatment of fungal infections depends on the kind of the target fungus and the type of infection. As the administration form, there are, for example, oral administration and injection administration. As these administration methods have advantages and disadvantages, both methods of administration are required for a preferable agent for the treatment of fungal infection. Although the triazole agents for the treatment of fungal infection indicated above have excellent antifungal activity, they also have the disadvantage of difficulty in administration by injection because of their low solubility in water.

In order to improve the low solubility in water, the conversion of the hydroxy group into an ester group for increasing the water solubility may be considered. However, as the hydroxy group which these therapeutic agents have in common is a tertiary hydroxy group, there is the disadvantage that the said ester group is not cleaved promptly in vivo after administration owing to its low reactivity, and consequently that the active substance is not released efficiently. Ester compounds interrupted by a methylenedioxy group generate formaldehyde upon cleavage of the ester.

The problem to be resolved by the present invention is to afford triazole compounds esterified on the tertiary hydroxy group which have high solubility in water, can be cleaved in vivo promptly, and are safe compounds because no formaldehyde is generated upon cleavage. Triazole compounds having an ester group on the tertiary hydroxy group relating to the present invention have not been known so far.

SUMMARY OF THE INVENTION

The present inventors have designed the ester group at the tertiary hydroxy group relating to the present invention, conducted synthesis, and have found that the triazole compounds relating to the present invention are useful as medicaments (especially as antifungals) (and especially for injection), because these compounds can be produced at low cost and with ease, have superior chemical stability and high water solubility, undergo prompt cleavage of the ester group in vivo with high percentages of conversion to exhibit excellent antifungal activity, do not generate formaldehyde upon cleavage, have high organ selectivity, and exhibit favorable pharmacokinetics and a high degree of safety, thereby leading to completion of the present invention.

The present invention relates to a triazole compound of the general formula (I) or a pharmacologically acceptable salt thereof:

[wherein, X represents a group of general formula (II),

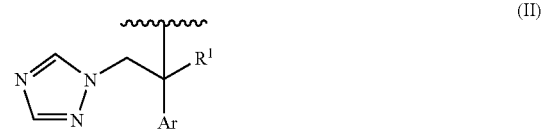

(wherein, Ar represents a $C_6$-$C_{10}$ aryl group which may optionally be substituted with 1 to 3 same or different group(s) selected from the group consisting of a halogen atom and a halogenated $C_1$-$C_6$ alkyl group, and $R^1$ represents an organic residue group) (provided that the compound of formula X—OH has antifungal activity), L represents a group of general formula —$L^a$—$L^b$—
[wherein, $L^a$ represents a single bond, an oxygen atom, a $C_6$-$C_{10}$ aryl group which may optionally be substituted with 1 to 3 same or different group(s) selected from the group consisting of Substituent group α, a heterocyclic group which may optionally be substituted with 1 to 3 same or different group(s) selected from the group consisting of Substituent group α, or a $C_3$-$C_7$ cycloalkyl group which may optionally be substituted with 1 to 3 same or different group(s) selected from the group consisting of Substituent group α, and $L^b$ represents a $C_1$-$C_5$ alkylene group which may optionally be substituted with 1 to 3 same or different group(s) selected from the group consisting of Substituent group α], and R represents a hydrogen atom, a $C_1$-$C_6$ alkanoyl group which may optionally be substituted with 1 to 3 same or different group(s) selected from the group consisting of Substituent group β, a group of formula —C(O)—$NR^2R^3$ (wherein, $R^2$ and $R^3$ are the same or different and independently represent a hydrogen atom or a $C_1$-$C_6$ alkyl group, or $R^2$ and $R^3$, together with the nitrogen atom to which they are attached, form a 4- to 7-membered heterocyclic group containing nitrogen atom(s)) or a —P(=O)(OH)$_2$ group]

<Substituent Group α> a $C_1$-$C_6$ alkyl group, a $C_1$-$C_6$ alkoxy group, a halogen atom, a cyano group, a hydroxy group, an amino group, a $C_1$-$C_6$ alkylamino group, a di $C_1$-$C_6$ alkylamino group, an amino $C_1$-$C_6$ alkyl group, a $C_1$-$C_6$ alkylamino-$C_1$-$C_6$ alkyl group, a di $C_1$-$C_6$ alkylamino-$C_1$-$C_6$ alkyl group, a carboxy group, a —O—P(=O)(OH)$_2$ group, and a $C_1$-$C_6$ alkyl group substituted with one —O—P(=O)(OH)$_2$ group.

<Substituent Group β> a hydroxy group, a —Q—$NR^{2'}R^{3'}$ group [wherein, Q represents a single bond or a carbonyl group, and $R^{2'}$ and $R^{3'}$ are the same or different and independently represent a hydrogen atom or a $C_1$-$C_6$ alkyl group, or $R^{2'}$ and $R^{3'}$, together with the nitrogen atom to which they are attached, form a 4- to 7-membered heterocyclic group containing nitrogen atom(s) (said heterocyclic group containing nitrogen atom(s) may optionally be substituted with 1 or 2 same or different $C_1$-$C_6$ alkyl group(s))], a carboxy group, an —O—P(=O)(OH)$_2$ group and a —SO$_3$H group.

DETAILED DESCRIPTION OF THE INVENTION

Of the above compounds of the said general formula (I) and pharmacologically acceptable salts thereof, the preferred compounds are:

(1) a triazole compound or a pharmacologically acceptable salt thereof, wherein $L^a$ represents a $C_6$-$C_{10}$ aryl group which may optionally be substituted with 1 to 3 same or different group(s) selected from the group consisting of Substituent group α, a heterocyclic group which may optionally be substituted with 1 to 3 same or different group(s) selected from the group consisting of Substituent group α, or a $C_3$-$C_7$ cycloalkyl group which may optionally be substituted with 1 to 3 same or different group(s) selected from the group consisting of Substituent group α, (2) a triazole compound or a pharmacologically acceptable salt thereof, wherein the carbon atom in the group of —$L^a$— to which the group of formula X—O—C(=O)— is bonded and the carbon atom in the group of —$L^a$— to which the group of formula —$L^b$—O—R is bonded are adjacent to each other, (3) a triazole compound or a pharmacologically acceptable salt thereof, wherein $L^b$ represents a methylene group or a methylene group which is substituted with 1 or 2 same or different group(s) selected from the group consisting of Substituent group α, (4) a triazole compound or a pharmacologically acceptable salt thereof, wherein L represents an -(o-phenylene)-CH$_2$— group or an -(o-phenylene)-CH$_2$— group which is substituted with one group selected from the group consisting of Substituent group α, (5) a triazole compound or a pharmacologically acceptable salt thereof, wherein L represents an -(o-phenylene)-CH$_2$— group which is substituted with one group selected from the group consisting of Substituent group α, (6) a triazole compound or a pharmacologically acceptable salt thereof, wherein R represents a hydrogen atom, (7) a triazole compound or a pharmacologically acceptable salt thereof, wherein R represents a $C_1$-$C_6$ alkanoyl group which may optionally be substituted with 1 to 3 same or different group(s) selected from the group consisting of Substituent group β, (8) a triazole compound or a pharmacologically acceptable salt thereof, wherein R represents a —P(=O)(OH)$_2$ group, (9) a triazole compound or a pharmacologically acceptable salt thereof, wherein Substituent group α represents Substituent group α1 which consists of a methyl group, a methoxy group, a halogen atom, a cyano group and a —CH$_2$—O—P(=O)(OH)$_2$ group,

(10) a triazole compound or a pharmacologically acceptable salt thereof, wherein Substituent group β represents Substituent group β1 which consists of an amino group, a $C_1$-$C_6$ alkylamino group and a di $C_1$-$C_6$ alkylamino group,

(11) a triazole compound or a pharmacologically acceptable salt thereof, wherein Substituent group β represents a di $C_1$-$C_6$ alkylamino group,

(12) a triazole compound or a pharmacologically acceptable salt thereof, wherein Substituent group β represents an N,N-dimethylamino group,

(13) a triazole compound or a pharmacologically acceptable salt thereof, wherein Substituent group β represents a carboxy group,

(14) a triazole compound or a pharmacologically acceptable salt thereof, wherein Substituent group β represents a 4- to 7-membered heterocyclic group containing nitrogen atom(s) (said heterocyclic group containing nitrogen atom(s) may optionally be substituted with 1 or 2 same or different $C_1$-$C_6$ alkyl group(s)),

(15) a triazole compound or a pharmacologically acceptable salt thereof, wherein Substituent group β represents a 4- to 7-membered heterocyclic group containing nitrogen atom(s) (said heterocyclic group containing nitrogen atom(s) is substituted with 1 or 2 same or different $C_1$-$C_6$ alkyl group(s)),

(16) a triazole compound or a pharmacologically acceptable salt thereof, wherein Substituent group β represents a 4-methyl-1-piperazinyl group,

(17) a triazole compound or a pharmacologically acceptable salt thereof, wherein Substituent group β represents a group of formula —C(O)—W [wherein, W represents a 4- to 7-membered heterocyclic group containing nitrogen atom(s) (said heterocyclic group containing nitrogen atom(s) may optionally be substituted with 1 or 2 same or different $C_1$-$C_6$ alkyl group(s))],

(18) a triazole compound or a pharmacologically acceptable salt thereof, wherein Substituent group β represents a group of formula —C(O)—$W^1$ [wherein, $W^1$ represents a 4- to 7-membered heterocyclic group containing nitrogen atom(s) (said heterocyclic group containing nitrogen atom(s) is substituted with 1 or 2 same or different $C_1$-$C_6$ alkyl group(s))],

(19) a triazole compound or a pharmacologically acceptable salt thereof, wherein Substituent group β represents a (4-methyl-1-piperazinyl)carbonyl group,

(20) a triazole compound or a pharmacologically acceptable salt thereof, wherein X represents a group of general formula (III),

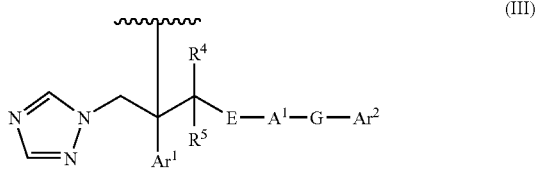

(III)

[wherein, $Ar^1$ represents a phenyl group which may optionally be substituted with 1 to 3 same or different group(s) selected from the group consisting of a halogen atom and a trifluoromethyl group, $Ar^2$ represents a phenyl group which may optionally be substituted with 1 to 5 same or different group(s) selected from the group consisting of Substituent group γ, a monocyclic heteroaryl group which may optionally be substituted with 1 to 5 same or different group(s) selected from the group consisting of Substituent group γ, a naphthyl group which may optionally be substituted with 1 to 5 same or different group(s) selected from the group consisting of Substituent group γ, or a fused bicyclic heteroaryl group which may optionally be substituted with 1 to 5 same or different group(s) selected from the group consisting of Substituent group γ, E represents a methylene group or a group of formula —S(O)$_{n1}$— (wherein, n1 is an integer from 0 to 2), $A^1$ represents a $C_4$-$C_7$ cycloalkyl group or a heterocyclyl group, $R^4$ and $R^5$ independently represent a hydrogen atom or a $C_1$-$C_6$ alkyl group, G represents a group of formula (Ga)

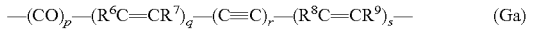

(Ga)

(wherein, $R^6$, $R^7$, $R^8$ and $R^9$ independently represent a hydrogen atom or a $C_1$-$C_6$ alkyl group which may optionally be substituted with 1 to 5 same or different halogen atom(s), p is an integer 0 or 1, q is an integer from 0 to 3, and r and s independently are an integer from 0 to 2), or G represents a group of formula (Gb)

—Φ—CO—NR$^ψ$—T— (Gb)

(wherein, φ represents a phenylene group which may optionally be substituted with 1 or 2 same or different group(s) selected from the group consisting of a fluorine atom and a chlorine atom, or a naphthylene group which may optionally be substituted with 1 or 2 same or different group(s) selected from the group consisting of a fluorine atom and a chlorine atom, $R^ψ$ represents a hydrogen atom or a $C_1$-$C_6$ alkyl group, and T represents a single bond or a straight or branched chain $C_1$-$C_8$ alkylene group)],

(21) a triazole compound or a pharmacologically acceptable salt thereof according to (20), wherein $Ar^2$ represents a phenyl group which may optionally be substituted with 1 to 5 same or different group(s) selected from the group consisting of Substituent group γ, or a monocyclic heteroaryl group which may optionally be substituted with 1 to 5 same or different group(s) selected from the group consisting of Substituent group γ, E represents a group of formula —S(O)$_{n1}$— (wherein, n1 is an integer from 0 to 2), $R^4$ represents a $C_1$-$C_4$ alkyl group, $R^5$ represents a hydrogen atom or a $C_1$-$C_4$ alkyl group, G represents a group of formula (Ga')

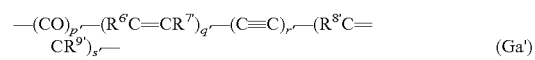

(Ga')

(wherein, $R^{6'}$, $R^{7'}$, $R^{8'}$ and $R^{9'}$ independently represent a hydrogen atom or a $C_1$-$C_6$ alkyl group which may optionally be substituted with 1 to 5 same or different halogen atom(s), p' is an integer 0 or 1, and q', r' and s' independently are an integer from 0 to 2),

(22) a triazole compound or a pharmacologically acceptable salt thereof, wherein X represents a group of general formula (IV),

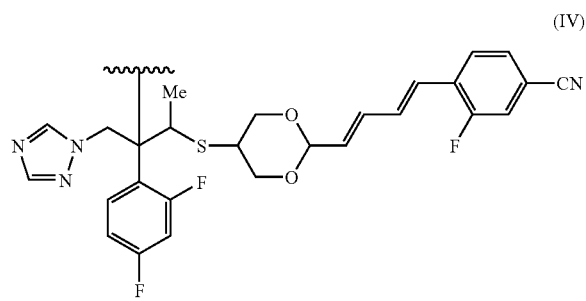

(IV)

(23) a triazole compound or a pharmacologically acceptable salt thereof according to (20), wherein E represents a methylene group, $A^1$ represents a group selected from the group consisting of

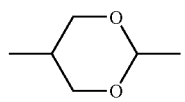

(B1)

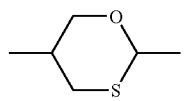

(B2)

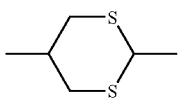

G represents a group of formula (Ga")

—(HC=CH))$_{q''}$—(C≡C)$_{r''}$—(HC=CH)$_{s''}$— (Ga")

(wherein, q" is an integer from 0 to 3, and r" and s" independently are an integer from 0 to 2, provided that total of q", r" and s" is 3 or less),

(24) a triazole compound or a pharmacologically acceptable salt thereof, wherein X represents a group of general formula (V),

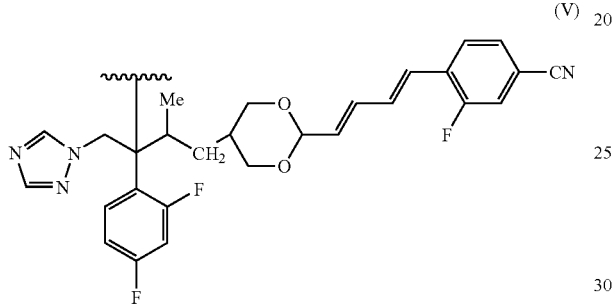

(25) a triazole compound or a pharmacologically acceptable salt thereof according to (20), wherein Ar$^2$ represents a naphthyl group which may optionally be substituted with 1 to 5 same or different group(s) selected from the group consisting of Substituent group γ, or a fused bicyclic heteroaryl group which may optionally be substituted with 1 to 5 same or different group(s) selected from the group consisting of Substituent group γ, E represents a group of formula —S(O)$_{n1}$— (wherein, n1 is an integer from 0 to 2), R$^4$ represents a C$_1$-C$_6$ alkyl group, R$^5$ represents a hydrogen atom, G represents a group of formula (Ga')

—(CO)$_{p'}$—(R$^{6'}$C=CR$^{7'}$)$_{q'}$—(C≡C)$_{r'}$—(R$^{8'}$C=CR$^{9'}$)$_{s'}$— (Ga')

(wherein, R$^{6'}$, R$^{7'}$, R$^{8'}$ and R$^{9'}$ independently represent a hydrogen atom or a C$_1$-C$_6$ alkyl group which may optionally be substituted with 1 to 5 same or different halogen atom(s), p' is an integer 0 or 1, and q', r' and s' independently are an integer from 0 to 2),

(26) a triazole compound or a pharmacologically acceptable salt thereof according to (20), wherein Ar$^2$ represents a phenyl group which may optionally be substituted with 1 to 5 same or different group(s) selected from the group consisting of Substituent group γ, or a naphthyl group which may optionally be substituted with 1 to 5 same or different group(s) selected from the group consisting of Substituent group γ, E represents a methylene group or a sulfur atom, R$^5$ represents a hydrogen atom, and G represents a group of formula (Gb)

—Φ—CO—NR$^{ψ}$—T— (Gb)

(wherein, φ represents a phenylene group which may optionally be substituted with 1 or 2 same or different group(s) selected from the group consisting of a fluorine atom and a chlorine atom, or a naphthylene group which may optionally be substituted with 1 or 2 same or different group(s) selected from the group consisting of a fluorine atom and a chlorine atom, R$^ψ$ represents a hydrogen atom or a C$_1$-C$_6$ alkyl group, and T represents a single bond or a straight or branched chain C$_1$-C$_8$ alkylene group),

(27) a triazole compound or a pharmacologically acceptable salt thereof, wherein X represents a group of formula (VI),

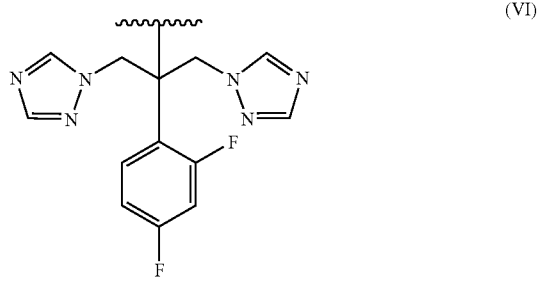

(28) a triazole compound or a pharmacologically acceptable salt thereof, wherein X represents a group of formula (VII),

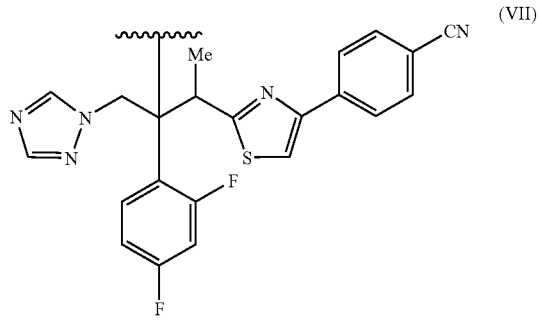

(29) a triazole compound or a pharmacologically acceptable salt thereof, wherein X represents a group of formula (VIII),

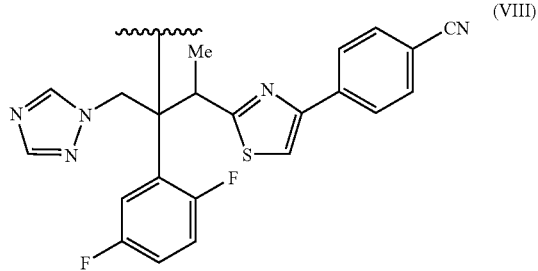

(30) a triazole compound or a pharmacologically acceptable salt thereof, wherein X represents a group of formula (IX),

(31) a triazole compound or a pharmacologically acceptable salt thereof, wherein X represents a group of formula (X),

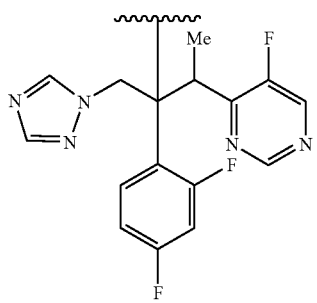

(IX)

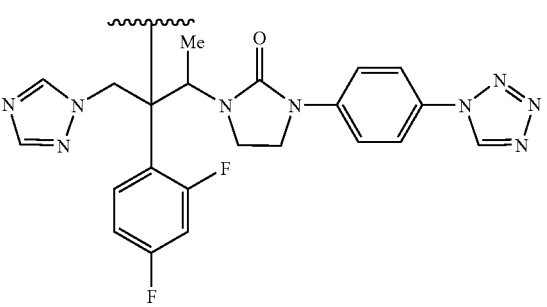

(X)

(32) a triazole compound or a pharmacologically acceptable salt thereof, wherein X represents a group of formula (XI),

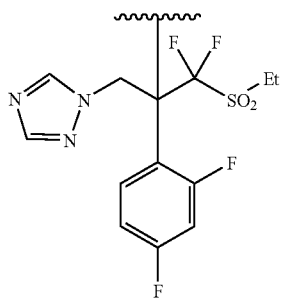

(XI)

(33) a triazole compound or a pharmacologically acceptable salt thereof, wherein X represents a group of formula (XII),

(34) a triazole compound or a pharmacologically acceptable salt thereof wherein, X represents a group of formula (XIII).

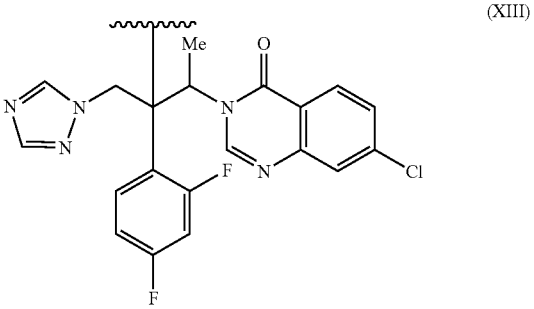

(XIII)

<Substituent Group γ> a halogen atom, a hydroxy group, a mercapto group, a nitro group, an amino group, a cyano group, a carboxy group, a $C_1$-$C_6$ alkyl group which may optionally be substituted with 1 to 5 same or different group(s) selected from the group consisting of Substituent group ζ, a $C_1$-$C_6$ alkoxy group which may optionally be substituted with 1 to 5 same or different group(s) selected from the group consisting of Substituent group ζ, a $C_1$-$C_6$ alkanoyl group which may optionally be substituted with 1 to 5 same or different group(s) selected from the group consisting of Substituent group ζ, a $C_2$-$C_6$ alkanoyloxy group which may optionally be substituted with 1 to 5 same or different group(s) selected from the group consisting of Substituent group ζ, a $C_2$-$C_7$ alkoxycarbonyl group, a $C_2$-$C_5$ alkanoylamino group, a group of formula —C(O)—NR$^{2a}$R$^{3a}$ (wherein, R$^{2a}$ and R$^{3a}$ independently represent a hydrogen atom or a $C_1$-$C_6$ alkyl group, or R$^{2a}$ and R$^{3a}$, together with the nitrogen atom to which they are attached, form a 4- to 7-membered heterocyclic group containing nitrogen atom(s), a group of formula —S(O)$_{\mu1}$—R$^{\xi1}$ (wherein, μ1 is an integer from 0 to 2 and R$^{\xi1}$ represents a $C_1$-$C_6$ alkyl group which may optionally be substituted with 1 to 5 same or different group(s) selected from the group consisting of Substituent group η), a group of formula —S(O)$^{\mu2}$—O—R$^{\xi2}$ (wherein, μ2 is an integer from 0 to 2 and R$^{\xi2}$ represents a $C_1$-$C_6$ alkyl group which may optionally be substituted with 1 to 5 same or different group(s) selected from the group consisting of Substituent group η), a group of formula —O—S(O)$_{\mu3}$—R$^{\xi3}$ (wherein, μ3

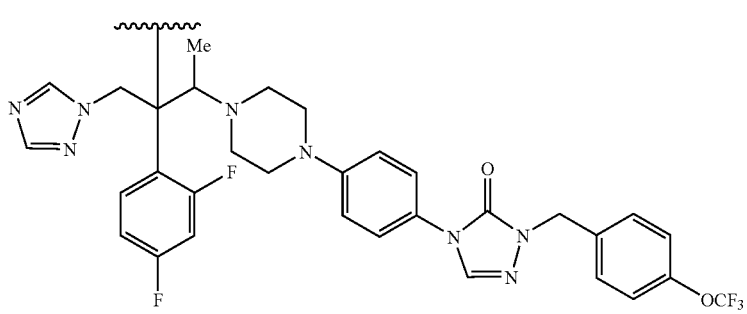

(XII)

is an integer from 0 to 2 and $R^{\xi 3}$ represents a $C_1$-$C_6$ alkyl group which may optionally be substituted with 1 to 5 same or different group(s) selected from the group consisting of Substituent group η), an imidazolyl group which may optionally be substituted with 1 or 2 same or different group(s) selected from the group consisting of Substituent group δ, a pyrazolyl group which may optionally be substituted with 1 or 2 same or different group(s) selected from the group consisting of Substituent group δ, a triazolyl group which may optionally be substituted with 1 or 2 same or different group(s) selected from the group consisting of Substituent group δ, a tetrazolyl group which may optionally be substituted with 1 or 2 same or different group(s) selected from the group consisting of Substituent group δ, a $C_2$-$C_6$ alkenyl group, a $C_2$-$C_6$ alkynyl group, a $C_3$-$C_6$ cycloalkyl group, and a $C_1$-$C_6$ alkyl group which is substituted with a $C_3$-$C_6$ cycloalkyl group.

<Substituent Group δ>
a $C_1$-$C_4$ alkyl group, a $C_1$-$C_4$ alkyl group which is substituted with 1 to 5 same or different halogen atom(s), and a halogen atom.

<Substituent Group ζ>
a halogen atom, a hydroxy group, a cyano group, and a $C_1$-$C_6$ alkoxy group.

<Substituent Group η>
a halogen atom and a hydroxy group.

Alternatively, the present invention relates in part to triazole compounds represented by the following general formula (I') shown below and pharmacologically acceptable salts thereof:

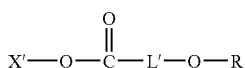

(I')

X' represents a group of general formula (II'),

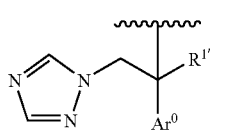

(II')

[wherein,
Ar⁰ represents a $C_6$-$C_{10}$ aryl group which may optionally be substituted with group(s) selected from the group consisting of a halogen atom and a halogenated $C_1$-$C_6$ alkyl group, and
R¹' represents an organic residue group] provided that the compound of formula X'—OH has antifungal activity,
L' represents a $C_3$-$C_4$ alkylene group which may optionally be substituted with 1 to 3 group(s) selected from the group consisting of Substituent group α0 described hereinafter, an —O—($C_2$-$C_3$ alkylene) group which may optionally be substituted with 1 to 3 group(s) selected from the group consisting of Substituent group α0 described hereinafter, an- (adjacently substituted $C_6$-$C_{10}$ aryl)-CH$_2$— group which may optionally be substituted with 1 to 3 group(s) selected from the group consisting of Substituent group α0 described hereinafter, or an- (adjacently substituted $C_3$-$C_7$ cycloalkyl) —CH$_2$— group which may optionally be substituted with 1 to 3 group(s) selected from the group consisting of Substituent group α0 described hereinafter, and
R' represents a hydrogen atom, a $C_1$-$C_6$ alkanoyl group, a $C_1$-$C_6$ alkanoyl group which is substituted with 1 to 3 group(s) selected from the group consisting of Substituent group β0, or a —P(=O)(OH)$_2$ group.

Substituent group α0 represents a group selected from the group consisting of a $C_1$-$C_6$ alkyl group, a $C_1$-$C_6$ alkoxy group, a halogen atom, a cyano group, a hydroxy group, an —NR$^{20}$R$^{30}$ group (wherein, R$^{20}$ and R$^{30}$ independently represent a hydrogen atom or a $C_1$-$C_6$ alkyl group), a group of formula —($C_1$-$C_6$ alkyl)NR$^{20}$R$^{30}$ (wherein, R$^{20}$ and R$^{30}$ have the same meanings as defined above), a carboxy group, a group of formula —OP(O)(OH)$_2$ and a group of formula —($C_1$-$C_6$ alkyl)OP(O)(OH)$_2$.

Substituent group β0 represents a group selected from the group consisting of a hydroxy group, an amino group, a carboxy group, a group of formula —OP(O)(OH)$_2$ and a group of formula —SO$_3$H.

The "aryl group" is an aromatic hydrocarbon ring group, and the $C_6$-$C_{10}$ aryl group, for example, can be a phenyl, a 1-naphthyl or a 2-naphthyl group, and is preferably a phenyl group.

The "halogen atom", for example, can be a fluorine atom, a chlorine atom, a bromine atom or an iodine atom, and is preferably a fluorine atom or a chlorine atom.

The "alkyl group" is a straight or branched chain saturated hydrocarbon group, and the $C_1$-$C_4$ alkyl group, for example, can be a methyl, an ethyl, a propyl, an isopropyl, a butyl, an isobutyl, a s-butyl or a t-butyl group, and the $C_1$-$C_6$ alkyl group, for example, can be, in addition to the above alkyl groups, a pentyl, a s-pentyl, an isopentyl, a 2-methylbutyl, a neopentyl, a 1-ethylpropyl, a hexyl, a 4-methylpentyl (an isohexyl), a 3-methylpentyl, a 2-methylpentyl, a 1-methylpentyl (a s-hexyl), a 3,3-dimethylbutyl, a 2,2-dimethylbutyl, a 1,1-dimethylbutyl, a 1,2-dimethylbutyl, a 1,3-dimethylbutyl, a 2,3-dimethylbutyl or a 2-ethylbutyl group, and is preferably a $C_1$-$C_4$ alkyl group, more preferably a $C_1$-$C_2$ alkyl group, most preferably a methyl group.

The "alkoxy group" is a straight or branched chain alkoxy group, and the $C_1$-$C_4$ alkoxy group, for example, can be a methoxy, an ethoxy, a propoxy, an isopropoxy, a butoxy, an isobutoxy, a s-butoxy or a t-butoxy group, and the $C_1$-$C_6$ alkoxy group, for example, can be, in addition to the above alkoxy groups, a pentoxy, an isopentoxy, a 2-methylbutoxy, a neopentoxy, a 1-ethylpropoxy, a hexyloxy, a 4-methylpentoxy, a 3-methylpentoxy, a 2-methylpentoxy, a 3,3-dimethylbutoxy, a 2,2-dimethylbutoxy, a 1,1-dimethylbutoxy, a 1,2-dimethylbutoxy, a 1,3-dimethylbutoxy, a 2,3-dimethylbutoxy or a 2-ethylbutoxy group, and is preferably a $C_1$-$C_4$ alkoxy group, more preferably a $C_1$-$C_2$ alkoxy group, most preferably a methoxy group.

The "halogenated alkyl group" is a monovalent group in which hydrogen atom(s) of the said alkyl group is (are) substituted with 1 to 5 halogen atom(s), and the $C_1$-$C_6$ halogenated alkyl group, for example, can be a trifluoromethyl, a trichloromethyl, a difluoromethyl, a dichloromethyl, a dibromomethyl, a fluoromethyl, a 2,2,2-trifluoroethyl, a 2,2,2-trichloroethyl, a 2-bromoethyl, a 2-chloroethyl, a 2-fluoroethyl, a 2-iodoethyl, a pentafluoroethyl, a 3-chloropropyl, a 4-fluorobutyl, a 6-iodohexyl or a 2,2-dibromoethyl group, and is preferably a $C_1$-$C_4$ halogenated alkyl group, more preferably a $C_1$-$C_2$ halogenated alkyl group, most preferably a trifluoromethyl group.

The "alkylene group" is a divalent group derived from a straight-chain saturated hydrocarbon in which both end hydrogen atoms are removed, for example, can be a methylene (—(CH$_2$)—), an ethylene (—(CH$_2$)$_2$—), a trimethylene (—(CH$_2$)$_3$—) or a tetramethylene (—(CH$_2$)$_4$—) group, and where L$^a$ is a single bond, the alkylene group is preferably a trimethylene group; where L$^a$ is an oxygen atom, the alkylene group is preferably an ethylene group; where L$^a$ is a C$_6$-C$_{10}$ aryl group which may optionally be substituted with 1 to 3 same or different group(s) selected from the group consisting of Substituent group α, a heterocyclic group which may optionally be substituted with 1 to 3 same or different group(s) selected from the group consisting of Substituent group α, or a C$_3$-C$_7$ cycloalkyl group which may optionally be substituted with 1 to 3 same or different group(s) selected from the group consisting of Substituent group α, the alkylene group is preferably a methylene group; and, in L', the —O—(C$_2$-C$_3$ alkylene) group, for example, can be an —O—(CH$_2$)$_2$— group or an —O—(CH$_2$)$_3$— group, and is preferably an —O—(CH$_2$)$_2$— group.

The "alkanoyl group" is a monovalent group in which a hydrogen atom or an alkyl group as defined above is bonded to a carbonyl group, and the C$_1$-C$_6$ alkanoyl group, for example, can be a formyl, an acetyl, a propionyl, a butyryl, an isobutyryl, a pentanoyl, a pivaloyl, a valeryl or an isovaleryl group, and is preferably a C$_1$-C$_4$ alkanoyl group.

The "alkanoyloxy group" is a group in which an oxygen atom is substituted with an alkanoyl group as defined above, and the C$_2$-C$_6$ alkanoyloxy group, for example, can be an acetyloxy, a propionyloxy, a butyryloxy, an isobutyryloxy, a pentanoyloxy, a pivaloyloxy, a valeryloxy or an isovaleryloxy group, and is preferably a C$_1$-C$_4$ alkanoyloxy group.

The "alkanoylamino group" is a group in which an amino group is substituted with an alkanoyl group as defined above, and the C$_2$-C$_6$ alkanoylamino group, for example, can be an acetylamino, a propionylamino, a butyrylamino, an isobutyrylamino, a pentanoylamino, a pivaloylamino, a valerylamino or an isovalerylamino group, and is preferably a C$_1$-C$_4$ alkanoylamino group.

The "alkoxycarbonyl group" is a group in which a carbonyl group is substituted with an alkoxy group as defined above, and the C$_2$-C$_6$ alkoxycarbonyl group, for example, can be a methoxycarbonyl, an ethoxycarbonyl, a propoxycarbonyl, an isopropoxycarbonyl, a butoxycarbonyl, an isobutoxycarbonyl, a s-butoxycarbonyl, a t-butoxycarbonyl, a pentoxycarbonyl, an isopentoxycarbonyl, a 2-methylbutoxycarbonyl, a neopentoxycarbonyl or a 1-ethylpropoxycarbonyl group, and the C$_2$-C$_7$ alkoxycarbonyl group, for example, can be, in addition to the above alkoxycarbonyl groups, a hexyloxycarbonyl, a 4-methylpentoxycarbonyl, a 3-methylpentoxycarbonyl, a 2-methylpentoxycarbonyl, a 3,3-dimethylbutoxycarbonyl, a 2,2-dimethylbutoxycarbonyl, a 1,1-dimethylbutoxycarbonyl, a 1,2-dimethylbutoxycarbonyl, a 1,3-dimethylbutoxycarbonyl, a 2,3-dimethylbutoxycarbonyl or a 2-ethylbutoxycarbonyl group, and is preferably a C$_2$-C$_5$ alkoxycarbonyl group, more preferably a C$_2$-C$_3$ alkoxycarbonyl group, most preferably an ethoxycarbonyl group.

The "C$_1$-C$_6$ alkylamino group" is a group in which an amino group is substituted with one C$_1$-C$_6$ alkyl group as defined above, and, for example, can be a methylamino, an ethylamino, a n-propylamino, an isopropylamino, a n-butylamino, an isobutylamino, a s-butylamino, a tert-butylamino, a n-pentylamino, isopentylamino, a 2-methylbutylamino, a neopentylamino, a 1-ethylpropylamino, a n-hexylamino, an isohexylamino, a 4-methylpentylamino, a 3-methylpentylamino, a 2-methylpentylamino, a 1-methylpentylamino, a 3,3-dimethylbutylamino, a 2,2-dimethylbutylamino, a 1,1-dimethylbutylamino, a 1,2-dimethylbutylamino, a 1,3-dimethylbutylamino, a 2,3-dimethylbutylamino or a 2-ethylbutylamino group, and is preferably a methylamino group.

The "di C$_1$-C$_6$ alkylamino group" is a group in which an amino group is substituted with two C$_1$-C$_6$ alkyl groups as defined above, and, for example, can be a straight- or branched-chain dialkylamino group having a carbon number of 2-12 such as a dimethylamino, a diethylamino, an ethylmethylamino, a dipropylamino, a diisopropylamino, a dibutylamino, a diisobutylamino, a di(s-butyl)amino, a di(t-butyl)amino, a dipentylamino, a diisopentylamino, a dineopentylamino, a di(1-ethylpropyl)amino, a dihexylamino or a diisohexylamino group, and is preferably a dimethylamino or a diethylamino group, more preferably a diethylamino group.

The "—NR$^{20}$R$^{30}$ group (R$^{20}$ and R$^{30}$ independently represent a hydrogen atom or a C$_1$-C$_6$ alkyl group)" is an amino group, a "C$_1$-C$_6$ alkylamino group" or a "di C$_1$-C$_6$ alkylamino group", and is preferably an amino, a dimethylamino or a diethylamino group, more preferably a diethylamino group.

The "amino-C$_1$-C$_6$ alkyl group" is a group in which a C$_1$-C$_6$ alkyl group as defined above is substituted with one amino group, and, for example, can be an aminomethyl, an aminoethyl, an aminopropyl, an aminobutyl, an aminohexyl or a 2 aminoethyl group, and is preferably an aminomethyl group.

The "C$_1$-C$_6$ alkylamino-C$_1$-C$_6$ alkyl group" is a group in which the amino group of the amino-C$_1$-C$_6$ alkyl group as defined above is substituted with one C$_1$-C$_6$ alkyl group as defined above, and, for example, can be a methylaminomethyl, an ethylaminomethyl, a propylaminomethyl, an isopropylaminomethyl, a butylaminomethyl, a pentylaminomethyl or a hexylaminomethyl group, and is preferably a methylaminomethyl group.

The "di C$_1$-C$_6$ alkylamino-C$_1$-C$_6$ alkyl group" is a group in which the amino group of the amino-C$_1$-C$_6$ alkyl group as defined above is substituted with two C$_1$-C$_6$ alkyl groups as defined above, and, for example, can be a dimethylaminomethyl, a diethylaminomethyl, a diisopropylaminomethyl, a dimethylaminoethyl, a diethylaminoethyl, a dimethylaminopropyl, a diethylaminopropyl, a diethylaminobutyl, a diethylaminopentyl or a diethylaminohexyl group, and is preferably a diethylaminomethyl group.

The "—(C$_1$-C$_6$ alkyl)NR$^{20}$R$^{30}$" group is a group in which a C$_1$-C$_6$ alkyl group as defined above is substituted with one group of formula —NR$^{20}$R$^{30}$ as defined above, and is an "amino-C$_1$-C$_6$ alkyl group", a "C$_1$-C$_6$ alkylamino-C$_1$-C$_6$ alkyl group" or a "di C$_1$-C$_6$ alkylamino-C$_1$-C$_6$ alkyl group", and is preferably a —CH$_2$—NR$^{20}$R$^{30}$ group, more preferably a diethylaminomethyl group.

The "cycloalkyl group" is a cyclic saturated aliphatic hydrocarbon group, and the C$_3$-C$_7$ cycloalkyl group, for example, can be a cyclopropyl, a cyclobutyl, a cyclopentyl, a cyclohexyl or a cycloheptyl group, and is preferably a C$_3$-C$_6$ cycloalkyl group.

The "heterocyclic group containing nitrogen atom(s)" is a 4- to 7-membered heterocyclic group having 1 to 3 nitrogen atom(s), and, for example, can be a pyrrolyl, a pyrazolyl, an imidazolyl, an oxazolyl, an isoxazolyl, a thiazolyl, an isothiazolyl, a 1,2,3-oxadiazolyl, a triazolyl, a thiadiazolyl, a tetrazolyl, a pyridyl, a pyridazinyl, a pyrimidinyl, a pyrazinyl, an azetidinyl, a thiolanyl, a pyrrolidinyl, an imidazolidinyl, an oxazolidinyl, an isoxazolidinyl, a thiazolidinyl, an isothiazolidinyl, a piperidinyl, a piperazyl, a morpholinyl, a thiomorpholinyl, a pyrazolinyl, a pyrrolinyl, an imidazolinyl, an azepinyl, an azepanyl or a diazepinyl group, and is preferably a saturated 4- to 7-membered heterocyclic group, more preferably a piperazinyl group.

The "monocyclic heteroaryl group" is a 5- or 6-membered monocyclic aromatic heterocyclic group having 1 to 4 heteroatom(s) selected from the group consisting of oxygen atom(s), nitrogen atom(s) and sulfur atom(s), and, for example, can be a 5-membered monocyclic heteroaryl group such as a furyl, a thienyl, a pyrrolyl, a pyrazolyl, an imidazolyl, an oxazolyl, an isoxazolyl, a thiazolyl, an isothiazolyl, a 1,2,3-oxadiazolyl, a triazolyl, a thiadiazolyl or a tetrazolyl group; or a 6-membered monocyclic heteroaryl group such as a pyridyl, a pyridazinyl, a pyrimidinyl or a pyrazinyl group; and is preferably a 5-membered monocyclic heteroaryl group, more preferably a furyl, a thienyl or a pyridyl group.

The "heterocyclyl group" is a 4- to 6-membered non-aromatic heterocyclic group having 1 to 3 heteroatom(s) selected from the group consisting of oxygen atom(s), nitrogen atom(s) and sulfur atom(s), and, for example, can be a 4-membered heterocyclyl group such as an oxetanyl, a thietanyl or an azetidinyl group; a 5-membered heterocyclyl group such as a tetrahydrofuryl, a thiolanyl, a pyrrolidinyl, an imidazolidinyl, an oxazolidinyl, an isoxazolidinyl, a thiazolidinyl or an isothiazolidinyl group; or a 6-membered heterocyclyl group such as a dioxanyl, an oxathianyl, a dithianyl, a tetrahydropyranyl, a thianyl, a piperizinyl, a piperazyl, a morpholinyl or a thiomorpholinyl group; and is preferably a 6-membered heterocyclyl group, more preferably a dioxanyl, an oxathianyl or a dithianyl group.

The "fused bicyclic heteroaryl group" is a fused bicyclic aromatic heterocyclic group having 1 to 3 heteroatom(s) selected from the group consisting of oxygen atom(s), nitrogen atom(s) and sulfur atom(s), and, for example, can be a 9-membered polycyclic heteroaryl group such as an isobenzofuranyl, a benzofuranyl, an isobenzothiophenyl, a benzothiophenyl, an indolizinyl, an isoindolyl, an indolyl, a benzoxazolyl or a benzothiazolyl group; or a 10-membered polycyclic heteroaryl group such as a chromenyl, an isoquinolyl, a quinolyl or a quinazolinyl group; and is preferably a quinolyl, a benzothiophenyl or an indolyl group.

The "heterocyclic group" includes the "heterocyclic group containing nitrogen atom(s)", the "monocyclic heteroaryl group", the "heterocyclyl group" and the "fused bicyclic heteroaryl group" as defined above, and is preferably a "monocyclic heteroaryl group" or a "heterocyclyl group", more preferably a "monocyclic heteroaryl group".

In the general formula (I'), the- (adjacently substituted $C_6$-$C_{10}$ aryl)-$CH_2$— group, and the- (adjacently substituted $C_3$-$C_7$ cycloalkyl)-$CH_2$— group in the definition of L' have the same meanings as in "the carbon atom in the —$L^a$— group to which the X—O—C(=O)— group is bonded and the carbon atom in the —$L^a$— group to which the —$L^b$—O—R group is bonded are adjacent to each other".

That is, adjacent carbon atoms in the aryl moiety or cycloalkyl moiety are substituted. The structure is shown below.

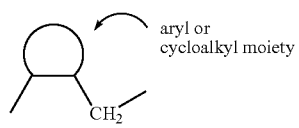
aryl or cycloalkyl moiety

Provided that when the aryl moiety in the- (adjacently substituted $C_6$-$C_{10}$ aryl)-$CH_2$— group is a naphthalene, the substituted positions on the naphthalene ring may be the 1 and 8 positions.

When R is a non-hydrophilic group, that is, when R is a $C_1$-$C_6$ alkanoyl group, Substituent group α is preferably selected from Substituent group α2 consisting of a hydroxy group, an amino group, a $C_1$-$C_6$ alkylamino group, a di $C_1$-$C_6$ alkylamino group, an amino-$C_1$-$C_6$ alkyl group, a $C_1$-$C_6$ alkyl-amino-$C_1$-$C_6$ alkyl group, a di $C_1$-$C_6$ alkyl-amino-$C_1$-$C_6$ alkyl group, a carboxy group, an —O—P(=O)(OH)$_2$ group, and a $C_1$-$C_6$ alkyl group substituted with one —O—P(=O)(OH)$_2$ group.

When $R^1$ is an organic residue group, there is no particular limitation on the nature of the "organic residue group", provided that the group contains carbon atoms and the compound of formula X—OH including $R^1$ exhibits antifungal activity.

The "antifungal activity" of the compound means that the compound is expected to be used for the treatment of mycotic infection (mycosis) such as deep mycosis, deep dermatomycosis, epidermomycosis and the like, and whether the specific compound has such an effect can be judged easily by persons skilled in the art according to the methods described below.

Such methods are ones comprising the determination of the MIC (minimum inhibitory concentration) of the compound against typical fungus such as Candida, Aspergillus, Cryptococcus neoformans or Trichophyton, according to the method (M27-A, M38-P) standardized by NCCLS (National Committee for Clinical Laboratory Standards) or the method (described in Journal of Clinical Microbiology, 38, 341-344 (2000)), and if the MIC is equal to or lower than the standard (preferably 64 µg/mL), the compound is judged active against fungi.

"The pharmacologically acceptable salt" of the compound of the present invention is a salt generally used in pharmaceutical compounds of an acidic group such as a carboxy group, a —P(=O)(OH)$_2$ group or a —SO$_3$H group, or of a basic group such as a triazole group, an amino group or a piperidyl group.

The salts formed with an acidic group of general formula (I), for example, can be alkali metal salts (e.g. sodium salts, potassium salts and lithium salts); alkaline earth metal salts (e.g. calcium salts and magnesium salts); metal salts (e.g. aluminum salts, iron salts, zinc salts, copper salts, nickel salts and cobalt salts); inorganic salts (e.g. ammonium salts); and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-N-phenethylamine salts, piperazine salts, tetramethylammonium salts and tris(hydroxymethyl)aminomethane salts).

The salts formed with a basic group of general formula (I), for example, can be hydrohalide acid salts (e.g. hydrofluorides, hydrochlorides, hydrobromides and hydroiodides); inorganic acid salts (e.g. nitrates, perchlorates, sulfates and phosphates); lower alkanesulfonates (e.g. methanesulfonates, trifluoromethanesulfonates and ethanesulfonates); arylsulfonates (e.g. benzenesulfonate and p-toluenesulfonate); amino acid salts (e.g. ornithine salts and glutamates); and carboxylic acid salts (e.g. fumarates, succinates, citrates, tartrates, oxalates and maleates).

The compounds of the present invention can sometimes absorb water or form a hydrate upon exposure to the atmosphere or when recrystallized, and such hydrates are also included within the scope of the triazole compound or a pharmacologically acceptable salt thereof of the present invention.

Additionally, certain other solvents may be taken up by the compounds of the present invention to produce solvates, which also form a part of the triazole compound or a pharmacologically acceptable salt thereof of the present invention.

The compounds of the present invention involve various isomers. For example, the compound of general formula (II) contains asymmetric carbons, and based on these carbons, stereoisomers exist in the compounds of the invention.

Alternatively, the group $R^1$ of the compound of general formula (II) may have asymmetric carbons and carbon-carbon double bond(s), the compounds of the present invention involve various stereoisomers.

Accordingly, the present invention covers both the individual isomers and mixtures thereof in any proportion.

Such stereoisomers can be prepared by using stereospecific starting compounds, or by synthesizing the compounds of the present invention according to methods of asymmetric synthesis or asymmetric induction, or by conventional optical resolution methods or separating methods.

The ester part of the triazole compound of the present invention includes, for example, the groups described in Example Tables 1, 1A, 2, 2A, 2B, 2C and 3, but the scope of the invention is not limited to those groups.

Further, the mark ["] represents the same chemical structure as the structure above it.

The abbreviations in the Tables represent the following structural formulas.

| Abbreviation | Structural formula |
|---|---|
| 1-Azt | —N⟨△⟩ |
| 1-Pyrd | —N⟨pentagon⟩ |
| 1-Pip | —N⟨hexagon⟩ |
| 1-Azp | —N⟨heptagon⟩ |
| Mor | —N⟨hexagon with O⟩ |
| Thz | —N⟨hexagon with S⟩ |

-continued

| Abbreviation | Structural formula |
|---|---|
| 4-Me-1-Piz | 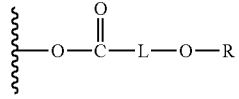 |

EXAMPLE TABLE 1

$$\xi\text{—O—}\overset{\overset{\displaystyle O}{\|}}{C}\text{—L—O—R}$$

| Example No. | L | R |
|---|---|---|
| 1-1 | CH$_2$CH$_2$CH$_2$ | H |
| 1-2 | CH$_2$CH$_2$CH$_2$ | CHO |
| 1-3 | CH$_2$CH$_2$CH$_2$ | CONH$_2$ |
| 1-4 | CH$_2$CH$_2$CH$_2$ | C(=O)COOH |
| 1-5 | CH$_2$CH$_2$CH$_2$ | COCH$_3$ |
| 1-6 | CH$_2$CH$_2$CH$_2$ | COCH$_2$NH$_2$ |
| 1-7 | CH$_2$CH$_2$CH$_2$ | COCH$_2$COOH |
| 1-8 | CH$_2$CH$_2$CH$_2$ | COCH$_2$CH$_2$OH |
| 1-9 | CH$_2$CH$_2$CH$_2$ | COCH$_2$CH$_2$NH$_2$ |
| 1-10 | CH$_2$CH$_2$CH$_2$ | COCH$_2$CH$_2$COOH |
| 1-11 | CH$_2$CH$_2$CH$_2$ | COCH(CH$_3$)NH$_2$ |
| 1-12 | CH$_2$CH$_2$CH$_2$ | COCH(CH$_3$)COOH |
| 1-13 | CH$_2$CH$_2$CH$_2$ | COCH$_2$CH$_2$CH$_2$OH |
| 1-14 | CH$_2$CH$_2$CH$_2$ | COCH$_2$CH$_2$CH$_2$NH$_2$ |
| 1-15 | CH$_2$CH$_2$CH$_2$ | COCH$_2$CH$_2$CH$_2$COOH |
| 1-16 | CH$_2$CH$_2$CH$_2$ | COC(CH$_3$)$_2$COOH |
| 1-17 | CH$_2$CH$_2$CH$_2$ | COC(CH$_3$)$_2$CH$_2$OH |
| 1-18 | CH$_2$CH$_2$CH$_2$ | COC(CH$_3$)$_2$CH$_2$NH$_2$ |
| 1-19 | CH$_2$CH$_2$CH$_2$ | COC(CH$_3$)$_2$CH$_2$COOH |
| 1-20 | CH$_2$CH$_2$CH$_2$ | COCH(NH$_2$)COOH |
| 1-21 | CH$_2$CH$_2$CH$_2$ | COCH(NH$_2$)CH$_2$COOH |
| 1-22 | CH$_2$CH$_2$CH$_2$ | COCH$_2$CH(NH$_2$)COOH |
| 1-23 | CH$_2$CH$_2$CH$_2$ | COCH(NH$_2$)CH$_2$CH$_2$COOH |
| 1-24 | CH$_2$CH$_2$CH$_2$ | COCH$_2$CH$_2$CH(NH$_2$)COOH |
| 1-25 | CH$_2$CH$_2$CH$_2$ | P(=O)(OH)$_2$ |
| 1-26 | CF$_2$CH$_2$CH$_2$ | H |
| 1-27 | CF$_2$CH$_2$CH$_2$ | COCH$_2$COOH |
| 1-28 | CF$_2$CH$_2$CH$_2$ | COCH$_2$CH$_2$COOH |
| 1-29 | CF$_2$CH$_2$CH$_2$ | COCH$_2$CH$_2$CH$_2$COOH |
| 1-30 | CF$_2$CH$_2$CH$_2$ | P(=O)(OH)$_2$ |
| 1-31 | C(CH$_3$)$_2$CH$_2$CH$_2$ | H |
| 1-32 | C(CH$_3$)$_2$CH$_2$CH$_2$ | COCH$_2$COOH |
| 1-33 | C(CH$_3$)$_2$CH$_2$CH$_2$ | COCH$_2$CH$_2$COOH |
| 1-34 | C(CH$_3$)$_2$CH$_2$CH$_2$ | COCH$_2$CH$_2$CH$_2$COOH |
| 1-35 | C(CH$_3$)$_2$CH$_2$CH$_2$ | P(=O)(OH)$_2$ |
| 1-36 | CH$_2$C(CH$_3$)$_2$CH$_2$ | H |
| 1-37 | CH$_2$C(CH$_3$)$_2$CH$_2$ | COCH$_2$COOH |
| 1-38 | CH$_2$C(CH$_3$)$_2$CH$_2$ | COCH$_2$CH$_2$COOH |
| 1-39 | CH$_2$C(CH$_3$)$_2$CH$_2$ | COCH$_2$CH$_2$CH$_2$COOH |
| 1-40 | CH$_2$C(CH$_3$)$_2$CH$_2$ | P(=O)(OH)$_2$ |
| 1-41 | CH$_2$CH$_2$CH(COOH) | H |
| 1-42 | CH$_2$CH$_2$CH(COOH) | COCH$_3$ |
| 1-43 | CH$_2$CH$_2$CH(COOH) | COCH$_2$NH$_2$ |
| 1-44 | CH$_2$CH$_2$CH(COOH) | COCH$_2$COOH |
| 1-45 | CH$_2$CH$_2$CH(COOH) | COCH$_2$CH$_2$COOH |
| 1-46 | CH$_2$CH$_2$CH(COOH) | COCH$_2$CH$_2$CH$_2$COOH |
| 1-47 | CH$_2$CH$_2$CH(COOH) | P(=O)(OH)$_2$ |
| 1-48 | CH$_2$CH$_2$CH$_2$CH$_2$ | H |
| 1-49 | CH$_2$CH$_2$CH$_2$CH$_2$ | COCH$_2$COOH |
| 1-50 | CH$_2$CH$_2$CH$_2$CH$_2$ | COCH$_2$CH$_2$COOH |
| 1-51 | CH$_2$CH$_2$CH$_2$CH$_2$ | COCH$_2$CH$_2$CH$_2$COOH |
| 1-52 | CH$_2$CH$_2$CH$_2$CH$_2$ | P(=O)(OH)$_2$ |
| 1-53 | CF$_2$CH$_2$CH$_2$CH$_2$ | H |
| 1-54 | CF$_2$CH$_2$CH$_2$CH$_2$ | COCH$_2$COOH |
| 1-55 | CF$_2$CH$_2$CH$_2$CH$_2$ | COCH$_2$CH$_2$COOH |
| 1-56 | CF$_2$CH$_2$CH$_2$CH$_2$ | COCH$_2$CH$_2$CH$_2$COOH |
| 1-57 | CF$_2$CH$_2$CH$_2$CH$_2$ | P(=O)(OH)$_2$ |
| 1-58 | C(CH$_3$)$_2$CH$_2$CH$_2$CH$_2$ | H |
| 1-59 | C(CH$_3$)$_2$CH$_2$CH$_2$CH$_2$ | COCH$_2$COOH |

EXAMPLE TABLE 1-continued

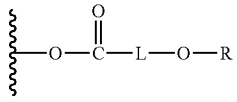

| Example No. | L | R |
|---|---|---|
| 1-60 | C(CH$_3$)$_2$CH$_2$CH$_2$CH$_2$ | COCH$_2$CH$_2$COOH |
| 1-61 | C(CH$_3$)$_2$CH$_2$CH$_2$CH$_2$ | P(=O)(OH)$_2$ |
| 1-62 | CH$_2$C(CH$_3$)$_2$CH$_2$CH$_2$ | H |
| 1-63 | CH$_2$C(CH$_3$)$_2$CH$_2$CH$_2$ | COCH$_2$COOH |
| 1-64 | CH$_2$C(CH$_3$)$_2$CH$_2$CH$_2$ | COCH$_2$CH$_2$COOH |
| 1-65 | CH$_2$C(CH$_3$)$_2$CH$_2$CH$_2$ | P(=O)(OH)$_2$ |
| 1-66 | CH$_2$CH$_2$C(CH$_3$)$_2$CH$_2$ | H |
| 1-67 | CH$_2$CH$_2$C(CH$_3$)$_2$CH$_2$ | COCH$_2$COOH |
| 1-68 | CH$_2$CH$_2$C(CH$_3$)$_2$CH$_2$ | COCH$_2$CH$_2$COOH |
| 1-69 | CH$_2$CH$_2$C(CH$_3$)$_2$CH$_2$ | P(=O)(OH)$_2$ |
| 1-70 | OCH$_2$CH$_2$ | H |
| 1-71 | OCH$_2$CH$_2$ | CHO |
| 1-72 | OCH$_2$CH$_2$ | CONH$_2$ |
| 1-73 | OCH$_2$CH$_2$ | C(=O)COOH |
| 1-74 | OCH$_2$CH$_2$ | COCH$_2$OH |
| 1-75 | OCH$_2$CH$_2$ | COCH$_2$NH$_2$ |
| 1-76 | OCH$_2$CH$_2$ | COCH$_2$COOH |
| 1-77 | OCH$_2$CH$_2$ | COCH$_2$CH$_2$OH |
| 1-78 | OCH$_2$CH$_2$ | COCH$_2$CH$_2$NH$_2$ |
| 1-79 | OCH$_2$CH$_2$ | COCH$_2$CH$_2$COOH |
| 1-80 | OCH$_2$CH$_2$ | COCH(CH$_3$)NH$_2$ |
| 1-81 | OCH$_2$CH$_2$ | COCH(CH$_3$)COOH |
| 1-82 | OCH$_2$CH$_2$ | COCH$_2$CH$_2$CH$_2$OH |
| 1-83 | OCH$_2$CH$_2$ | COCH$_2$CH$_2$CH$_2$NH$_2$ |
| 1-84 | OCH$_2$CH$_2$ | COCH$_2$CH$_2$CH$_2$COOH |
| 1-85 | OCH$_2$CH$_2$ | COC(CH$_3$)$_2$COOH |
| 1-86 | OCH$_2$CH$_2$ | COC(CH$_3$)$_2$CH$_2$OH |
| 1-87 | OCH$_2$CH$_2$ | COC(CH$_3$)$_2$CH$_2$NH$_2$ |
| 1-88 | OCH$_2$CH$_2$ | COC(CH$_3$)$_2$CH$_2$COOH |
| 1-89 | OCH$_2$CH$_2$ | COCH(NH$_2$)COOH |
| 1-90 | OCH$_2$CH$_2$ | COCH(NH$_2$)CH$_2$COOH |
| 1-91 | OCH$_2$CH$_2$ | COCH$_2$CH(NH$_2$)COOH |
| 1-92 | OCH$_2$CH$_2$ | COCH(NH$_2$)CH$_2$CH$_2$COOH |
| 1-93 | OCH$_2$CH$_2$ | COCH$_2$CH$_2$CH(NH$_2$)COOH |
| 1-94 | OCH$_2$CH$_2$ | P(=O)(OH)$_2$ |
| 1-95 | OCH$_2$CH$_2$CH$_2$ | H |
| 1-96 | OCH$_2$CH$_2$CH$_2$ | COCH$_2$COOH |
| 1-97 | OCH$_2$CH$_2$CH$_2$ | COCH$_2$CH$_2$COOH |
| 1-98 | OCH$_2$CH$_2$CH$_2$ | COCH$_2$CH$_2$CH$_2$COOH |
| 1-99 | OCH$_2$CH$_2$CH$_2$ | P(=O)(OH)$_2$ |
| 1-100 | OCH$_2$C(CH$_3$)$_2$CH$_2$ | H |
| 1-101 | OCH$_2$C(CH$_3$)$_2$CH$_2$ | COCH$_2$COOH |
| 1-102 | OCH$_2$C(CH$_3$)$_2$CH$_2$ | COCH$_2$CH$_2$COOH |
| 1-103 | OCH$_2$C(CH$_3$)$_2$CH$_2$ | P(=O)(OH)$_2$ |
| 1-104 | CH$_2$CH$_2$CH(CH$_2$N(C$_2$H$_5$)$_2$) | H |
| 1-105 | CH$_2$CH$_2$CH(CH$_2$N(C$_2$H$_5$)$_2$) | COCH$_3$ |
| 1-106 | CH$_2$CH$_2$CH(CH$_2$N(C$_2$H$_5$)$_2$) | P(=O)(OH)$_2$ |

EXAMPLE TABLE 1A

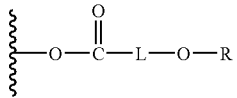

| Example No. | L | R |
|---|---|---|
| 1A-1 | CH$_2$ | H |
| 1A-2 | CH$_2$ | COCH$_2$CH$_2$COOH |
| 1A-3 | CH$_2$ | P(=O)(OH)$_2$ |
| 1A-4 | CH$_2$CH$_2$ | H |
| 1A-5 | CH$_2$CH$_2$ | P(=O)(OH)$_2$ |
| 1A-6 | CH$_2$CH$_2$CH$_2$ | COCH$_2$NHCH$_3$ |
| 1A-7 | CH$_2$CH$_2$CH$_2$ | COCH$_2$N(CH$_3$)$_2$ |
| 1A-8 | CH$_2$CH$_2$CH$_2$ | COCH$_2$-(1-Pyrd) |
| 1A-9 | CH$_2$CH$_2$CH$_2$ | COCH$_2$-(4-Me-1-Piz) |

EXAMPLE TABLE 1A-continued

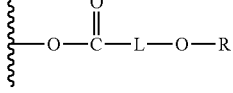

| Example No. | L | R |
|---|---|---|
| 1A-10 | CH$_2$CH$_2$CH$_2$ | COCH$_2$CH$_2$N(CH$_3$)$_2$ |
| 1A-11 | CH$_2$CH$_2$CH$_2$ | COCH$_2$CH$_2$-(1-Pyrd) |
| 1A-12 | CH$_2$CH$_2$CH$_2$ | COCH$_2$CH$_2$-(4-Me-1-Piz) |
| 1A-13 | CH$_2$CH$_2$CH$_2$ | COCH$_2$CH$_2$CO-(4-Me-1-Piz) |
| 1A-14 | CH$_2$CH$_2$CH$_2$ | COCH$_2$CH$_2$CH$_2$N(CH$_3$)$_2$ |
| 1A-15 | CH$_2$CH$_2$CH$_2$ | COCH$_2$CH$_2$CH$_2$-(1-Pyrd) |
| 1A-16 | CH$_2$CH$_2$CH$_2$ | COCH$_2$CH$_2$CH$_2$-(4-Me-1-Piz) |
| 1A-17 | OCH$_2$CH$_2$ | COCH$_2$NHCH$_3$ |
| 1A-18 | OCH$_2$CH$_2$ | COCH$_2$N(CH$_3$)$_2$ |
| 1A-19 | OCH$_2$CH$_2$ | COCH$_2$-(1-Pyrd) |
| 1A-20 | OCH$_2$CH$_2$ | COCH$_2$-(4-Me-1-Piz) |
| 1A-21 | OCH$_2$CH$_2$ | COCH$_2$CH$_2$CO-(4-Me-1-Piz) |
| 1A-22 | CF$_2$CH$_2$CH$_2$ | COCH$_2$NHCH$_3$ |
| 1A-23 | CF$_2$CH$_2$CH$_2$ | COCH$_2$N(CH$_3$)$_2$ |
| 1A-24 | CF$_2$CH$_2$CH$_2$ | COCH$_2$-(1-Pyrd) |
| 1A-25 | CF$_2$CH$_2$CH$_2$ | COCH$_2$-(4-Me-1-Piz) |
| 1A-26 | CF$_2$CH$_2$CH$_2$ | COCH$_2$CH$_2$CO-(4-Me-1-Piz) |
| 1A-27 | C(CH$_3$)$_2$CH$_2$CH$_2$ | COCH$_2$NHCH$_3$ |
| 1A-28 | C(CH$_3$)$_2$CH$_2$CH$_2$ | COCH$_2$N(CH$_3$)$_2$ |
| 1A-29 | C(CH$_3$)$_2$CH$_2$CH$_2$ | COCH$_2$-(1-Pyrd) |
| 1A-30 | C(CH$_3$)$_2$CH$_2$CH$_2$ | COCH$_2$-(4-Me-1-Piz) |
| 1A-31 | C(CH$_3$)$_2$CH$_2$CH$_2$ | COCH$_2$CH$_2$CO-(4-Me-1-Piz) |
| 1A-32 | CH$_2$C(CH$_3$)$_2$CH$_2$ | COCH$_2$NHCH$_3$ |
| 1A-33 | CH$_2$C(CH$_3$)$_2$CH$_2$ | COCH$_2$N(CH$_3$)$_2$ |
| 1A-34 | CH$_2$C(CH$_3$)$_2$CH$_2$ | COCH$_2$-(1-Pyrd) |
| 1A-35 | CH$_2$C(CH$_3$)$_2$CH$_2$ | COCH$_2$-(4-Me-1-Piz) |
| 1A-36 | CH$_2$C(CH$_3$)$_2$CH$_2$ | COCH$_2$CH$_2$CO-(4-Me-1-Piz) |

EXAMPLE TABLE 2

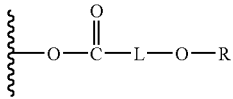

| Example No. | L | R |
|---|---|---|
| 2-1 | 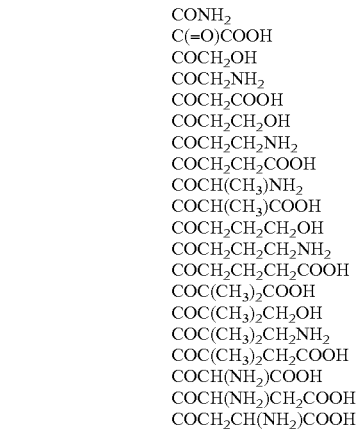 | H |
| 2-2 | " | CHO |
| 2-3 | " | CONH$_2$ |
| 2-4 | " | C(=O)COOH |
| 2-5 | " | COCH$_2$OH |
| 2-6 | " | COCH$_2$NH$_2$ |
| 2-7 | " | COCH$_2$COOH |
| 2-8 | " | COCH$_2$CH$_2$OH |
| 2-9 | " | COCH$_2$CH$_2$NH$_2$ |
| 2-10 | " | COCH$_2$CH$_2$COOH |
| 2-11 | " | COCH(CH$_3$)NH$_2$ |
| 2-12 | " | COCH(CH$_3$)COOH |
| 2-13 | " | COCH$_2$CH$_2$CH$_2$OH |
| 2-14 | " | COCH$_2$CH$_2$CH$_2$NH$_2$ |
| 2-15 | " | COCH$_2$CH$_2$CH$_2$COOH |
| 2-16 | " | COC(CH$_3$)$_2$COOH |
| 2-17 | " | COC(CH$_3$)$_2$CH$_2$OH |
| 2-18 | " | COC(CH$_3$)$_2$CH$_2$NH$_2$ |
| 2-19 | " | COC(CH$_3$)$_2$CH$_2$COOH |
| 2-20 | " | COCH(NH$_2$)COOH |
| 2-21 | " | COCH(NH$_2$)CH$_2$COOH |
| 2-22 | " | COCH$_2$CH(NH$_2$)COOH |

EXAMPLE TABLE 2-continued $$\{-O-\overset{O}{\underset{\|}{C}}-L-O-R$$

| Example No. | L | R |
|---|---|---|
| 2-23 | " | COCH(NH$_2$)CH$_2$CH$_2$COOH |
| 2-24 | " | COCH$_2$CH$_2$CH(NH$_2$)COOH |
| 2-25 | " | P(=O)(OH)$_2$ |
| 2-26 | 2-cyanophenylene (NC at position) | H |
| 2-27 | " | P(=O)(OH)$_2$ |
| 2-28 | 4-cyanophenylene | H |
| 2-29 | " | P(=O)(OH)$_2$ |
| 2-30 | 4-CN phenylene | H |
| 2-31 | " | P(=O)(OH)$_2$ |
| 2-32 | indoline-CN | H |
| 2-33 | " | P(=O)(OH)$_2$ |
| 2-34 | 3-F phenylene | H |
| 2-35 | " | P(=O)(OH)$_2$ |
| 2-36 | 4-F phenylene | H |
| 2-37 | " | COCH$_2$COOH |

EXAMPLE TABLE 2-continued $$\{-O-\overset{O}{\underset{\|}{C}}-L-O-R$$

| Example No. | L | R |
|---|---|---|
| 2-38 | 5-F phenylene | COCH$_2$CH$_2$COOH |
| 2-39 | " | COCH$_2$CH$_2$CH$_2$COOH |
| 2-40 | " | P(=O)(OH)$_2$ |
| 2-41 | 4-F phenylene (1,3-sub) | H |
| 2-42 | " | COCH$_2$COOH |
| 2-43 | " | COCH$_2$CH$_2$COOH |
| 2-44 | " | COCH$_2$CH$_2$CH$_2$COOH |
| 2-45 | " | P(=O)(OH)$_2$ |
| 2-46 | " | H |
| 2-47 | " | COCH$_2$COOH |
| 2-48 | " | COCH$_2$CH$_2$COOH |
| 2-49 | " | COCH$_2$CH$_2$CH$_2$COOH |
| 2-50 | " | P(=O)(OH)$_2$ |
| 2-51 | 3-CH$_3$ phenylene | H |
| 2-52 | " | P(=O)(OH)$_2$ |
| 2-53 | 4-CH$_3$ phenylene | H |
| 2-54 | " | P(=O)(OH)$_2$ |
| 2-55 | 5-CH$_3$ phenylene | H |
| 2-56 | " | P(=O)(OH)$_2$ |

EXAMPLE TABLE 2-continued $$\text{-O-C(=O)-L-O-R}$$

| Example No. | L | R |
|---|---|---|
| 2-57 | 4-methyl-indane-1,7-diyl | H |
| 2-58 | " | COCH$_2$COOH |
| 2-59 | " | COCH$_2$CH$_2$COOH |
| 2-60 | " | COCH$_2$CH$_2$CH$_2$COOH |
| 2-61 | " | P(=O)(OH)$_2$ |
| 2-62 | 4-methoxy-indane-1,7-diyl | H |
| 2-63 | " | COCH$_2$COOH |
| 2-64 | " | COCH$_2$CH$_2$COOH |
| 2-65 | " | COCH$_2$CH$_2$CH$_2$COOH |
| 2-66 | " | P(=O)(OH)$_2$ |
| 2-67 | 2-carboxy-benzene-1,3-diylmethyl | H |
| 2-68 | " | COCH$_3$ |
| 2-69 | " | COCH$_2$COOH |
| 2-70 | " | P(=O)(OH)$_2$ |
| 2-71 | 4-carboxy-benzene-1,2-diylmethyl | H |
| 2-72 | " | COCH$_3$ |
| 2-73 | " | COCH$_2$COOH |
| 2-74 | " | P(=O)(OH)$_2$ |
| 2-75 | 4-carboxy-benzene-1,3-diylmethyl | H |
| 2-76 | " | COCH$_3$ |
| 2-77 | " | COCH$_2$COOH |
| 2-78 | " | P(=O)(OH)$_2$ |
| 2-79 | 7-carboxy-indane-1,4-diyl | H |
| 2-80 | " | COCH$_3$ |
| 2-81 | " | COCH$_2$COOH |
| 2-82 | " | P(=O)(OH)$_2$ |
| 2-83 | 2-(phosphonooxymethyl)-benzene-1,3-diylmethyl | H |
| 2-84 | " | COCH$_3$ |
| 2-85 | " | COCH$_2$COOH |
| 2-86 | 4-(phosphonooxymethyl)-benzene-1,2-diylmethyl | H |
| 2-87 | " | COCH$_3$ |
| 2-88 | " | COCH$_2$COOH |
| 2-89 | 4-(phosphonooxymethyl)-benzene-1,3-diylmethyl | H |
| 2-90 | " | COCH$_3$ |
| 2-91 | " | COCH$_2$COOH |
| 2-92 | 7-(phosphonooxymethyl)-indane-1,4-diyl | H |
| 2-93 | " | COCH$_3$ |
| 2-94 | " | COCH$_2$COOH |
| 2-95 | 2-isopropyl-phenylene | H |

EXAMPLE TABLE 2-continued structure: ⌇-O-C(=O)-L-O-R

| Example No. | L | R |
|---|---|---|
| 2-96 | " | P(=O)(OH)₂ |
| 2-97 | 1,2-phenylene with C(CH₃)₂ linker | H |
| 2-98 | " | P(=O)(OH)₂ |
| 2-99 | 1,8-naphthalenediyl with CH₂ | H |
| 2-100 | " | P(=O)(OH)₂ |
| 2-101 | 3-Cl-1,2-phenylene with CH₂ | H |
| 2-102 | " | P(=O)(OH)₂ |
| 2-103 | 4-Cl-1,2-phenylene with CH₂ | H |
| 2-104 | " | P(=O)(OH)₂ |
| 2-105 | 5-Cl-1,2-phenylene with CH₂ | H |
| 2-106 | " | P(=O)(OH)₂ |
| 2-107 | 3-Cl-1,2-phenylene with CH₂ (alt) | H |
| 2-108 | " | P(=O)(OH)₂ |

EXAMPLE TABLE 2A structure: ⌇-O-C(=O)-L-O-R

| Example No. | L | R |
|---|---|---|
| 2A-1 | 1,2-phenylene with CH₂ | COCH₂NHCH₃ |
| 2A-2 | " | COCH₂N(CH₃)₂ |
| 2A-3 | " | COCH₂-(1-Azt) |
| 2A-4 | " | COCH₂-(1-Pyrd) |
| 2A-5 | " | COCH₂-(1-Pip) |
| 2A-6 | " | COCH₂-(1-Azp) |
| 2A-7 | " | COCH₂Mor |
| 2A-8 | " | COCH₂Thz |
| 2A-9 | " | COCH₂-(4-Me-1-Piz) |
| 2A-10 | " | COCH₂CONH₂ |
| 2A-11 | " | COCH₂CONHCH₃ |
| 2A-12 | " | COCH₂CON(CH₃)₂ |
| 2A-13 | " | COCH₂CO-(1-Azt) |
| 2A-14 | " | COCH₂CO-(1-Pyrd) |
| 2A-15 | " | COCH₂CO-(1-Pip) |
| 2A-16 | " | COCH₂CO-(1-Azp) |
| 2A-17 | " | COCH₂COMor |
| 2A-18 | " | COCH₂COThz |
| 2A-19 | " | COCH₂CO-(4-Me-1-Piz) |
| 2A-20 | " | COCH₂CH₂NHCH₃ |
| 2A-21 | " | COCH₂CH₂N(CH₃)₂ |
| 2A-22 | " | COCH₂CH₂-(1-Azt) |
| 2A-23 | " | COCH₂CH₂-(1-Pyrd) |
| 2A-24 | " | COCH₂CH₂-(1-Pip) |
| 2A-25 | " | COCH₂CH₂-(1-Azp) |
| 2A-26 | " | COCH₂CH₂Mor |
| 2A-27 | " | COCH₂CH₂Thz |
| 2A-28 | " | COCH₂CH₂-(4-Me-1-Piz) |
| 2A-29 | " | COCH₂CH₂CONH₂ |
| 2A-30 | " | COCH₂CH₂CONHCH₃ |
| 2A-31 | " | COCH₂CH₂CON(CH₃)₂ |
| 2A-32 | " | COCH₂CH₂CO-(1-Azt) |
| 2A-33 | " | COCH₂CH₂CO-(1-Pyrd) |
| 2A-34 | " | COCH₂CH₂CO-(1-Pip) |
| 2A-35 | " | COCH₂CH₂CO-(1-Azp) |
| 2A-36 | " | COCH₂CH₂COMor |
| 2A-37 | " | COCH₂CH₂COThz |
| 2A-38 | " | COCH₂CH₂CO-(4-Me-1-Piz) |
| 2A-39 | " | COCH₂CH₂CH₂NHCH₃ |
| 2A-40 | " | COCH₂CH₂CH₂N(CH₃)₂ |
| 2A-41 | " | COCH₂CH₂CH₂-(1-Azt) |
| 2A-42 | " | COCH₂CH₂CH₂-(1-Pyrd) |
| 2A-43 | " | COCH₂CH₂CH₂-(1-Pip) |
| 2A-44 | " | COCH₂CH₂CH₂-(1-Azp) |
| 2A-45 | " | COCH₂CH₂CH₂Mor |
| 2A-46 | " | COCH₂CH₂CH₂Thz |
| 2A-47 | " | COCH₂CH₂CH₂-(4-Me-1-Piz) |
| 2A-48 | " | COCH₂CH₂CH₂CONH₂ |
| 2A-49 | " | COCH₂CH₂CH₂CONHCH₃ |
| 2A-50 | " | COCH₂CH₂CH₂CON(CH₃)₂ |
| 2A-51 | " | COCH₂CH₂CH₂CO-(1-Azt) |
| 2A-52 | " | COCH₂CH₂CH₂CO-(1-Pyrd) |
| 2A-53 | " | COCH₂CH₂CH₂CO-(1-Pip) |
| 2A-54 | " | COCH₂CH₂CH₂CO-(1-Azp) |
| 2A-55 | " | COCH₂CH₂CH₂COMor |
| 2A-56 | " | COCH₂CH₂CH₂COThz |
| 2A-57 | " | COCH₂CH₂CH₂CO-(4-Me-1-Piz) |
| 2A-58 | " | COCH(CH₃)NHCH₃ |
| 2A-59 | " | COCH(CH₃)NH(CH₃)₂ |
| 2A-60 | " | COC(CH₃)₂NHCH₃ |
| 2A-61 | " | COC(CH₃)₂N(CH₃)₂ |
| 2A-62 | " | COCH[N(CH₃)₂]CON(CH₃)₂ |

EXAMPLE TABLE 2A-continued

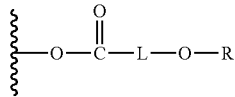

| Example No. | L | R |
|---|---|---|
| 2A-63 | " | COCH[N(CH₃)₂]CO-(1-Azt) |
| 2A-64 | " | COCH[N(CH₃)₂]CO-(1-Pyrd) |
| 2A-65 | " | COCH[N(CH₃)₂]CO-(1-Pip) |
| 2A-66 | " | COCH[N(CH₃)₂]CO-(1-Azp) |
| 2A-67 | " | COCH[N(CH₃)₂]COMor |
| 2A-68 | " | COCH[N(CH₃)₂]COThz |
| 2A-69 | " | COCH[N(CH₃)₂]CO-(4-Me-1-Piz) |
| 2A-70 | " | COCH[N(CH₃)₂]-CH₂CON(CH₃)₂ |
| 2A-71 | " | COCH[N(CH₃)₂]-CH₂CO-(1-Azt) |
| 2A-72 | " | COCH[N(CH₃)₂]-CH₂CO-(1-Pyrd) |
| 2A-73 | " | COCH[N(CH₃)₂]CH₂CO-(1-Pip) |
| 2A-74 | " | COCH[N(CH₃)₂]CH₂CO-(1-Azp) |
| 2A-75 | " | COCH[N(CH₃)₂]CH₂COMor |
| 2A-76 | " | COCH[N(CH₃)₂]CH₂COThz |
| 2A-77 | " | COCH[N(CH₃)₂]CH₂CO-(4-Me-1-Piz) |
| 2A-78 | " | COCH₂CH[N(CH₃)₂]CON(CH₃)₂ |
| 2A-79 | " | COCH₂CH[N(CH₃)₂]CO-(1-Azt) |
| 2A-80 | " | COCH₂CH[N(CH₃)₂]CO-(1-Pyrd) |
| 2A-81 | " | COCH₂CH[N(CH₃)₂]CO-(1-Pip) |
| 2A-82 | " | COCH₂CH[N(CH₃)₂]CO-(1-Azp) |
| 2A-83 | " | COCH₂CH[N(CH₃)₂]COMor |
| 2A-84 | " | COCH₂CH[N(CH₃)₂]COThz |
| 2A-85 | " | COCH₂CH[N(CH₃)₂]CO-(4-Me-1-Piz) |
| 2A-86 | " | COCH[N(CH₃)₂]-CH₂CH₂CON(CH₃)₂ |
| 2A-87 | " | COCH[N(CH₃)₂]-CH₂CH₂CO-(1-Azt) |
| 2A-88 | " | COCH[N(CH₃)₂]-CH₂CH₂CO-(1-Pyrd) |
| 2A-89 | " | COCH[N(CH₃)₂]-CH₂CH₂CO-(1-Pip) |
| 2A-90 | " | COCH[N(CH₃)₂]-CH₂CH₂CO-(1-Azp) |
| 2A-91 | " | COCH[N(CH₃)₂]-CH₂CH₂COMor |
| 2A-92 | " | COCH[N(CH₃)₂]-CH₂CH₂COThz |
| 2A-93 | " | COCH[N(CH₃)₂]-CH₂CH₂CO-(4-Me-1-Piz) |
| 2A-94 | " | COCH₂CH₂CH[N(CH₃)₂]-CON(CH₃)₂ |
| 2A-95 | " | COCH₂CH₂CH[N(CH₃)₂]CO-(1-Azt) |
| 2A-96 | " | COCH₂CH₂CH[N(CH₃)₂]CO-(1-Pyrd) |
| 2A-97 | " | COCH₂CH₂CH[N(CH₃)₂]CO-(1-Pip) |
| 2A-98 | " | COCH₂CH₂CH[N(CH₃)₂]CO-(1-Azp) |
| 2A-99 | " | COCH₂CH₂CH-[N(CH₃)₂]COMor |
| 2A-100 | " | COCH₂CH₂CH-[N(CH₃)₂]COThz |
| 2A-101 | " | COCH₂CH₂CH-[N(CH₃)₂]CO-(4-Me-1-Piz) |

EXAMPLE TABLE 2A-continued

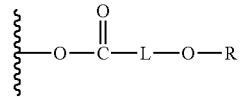

| Example No. | L | R |
|---|---|---|
| 2A-102 | 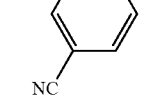 | CONH₂ |
| 2A-103 | " | C(=O)COOH |
| 2A-104 | " | COCH₂OH |
| 2A-105 | " | COCH₂NH₂ |
| 2A-106 | " | COCH₂COOH |
| 2A-107 | " | COCH₂CH₂NH₂ |
| 2A-108 | " | COCH₂CH₂COOH |
| 2A-109 | " | COCH₂CH₂CH₂OH |
| 2A-110 | " | COCH₂CH₂CH₂NH₂ |
| 2A-111 | " | COCH₂CH₂CH₂COOH |
| 2A-112 | " | COCH₂NHCH₃ |
| 2A-113 | " | COCH₂N(CH₃)₂ |
| 2A-114 | " | COCH₂-(1-Azt) |
| 2A-115 | " | COCH₂-(1-Pyrd) |
| 2A-116 | " | COCH₂-(1-Pip) |
| 2A-117 | " | COCH₂-(1-Azp) |
| 2A-118 | " | COCH₂Mor |
| 2A-119 | " | COCH₂Thz |
| 2A-120 | " | COCH₂-(4-Me-1-Piz) |
| 2A-121 | " | COCH₂CONH₂ |
| 2A-122 | " | COCH₂CONHCH₃ |
| 2A-123 | " | COCH₂CON(CH₃)₂ |
| 2A-124 | " | COCH₂CO-(1-Azt) |
| 2A-125 | " | COCH₂CO-(1-Pyrd) |
| 2A-126 | " | COCH₂CO-(1-Pip) |
| 2A-127 | " | COCH₂CO-(1-Azp) |
| 2A-128 | " | COCH₂COMor |
| 2A-129 | " | COCH₂COThz |
| 2A-130 | " | COCH₂CO-(4-Me-1-Piz) |
| 2A-131 | " | COCH₂CH₂NHCH₃ |
| 2A-132 | " | COCH₂CH₂N(CH₃)₂ |
| 2A-133 | " | COCH₂CH₂-(1-Azt) |
| 2A-134 | " | COCH₂CH₂-(1-Pyrd) |
| 2A-135 | " | COCH₂CH₂-(1-Pip) |
| 2A-136 | " | COCH₂CH₂-(1-Azp) |
| 2A-137 | " | COCH₂CH₂Mor |
| 2A-133 | " | COCH₂CH₂Thz |
| 2A-139 | " | COCH₂CH₂-(4-Me-1-Piz) |
| 2A-140 | " | COCH₂CH₂CONH₂ |
| 2A-141 | " | COCH₂CH₂CONHCH₃ |
| 2A-142 | " | COCH₂CH₂CON(CH₃)₂ |
| 2A-143 | " | COCH₂CH₂CO-(1-Azt) |
| 2A-144 | " | COCH₂CH₂CO-(1-Pyrd) |
| 2A-145 | " | COCH₂CH₂CO-(1-Pip) |
| 2A-146 | " | COCH₂CH₂CO-(1-Azp) |
| 2A-147 | " | COCH₂CH₂COMor |
| 2A-148 | " | COCH₂CH₂COThz |
| 2A-149 | " | COCH₂CH₂CO-(4-Me-1-Piz) |
| 2A-150 | " | COCH₂CH₂CH₂NHCH₃ |
| 2A-151 | " | COCH₂CH₂CH₂N(CH₃)₂ |
| 2A-152 | " | COCH₂CH₂CH₂-(1-Azt) |
| 2A-153 | " | COCH₂CH₂CH₂-(1-Pyrd) |
| 2A-154 | " | COCH₂CH₂CH₂-(1-Pip) |
| 2A-155 | " | COCH₂CH₂CH₂-(1-Azp) |
| 2A-156 | " | COCH₂CH₂CH₂Mor |
| 2A-157 | " | COCH₂CH₂CH₂Thz |
| 2A-158 | " | COCH₂CH₂CH₂-(4-Me-1-Piz) |
| 2A-159 | " | COCH₂CH₂CH₂CONH₂ |
| 2A-160 | " | COCH₂CH₂CH₂CONHCH₃ |
| 2A-161 | " | COCH₂CH₂CH₂CON(CH₃)₂ |

EXAMPLE TABLE 2A-continued $$\xi\text{—O—}\overset{\overset{\text{O}}{\|}}{\text{C}}\text{—L—O—R}$$

| Example No. | L | R |
|---|---|---|
| 2A-162 | " | COCH$_2$CH$_2$CH$_2$CO-(1-Azt) |
| 2A-163 | " | COCH$_2$CH$_2$CH$_2$CO-(1-Pyrd) |
| 2A-164 | " | COCH$_2$CH$_2$CH$_2$CO-(1-Pip) |
| 2A-165 | " | COCH$_2$CH$_2$CH$_2$CO-(1-Azp) |
| 2A-166 | " | COCH$_2$CH$_2$CH$_2$COMor |
| 2A-167 | " | COCH$_2$CH$_2$CH$_2$COThz |
| 2A-168 | " | COCH$_2$CH$_2$CH$_2$CO-(4-Me-1-Piz) |
| 2A-169 | " | COCH(CH$_3$)NHCH$_3$ |
| 2A-170 | " | COCH(CH$_3$)NH(CH$_3$)$_2$ |
| 2A-171 | " | COC(CH$_3$)$_2$NHCH$_3$ |
| 2A-172 | " | COC(CH$_3$)$_2$N(CH$_3$)$_2$ |
| 2A-173 | " | COCH[N(CH$_3$)$_2$]CON(CH$_3$)$_2$ |
| 2A-174 | " | COCH[N(CH$_3$)$_2$]CO-(1-Azt) |
| 2A-175 | " | COCH[N(CH$_3$)$_2$]CO-(1-Pyrd) |
| 2A-176 | " | COCH[N(CH$_3$)$_2$]CO-(1-Pip) |
| 2A-177 | " | COCH[N(CH$_3$)$_2$]CO-(1-Azp) |
| 2A-178 | " | COCH[N(CH$_3$)$_2$]COMor |
| 2A-180 | " | COCH[N(CH$_3$)$_2$]CO-(4-Me-1-Piz) |
| 2A-183 | " | COCH[N(CH$_3$)$_2$]CH$_2$CO-(1-Pyrd) |
| 2A-184 | " | COCH[N(CH$_3$)$_2$]CH$_2$CO-(1-Pip) |
| 2A-185 | " | COCH[N(CH$_3$)$_2$]CH$_2$CO-(1-Azp) |
| 2A-186 | " | COCH[N(CH$_3$)$_2$]CH$_2$COMor |
| 2A-187 | " | COCH[N(CH$_3$)$_2$]CH$_2$COThz |
| 2A-188 | " | COCH[N(CH$_3$)$_2$]CH$_2$CO-(4-Me-1-Piz) |
| 2A-189 | " | COCH$_2$CH[N(CH$_3$)$_2$]-CON(CH$_3$)$_2$ |
| 2A-190 | " | COCH$_2$CH[N(CH$_3$)$_2$]CO-(1-Azt) |
| 2A-191 | " | COCH$_2$CH[N(CH$_3$)$_2$]CO-(1-Pyrd) |
| 2A-192 | " | COCH$_2$CH[N(CH$_3$)$_2$]CO-(1-Pip) |
| 2A-193 | " | COCH$_2$CH[N(CH$_3$)$_2$]CO-(1-Azp) |
| 2A-194 | " | COCH$_2$CH [N(CH$_3$)$_2$]COMor |
| 2A-195 | " | COCH$_2$CH[N(CH$_3$)$_2$]COThz |
| 2A-196 | " | COCH$_2$CH[N(CH$_3$)$_2$]CO-(4-Me-1-Piz) |
| 2A-197 | " | COCH[N(CH$_3$)$_2$]-CH$_2$CH$_2$CON(CH$_3$)$_2$ |
| 2A-198 | " | COCH[N(CH$_3$)$_2$]-CH$_2$CH$_2$CO-(1-Azt) |
| 2A-199 | " | COCH[N(CH$_3$)$_2$]CH$_2$CH$_2$CO-(1-Pyrd) |
| 2A-200 | " | COCH[N(CH$_3$)$_2$]CH$_2$CH$_2$CO-(1-Pip) |
| 2A-201 | " | COCH[N(CH$_3$)$_2$]CH$_2$CH$_2$CO-(1-Azp) |
| 2A-202 | " | COCH[N(CH$_3$)$_2$]-CH$_2$CH$_2$COMor |
| 2A-203 | " | COCH[N(CH$_3$)$_2$]-CH$_2$CH$_2$COThz |
| 2A-204 | " | COCH[N(CH$_3$)$_2$]CH$_2$CH$_2$CO-(4-Me-1-Piz) |
| 2A-205 | " | COCH$_2$CH$_2$CH[N(CH$_3$)$_2$]-CON(CH$_3$)$_2$ |
| 2A-206 | " | COCH$_2$CH$_2$CH[N(CH$_3$)$_2$]CO-(1-Azt) |
| 2A-207 | " | COCH$_2$CH$_2$CH[N(CH$_3$)$_2$]CO-(1-Pyrd) |
| 2A-208 | " | COCH$_2$CH$_2$CH[N(CH$_3$)$_2$]CO-(1-Pip) |
| 2A-209 | " | COCH$_2$CH$_2$CH[N(CH$_3$)$_2$]CO-(1-Azp) |
| 2A-210 | " | COCH$_2$CH$_2$CH-[N(CH$_3$)$_2$]COMor |
| 2A-211 | " | COCH$_2$CH$_2$CH-[N(CH$_3$)$_2$]COThz |
| 2A-212 | " | COCH$_2$CH$_2$CH[N(CH$_3$)$_2$]CO-(4-Me-1-Piz) |

EXAMPLE TABLE 2B $$\xi\text{—O—}\overset{\overset{\text{O}}{\|}}{\text{C}}\text{—L—O—R}$$

| Example No. | L | R |
|---|---|---|
| 2B-1 | 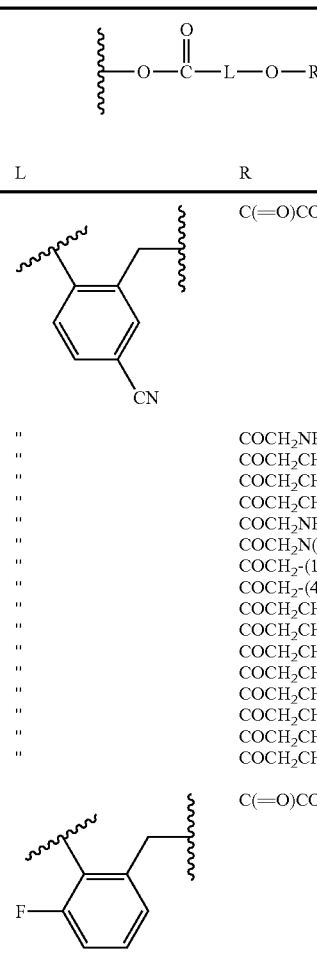 | C(=O)COOH |
| 2B-2 | " | COCH$_2$NH$_2$ |
| 2B-3 | " | COCH$_2$CH$_2$NH$_2$ |
| 2B-4 | " | COCH$_2$CH$_2$CH$_2$NH$_2$ |
| 2B-5 | " | COCH$_2$CH$_2$COOH |
| 2B-6 | " | COCH$_2$NHCH$_3$ |
| 2B-7 | " | COCH$_2$N(CH$_3$)$_2$ |
| 2B-8 | " | COCH$_2$-(1-Pyrd) |
| 2B-9 | " | COCH$_2$-(4-Me-1-Piz) |
| 2B-10 | " | COCH$_2$CH$_2$NHCH$_3$ |
| 2B-11 | " | COCH$_2$CH$_2$N(CH$_3$)$_2$ |
| 2B-12 | " | COCH$_2$CH$_2$-(1-Pyrd) |
| 2B-13 | " | COCH$_2$CH$_2$-(4-Me-1-Piz) |
| 2B-14 | " | COCH$_2$CH$_2$CO-(4-Me-1-Piz) |
| 2B-15 | " | COCH$_2$CH$_2$CH$_2$N(CH$_3$)$_2$ |
| 2B-16 | " | COCH$_2$CH$_2$CH$_2$-(1-Pyrd) |
| 2B-17 | " | COCH$_2$CH$_2$CH$_2$-(4-Me-1-Piz) |
| 2B-18 | 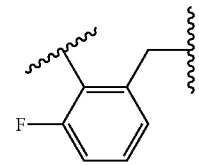 | C(=O)COOH |
| 2B-19 | " | COCH$_2$NH$_2$ |
| 2B-20 | " | COCH$_2$CH$_2$NH$_2$ |
| 2B-21 | " | COCH$_2$CH$_2$CH$_2$NH$_2$ |
| 2B-22 | " | COCH$_2$CH$_2$COOH |
| 2B-23 | " | COCH$_2$NHCH$_3$ |
| 2B-24 | " | COCH$_2$N(CH$_3$)$_2$ |
| 2B-25 | " | COCH$_2$-(1-Pyrd) |
| 2B-26 | " | COCH$_2$-(4-Me-1-Piz) |
| 2B-27 | " | COCH$_2$CH$_2$NHCH$_3$ |
| 2B-28 | " | COCH$_2$CH$_2$N(CH$_3$)$_2$ |
| 2B-29 | " | COCH$_2$CH$_2$-(1-Pyrd) |
| 2B-30 | " | COCH$_2$CH$_2$-(4-Me-1-Piz) |
| 2B-31 | " | COCH$_2$CH$_2$CO-(4-Me-1-Piz) |
| 2B-32 | " | COCH$_2$CH$_2$CH$_2$N(CH$_3$)$_2$ |
| 2B-33 | " | COCH$_2$CH$_2$CH$_2$-(1-Pyrd) |
| 2B-34 | " | COCH$_2$CH$_2$CH$_2$-(4-Me-1-Piz) |

EXAMPLE TABLE 2B-continued

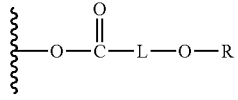

| Example No. | L | R |
|---|---|---|
| 2B-35 | 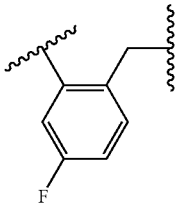 | C(=O)COOH |
| 2B-36 | " | COCH$_2$NH$_2$ |
| 2B-37 | " | COCH$_2$CH$_2$NH$_2$ |
| 2B-38 | " | COCH$_2$CH$_2$CH$_2$NH$_2$ |
| 2B-39 | " | COCH$_2$OH |
| 2B-40 | " | COCH$_2$NHCH$_3$ |
| 2B-41 | " | COCH$_2$N(CH$_3$)$_2$ |
| 2B-42 | " | COCH$_2$-(1-Pyrd) |
| 2B-43 | " | COCH$_2$-(4-Me-1-Piz) |
| 2B-44 | " | COCH$_2$CH$_2$NHCH$_3$ |
| 2B-45 | " | COCH$_2$CH$_2$N(CH$_3$)$_2$ |
| 2B-46 | " | COCH$_2$CH$_2$-(1-Pyrd) |
| 2B-47 | " | COCH$_2$CH$_2$-(4-Me-1-Piz) |
| 2B-48 | " | COCH$_2$CH$_2$CO-(4-Me-1-Piz) |
| 2B-49 | " | COCH$_2$CH$_2$CH$_2$N(CH$_3$)$_2$ |
| 2B-50 | " | COCH$_2$CH$_2$CH$_2$-(1-Pyrd) |
| 2B-51 | " | COCH$_2$CH$_2$CH$_2$-(4-Me-1-Piz) |
| 2B-52 | 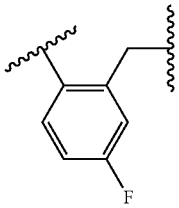 | C(=O)COOH |
| 2B-53 | " | COCH$_2$NH$_2$ |
| 2B-54 | " | COCH$_2$CH$_2$NH$_2$ |
| 2B-55 | " | COCH$_2$CH$_2$CH$_2$NH$_2$ |
| 2B-56 | " | COCH$_2$OH |
| 2B-57 | " | COCH$_2$NHCH$_3$ |
| 2B-58 | " | COCH$_2$N(CH$_3$)$_2$ |
| 2B-59 | " | COCH$_2$-(1-Pyrd) |
| 2B-60 | " | COCH$_2$-(4-Me-1-Piz) |
| 2B-61 | " | COCH$_2$CH$_2$NHCH$_3$ |
| 2B-62 | " | COCH$_2$CH$_2$N(CH$_3$)$_2$ |
| 2B-63 | " | COCH$_2$CH$_2$-(1-Pyrd) |
| 2B-64 | " | COCH$_2$CH$_2$-(4-Me-1-Piz) |
| 2B-65 | " | COCH$_2$CH$_2$CO-(4-Me-1-Piz) |
| 2B-66 | " | COCH$_2$CH$_2$CH$_2$N(CH$_3$)$_2$ |
| 2B-67 | " | COCH$_2$CH$_2$CH$_2$-(1-Pyrd) |
| 2B-68 | " | COCH$_2$CH$_2$CH$_2$-(4-Me-1-Piz) |
| 2B-69 | 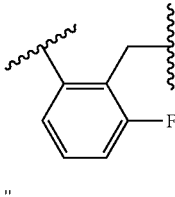 | C(=O)COOH |
| 2B-70 | " | COCH$_2$NH$_2$ |
| 2B-71 | " | COCH$_2$CH$_2$NH$_2$ |
| 2B-72 | " | COCH$_2$CH$_2$CH$_2$NH$_2$ |
| 2B-73 | " | COCH$_2$OH |
| 2B-74 | " | COCH$_2$NHCH$_3$ |
| 2B-75 | " | COCH$_2$N(CH$_3$)$_2$ |

EXAMPLE TABLE 2B-continued

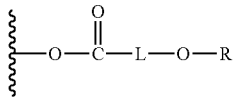

| Example No. | L | R |
|---|---|---|
| 2B-76 | " | COCH$_2$-(1-Pyrd) |
| 2B-77 | " | COCH$_2$-(4-Me-1-Piz) |
| 2B-78 | " | COCH$_2$CH$_2$NHCH$_3$ |
| 2B-79 | " | COCH$_2$CH$_2$N(CH$_3$)$_2$ |
| 2B-80 | " | COCH$_2$CH$_2$-(1-Pyrd) |
| 2B-81 | " | COCH$_2$CH$_2$-(4-Me-1-Piz) |
| 2B-82 | " | COCH$_2$CH$_2$CO-(4-Me-1-Piz) |
| 2B-83 | " | COCH$_2$CH$_2$CH$_2$N(CH$_3$)$_2$ |
| 2B-84 | " | COCH$_2$CH$_2$CH$_2$-(1-Pyrd) |
| 2B-85 | " | COCH$_2$CH$_2$CH$_2$-(4-Me-1-Piz) |
| 2B-86 | 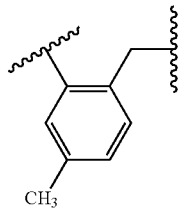 | COCH$_2$OH |
| 2B-87 | " | C(=O)COOH |
| 2B-88 | " | COCH$_2$NH$_2$ |
| 2B-89 | " | COCH$_2$CH$_2$NH$_2$ |
| 2B-90 | " | COCH$_2$CH$_2$CH$_2$NH$_2$ |
| 2B-91 | " | COCH$_2$CH$_2$COOH |
| 2B-92 | " | CONH$_2$ |
| 2B-93 | " | COCH$_2$NHCH$_3$ |
| 2B-94 | " | COCH$_2$N(CH$_3$)$_2$ |
| 2B-95 | " | COCH$_2$-(1-Pyrd) |
| 2B-96 | " | COCH$_2$-(4-Me-1-Piz) |
| 2B-97 | " | COCH$_2$CH$_2$NHCH$_3$ |
| 2B-98 | " | COCH$_2$CH$_2$N(CH$_3$)$_2$ |
| 2B-99 | " | COCH$_2$CH$_2$-(1-Pyrd) |
| 2B-100 | " | COCH$_2$CH$_2$-(4-Me-1-Piz) |
| 2B-101 | " | COCH$_2$CH$_2$CO-(4-Me-1-Piz) |
| 2B-102 | " | COCH$_2$CH$_2$CH$_2$N(CH$_3$)$_2$ |
| 2B-103 | " | COCH$_2$CH$_2$CH$_2$-(1-Pyrd) |
| 2B-104 | " | COCH$_2$CH$_2$CH$_2$-(4-Me-1-Piz) |
| 2B-105 | 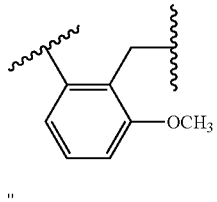 | C(=O)COOH |
| 2B-106 | " | COCH$_2$NH$_2$ |
| 2B-107 | " | COCH$_2$CH$_2$NH$_2$ |
| 2B-108 | " | COCH$_2$CH$_2$CH$_2$NH$_2$ |
| 2B-109 | " | COCH$_2$OH |
| 2B-110 | " | COCH$_2$NHCH$_3$ |
| 2B-111 | " | COCH$_2$N(CH$_3$)$_2$ |
| 2B-112 | " | COCH$_2$-(1-Pyrd) |
| 2B-113 | " | COCH$_2$-(4-Me-1-Piz) |
| 2B-114 | " | COCH$_2$CH$_2$NHCH$_3$ |
| 2B-115 | " | COCH$_2$CH$_2$N(CH$_3$)$_2$ |
| 2B-116 | " | COCH$_2$CH$_2$-(1-Pyrd) |
| 2B-117 | " | COCH$_2$CH$_2$-(4-Me-1-Piz) |
| 2B-118 | " | COCH$_2$CH$_2$CO-(4-Me-1-Piz) |
| 2B-119 | " | COCH$_2$CH$_2$CH$_2$N(CH$_3$)$_2$ |
| 2B-120 | " | COCH$_2$CH$_2$CH$_2$-(1-Pyrd) |
| 2B-121 | " | COCH$_2$CH$_2$CH$_2$-(4-Me-1-Piz) |

EXAMPLE TABLE 2B-continued $$\wavy-O-\overset{O}{\underset{\|}{C}}-L-O-R$$

| Example No. | L | R |
|---|---|---|
| 2B-122 | 2-CH2-, 5-CH3O phenyl (CH2 linker) | H |
| 2B-123 | " | C(=O)COOH |
| 2B-124 | " | COCH2NH2 |
| 2B-125 | " | COCH2CH2NH2 |
| 2B-126 | " | COCH2CH2CH2NH2 |
| 2B-127 | " | COCH2CH2CH2COOH |
| 2B-128 | " | P(=O)(OH)2 |
| 2B-129 | " | COCH2NHCH3 |
| 2B-130 | " | COCH2N(CH3)2 |
| 2B-131 | " | COCH2-(1-Pyrd) |
| 2B-132 | " | COCH2-(4-Me-1-Piz) |
| 2B-133 | " | COCH2CH2NHCH3 |
| 2B-134 | " | COCH2CH2N(CH3)2 |
| 2B-135 | " | COCH2CH2-(1-Pyrd) |
| 2B-136 | " | COCH2CH2-(4-Me-1-Piz) |
| 2B-137 | " | COCH2CH2CO-(4-Me-1-Piz) |
| 2B-138 | " | COCH2CH2CH2N(CH3)2 |
| 2B-139 | " | COCH2CH2CH2-(1-Pyrd) |
| 2B-140 | " | COCH2CH2CH2-(4-Me-1-Piz) |
| 2B-141 | 2-CH2-, 4-Cl phenyl | C(=O)COOH |
| 2B-142 | " | COCH2NH2 |
| 2B-143 | " | COCH2CH2NH2 |
| 2B-144 | " | COCH2CH2CH2NH2 |
| 2B-145 | " | COCH2CH2CH2COOH |
| 2B-146 | " | COCH2NHCH3 |
| 2B-147 | " | COCH2N(CH3)2 |
| 2B-148 | " | COCH2-(1-Pyrd) |
| 2B-149 | " | COCH2-(4-Me-1-Piz) |
| 2B-150 | " | COCH2CH2NHCH3 |
| 2B-151 | " | COCH2CH2N(CH3)2 |
| 2B-152 | " | COCH2CH2-(1-Pyrd) |
| 2B-153 | " | COCH2CH2-(4-Me-1-Piz) |
| 2B-154 | " | COCH2CH2CO-(4-Me-1-Piz) |
| 2B-155 | " | COCH2CH2CH2N(CH3)2 |
| 2B-156 | " | COCH2CH2CH2-(1-Pyrd) |
| 2B-157 | " | COCH2CH2CH2-(4-Me-1-Piz) |
| 2B-158 | 2-CH2-, 6-Cl phenyl | C(=O)COOH |
| 2B-159 | " | COCH2NH2 |
| 2B-160 | " | COCH2CH2NH2 |
| 2B-161 | " | COCH2CH2CH2NH2 |
| 2B-162 | " | COCH2CH2CH2COOH |
| 2B-163 | " | COCH2NHCH3 |
| 2B-164 | " | COCH2N(CH3)2 |
| 2B-165 | " | COCH2-(1-Pyrd) |
| 2B-166 | " | COCH2-(4-Me-1-Piz) |
| 2B-167 | " | COCH2CH2NHCH3 |
| 2B-168 | " | COCH2CH2N(CH3)2 |
| 2B-169 | " | COCH2CH2-(1-Pyrd) |
| 2B-170 | " | COCH2CH2-(4-Me-1-Piz) |
| 2B-171 | " | COCH2CH2CO-(4-Me-1-Piz) |
| 2B-172 | " | COCH2CH2CH2N(CH3)2 |
| 2B-173 | " | COCH2CH2CH2-(1-Pyrd) |
| 2B-174 | " | COCH2CH2CH2-(4-Me-1-Piz) |

EXAMPLE TABLE 2C $$\wavy-O-\overset{O}{\underset{\|}{C}}-L-O-R$$

| Example No. | L | R |
|---|---|---|
| 2C-1 | 2,3-disubstituted furan (CH2 linker) | H |
| 2C-2 | " | COCH2NH2 |
| 2C-3 | " | P(=O)(OH)2 |
| 2C-4 | " | COCH2NHCH3 |
| 2C-5 | " | COCH2N(CH3)2 |
| 2C-6 | " | COCH2-(1-Pyrd) |
| 2C-7 | " | COCH2-(4-Me-1-Piz) |
| 2C-8 | " | COCH2CH2NHCH3 |
| 2C-9 | " | COCH2CH2N(CH3)2 |
| 2C-10 | " | COCH2CH2-(1-Pyrd) |
| 2C-11 | " | COCH2CH2-(4-Me-1-Piz) |
| 2C-12 | " | COCH2CH2CO-(4-Me-1-Piz) |
| 2C-13 | " | COCH2CH2N(CH3)2 |
| 2C-14 | " | COCH2CH2CH2-(1-Pyrd) |
| 2C-15 | " | COCH2CH2COOH |
| 2C-16 | 3,4-disubstituted furan (CH2 linker) | H |
| 2C-17 | " | COCH2NH2 |
| 2C-18 | " | P(=O)(OH)2 |
| 2C-19 | " | COCH2NHCH3 |
| 2C-20 | " | COCH2N(CH3)2 |
| 2C-21 | " | COCH2-(1-Pyrd) |
| 2C-22 | " | COCH2-(4-Me-1-Piz) |
| 2C-23 | " | COCH2CH2NHCH3 |
| 2C-24 | " | COCH2CH2N(CH3)2 |
| 2C-25 | " | COCH2CH2-(1-Pyrd) |
| 2C-26 | " | COCH2CH2-(4-Me-1-Piz) |
| 2C-27 | " | COCH2CH2CO-(4-Me-1-Piz) |
| 2C-28 | " | COCH2CH2CH2N(CH3)2 |

EXAMPLE TABLE 2C-continued $$\wwavy-O-\underset{\underset{O}{\|}}{C}-L-O-R$$

| Example No. | L | R |
|---|---|---|
| 2C-29 | " | COCH$_2$CH$_2$CH$_2$-(1-Pyrd) |
| 2C-30 | " | COCH$_2$CH$_2$COOH |
| 2C-31 | 3-furyl-2-CH$_2$ | H |
| 2C-32 | " | COCH$_2$NH$_2$ |
| 2C-33 | " | P(=O)(OH)$_2$ |
| 2C-34 | " | COCH$_2$NHCH$_3$ |
| 2C-35 | " | COCH$_2$N(CH$_3$)$_2$ |
| 2C-36 | " | COCH$_2$-(1-Pyrd) |
| 2C-37 | " | COCH$_2$-(4-Me-1-Piz) |
| 2C-38 | " | COCH$_2$CH$_2$NHCH$_3$ |
| 2C-39 | " | COCH$_2$CH$_2$N(CH$_3$)$_2$ |
| 2C-40 | " | COCH$_2$CH$_2$-(1-Pyrd) |
| 2C-41 | " | COCH$_2$CH$_2$-(4-Me-1-Piz) |
| 2C-42 | " | COCH$_2$CH$_2$CO-(4-Me-1-Piz) |
| 2C-43 | " | COCH$_2$CH$_2$CH$_2$N(CH$_3$)$_2$ |
| 2C-44 | " | COCH$_2$CH$_2$CH$_2$-(1-Pyrd) |
| 2C-45 | " | COCH$_2$CH$_2$COOH |
| 2C-46 | 2-thienyl-3-CH$_2$ | H |
| 2C-47 | " | COCH$_2$NH$_2$ |
| 2C-48 | " | P(=O)(OH)$_2$ |
| 2C-49 | " | COCH$_2$NHCH$_3$ |
| 2C-50 | " | COCH$_2$N(CH$_3$)$_2$ |
| 2C-51 | " | COCH$_2$-(1-Pyrd) |
| 2C-52 | " | COCH$_2$-(4-Me-1-Piz) |
| 2C-53 | " | COCH$_2$CH$_2$NHCH$_3$ |
| 2C-54 | " | COCH$_2$CH$_2$N(CH$_3$)$_2$ |
| 2C-55 | " | COCH$_2$CH$_2$-(1-Pyrd) |
| 2C-56 | " | COCH$_2$CH$_2$-(4-Me-1-Piz) |
| 2C-57 | " | COCH$_2$CH$_2$CO-(4-Me-1-Piz) |
| 2C-58 | " | COCH$_2$CH$_2$CH$_2$N(CH$_3$)$_2$ |
| 2C-59 | " | COCH$_2$CH$_2$CH$_2$-(1-Pyrd) |
| 2C-60 | " | COCH$_2$CH$_2$COOH |
| 2C-61 | 3,4-thienyl-diCH$_2$ | H |
| 2C-62 | " | COCH$_2$NH$_2$ |
| 2C-63 | " | P(=O)(OH)$_2$ |
| 2C-64 | " | COCH$_2$NHCH$_3$ |
| 2C-65 | " | COCH$_2$N(CH$_3$)$_2$ |
| 2C-66 | " | COCH$_2$-(1-Pyrd) |
| 2C-67 | " | COCH$_2$-(4-Me-1-Piz) |
| 2C-68 | " | COCH$_2$CH$_2$NHCH$_3$ |
| 2C-69 | " | COCH$_2$CH$_2$N(CH$_3$)$_2$ |
| 2C-70 | " | COCH$_2$CH$_2$-(1-Pyrd) |
| 2C-71 | " | COCH$_2$CH$_2$-(4-Me-1-Piz) |
| 2C-72 | " | COCH$_2$CH$_2$CO-(4-Me-1-Piz) |
| 2C-73 | " | COCH$_2$CH$_2$CH$_2$N(CH$_3$)$_2$ |
| 2C-74 | " | COCH$_2$CH$_2$CH$_2$-(1-Pyrd) |
| 2C-75 | " | COCH$_2$CH$_2$COOH |
| 2C-76 | 3-thienyl-2-CH$_2$ | H |
| 2C-77 | " | COCH$_2$NH$_2$ |
| 2C-78 | " | P(=O)(OH)$_2$ |
| 2C-79 | " | COCH$_2$NHCH$_3$ |
| 2C-80 | " | COCH$_2$N(CH$_3$)$_2$ |
| 2C-81 | " | COCH$_2$-(1-Pyrd) |
| 2C-82 | " | COCH$_2$-(4-Me-1-Piz) |
| 2C-83 | " | COCH$_2$CH$_2$NHCH$_3$ |
| 2C-84 | " | COCH$_2$CH$_2$N(CH$_3$)$_2$ |
| 2C-85 | " | COCH$_2$CH$_2$-(1-Pyrd) |
| 2C-86 | " | COCH$_2$CH$_2$-(4-Me-1-Piz) |
| 2C-87 | " | COCH$_2$CH$_2$CO-(4-Me-1-Piz) |
| 2C-88 | " | COCH$_2$CH$_2$CH$_2$N(CH$_3$)$_2$ |
| 2C-89 | " | COCH$_2$CH$_2$CH$_2$-(1-Pyrd) |
| 2C-90 | " | COCH$_2$CH$_2$COOH |
| 2C-91 | 2-pyridyl-3-CH$_2$ | H |
| 2C-92 | " | COCH$_2$NH$_2$ |
| 2C-93 | " | P(=O)(OH)$_2$ |
| 2C-94 | " | COCH$_2$NHCH$_3$ |
| 2C-95 | " | COCH$_2$N(CH$_3$)$_2$ |
| 2C-96 | " | COCH$_2$-(1-Pyrd) |
| 2C-97 | " | COCH$_2$-(4-Me-1-Piz) |
| 2C-98 | " | COCH$_2$CH$_2$NHCH$_3$ |
| 2C-99 | " | COCH$_2$CH$_2$N(CH$_3$)$_2$ |
| 2C-100 | " | COCH$_2$CH$_2$-(1-Pyrd) |
| 2C-101 | " | COCH$_2$CH$_2$-(4-Me-1-Piz) |
| 2C-102 | " | COCH$_2$CH$_2$CO-(4-Me-1-Piz) |
| 2C-103 | " | COCH$_2$CH$_2$CH$_2$N(CH$_3$)$_2$ |
| 2C-104 | " | COCH$_2$CH$_2$CH$_2$-(1-Pyrd) |
| 2C-105 | " | COCH$_2$CH$_2$COOH |
| 2C-106 | 3-pyridyl-4-CH$_2$ | H |
| 2C-107 | " | COCH$_2$NH$_2$ |
| 2C-108 | " | P(=O)(OH)$_2$ |
| 2C-109 | " | COCH$_2$NHCH$_3$ |
| 2C-110 | " | COCH$_2$N(CH$_3$)$_2$ |
| 2C-111 | " | COCH$_2$-(1-Pyrd) |
| 2C-112 | " | COCH$_2$-(4-Me-1-Piz) |
| 2C-113 | " | COCH$_2$CH$_2$NHCH$_3$ |
| 2C-114 | " | COCH$_2$CH$_2$N(CH$_3$)$_2$ |
| 2C-115 | " | COCH$_2$CH$_2$-(1-Pyrd) |
| 2C-116 | " | COCH$_2$CH$_2$-(4-Me-1-Piz) |
| 2C-117 | " | COCH$_2$CH$_2$CO-(4-Me-1-Piz) |

EXAMPLE TABLE 2C-continued $$\xi\text{—}O\text{—}\overset{\overset{O}{\|}}{C}\text{—}L\text{—}O\text{—}R$$

| Example No. | L | R |
|---|---|---|
| 2C-118 | " | COCH$_2$CH$_2$CH$_2$N(CH$_3$)$_2$ |
| 2C-119 | " | COCH$_2$CH$_2$CH$_2$-(1-Pyrd) |
| 2C-120 | " | COCH$_2$CH$_2$COOH |
| 2C-121 | [4-CH$_2$-3-pyridyl group] | H |
| 2C-122 | " | COCH$_2$NH$_2$ |
| 2C-123 | " | P(=O)(OH)$_2$ |
| 2C-124 | " | COCH$_2$NHCH$_3$ |
| 2C-125 | " | COCH$_2$N(CH$_3$)$_2$ |
| 2C-126 | " | COCH$_2$-(1-Pyrd) |
| 2C-127 | " | COCH$_2$-(4-Me-1-Piz) |
| 2C-128 | " | COCH$_2$CH$_2$NHCH$_3$ |
| 2C-129 | " | COCH$_2$CH$_2$N(CH$_3$)$_2$ |
| 2C-130 | " | COCH$_2$CH$_2$-(1-Pyrd) |
| 2C-131 | " | COCH$_2$CH$_2$-(4-Me-1-Piz) |
| 2C-132 | " | COCH$_2$CH$_2$CO-(4-Me-1-Piz) |
| 2C-133 | " | COCH$_2$CH$_2$CH$_2$N(CH$_3$)$_2$ |
| 2C-134 | " | COCH$_2$CH$_2$CH$_2$-(1-Pyrd) |
| 2C-135 | " | COCH$_2$CH$_2$COOH |
| 2C-136 | [3-CH$_2$-2-pyridyl group] | H |
| 2C-137 | " | COCH$_2$NH$_2$ |
| 2C-138 | " | P(=O)(OH)$_2$ |
| 2C-139 | " | COCH$_2$NHCH$_3$ |
| 2C-140 | " | COCH$_2$N(CH$_3$)$_2$ |
| 2C-141 | " | COCH$_2$-(1-Pyrd) |
| 2C-142 | " | COCH$_2$-(4-Me-1-Piz) |
| 2C-143 | " | COCH$_2$CH$_2$NHCH$_3$ |
| 2C-144 | " | COCH$_2$CH$_2$N(CH$_3$)$_2$ |
| 2C-145 | " | COCH$_2$CH$_2$-(1-Pyrd) |
| 2C-146 | " | COCH$_2$CH$_2$-(4-Me-1-Piz) |
| 2C-147 | " | COCH$_2$CH$_2$CO-(4-Me-1-Piz) |
| 2C-148 | " | COCH$_2$CH$_2$CH$_2$N(CH$_3$)$_2$ |
| 2C-149 | " | COCH$_2$CH$_2$CH$_2$-(1-Pyrd) |
| 2C-150 | " | COCH$_2$CH$_2$COOH |

EXAMPLE TABLE 3

$$\xi\text{—}O\text{—}\overset{\overset{O}{\|}}{C}\text{—}L\text{—}O\text{—}R$$

| Example No. | L | R |
|---|---|---|
| 3-1 | [cyclopropyl-CH$_2$ linker] | H |
| 3-2 | " | P(=O)(OH)$_2$ |
| 3-3 | [cyclopropyl-CH$_2$ linker with HO$_2$C substituent] | H |
| 3-4 | " | COCH$_3$ |
| 3-5 | " | COCH$_2$COOH |
| 3-6 | " | P(=O)(OH)$_2$ |
| 3-7 | [cyclopropyl-CH$_2$ linker with CO$_2$H on quaternary C] | H |
| 3-8 | " | COCH$_3$ |
| 3-9 | " | COCH$_2$COOH |
| 3-10 | " | P(=O)(OH)$_2$ |
| 3-11 | [cyclopropyl-CH$_2$ linker with H$_2$O$_3$PO-CH$_2$ substituent] | H |
| 3-12 | [cyclopropyl-CH$_2$ linker with H$_2$O$_3$PO-CH$_2$ substituent] | COCH$_3$ |
| 3-13 | " | COCH$_2$COOH |
| 3-14 | [cyclopropyl-CH$_2$ linker with -CH$_2$OPO$_3$H$_2$ substituent] | H |
| 3-15 | " | COCH$_3$ |
| 3-16 | " | COCH$_2$COOH |
| 3-17 | [cyclobutyl-CH$_2$ linker] | H |
| 3-18 | " | P(=O)(OH)$_2$ |
| 3-19 | [cyclopentyl-CH$_2$ linker] | H |
| 3-20 | " | P(=O)(OH)$_2$ |

EXAMPLE TABLE 3-continued $$\{-O-\overset{\overset{O}{\|}}{C}-L-O-R\}$$

| Example No. | L | R |
|---|---|---|
| 3-21 | (cyclohexane-1,2-diyl) | H |
| 3-22 | " | P(=O)(OH)$_2$ |

In the above Tables, preferred groups are groups of Example No.: 1-1, 1-6, 1-7, 1-9, 1-10, 1-11, 1-12, 1-14, 1-15, 1-20, 1-21, 1-22, 1-23, 1-24, 1-25, 1-30, 1-35, 1-40, 1-42, 1-43, 1-44, 1-45, 1-46, 1-47, 1-52, 1-57, 1-61, 1-65, 1-69, 1-70, 1-75, 1-76, 1-78, 1-79, 1-80, 1-81, 1-83, 1-84, 1-89, 1-90, 1-91, 1-92, 1-93, 1-94, 1-99, 1-103, 2-1, 2-6, 2-7, 2-9, 2-10, 2-11, 2-12, 2-14, 2-15, 2-20, 2-21, 2-22, 2-23, 2-24, 2-25, 2-29, 2-31, 2-33, 2-35, 2-40, 2-45, 2-50, 2-61, 2-66, 2-72, 2-73, 2-74, 2-76, 2-77, 2-78, 2-80, 2-81, 2-82, 2-87, 2-88, 2-90, 2-91, 2-93, 2-94, 2-98, 2-100, 3-2, 3-4, 3-5, 3-6, 3-8, 3-9, 3-10, 3-12, 3-13, 3-15, 3-16, 3-18, 3-20, 3-22, 1A-1, 1A-2, 1A-3, 1A-6, 1A-7, 1A-9, 1A-10, 1A-12, 1A-13, 1A-14, 1A-17, 1A-18, 1A-20, 1A-21, 1A-22, 1A-23, 1A-25, 1A-26, 1A-27, 1A-28, 1A-30, 1A-31, 1A-32, 1A-33, 1A-35, 1A-36, 2A-1, 2A-2, 2A-3, 2A-4, 2A-5, 2A-6, 2A-7, 2A-8, 2A-9, 2A-20, 2A-21, 2A-22, 2A-23, 2A-24, 2A-25, 2A-26, 2A-27, 2A-28, 2A-38, 2A-39, 2A-40, 2A-57, 2A-105, 2A-106, 2A-107, 2A-108, 2A-109, 2A-110, 2A-111, 2A-112, 2A-113, 2A-114, 2A-115, 2A-116, 2A-117, 2A-118, 2A-119, 2A-120, 2A-131, 2A-132, 2A-133, 2A-134, 2A-135, 2A-136, 2A-137, 2A-138, 2A-139, 2A-149, 2A-150, 2A-151, 2A-168, 2B-6, 2B-7, 2B-9, 2B-10, 2B-11, 2B-14, 2B-23, 2B-24, 2B-26, 2B-27, 2B-28, 2B-31, 2B-40, 2B-41, 2B-43, 2B-44, 2B-45, 2B-48, 2B-57, 2B-58, 2B-60, 2B-61, 2B-62, 2B-65, 2B-74, 2B-75, 2B-77, 2B-78, 2B-79, 2B-82, 2B-92, 2B-93, 2B-94, 2B-96, 2B-97, 2B-98, 2B-101, 2B-128, 2B-146, 2B-147, 2B-148, 2B-149, 2B-150, 2B-151, 2B-154, 2B-163, 2B-164, 2B-166, 2B-171, 2C-3, 2C-7, 2C-12, 2C-18, 2C-22, 2C-27, 2C-33, 2C-37, 2C-42, 2C-48, 2C-52, 2C-57, 2C-78, 2C-82, 2C-87, 2C-97, 2C-102, 2C-112, 2C-117, 2C-127, 2C-132, 2C-142 and 2C-147.

more preferred groups are groups of Example No.: 1-7, 1-10, 1-15, 1-25, 1-30, 1-35, 1-40, 1-42, 1-47, 1-76, 1-79, 1-84, 1-94, 2-7, 2-10, 2-15, 2-25, 2-29, 2-31, 2-33, 2-35, 2-40, 2-45, 2-50, 2-61, 2-66, 2-87, 2-90, 2-100, 3-4, 3-6, 3-10, 3-12, 1A-9, 1A-13, 2A-1, 2A-2, 2A-9, 2A-20, 2A-21, 2A-22, 2A-28, 2A-38, 2A-39, 2A-40, 2A-57, 2A-105, 2A-107, 2A-108, 2A-110, 2A-111, 2A-112, 2A-113, 2A-120, 2A-131, 2A-132, 2A-139, 2A-149, 2A-150, 2A-151, 2A-168, 2B-7, 2B-9, 2B-14, 2B-24, 2B-26, 2B-31, 2B-41, 2B-43, 2B-58, 2B-60, 2B-65, 2B-75, 2B-77, 2B-82, 2B-92, 2B-94, 2B-96, 2B-101, 2B-128, 2B-147, 2B-149, 2B-154, 2B-164, 2B-166 and 2B-171.

still more preferred groups are groups of Example No.: 2-25, 2-29, 2A-9, 2A-28, 2A-38, 2A-120, 2A-139 and 2A-149.

The triazole compound of the present invention includes, for example, the compounds described in Example Tables 4, 4A, 5, 5A, 5B, 5C and 6, but the scope of the invention is not limited to those compounds.

EXAMPLE TABLE 4

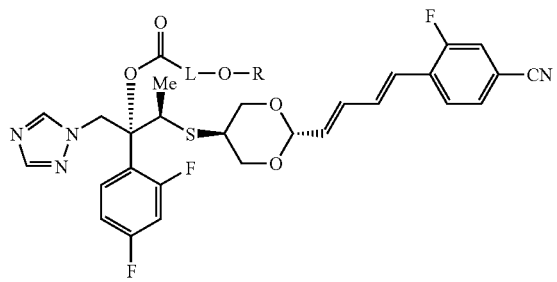

| Example No. | L | R |
|---|---|---|
| 4-1 | CH$_2$CH$_2$CH$_2$ | H |
| 4-2 | CH$_2$CH$_2$CH$_2$ | COCH$_3$ |
| 4-3 | CH$_2$CH$_2$CH$_2$ | COCH$_2$NH$_2$ |
| 4-4 | CH$_2$CH$_2$CH$_2$ | COCH$_2$COOH |
| 4-5 | CH$_2$CH$_2$CH$_2$ | COCH$_2$CH$_2$NH$_2$ |
| 4-6 | CH$_2$CH$_2$CH$_2$ | COCH$_2$CH$_2$COOH |
| 4-7 | CH$_2$CH$_2$CH$_2$ | COCH(CH$_3$)NH$_2$ |
| 4-8 | CH$_2$CH$_2$CH$_2$ | COCH(CH$_3$)COOH |
| 4-9 | CH$_2$CH$_2$CH$_2$ | COCH$_2$CH$_2$CH$_2$NH$_2$ |
| 4-10 | CH$_2$CH$_2$CH$_2$ | COCH$_2$CH$_2$CH$_2$COOH |
| 4-11 | CH$_2$CH$_2$CH$_2$ | COCH(NH$_2$)COOH |
| 4-12 | CH$_2$CH$_2$CH$_2$ | COCH(NH$_2$)CH$_2$COOH |
| 4-13 | CH$_2$CH$_2$CH$_2$ | COCH$_2$CH(NH$_2$)COOH |
| 4-14 | CH$_2$CH$_2$CH$_2$ | COCH(NH$_2$)CH$_2$CH$_2$COOH |
| 4-15 | CH$_2$CH$_2$CH$_2$ | COCH$_2$CH$_2$CH(NH$_2$)COOH |
| 4-16 | CH$_2$CH$_2$CH$_2$ | P(=O)(OH)$_2$ |
| 4-17 | CF$_2$CH$_2$CH$_2$ | P(=O)(OH)$_2$ |
| 4-18 | C(CH$_3$)$_2$CH$_2$CH$_2$ | P(=O)(OH)$_2$ |
| 4-19 | CH$_2$C(CH$_3$)$_2$CH$_2$ | P(=O)(OH)$_2$ |
| 4-20 | CH$_2$CH$_2$CH(COOH) | COCH$_3$ |
| 4-21 | CH$_2$CH$_2$CH(COOH) | COCH$_2$NH$_2$ |
| 4-22 | CH$_2$CH$_2$CH(COOH) | COCH$_2$COOH |
| 4-23 | CH$_2$CH$_2$CH(COOH) | COCH$_2$CH$_2$COOH |
| 4-24 | CH$_2$CH$_2$CH(COOH) | COCH$_2$CH$_2$COOH |
| 4-25 | CH$_2$CH$_2$CH(COOH) | P(=O)(OH)$_2$ |
| 4-26 | CH$_2$CH$_2$CH$_2$CH$_2$ | P(=O)(OH)$_2$ |
| 4-27 | CF$_2$CH$_2$CH$_2$CH$_2$ | P(=O)(OH)$_2$ |
| 4-28 | C(CH$_3$)$_2$CH$_2$CH$_2$CH$_2$ | P(=O)(OH)$_2$ |
| 4-29 | CH$_2$C(CH$_3$)$_2$CH$_2$CH$_2$ | P(=O)(OH)$_2$ |
| 4-30 | CH$_2$CH$_2$C(CH$_3$)$_2$CH$_2$ | P(=O)(OH)$_2$ |
| 4-31 | OCH$_2$CH$_2$ | H |
| 4-32 | OCH$_2$CH$_2$ | COCH$_2$NH$_2$ |
| 4-33 | OCH$_2$CH$_2$ | COCH$_2$COOH |
| 4-34 | OCH$_2$CH$_2$ | COCH$_2$CH$_2$NH$_2$ |
| 4-35 | OCH$_2$CH$_2$ | COCH$_2$CH$_2$COOH |
| 4-36 | OCH$_2$CH$_2$ | COCH(CH$_3$)NH$_2$ |
| 4-37 | OCH$_2$CH$_2$ | COCH(CH$_3$)COOH |
| 4-38 | OCH$_2$CH$_2$ | COCH$_2$CH$_2$CH$_2$NH$_2$ |
| 4-39 | OCH$_2$CH2 | COCH$_2$CH$_2$CH$_2$COOH |
| 4-40 | OCH$_2$CH$_2$ | COCH(NH$_2$)COOH |
| 4-41 | OCH$_2$CH$_2$ | COCH(NH$_2$)CH$_2$COOH |
| 4-42 | OCH$_2$CH$_2$ | COCH$_2$CH(NH$_2$)COOH |
| 4-43 | OCH$_2$CH$_2$ | COCH(NH$_2$)CH$_2$CH$_2$COOH |
| 4-44 | OCH$_2$CH$_2$ | COCH$_2$CH$_2$CH(NH$_2$)COOH |
| 4-45 | OCH$_2$CH$_2$ | P(=O)(OH)$_2$ |
| 4-46 | OCH$_2$CH$_2$CH$_2$ | P(=O)(OH)$_2$ |
| 4-47 | OCH$_2$C(CH$_3$)$_2$CH$_2$ | P(=O)(OH)$_2$ |
| 4-48 | CH$_2$CH$_2$CH(CH$_2$N(C$_2$H$_5$)$_2$) | H |
| 4-49 | CH$_2$CH$_2$CH(CH$_2$N(C$_2$H$_5$)$_2$) | COCH$_3$ |
| 4-50 | CH$_2$CH$_2$CH(CH$_2$N(C$_2$H$_5$)$_2$) | P(=O)(OH)$_2$ |

EXAMPLE TABLE 4A

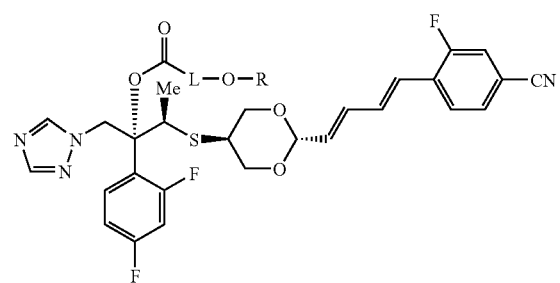

| Example No. | L | R |
|---|---|---|
| 4A-1 | CH$_2$ | H |
| 4A-2 | CH$_2$ | COCH$_2$CH$_2$COOH |
| 4A-3 | CH$_2$ | P(=O)(OH)$_2$ |
| 4A-4 | CH$_2$CH$_2$CH$_2$ | COCH$_2$NHCH$_3$ |
| 4A-5 | CH$_2$CH$_2$CH$_2$ | COCH$_2$N(CH$_3$)$_2$ |
| 4A-6 | CH$_2$CH$_2$CH$_2$ | COCH$_2$-(4-Me-1-Piz) |
| 4A-7 | CH$_2$CH$_2$CH$_2$ | COCH$_2$CH$_2$N(CH$_3$)$_2$ |
| 4A-8 | CH$_2$CH$_2$CH$_2$ | COCH$_2$CH$_2$-(4-Me-1-Piz) |
| 4A-9 | CH$_2$CH$_2$CH$_2$ | COCH$_2$CH$_2$CO-(4-Me-1-Piz) |
| 4A-10 | CH$_2$CH$_2$CH$_2$ | COCH$_2$CH$_2$CH$_2$N(CH$_3$)$_2$ |
| 4A-11 | OCH$_2$CH$_2$ | COCH$_2$NHCH$_3$ |
| 4A-12 | OCH$_2$CH$_2$ | COCH$_2$N(CH$_3$)$_2$ |
| 4A-13 | OCH$_2$CH$_2$ | COCH$_2$-(4-Me-1-Piz) |
| 4A-14 | OCH$_2$CH$_2$ | COCH$_2$CH$_2$CO-(4-Me-1-Piz) |

EXAMPLE TABLE 5

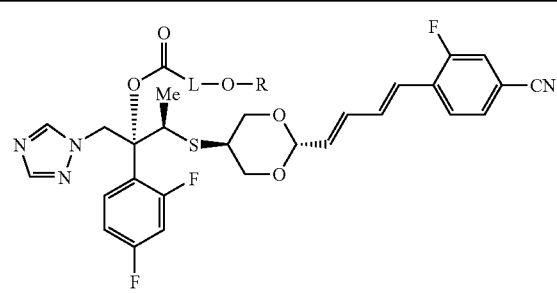

| Example No. | L | R |
|---|---|---|
| 5-1 | (2-substituted benzyl) | H |
| 5-2 | " | COCH$_2$NH$_2$ |
| 5-3 | " | COCH$_2$COOH |
| 5-4 | " | COCH$_2$CH$_2$NH$_2$ |
| 5-5 | " | COCH$_2$CH$_2$COOH |
| 5-6 | " | COCH(CH$_3$)NH$_2$ |
| 5-7 | " | COCH(CH$_3$)COOH |
| 5-8 | " | COCH$_2$CH$_2$CH$_2$NH$_2$ |
| 5-9 | " | COCH$_2$CH$_2$CH$_2$COOH |
| 5-10 | " | COCH(NH$_2$)COOH |
| 5-11 | " | COCH(NH$_2$)CH$_2$COOH |
| 5-12 | (3-substituted benzyl) | COCH$_2$CH(NH$_2$)COOH |

EXAMPLE TABLE 5-continued

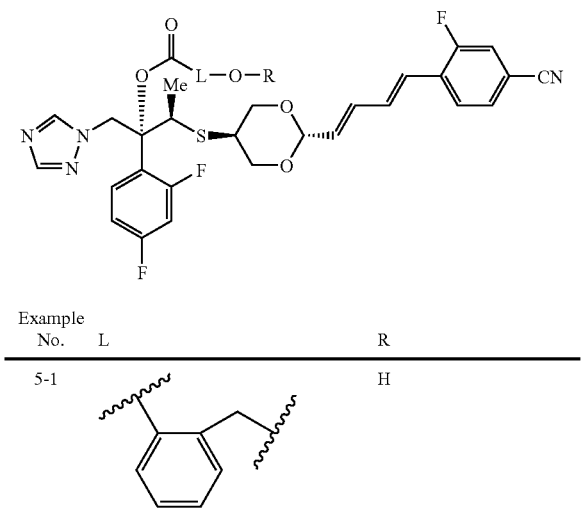

| Example No. | L | R |
|---|---|---|
| 5-13 | " | COCH(NH$_2$)CH$_2$COOH |
| 5-14 | " | COCH$_2$CH$_2$CH(NH$_2$)COOH |
| 5-15 | " | P(=O)(OH)$_2$ |
| 5-16 | (5-cyano-1,2-substituted phenyl) | P(=O)(OH)$_2$ |
| 5-17 | (4-cyano-1,2-substituted phenyl) | P(=O)(OH)$_2$ |
| 5-18 | (4-cyano-indane-substituted) | P(=O)(OH)$_2$ |
| 5-19 | (3-fluoro-1,2-substituted phenyl) | P(=O)(OH)$_2$ |
| 5-20 | (4-fluoro-1,2-substituted phenyl) | P(=O)(OH)$_2$ |
| 5-21 | (4-fluoro-1,3-substituted phenyl) | P(=O)(OH)$_2$ |

EXAMPLE TABLE 5-continued

| Example No. | L | R |
|---|---|---|
| 5-22 | [indane-F] | P(=O)(OH)$_2$ |
| 5-23 | [indane-CH$_3$] | P(=O)(OH)$_2$ |
| 5-24 | [indane-OCH$_3$] | P(=O)(OH)$_2$ |
| 5-25 | [benzene with HO$_2$C] | COCH$_3$ |
| 5-26 | " | COCH$_2$COOH |
| 5-27 | " | P(=O)(OH)$_2$ |
| 5-28 | [benzene with CO$_2$H] | COCH$_3$ |
| 5-29 | " | COCH$_2$COOH |
| 5-30 | " | P(=O)(OH)$_2$ |
| 5-31 | [indane-CO$_2$H] | COCH$_3$ |
| 5-32 | " | COCH$_2$COOH |
| 5-33 | " | P(=O)(OH)$_2$ |
| 5-34 | [benzene-CH$_2$OPO$_3$H$_2$] | COCH$_3$ |
| 5-35 | [benzene-CH$_2$OPO$_3$H$_2$] | COCH$_2$COOH |
| 5-36 | [benzene-CH$_2$OPO$_3$H$_2$] | COCH$_3$ |
| 5-37 | " | COCH$_2$COOH |
| 5-38 | [indane-CH$_2$OPO$_3$H$_2$] | COCH$_3$ |
| 5-39 | " | COCH$_2$COOH |
| 5-40 | [benzene-C(CH$_3$)$_2$] | P(=O)(OH)$_2$ |
| 5-41 | [naphthalene] | P(=O)(OH)$_2$ |

EXAMPLE TABLE 5-continued
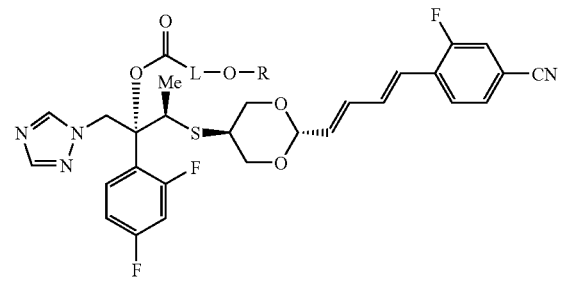
| Example No. | L | R |
|---|---|---|
| 5-42 | (2-Cl phenyl-CH2) | P(=O)(OH)2 |
| 5-43 | (4-Cl phenyl-CH2) | P(=O)(OH)2 |
EXAMPLE TABLE 5-continued
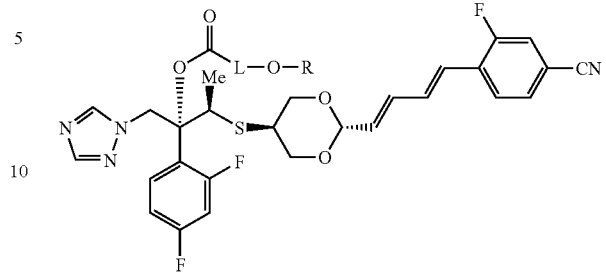
| Example No. | L | R |
|---|---|---|
| 5-44 | (5-Cl phenyl-CH2) | P(=O)(OH)2 |
| 5-45 | (Cl-indanyl) | P(=O)(OH)2 |
EXAMPLE TABLE 5A
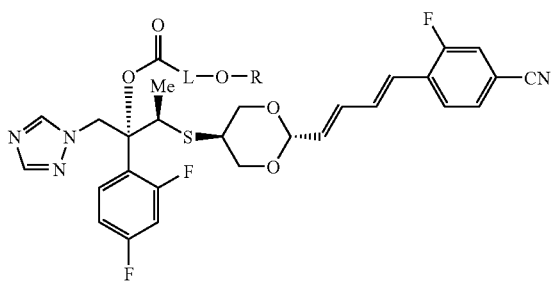
| Example No. | L | R |
|---|---|---|
| 5A-1 | (phenyl-CH2) | COCH2NHCH3 |
| 5A-2 | " | COCH2N(CH3)2 |
| 5A-3 | " | COCH2-(1-Azt) |
| 5A-4 | " | COCH2-(1-Pyrd) |
| 5A-5 | " | COCH2-(1-Pip) |
| 5A-6 | " | COCH2-(1-Azp) |
| 5A-7 | " | COCH2Mor |
| 5A-8 | " | COCH2Thz |

EXAMPLE TABLE 5A-continued

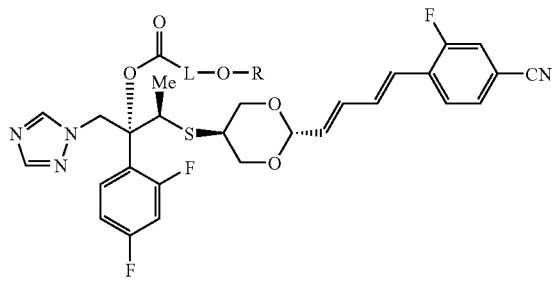

| Example No. | L | R |
|---|---|---|
| 5A-9 | " | COCH$_2$-(4-Me-1-Piz) |
| 5A-10 | " | COCH$_2$CO-(4-Me-1-Piz) |
| 5A-11 | " | COCH$_2$CH$_2$NHCH$_3$ |
| 5A-12 | " | COCH$_2$CH$_2$N(CH$_3$)$_2$ |
| 5A-13 | " | COCH$_2$CH$_2$-(1-Azt) |
| 5A-14 | " | COCH$_2$CH$_2$-(1-Pyrd) |
| 5A-15 | " | COCH$_2$CH$_2$-(1-Pip) |
| 5A-16 | " | COCH$_2$CH$_2$-(1-Azp) |
| 5A-17 | " | COCH$_2$CH$_2$Mor |
| 5A-18 | " | COCH$_2$CH$_2$Thz |
| 5A-19 | " | COCH$_2$CH$_2$-(4-Me-1-Piz) |
| 5A-20 | " | COCH$_2$CH$_2$CO-(4-Me-1-Piz) |
| 5A-21 | " | COCH$_2$CH$_2$CH$_2$NHCH$_3$ |
| 5A-22 | " | COCH$_2$CH$_2$CH$_2$N(CH$_3$)$_2$ |
| 5A-23 | " | COCH$_2$CH$_2$CH$_2$-(1-Azt) |
| 5A-24 | " | COCH$_2$CH$_2$CH$_2$-(1-Pyrd) |
| 5A-25 | " | COCH$_2$CH$_2$CH$_2$-(1-Pip) |
| 5A-26 | " | COCH$_2$CH$_2$CH$_2$-(1-Azp) |
| 5A-27 | " | COCH$_2$CH$_2$CH$_2$Mor |
| 5A-28 | " | COCH$_2$CH$_2$CH$_2$Thz |
| 5A-29 | " | COCH$_2$CH$_2$CH$_2$-(4-Me-1-Piz) |
| 5A-30 | " | COCH$_2$CH$_2$CH$_2$CO-(4 -Me-1-Piz) |
| 5A-31 | " | COCH(CH$_3$)NHCH$_3$ |
| 5A-32 | " | COCH(CH$_3$)NH(CH$_3$)$_2$ |
| 5A-33 | " | COC(CH$_3$)$_2$NHCH$_3$ |
| 5A-34 | " | COC(CH$_3$)$_2$N(CH$_3$)$_2$ |
| 5A-35 | " | COCH[N(CH$_3$)$_2$]CON(CH$_3$)$_2$ |
| 5A-36 | 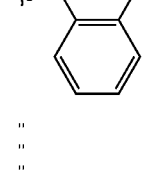 | COCH[N(CH$_3$)$_2$]CO-(1-Azt) |
| 5A-37 | " | COCH[N(CH$_3$)$_2$]CO-(1-Pyrd) |
| 5A-38 | " | COCH[N(CH$_3$)$_2$]CO-(1-Pip) |
| 5A-39 | " | COCH[N(CH$_3$)$_2$]CO-(1-Azp) |
| 5A-40 | " | COCH[N(CH$_3$)$_2$]COMor |
| 5A-41 | " | COCH[N(CH$_3$)$_2$]COThz |
| 5A-42 | " | COCH[N(CH$_3$)$_2$]CO-(4-Me-1-Piz) |
| 5A-43 | " | COCH[N(CH$_3$)$_2$]CH$_2$CON(CH$_3$)$_2$ |
| 5A-44 | " | COCH[N(CH$_3$)$_2$]CH$_2$CO-(1-Azt) |
| 5A-45 | " | COCH[N(CH$_3$)$_2$]CH$_2$CO-(1-Pyrd) |
| 5A-46 | " | COCH[N(CH$_3$)$_2$]CH$_2$CO-(1-Pip) |
| 5A-47 | " | COCH[N(CH$_3$)$_2$]CH$_2$CO-(1-Azp) |
| 5A-48 | " | COCH[N(CH$_3$)$_2$]CH$_2$COMor |
| 5A-49 | " | COCH[N(CH$_3$)$_2$]CH$_2$COThz |
| 5A-50 | " | COCH[N(CH$_3$)$_2$]CH$_2$CO-(4-Me-1-Piz) |
| 5A-51 | " | COCH$_2$CH[N(CH$_3$)$_2$]CON(CH$_3$)$_2$ |
| 5A-52 | " | COCH$_2$CH[N(CH$_3$)$_2$]CO-(1-Azt) |
| 5A-53 | " | COCH$_2$CH[N(CH$_3$)$_2$]CO-(1-Pyrd) |
| 5A-54 | " | COCH$_2$CH[N(CH$_3$)$_2$]CO-(1-Pip) |
| 5A-55 | " | COCH$_2$CH[N(CH$_3$)$_2$]CO-(1-Azp) |
| 5A-56 | " | COCH$_2$CH[N(CH$_3$)$_2$]COMor |
| 5A-57 | " | COCH$_2$CH[N(CH$_3$)$_2$]COThz |
| 5A-58 | " | COCH$_2$CH[N(CH$_3$)$_2$]CO-(4-Me-1-Piz) |
| 5A-59 | " | COCH[N(CH$_3$)$_2$]CH$_2$CH$_2$CON(CH$_3$)$_2$ |
| 5A-60 | " | COCH[N(CH$_3$)$_2$]CH$_2$CH$_2$CO-(1-Azt) |
| 5A-61 | " | COCH[N(CH$_3$)$_2$]CH$_2$CH$_2$CO-(1-Pyrd) |

EXAMPLE TABLE 5A-continued

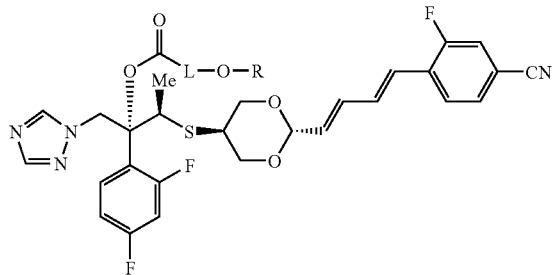

| Example No. | L | R |
|---|---|---|
| 5A-62 | " | COCH[N(CH₃)₂]CH₂CH₂CO-(1-Pip) |
| 5A-63 | " | COCH[N(CH₃)₂]CH₂CH₂CO-(1-Azp) |
| 5A-64 | " | COCH[N(CH₃)₂]CH₂CH₂COMor |
| 5A-65 | " | COCH[N(CH₃)₂]CH₂CH₂COThz |
| 5A-66 | " | COCH[N(CH₃)₂]CH₂CH₂CO-(4-Me-1-Piz) |
| 5A-67 | " | COCH₂CH₂CH[N(CH₃)₂]CON(CH₃)₂ |
| 5A-68 | " | COCH₂CH₂CH[N(CH₃)₂]CO-(1-Azt) |
| 5A-69 | " | COCH₂CH₂CH[N(CH₃)₂]CO-(1-Pyrd) |
| 5A-70 | " | COCH₂CH₂CH[N(CH₃)₂]CO-(1-Pip) |
| 5A-71 | " | COCH₂CH₂CH[N(CH₃)₂]CO-(1-Azp) |
| 5A-72 | " | COCH₂CH₂CH[N(CH₃)₂]COMor |
| 5A-73 | " | COCH₂CH₂CH[N(CH₃)₂]COThz |
| 5A-74 | " | COCH₂CH₂CH[N(CH₃)₂]CO-(4-Me-1-Piz) |
| 5A-75 | 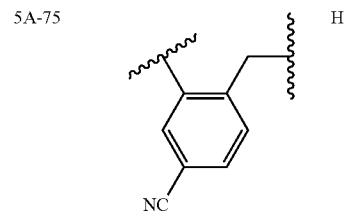 | H |
| 5A-76 | " | CONH₂ |
| 5A-77 | " | C(=O)COOH |
| 5A-78 | " | COCH₂OH |
| 5A-79 | " | COCH₂NH₂ |
| 5A-80 | " | COCH₂COOH |
| 5A-81 | " | COCH₂CH₂NH₂ |
| 5A-82 | " | COCH₂CH₂COOH |
| 5A-83 | " | COCH₂CH₂CH₂OH |
| 5A-84 | " | COCH₂CH₂CH₂NH₂ |
| 5A-35 | " | COCH₂CH₂CH₂COOH |
| 5A-86 | " | COCH₂NHCH₃ |
| 5A-87 | " | COCH₂N(CH₃)₂ |
| 5A-88 | " | COCH₂-(1-Azt) |
| 5A-89 | " | COCH₂-(1-Pyrd) |
| 5A-90 | " | COCH₂-(1-Pip) |
| 5A-91 | " | COCH₂-(1-Azp) |
| 5A-92 | " | COCH₂Mor |
| 5A-93 | " | COCH₂Thz |
| 5A-94 | " | COCH₂-(4-Me-1-Piz) |
| 5A-95 | " | COCH₂CO-(4-Me-1-Piz) |
| 5A-96 | " | COCH₂CH₂NHCH₃ |
| 5A-97 | " | COCH₂CH₂N(CH₃)₂ |
| 5A-98 | " | COCH₂CH₂-(1-Azt) |
| 5A-99 | " | COCH₂CH₂-(1-Pyrd) |
| 5A-100 | " | COCH₂CH₂-(1-Pip) |
| 5A-101 | " | COCH₂CH₂-(1-Azp) |
| 5A-102 | " | COCH₂CH₂Mor |
| 5A-103 | " | COCH₂CH₂Thz |
| 5A-104 | " | COCH₂CH₂-(4-Me-1-Piz) |
| 5A-105 | " | COCH₂CH₂CO-(4-Me-1-Piz) |
| 5A-106 | " | COCH₂CH₂CH₂NHCH₃ |
| 5A-107 | " | COCH₂CH₂CH₂N(CH₃)₂ |
| 5A-108 | " | COCH₂CH₂CH₂-(1-Azt) |
| 5A-109 | " | COCH₂CH₂CH₂-(1-Pyrd) |
| 5A-110 | " | COCH₂CH₂CH₂-(1-Pip) |
| 5A-111 | " | COCH₂CH₂CH₂-(1-Azp) |
| 5A-112 | " | COCH₂CH₂CH₂Mor |

EXAMPLE TABLE 5A-continued

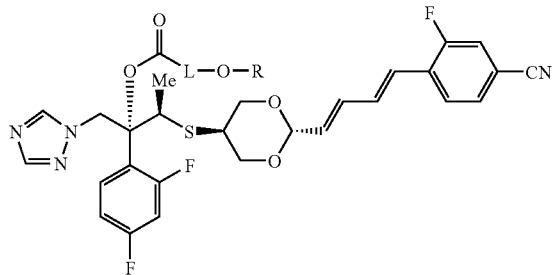

| Example No. | L | R |
|---|---|---|
| 5A-113 | " | COCH$_2$CH$_2$CH$_2$Thz |
| 5A-114 | " | COCH$_2$CH$_2$CH$_2$-(4-Me-1-Piz) |
| 5A-115 | " | COCH$_2$CH$_2$CH$_2$CO-(4-Me-1-Piz) |
| 5A-116 | (structure shown below) | COCH(CH$_3$)NHCH$_3$ |

(For 5A-116, L is:)

a benzyl linker with CN substituent on the phenyl ring

| Example No. | L | R |
|---|---|---|
| 5A-117 | " | COCH(CH$_3$)NH(CH$_3$)$_2$ |
| 5A-118 | " | COC(CH$_3$)$_2$NHCH$_3$ |
| 5A-119 | " | COC(CH$_3$)$_2$N(CH$_3$)$_2$ |
| 5A-120 | " | COCH[N(CH$_3$)$_2$]CON(CH$_3$)$_2$ |
| 5A-121 | " | COCH[N(CH$_3$)$_2$]CO-(1-Azt) |
| 5A-122 | " | COCH[N(CH$_3$)$_2$]CO-(1-Pyrd) |
| 5A-123 | " | COCH[N(CH$_3$)$_2$]CO-(1-Pip) |
| 5A-124 | " | COCH[N(CH$_3$)$_2$]CO-(1-Azp) |
| 5A-125 | " | COCH[N(CH$_3$)$_2$]COMor |
| 5A-126 | " | COCH[N(CH$_3$)$_2$]COThz |
| 5A-127 | " | COCH[N(CH$_3$)$_2$]CO-(4-Me-1-Piz) |
| 5A-128 | " | COCH[N(CH$_3$)$_2$]CH$_2$CON(CH$_3$)$_2$ |
| 5A-129 | " | COCH[N(CH$_3$)$_2$]CH$_2$CO-(1-Azt) |
| 5A-130 | " | COCH[N(CH$_3$)$_2$]CH$_2$CO-(1-Pyrd) |
| 5A-131 | " | COCH[N(CH$_3$)$_2$]CH$_2$CO-(1-Pip) |
| 5A-132 | " | COCH[N(CH$_3$)$_2$]CH$_2$CO-(1-Azp) |
| 5A-133 | " | COCH[N(CH$_3$)$_2$]CH$_2$COMor |
| 5A-134 | " | COCH[N(CH$_3$)$_2$]CH$_2$COThz |
| 5A-135 | " | COCH[N(CH$_3$)$_2$]CH$_2$CO-(4-Me-1-Piz) |
| 5A-136 | " | COCH$_2$CH[N(CH$_3$)$_2$]CON(CH$_3$)$_2$ |
| 5A-137 | " | COCH$_2$CH[N(CH$_3$)$_2$]CO-(1-Azt) |
| 5A-138 | " | COCH$_2$CH[N(CH$_3$)$_2$]CO-(1-Pyrd) |
| 5A-139 | " | COCH$_2$CH[N(CH$_3$)$_2$]CO-(1-Pip) |
| 5A-140 | " | COCH$_2$CH[N(CH$_3$)$_2$]CO-(1-Azp) |
| 5A-141 | " | COCH$_2$CH[N(CH$_3$)$_2$]COMor |
| 5A-142 | " | COCH$_2$CH[N(CH$_3$)$_2$]COThz |
| 5A-143 | " | COCH$_2$CH[N(CH$_3$)$_2$]CO-(4-Me-1-Piz) |
| 5A-144 | " | COCH[N(CH$_3$)$_2$]CH$_2$CH$_2$CON(CH$_3$)$_2$ |
| 5A-145 | " | COCH[N(CH$_3$)$_2$]CH$_2$CH$_2$CO-(1-Azt) |
| 5A-146 | " | COCH[N(CH$_3$)$_2$]CH$_2$CH$_2$CO-(1-Pyrd) |
| 5A-147 | " | COCH[N(CH$_3$)$_2$]CH$_2$CH$_2$CO-(1-Pip) |
| 5A-148 | " | COCH[N(CH$_3$)$_2$]CH$_2$CH$_2$CO-(1-Azp) |
| 5A-149 | " | COCH[N(CH$_3$)$_2$]CH$_2$CH$_2$COMor |
| 5A-150 | " | COCH[N(CH$_3$)$_2$]CH$_2$CH$_2$COThz |
| 5A-151 | " | COCH[N(CH$_3$)$_2$]CH$_2$CH$_2$CO-(4-Me-1-Piz) |
| 5A-152 | " | COCH$_2$CH$_2$CH[N(CH$_3$)$_2$]CON(CH$_3$)$_2$ |
| 5A-153 | " | COCH$_2$CH$_2$CH[N(CH$_3$)$_2$]CO-(1-Azt) |
| 5A-154 | " | COCH$_2$CH$_2$CH[N(CH$_3$)$_2$]CO-(1-Pyrd) |
| 5A-155 | " | COCH$_2$CH$_2$CH[N(CH$_3$)$_2$]CO-(1-Pip) |
| 5A-156 | " | COCH$_2$CH$_2$CH[N(CH$_3$)$_2$]CO-(1-Azp) |
| 5A-157 | " | COCH$_2$CH$_2$CH[N(CH$_3$)$_2$]COMor |
| 5A-158 | " | COCH$_2$CH$_2$CH[N(CH$_3$)$_2$]COThz |
| 5A-159 | " | COCH$_2$CH$_2$CH[N(CH$_3$)$_2$]CO-(4-Me-1-Piz) |

EXAMPLE TABLE 5B

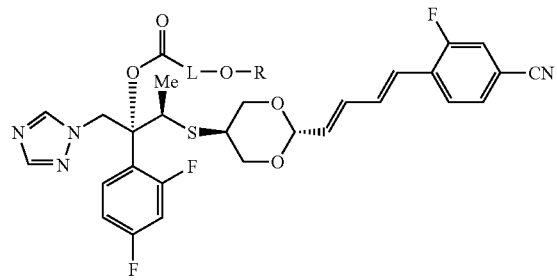

| Example No. | L | R |
|---|---|---|
| 5B-1 | (3-CN-benzyl linker) | C(=O)COOH |
| 5B-2 | " | COCH$_2$NH$_2$ |
| 5B-3 | " | COCH$_2$CH$_2$NH$_2$ |
| 5B-4 | " | COCH$_2$CH$_2$CH$_2$NH$_2$ |
| 5B-5 | " | COCH$_2$CH$_2$COOH |
| 5B-6 | " | COCH$_2$NHCH$_3$ |
| 5B-7 | " | COCH$_2$N(CH$_3$)$_2$ |
| 5B-8 | " | COCH$_2$-(1-Pyrd) |
| 5B-9 | " | COCH$_2$-(4-Me-1-Piz) |
| 5B-10 | " | COCH$_2$CH$_2$NHCH$_3$ |
| 5B-11 | " | COCH$_2$CH$_2$N(CH$_3$)$_2$ |
| 5B-12 | " | COCH$_2$CH$_2$-(1-Pyrd) |
| 5B-13 | " | COCH$_2$CH$_2$-(4-Me-1-Piz) |
| 5B-14 | " | COCH$_2$CH$_2$CO-(4-Me-1-Piz) |
| 5B-15 | " | COCH$_2$CH$_2$CH$_2$N(CH$_3$)$_2$ |
| 5B-16 | " | COCH$_2$CH$_2$CH$_2$-(1-Pyrd) |
| 5B-17 | " | COCH$_2$CH$_2$CH$_2$-(4-Me-1-Piz) |
| 5B-18 | (3-F-benzyl linker) | C(=O)COOH |
| 5B-19 | " | COCH$_2$NH$_2$ |
| 5B-20 | " | COCH$_2$CH$_2$NH$_2$ |
| 5B-21 | " | COCH$_2$CH$_2$CH$_2$NH$_2$ |
| 5B-22 | " | COCH$_2$CH$_2$COOH |
| 5B-23 | " | COCH$_2$NHCH$_3$ |
| 5B-24 | " | COCH$_2$N(CH$_3$)$_2$ |
| 5B-25 | " | COCH$_2$-(1-Pyrd) |
| 5B-26 | " | COCH$_2$-(4-Me-1-Piz) |
| 5B-27 | " | COCH$_2$CH$_2$NHCH$_3$ |
| 5B-28 | " | COCH$_2$CH$_2$N(CH$_3$)$_2$ |
| 5B-29 | " | COCH$_2$CH$_2$-(1-Pyrd) |
| 5B-30 | " | COCH$_2$CH$_2$-(4-Me-1-Piz) |
| 5B-31 | " | COCH$_2$CH$_2$CO-(4-Me-1-Piz) |
| 5B-32 | " | COCH$_2$CH$_2$CH$_2$N(CH$_3$)$_2$ |
| 5B-33 | " | COCH$_2$CH$_2$CH$_2$-(1-Pyrd) |
| 5B-34 | " | COCH$_2$CH$_2$CH$_2$-(4-Me-1-Piz) |

EXAMPLE TABLE 5B-continued

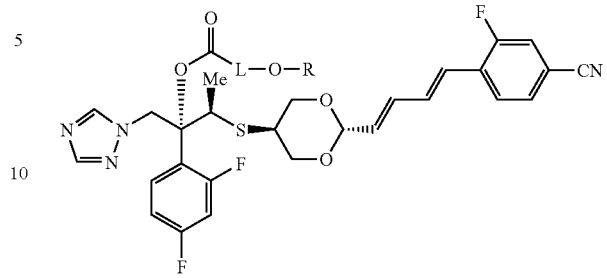

| Example No. | L | R |
|---|---|---|
| 5B-35 | (4-F-benzyl linker) | C(=O)COOH |
| 5B-36 | " | COCH$_2$NH$_2$ |
| 5B-37 | " | COCH$_2$CH$_2$NH$_2$ |
| 5B-38 | " | COCH$_2$CH$_2$CH$_2$NH$_2$ |
| 5B-39 | " | COCH$_2$CH$_2$COOH |
| 5B-40 | " | COCH$_2$NHCH$_3$ |
| 5B-41 | " | COCH$_2$N(CH$_3$)$_2$ |
| 5B-42 | " | COCH$_2$-(1-Pyrd) |
| 5B-43 | " | COCH$_2$-(4-Me-1-Piz) |
| 5B-44 | " | COCH$_2$CH$_2$NHCH$_3$ |
| 5B-45 | " | COCH$_2$CH$_2$N(CH$_3$)$_2$ |
| 5B-46 | " | COCH$_2$CH$_2$-(1-Pyrd) |
| 5B-47 | " | COCH$_2$CH$_2$-(4-Me-1-Piz) |
| 5B-48 | " | COCH$_2$CH$_2$CO-(4-Me-1-Piz) |
| 5B-49 | " | COCH$_2$CH$_2$CH$_2$N(CH$_3$)$_2$ |
| 5B-50 | " | COCH$_2$CH$_2$CH$_2$-(1-Pyrd) |
| 5B-51 | " | COCH$_2$CH$_2$CH$_2$-(4-Me-1-Piz) |
| 5B-52 | (5-F-benzyl linker) | C(=O)COOH |
| 5B-53 | " | COCH$_2$NH$_2$ |
| 5B-54 | " | COCH$_2$CH$_2$NH$_2$ |
| 5B-55 | " | COCH$_2$CH$_2$CH$_2$NH$_2$ |
| 5B-56 | " | COCH$_2$CH$_2$COOH |
| 5B-57 | " | COCH$_2$NHCH$_3$ |
| 5B-58 | " | COCH$_2$N(CH$_3$)$_2$ |
| 5B-59 | " | COCH$_2$-(1-Pyrd) |
| 5B-60 | " | COCH$_2$-(4-Me-1-Piz) |
| 5B-61 | " | COCH$_2$CH$_2$NHCH$_3$ |
| 5B-62 | " | COCH$_2$CH$_2$N(CH$_3$)$_2$ |
| 5B-63 | " | COCH$_2$CH$_2$-(1-Pyrd) |
| 5B-64 | " | COCH$_2$CH$_2$-(4-Me-1-Piz) |
| 5B-65 | " | COCH$_2$CH$_2$CO-(4-Me-1-Piz) |
| 5B-66 | " | COCH$_2$CH$_2$CH$_2$N(CH$_3$)$_2$ |
| 5B-67 | " | COCH$_2$CH$_2$CH$_2$-(1-Pyrd) |
| 5B-68 | " | COCH$_2$CH$_2$CH$_2$-(4-Me-1-Piz) |

EXAMPLE TABLE 5B-continued

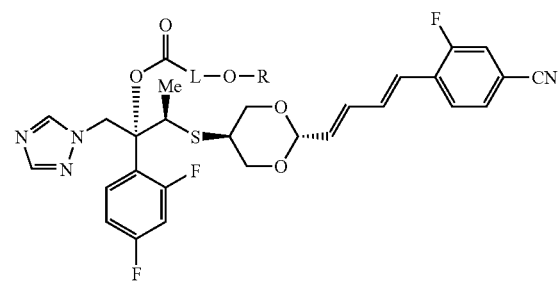

| Example No. | L | R |
|---|---|---|
| 5B-69 | 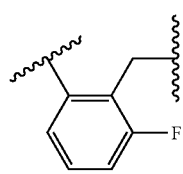 | C(=O)COOH |
| 5B-70 | " | COCH$_2$NH$_2$ |
| 5B-71 | " | COCH$_2$CH$_2$NH$_2$ |
| 5B-72 | " | COCH$_2$CH$_2$CH$_2$NH$_2$ |
| 5B-73 | " | COCH$_2$CH$_2$COOH |
| 5B-74 | " | COCH$_2$NHCH$_3$ |
| 5B-75 | " | COCH$_2$N(CH$_3$)$_2$ |
| 5B-76 | " | COCH$_2$-(1-Pyrd) |
| 5B-77 | " | COCH$_2$-(4-Me-1-Piz) |
| 5B-78 | " | COCH$_2$CH$_2$NHCH$_3$ |
| 5B-79 | " | COCH$_2$CH$_2$N(CH$_3$)$_2$ |
| 5B-80 | " | COCH$_2$CH$_2$-(1-Pyrd) |
| 5B-81 | " | COCH$_2$CH$_2$-(4-Me-1-Piz) |
| 5B-82 | " | COCH$_2$CH$_2$CO-(4-Me-1-Piz) |
| 5B-83 | " | COCH$_2$CH$_2$CH$_2$N(CH$_3$)$_2$ |
| 5B-84 | " | COCH$_2$CH$_2$CH$_2$-(1-Pyrd) |
| 5B-85 | " | COCH$_2$CH$_2$CH$_2$-(4-Me-1-Piz) |
| 5B-86 | 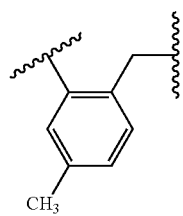 | H |
| 5B-87 | " | C(=O)COOH |
| 5B-88 | " | COCH$_2$NH$_2$ |
| 5B-89 | " | COCH$_2$CH$_2$NH$_2$ |
| 5B-90 | " | COCH$_2$CH$_2$CH$_2$NH$_2$ |
| 5B-91 | " | COCH$_2$CH$_2$COOH |
| 5B-92 | " | P(=O)(OH)$_2$ |
| 5B-93 | " | COCH$_2$NHCH$_3$ |
| 5B-94 | " | COCH$_2$N(CH$_3$)$_2$ |
| 5B-95 | " | COCH$_2$-(1-Pyrd) |
| 5B-96 | " | COCH$_2$-(4-Me-1-Piz) |
| 5B-97 | " | COCH$_2$CH$_2$NHCH$_3$ |
| 5B-98 | " | COCH$_2$CH$_2$N(CH$_3$)$_2$ |
| 5B-99 | " | COCH$_2$CH$_2$-(1-Pyrd) |
| 5B-100 | " | COCH$_2$CH$_2$-(4-Me-1-Piz) |
| 5B-101 | " | COCH$_2$CH$_2$CO-(4-Me-1-Piz) |
| 5B-102 | " | COCH$_2$CH$_2$CH$_2$N(CH$_3$)$_2$ |
| 5B-103 | " | COCH$_2$CH$_2$CH$_2$-(1-Pyrd) |
| 5B-104 | " | COCH$_2$CH$_2$CH$_2$-(4-Me-1-Piz) |

EXAMPLE TABLE 5B-continued

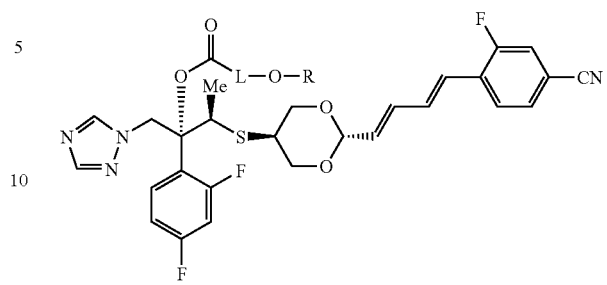

| Example No. | L | R |
|---|---|---|
| 5B-105 | (2-OCH$_3$ phenyl-CH$_2$) | C(=O)COOH |
| 5B-106 | " | COCH$_2$NH$_2$ |
| 5B-107 | " | COCH$_2$CH$_2$NH$_2$ |
| 5B-108 | " | COCH$_2$CH$_2$CH$_2$NH$_2$ |
| 5B-109 | " | COCH$_2$CH$_2$COOH |
| 5B-110 | " | COCH$_2$NHCH$_3$ |
| 5B-111 | " | COCH$_2$N(CH$_3$)$_2$ |
| 5B-112 | " | COCH$_2$-(1-Pyrd) |
| 5B-113 | " | COCH$_2$-(4-Me-1-Piz) |
| 5B-114 | " | COCH$_2$CH$_2$NHCH$_3$ |
| 5B-115 | " | COCH$_2$CH$_2$N(CH$_3$)$_2$ |
| 5B-116 | " | COCH$_2$CH$_2$-(1-Pyrd) |
| 5B-117 | " | COCH$_2$CH$_2$-(4-Me-1-Piz) |
| 5B-118 | " | COCH$_2$CH$_2$CO-(4-Me-1-Piz) |
| 5B-119 | " | COCH$_2$CH$_2$CH$_2$N(CH$_3$)$_2$ |
| 5B-120 | " | COCH$_2$CH$_2$CH$_2$-(1-Pyrd) |
| 5B-121 | " | COCH$_2$CH$_2$CH$_2$-(4-Me-1-Piz) |
| 5B-122 | (4-OCH$_3$ phenyl-CH$_2$) | H |
| 5B-123 | " | C(=O)COOH |
| 5B-124 | " | COCH$_2$NH$_2$ |
| 5B-125 | " | COCH$_2$CH$_2$NH$_2$ |
| 5B-126 | " | COCH$_2$CH$_2$CH$_2$NH$_2$ |
| 5B-127 | " | COCH$_2$CH$_2$COOH |
| 5B-128 | " | P(=O)(OH)$_2$ |
| 5B-129 | " | COCH$_2$NHCH$_3$ |
| 5B-130 | " | COCH$_2$N(CH$_3$)$_2$ |
| 5B-131 | " | COCH$_2$-(1-Pyrd) |
| 5B-132 | " | COCH$_2$-(4-Me-1-Piz) |
| 5B-133 | " | COCH$_2$CH$_2$NHCH$_3$ |
| 5B-134 | " | COCH$_2$CH$_2$N(CH$_3$)$_2$ |
| 5B-135 | " | COCH$_2$CH$_2$-(1-Pyrd) |
| 5B-136 | " | COCH$_2$CH$_2$-(4-Me-1-Piz) |
| 5B-137 | " | COCH$_2$CH$_2$CO-(4-Me-1-Piz) |
| 5B-138 | " | COCH$_2$CH$_2$CH$_2$N(CH$_3$)$_2$ |
| 5B-139 | " | COCH$_2$CH$_2$CH$_2$-(1-Pyrd) |
| 5B-140 | " | COCH$_2$CH$_2$CH$_2$-(4-Me-1-Piz) |

EXAMPLE TABLE 5B-continued

| Example No. | L | R |
|---|---|---|
| 5B-141 | 2-CH2-,4-Cl-phenyl | C(=O)COOH |
| 5B-142 | " | COCH$_2$NH$_2$ |
| 5B-143 | " | COCH$_2$CH$_2$NH$_2$ |
| 5B-144 | " | COCH$_2$CH$_2$CH$_2$NH$_2$ |
| 5B-145 | " | COCH$_2$CH$_2$COOH |
| 5B-146 | " | COCH$_2$NHCH$_3$ |
| 5B-147 | " | COCH$_2$N(CH$_3$)$_2$ |
| 5B-148 | " | COCH$_2$-(1-Pyrd) |
| 5B-149 | " | COCH$_2$-(4-Me-1-Piz) |
| 5B-150 | " | COCH$_2$CH$_2$NHCH$_3$ |
| 5B-151 | " | COCH$_2$CH$_2$N(CH$_3$)$_2$ |
| 5B-152 | " | COCH$_2$CH$_2$-(1-Pyrd) |
| 5B-153 | " | COCH$_2$CH$_2$-(4-Me-1-Piz) |
| 5B-154 | " | COCH$_2$CH$_2$CO-(4-Me-1-Piz) |
| 5B-155 | " | COCH$_2$CH$_2$CH$_2$N(CH$_3$)$_2$ |
| 5B-156 | " | COCH$_2$CH$_2$CH$_2$-(1-Pyrd) |
| 5B-157 | " | COCH$_2$CH$_2$CH$_2$-(4-Me-1-Piz) |
| 5B-158 | 2-CH2-,3-Cl-phenyl | C(=O)COOH |
| 5B-159 | " | COCH$_2$NH$_2$ |
| 5B-160 | " | COCH$_2$CH$_2$NH$_2$ |
| 5B-161 | " | COCH$_2$CH$_2$CH$_2$NH$_2$ |
| 5B-162 | " | COCH$_2$CH$_2$COOH |
| 5B-163 | " | COCH$_2$NHCH$_3$ |
| 5B-164 | " | COCH$_2$N(CH$_3$)$_2$ |
| 5B-165 | " | COCH$_2$-(1-Pyrd) |
| 5B-166 | " | COCH$_2$-(4-Me-1-Piz) |
| 5B-167 | " | COCH$_2$CH$_2$NHCH$_3$ |
| 5B-168 | " | COCH$_2$CH$_2$N(CH$_3$)$_2$ |
| 5B-169 | " | COCH$_2$CH$_2$-(1-Pyrd) |
| 5B-170 | " | COCH$_2$CH$_2$-(4-Me-1-Piz) |
| 5B-171 | " | COCH$_2$CH$_2$CO-(4-Me-1-Piz) |
| 5B-172 | " | COCH$_2$CH$_2$CH$_2$N(CH$_3$)$_2$ |
| 5B-173 | " | COCH$_2$CH$_2$CH$_2$-(1-Pyrd) |
| 5B-174 | " | COCH$_2$CH$_2$CH$_2$-(4-Me-1-Piz) |

EXAMPLE TABLE 5C

| Example No. | L | R |
|---|---|---|
| 5C-1 | 2,3-furan-diyl-CH$_2$ | H |
| 5C-2 | " | COCH$_2$NH$_2$ |
| 5C-3 | " | P(=O)(OH)$_2$ |
| 5C-4 | " | COCH$_2$NHCH$_3$ |
| 5C-5 | " | COCH$_2$N(CH$_3$)$_2$ |
| 5C-6 | " | COCH$_2$-(1-Pyrd) |
| 5C-7 | " | COCH$_2$-(4-Me-1-Piz) |
| 5C-8 | " | COCH$_2$CH$_2$NHCH$_3$ |
| 5C-9 | " | COCH$_2$CH$_2$N(CH$_3$)$_2$ |
| 5C-10 | " | COCH$_2$CH$_2$-(1-Pyrd) |
| 5C-11 | " | COCH$_2$CH$_2$-(4-Me-1-Piz) |
| 5C-12 | " | COCH$_2$CH$_2$CO-(4-Me-1-Piz) |
| 5C-13 | " | COCH$_2$CH$_2$CH$_2$N(CH$_3$)$_2$ |
| 5C-14 | " | COCH$_2$CH$_2$CH$_2$-(1-Pyrd) |
| 5C-15 | " | COCH$_2$CH$_2$COOH |
| 5C-16 | 3,4-furan-diyl-CH$_2$ | H |
| 5C-17 | " | COCH$_2$NH$_2$ |
| 5C-18 | " | P(=O)(OH)$_2$ |
| 5C-19 | " | COCH$_2$NHCH$_3$ |
| 5C-20 | " | COCH$_2$N(CH$_3$)$_2$ |
| 5C-21 | " | COCH$_2$-(1-Pyrd) |
| 5C-22 | " | COCH$_2$-(4-Me-1-Piz) |
| 5C-23 | " | COCH$_2$CH$_2$NHCH$_3$ |
| 5C-24 | " | COCH$_2$CH$_2$N(CH$_3$)$_2$ |
| 5C-25 | " | COCH$_2$CH$_2$-(1-Pyrd) |
| 5C-26 | " | COCH$_2$CH$_2$-(4-Me-1-Piz) |
| 5C-27 | " | COCH$_2$CH$_2$CO-(4-Me-1-Piz) |
| 5C-28 | " | COCH$_2$CH$_2$CH$_2$N(CH$_3$)$_2$ |
| 5C-29 | " | COCH$_2$CH$_2$CH$_2$-(1-Pyrd) |
| 5C-30 | " | COCH$_2$CH$_2$COOH |
| 5C-31 | 2,3-furan-diyl-CH$_2$ (isomer) | H |
| 5C-32 | " | COCH$_2$NH$_2$ |
| 5C-33 | " | P(=O)(OH)$_2$ |
| 5C-34 | " | COCH$_2$NHCH$_3$ |
| 5C-35 | " | COCH$_2$N(CH$_3$)$_2$ |
| 5C-36 | " | COCH$_2$-(1-Pyrd) |
| 5C-37 | " | COCH$_2$-(4-Me-1-Piz) |

EXAMPLE TABLE 5C-continued

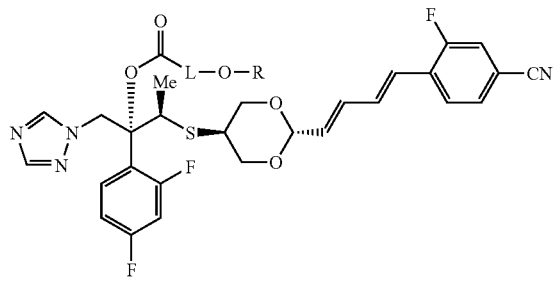

| Example No. | L | R |
|---|---|---|
| 5C-38 | " | COCH$_2$CH$_2$NHCH$_3$ |
| 5C-39 | " | COCH$_2$CH$_2$N(CH$_3$)$_2$ |
| 5C-40 | " | COCH$_2$CH$_2$-(1-Pyrd) |
| 5C-41 | " | COCH$_2$CH$_2$-(4-Me-1-Piz) |
| 5C-42 | " | COCH$_2$CH$_2$CO-(4-Me-1-Piz) |
| 5C-43 | " | COCH$_2$CH$_2$CH$_2$N(CH$_3$)$_2$ |
| 5C-44 | " | COCH$_2$CH$_2$CH$_2$-(1-Pyrd) |
| 5C-45 | " | COCH$_2$CH$_2$COOH |
| 5C-46 | (thiophene linker) | H |
| 5C-47 | " | COCH$_2$NH$_2$ |
| 5C-48 | " | P(=O)(OH)$_2$ |
| 5C-49 | " | COCH$_2$NHCH$_3$ |
| 5C-50 | " | COCH$_2$N(CH$_3$)$_2$ |
| 5C-51 | " | COCH$_2$-(1-Pyrd) |
| 5C-52 | " | COCH$_2$-(4-Me-1-Piz) |
| 5C-53 | " | COCH$_2$CH$_2$NHCH$_3$ |
| 5C-54 | " | COCH$_2$CH$_2$N(CH$_3$)$_2$ |
| 5C-55 | " | COCH$_2$CH$_2$-(1-Pyrd) |
| 5C-56 | " | COCH$_2$CH$_2$-(4-Me-1-Piz) |
| 5C-57 | " | COCH$_2$CH$_2$CO-(4-Me-1-Piz) |
| 5C-58 | " | COCH$_2$CH$_2$CH$_2$N(CH$_3$)$_2$ |
| 5C-59 | " | COCH$_2$CH$_2$CH$_2$-(1-Pyrd) |
| 5C-60 | " | COCH$_2$CH$_2$COOH |
| 5C-61 | (thiophene linker) | H |
| 5C-62 | " | COCH$_2$NH$_2$ |
| 5C-63 | " | P(=O)(OH)$_2$ |
| 5C-64 | " | COCH$_2$NHCH$_3$ |
| 5C-65 | " | COCH$_2$N(CH$_3$)$_2$ |
| 5C-66 | " | COCH$_2$-(1-Pyrd) |
| 5C-67 | " | COCH$_2$-(4-Me-1-Piz) |
| 5C-68 | " | COCH$_2$CH$_2$NHCH$_3$ |
| 5C-69 | " | COCH$_2$CH$_2$N(CH$_3$)$_2$ |
| 5C-70 | " | COCH$_2$CH$_2$-(1-Pyrd) |
| 5C-71 | " | COCH$_2$CH$_2$-(4-Me-1-Piz) |
| 5C-72 | " | COCH$_2$CH$_2$CO-(4-Me-1-Piz) |
| 5C-73 | " | COCH$_2$CH$_2$CH$_2$N(CH$_3$)$_2$ |
| 5C-74 | " | COCH$_2$CH$_2$CH$_2$-(1-Pyrd) |
| 5C-75 | " | COCH$_2$CH$_2$COOH |

EXAMPLE TABLE 5C-continued

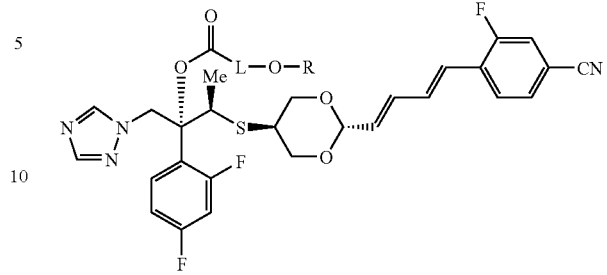

| Example No. | L | R |
|---|---|---|
| 5C-76 | (thiophene linker) | H |
| 5C-77 | " | COCH$_2$NH$_2$ |
| 5C-78 | " | P(=O)(OH)$_2$ |
| 5C-79 | " | COCH$_2$NHCH$_3$ |
| 5C-80 | " | COCH$_2$N(CH$_3$)$_2$ |
| 5C-81 | " | COCH$_2$-(1-Pyrd) |
| 5C-82 | " | COCH$_2$-(4-Me-1-Piz) |
| 5C-83 | " | COCH$_2$CH$_2$NHCH$_3$ |
| 5C-84 | " | COCH$_2$CH$_2$N(CH$_3$)$_2$ |
| 5C-85 | " | COCH$_2$CH$_2$-(1-Pyrd) |
| 5C-86 | " | COCH$_2$CH$_2$-(4-Me-1-Piz) |
| 5C-87 | " | COCH$_2$CH$_2$CO-(4-Me-1-Piz) |
| 5C-88 | " | COCH$_2$CH$_2$CH$_2$N(CH$_3$)$_2$ |
| 5C-89 | " | COCH$_2$CH$_2$CH$_2$-(1-Pyrd) |
| 5C-90 | " | COCH$_2$CH$_2$COOH |
| 5C-91 | (pyridine linker) | H |
| 5C-92 | " | COCH$_2$NH$_2$ |
| 5C-93 | " | P(=O)(OH)$_2$ |
| 5C-94 | " | COCH$_2$NHCH$_3$ |
| 5C-95 | " | COCH$_2$N(CH$_3$)$_2$ |
| 5C-96 | " | COCH$_2$-(1-Pyrd) |
| 5C-97 | " | COCH$_2$-(4-Me-1-Piz) |
| 5C-98 | " | COCH$_2$CH$_2$NHCH$_3$ |
| 5C-99 | " | COCH$_2$CH$_2$N(CH$_3$)$_2$ |
| 5C-100 | " | COCH$_2$CH$_2$-(1-Pyrd) |
| 5C-101 | " | COCH$_2$CH$_2$-(4-Me-1-Piz) |
| 5C-102 | " | COCH$_2$CH$_2$CO-(4-Me-1-Piz) |
| 5C-103 | " | COCH$_2$CH$_2$CH$_2$N(CH$_3$)$_2$ |
| 5C-104 | " | COCH$_2$CH$_2$CH$_2$-(1-Pyrd) |
| 5C-105 | " | COCH$_2$CH$_2$COOH |
| 5C-106 | (pyridine linker) | H |
| 5C-107 | " | COCH$_2$NH$_2$ |
| 5C-108 | " | P(=O)(OH)$_2$ |
| 5C-109 | " | COCH$_2$NHCH$_3$ |
| 5C-110 | " | COCH$_2$N(CH$_3$)$_2$ |
| 5C-111 | " | COCH$_2$-(1-Pyrd) |

EXAMPLE TABLE 5C-continued

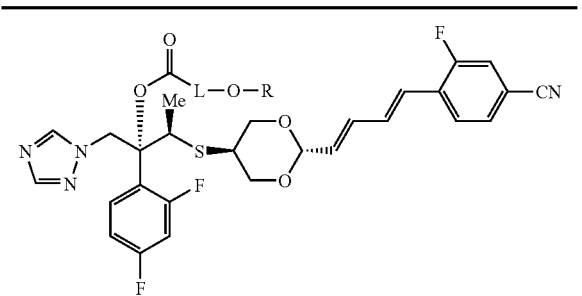

| Example No. | L | R |
|---|---|---|
| 5C-112 | " | COCH$_2$-(4-Me-1-Piz) |
| 5C-113 | " | COCH$_2$CH$_2$NHCH$_3$ |
| 5C-114 | " | COCH$_2$CH$_2$N(CH$_3$)$_2$ |
| 5C-115 | " | COCH$_2$CH$_2$-(1-Pyrd) |
| 5C-116 | " | COCH$_2$CH$_2$-(4-Me-1-Piz) |
| 5C-117 | " | COCH$_2$CH$_2$CO-(4-Me-1-Piz) |
| 5C-118 | " | COCH$_2$CH$_2$CH$_2$N(CH$_3$)$_2$ |
| 5C-119 | " | COCH$_2$CH$_2$CH$_2$-(1-Pyrd) |
| 5C-120 | " | COCH$_2$CH$_2$COOH |
| 5C-121 | (4-pyridyl-CH$_2$ group) | H |
| 5C-122 | " | COCH$_2$NH$_2$ |
| 5C-123 | " | P(=O)(OH)$_2$ |
| 5C-124 | " | COCH$_2$NHCH$_3$ |
| 5C-125 | " | COCH$_2$N(CH$_3$)$_2$ |
| 5C-126 | " | COCH$_2$-(1-Pyrd) |
| 5C-127 | " | COCH$_2$-(4-Me-1-Piz) |
| 5C-128 | " | COCH$_2$CH$_2$NHCH$_3$ |
| 5C-129 | " | COCH$_2$CH$_2$N(CH$_3$)$_2$ |
| 5C-130 | " | COCH$_2$CH$_2$-(1-Pyrd) |
| 5C-131 | " | COCH$_2$CH$_2$-(4-Me-1-Piz) |
| 5C-132 | " | COCH$_2$CH$_2$CO-(4-Me-1-Piz) |
| 5C-133 | " | COCH$_2$CH$_2$CH$_2$N(CH$_3$)$_2$ |
| 5C-134 | " | COCH$_2$CH$_2$CH$_2$-(1-Pyrd) |
| 5C-135 | " | COCH$_2$CH$_2$COOH |
| 5C-136 | (3-pyridyl-CH$_2$ group) | H |
| 5C-137 | " | COCH$_2$NH$_2$ |
| 5C-138 | " | P(=O)(OH)$_2$ |
| 5C-139 | " | COCH$_2$NHCH$_3$ |
| 5C-140 | " | COCH$_2$N(CH$_3$)$_2$ |
| 5C-141 | " | COCH$_2$-(1-Pyrd) |
| 5C-142 | " | COCH$_2$-(4-Me-1-Piz) |
| 5C-143 | " | COCH$_2$CH$_2$NHCH$_3$ |
| 5C-144 | " | COCH$_2$CH$_2$N(CH$_3$)$_2$ |
| 5C-145 | " | COCH$_2$CH$_2$-(1-Pyrd) |
| 5C-146 | " | COCH$_2$CH$_2$-(4-Me-1-Piz) |
| 5C-147 | " | COCH$_2$CH$_2$CO-(4-Me-1-Piz) |
| 5C-148 | " | COCH$_2$CH$_2$CH$_2$N(CH$_3$)$_2$ |
| 5C-149 | " | COCH$_2$CH$_2$CH$_2$-(1-Pyrd) |
| 5C-15C | " | COCH$_2$CH$_2$COOH |

EXAMPLE TABLE 6

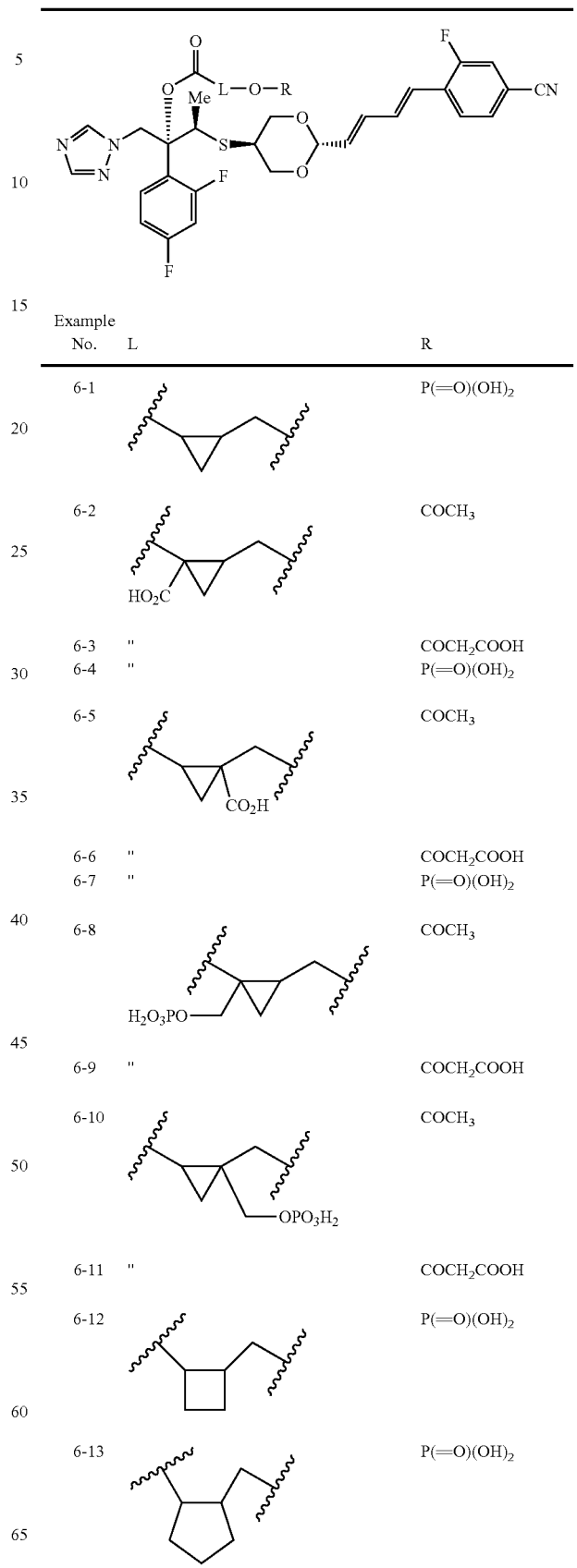

| Example No. | L | R |
|---|---|---|
| 6-1 | (cyclopropane-1,2-diyl) | P(=O)(OH)$_2$ |
| 6-2 | (cyclopropane with CO$_2$H) | COCH$_3$ |
| 6-3 | " | COCH$_2$COOH |
| 6-4 | " | P(=O)(OH)$_2$ |
| 6-5 | (cyclopropane with CO$_2$H) | COCH$_3$ |
| 6-6 | " | COCH$_2$COOH |
| 6-7 | " | P(=O)(OH)$_2$ |
| 6-8 | (cyclopropane with CH$_2$OPO$_3$H$_2$) | COCH$_3$ |
| 6-9 | " | COCH$_2$COOH |
| 6-10 | (cyclopropane with CH$_2$OPO$_3$H$_2$) | COCH$_3$ |
| 6-11 | " | COCH$_2$COOH |
| 6-12 | (cyclobutane-1,2-diyl) | P(=O)(OH)$_2$ |
| 6-13 | (cyclopentane-1,2-diyl) | P(=O)(OH)$_2$ |

EXAMPLE TABLE 6-continued

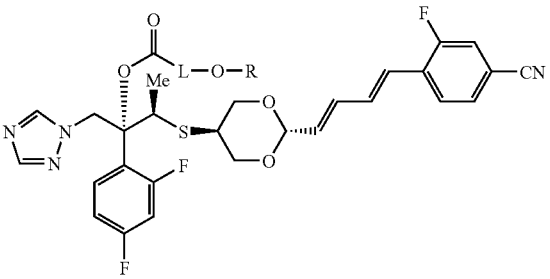

| Example No. | L | R |
|---|---|---|
| 6-14 | 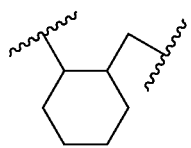 | P(=O)(OH)₂ |

In the above Tables, preferred compounds are compounds of Example No.: 4-3, 4-4, 4-5, 4-9, 4-15, 4-16, 4-17, 4-18, 4-19, 4-24, 4-32, 4-33, 4-34, 4-38, 4-44, 4-45, 5-2, 5-3, 5-5, 5-8, 5-9, 5-15, 5-16, 5-17, 5-18, 5-19, 5-20, 5-21, 5-22, 5-23, 5-24, 5-34, 5-36, 5-41, 5-45, 6-2, 6-4, 6-7, 6-8, 4A-6, 4A-9, 5A-1, 5A-2, 5A-9, 5A-11, 5A-12, 5A-19, 5A-20, 5A-21, 5A-22, 5A-29, 5A-30, 5A-79, 5A-82, 5A-84, 5A-85, 5A-86, 5A-87, 5A-94, 5A-96, 5A-97, 5A-104, 5A-105, 5A-106, 5A-107, 5A-114, 5A-115, 5B-9, 5B-15, 5B-26, 5B-31, 5B-43, 5B-48, 5B-60, 5B-65, 5B-77, 5B-82, 5B-92, 5B-96, 5B-101, 5B-113, 5B-118, 5B-128, 5B-132, 5B-137, 5B-149, 5B-154, 5B-166, 5B-171, 5C-3, 5C-7, 5C-12, 5C-18, 5C-22, 5C-27, 5C-33, 5C-37, 5C-42, 5C-48, 5C-52, 5C-57, 5C-63, 5C-67, 5C-72, 5C-78, 5C-82, 5C-87, 5C-93, 5C-97, 5C-102, 5C-108, 5C-112, 5C-117, 5C-123, 5C-127, 5C-132, 5C-138, 5C-142 and 5C-147.

still preferred compounds are as follows:

Example No. 4-16: Dihydrogen 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl phosphate, Example No. 4-19: Dihydrogen 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2,2-dimethyl-4-oxobutyl phosphate, Example No. 5-15: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate, Example No. 5-16: Dihydrogen 4-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate, Example No. 5-20: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-fluorobenzyl phosphate, Example No. 5-21: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-5-fluorobenzyl phosphate, Example No. 5-22: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-fluorobenzyl phosphate, Example No. 5-23: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methylbenzyl phosphate, Example No. 5-24: Dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methoxybenzyl phosphate, Example No. 5-41: Dihydrogen [8-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-1-naphthyl] methyl phosphate, Example No. 5-45: Dihydrogen 2-chloro-6-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate, Example No. 4A-6: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[2-(4-methyl-1-piperazinyl)acetoxy]butyrate, Example No. 4A-9: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[[4-(4-methyl-1-piperazinyl)-4-oxobutyryl]oxy]butyrate, Example No. 5A-1: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N-methylamino)acetoxy]methyl]benzoate, Example No. 5A-2: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N,N-dimethylamino)acetoxy]methyl]benzoate, Example No. 5A-9: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(4-methyl-1-piperazinyl)acetoxy]methyl]benzoate, Example No. 5A-11: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[3-(N-methylamino)propanoyl]oxymethyl]benzoate, Example No. 5A-12: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[3-(N,N-dimethylamino)propionyl]oxymethyl]benzoate, Example No. 5A-19: (1R,2R)-2-[[trans-2-[(1E,3E)-4-(4-Cyano-2-fluorophenyl)-1,3-butadienyl]-1,3-dioxan-5-yl]

thio]-1-(2,4-difluorophenyl)-1-[(1H-1,2,4-triazol-1-yl)methyl]propyl 2-[[3-(4-methyl-1-piperazinyl)propionyl]oxymethyl]benzoate, Example No. 5A-20: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(4-methyl-1-piperazinyl)-4-oxobutyryl]oxymethyl]benzoate, Example No. 5A-21: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(N-methylamino)butyryl]oxymethyl]benzoate, Example No. 5A-22: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(N,N-dimethylamino)butyryl]oxymethyl]benzoate, Example No. 5A-86: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(N-methylamino)acetoxy]methyl]benzoate, Example No. 5A-87: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(N,N-dimethylamino)acetoxy]methyl]benzoate, Example No. 5A-94: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(4-methyl-1-piperazinyl)acetoxy]methyl]benzoate, Example No. 5A-96: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(N-methylamino)propanoyl]oxymethyl]benzoate, Example No. 5A-97: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(N,N-dimethylamino)propanoyl]oxymethyl]benzoate, Example No. 5A-104: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(4-methyl-1-piperazinyl)propanoyl]oxymethyl]benzoate, Example No. 5A-105: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(4-methyl-1-piperazinyl)-4-oxobutyryl]oxymethyl]benzoate, Example No. 5A-106: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(N-methylamino)butyryl]oxymethyl]benzoate, and Example No. 5A-107: (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(N,N-dimethylamino)butyryl]oxymethyl]benzoate.

The compounds of the general formula (I) of the present invention can be prepared according to the following methods described below.

[Method A]

Method A is a method to prepare compounds (Ia) [compounds (Ia) are compounds of general formula (I) of the present invention wherein $L^\alpha$ is a single bond, a $C_6$-$C_{10}$ aryl group which may optionally be substituted with 1 to 3 same or different group(s) selected from the group consisting of Substituent group α, a heterocyclic group which may optionally be substituted with 1 to 3 same or different group(s) selected from the group consisting of Substituent group α, or a $C_3$-$C_7$ cycloalkyl group which may optionally be substituted with 1 to 3 same or different group(s) selected from the group consisting of Substituent group α, and R is a $C_1$-$C_6$ alkanoyl group which may optionally be substituted with 1 to 3 same or different group(s) selected from the group consisting of Substituent group β, a group of formula —C(O)—NR²R³ (wherein, $R^2$ and $R^3$ independently represent a hydrogen atom or a $C_1$-$C_6$ alkyl group, or $R^2$ and $R^3$, together with the nitrogen atom to which they are attached, form a 4- to 7-membered heterocyclic group containing nitrogen atom(s)) or a —P(=O) (OH)$_2$ group], and the reaction scheme is shown below.

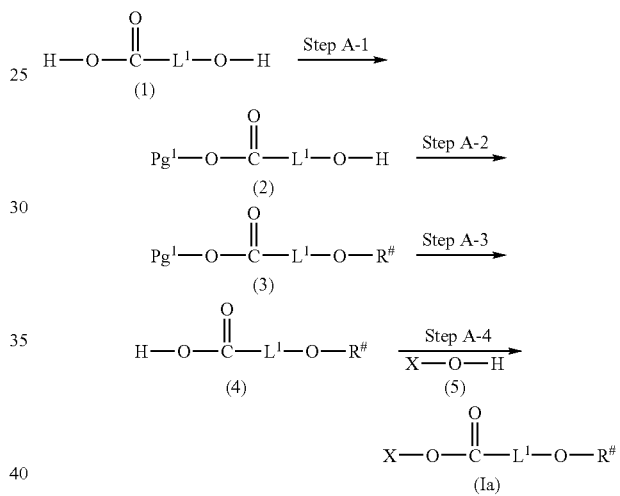

In the above reaction scheme, X is as defined above, $L^1$ is as defined for the above L (provided that $L^\alpha$ is not an oxygen atom), $R^\#$ is as defined for the above R (provided that R is not a hydrogen atom), and $Pg^1$ is a carboxyl protecting group.

Here, the protecting group $Pg^1$ is a protecting group of the ester type which is conventionally used in organic synthesis for the protection of carboxylic acids (examples of which are described in T. W. Greene et al., Protective Groups in Organic Synthesis, 3rd Edition, John Wiley & Sons, Inc. (1999)).

There is no particular restriction on the nature of this protecting group, provided that when the group $R^\#$ is introduced onto the alcoholic hydroxy group of compound (2) in Step A-2, the protecting group is not removed, but when the protecting group is removed in Step A-3, the deprotection can be carried out with no adverse effect on the compound (3). Examples of the protecting group include: an optionally substituted $C_1$-$C_{10}$ alkyl group such as methyl, ethyl, propyl, isopropyl, butyl, isobutyl, t-butyl, pentyl, isopentyl, 1-ethylpropyl, 1,1-dimethylpropyl, 2,2-dimethylpropyl, hexyl, isohexyl, 1,1-dimethylbutyl, 3,3-dimethylbutyl, 2,2-dimethylbutyl, heptyl, octyl, nonyl, decyl, methoxymethyl, methylthiomethyl, 2-(trimethylsilyl)ethoxymethyl, carbamoylmethyl, N-phthalimidomethyl, trichloroethyl, chloroethyl, chlorobutyl, chloropentyl, 2-(trimethylsilyl)ethyl, methylthioethyl, 2-(diphenylphosphino)ethyl, 2-(p-nitrophenylsulfenyl)ethyl or 2-(p-toluenesulfonyl)ethyl group; an optionally substituted $C_3$-$C_{10}$ alkenyl group such as allyl, cinnamyl or 3-buten-1-yl group; an optionally substituted $C_3$-$C_{10}$ cycloalkyl group such as cyclopropyl, cyclobutyl, cyclopentyl, cyclohexyl, methylcyclohexyl, cycloheptyl, cyclooctyl, cyclononyl or cyclodecyl group; an optionally substituted $C_4$-$C_{10}$ cycloalkyl-alkyl group such as cyclopropylmethyl, cyclobutylmethyl, cyclopentylmethyl, cyclohexylmethyl, cycloheptylmethyl, cyclooctylmethyl, cyclononylmethyl, cyclodecylmethyl, (cyclopropyl)ethyl, (cyclobutyl)ethyl, (cyclopentyl)ethyl, (cyclohexyl)ethyl, (cycloheptyl)ethyl or (cyclooctyl)ethyl group; an optionally substituted $C_6$-$C_{10}$ aryl group such as phenyl, tolyl or naphthyl group; an optionally substituted heterocyclic group such as tetrahydropyranyl, tetrahydrofuranyl or pyridyl group; an optionally substituted $C_7$-$C_{19}$ aralkyl group such as benzyl, phenethyl, 3-phenylpropyl, 1-methyl-1-phenylethyl, benzhydryl, trityl, fluorenyl, fluorenylmethyl, 9-anthrylmethyl, trimethylbenzyl, bromobenzyl, nitrobenzyl, methoxybenzyl or dimethoxybenzyl group; a $C_1$-$C_4$ alkyl group which is substituted with heterocyclic group(s), such as (1,3-dithian-2-yl)methyl, pyridylmethyl or 2-(2'-pyridyl)ethyl group; a ($C_7$-$C_{11}$ aralkyl)oxymethyl group such as benzyloxymethyl, phenethyloxymethyl or naphthylmethyloxymethyl group; a (substituted) arylcarbonylmethyl group such as phenacyl group; an optionally substituted 1-(acyloxy)methyl group such as acetoxymethyl, 1-(acetoxy)ethyl or pivaloyloxymethyl group; or a silyl group which is substituted with $C_1$-$C_6$ alkyl group(s) or phenyl group(s) such as trimethylsilyl, triethylsilyl, t-butyldimethylsilyl, triisopropylsilyl, isopropyldimethylsilyl, phenyldimethylsilyl, t-butyldiphenylsilyl or di(t-butyl)methylsilyl group.

Of these, a methyl, an ethyl, a propyl, an isopropyl, a t-butyl, a methoxymethyl, a methylthiomethyl, a 2-(trimethylsilyl)ethoxymethyl, a trichloroethyl, a chloroethyl, a 2-(trimethylsilyl)ethyl, an allyl, a cyclohexyl, a phenyl, a benzyl, a benzhydryl, a trityl, a fluorenyl, a fluorenylmethyl, a bromobenzyl, a nitrobenzyl, a methoxybenzyl, a benzyloxymethyl, a pivaloyloxymethyl, a trimethylsilyl, a triethylsilyl, a t-butyldimethylsilyl, a triisopropylsilyl, an isopropyldimethylsilyl, a phenyldimethylsilyl, a t-butyldiphenylsilyl or a di(t-butyl)methylsilyl group is preferred, a methyl, an ethyl, a t-butyl, a methoxymethyl, a methylthiomethyl, a 2-(trimethylsilyl)ethoxymethyl, a trichloroethyl, a chloroethyl, an allyl, a phenyl, a benzyl, a benzhydryl, a trityl, a nitrobenzyl, a methoxybenzyl, a benzyloxymethyl, a pivaloyloxymethyl, a triethylsilyl, a t-butyldimethylsilyl, a triisopropylsilyl, an isopropyldimethylsilyl or a t-butyldiphenylsilyl group is more preferred, a 2-(trimethylsilyl)ethoxymethyl, a benzyl, a 4-methoxybenzyl, a benzhydryl or a pivaloyloxymethyl group is still more preferred and a 4-methoxybenzyl group is most preferred.

The method is first to prepare a carboxyl-protected compound (2) by protecting the carboxy group of hydroxycarboxylic acid compound (1) (in Step A-1), then, to prepare compound (3) by introducing a group $R^\#$ onto the compound (2)(in Step A-2), then, to prepare a carboxylic acid compound (4) by deprotection of the compound (3) (in Step A-3), and finally to prepare compound (Ia) by esterification of the carboxylic acid compound (4) with an alcohol compound (5) (in Step A-4). Alternatively, compound (4) can be prepared directly by introducing a group $R^\#$ onto the alcohol group of the hydroxycarboxylic acid compound (1) without protecting the carboxy group.

Each step is described in detail as follows.

(Step A-1)

Step A-1 is a step to prepare compound (2) by protecting the carboxy group of hydroxycarboxylic acid compound (1), if necessary.

The hydroxycarboxylic acid compound (1) which is the starting material is commercially available, or if the compound is not commercially available, it can be prepared by Method F described below or by using methods well known in the art.

This step can be accomplished by protection reactions for a carboxy group, and the reactions are well known in the field of synthetic organic chemistry (examples of which are described in T. W. Greene et al., Protective Groups in Organic Synthesis, 2nd Edition, John Wiley & Sons, Inc. (1991)).

For example, the reaction can be carried out by Process 1 or Process 2 described below.

(Process 1)

A protected compound (2) is prepared by reacting compound (1) with an alkylating agent in a solvent under basic conditions.

The alkylating agent is a compound represented by the formula $Pg^1$—$Z^1$ (wherein, $Pg^1$ is as defined above, and $Z^1$ is a halogen atom or a leaving group) and, for example, can be a halide such as chloride, bromide or iodide; or a sulfonate such as methanesulfonate, trifluoromethanesulfonate or toluenesulfonate; and is preferably a halide.

The solvent to be used, for example, can be a hydrocarbon such as hexane, cyclohexane, benzene, toluene and the like; a halogenated hydrocarbon such as dichloromethane, dichloroethane and the like; a ketone such as acetone, 2-butanone and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably an amide (especially N,N-dimethylformamide).

The base to be used is not particularly limited provided that it is one that is usually used in the field of synthetic organic chemistry, and, for example, can be an alkali metal hydroxide such as sodium hydroxide, potassium hydroxide, lithium hydroxide and the like; an alkali metal carbonate such as sodium carbonate, potassium carbonate, cesium carbonate, sodium hydrogen carbonate and the like; an organic amine such as triethylamine, diisopropylethylamine, dicyclohexylamine, pyridine, lutidine, 4-(N,N-dimethylamino)pyridine, diazabicycloundecene, diazabicyclononene and the like; or an alkali metal alkoxide such as sodium methoxide and the like; and is preferably an alkali metal hydroxide (especially sodium hydroxide) or an alkali metal carbonate (especially sodium carbonate).

The reaction temperature is usually from 80° C. to 100° C.

The time required for the reaction varies mainly depending on the kind of protecting group, and is usually from 5 minutes to 3 hours (preferably from 15 minutes to 1 hour).

(Process 2)

The protected compound (2) can also be prepared by reacting compound (1) with a diazo compound in a solvent.

The diazo compound, for example, can be diazomethane, trimethylsilyldiazomethane or diphenyldiazomethane, and is preferably diphenyldiazomethane.

The solvent to be used, for example, can be a halogenated hydrocarbon such as dichloromethane, dichloroethane and the like; a ketone such as acetone, 2-butanone and the like; an ester such as ethyl acetate and the like; an alcohol such as methanol, ethanol and the like; or an ether such as diethyl ether, tetrahydrofuran, 1,4-dioxane, 1,2-dimethoxyethane and the like; and is preferably an ether (especially tetrahydrofuran).

The reaction temperature is usually from 0° C. to the boiling point of the solvent to be employed (preferably from 0° C. to room temperature).

The time required for the reaction varies mainly depending on the kind of diazo compound, and is usually from 0.5 hours to 24 hours (preferably from 0.5 hours to 6 hours).

After completion of the reaction, the compound (2) can be isolated from the reaction mixture by conventional methods. For example, it can be obtained by neutralizing the reaction mixture, adding an organic solvent which is not miscible with water to the reaction mixture or to the residue obtained after distilling off the solvent from the reaction mixture, washing the mixture with water, and then distilling off the solvent.

If necessary, the obtained compound (2) can be further purified by conventional methods, for example, recrystallization, reprecipitation, chromatography or the like.

(Step A-2)

Step A-2 is a step to prepare compound (3) by introducing a group $R^{\#}$ onto the alcoholic hydroxy group of compound (2), and the reaction can be carried out by using methods well known to those skilled in the art.

For example, when a $C_1$-$C_6$ alkanoyl group (said $C_1$-$C_6$ alkanoyl group may optionally be substituted with 1 to 3 same or different group(s) selected from the group consisting of Substituent group β) is introduced as the $R^{\#}$ group, the reaction can be carried out by reacting compound (2) with a reactive alkanoyl derivative in a solvent and usually in the presence of a base, or when a group of formula —C(O)—$NR^2R^3$ (wherein, $R^2$ and $R^3$ are as defined above) is introduced as the $R^{\#}$ group, the reaction can be carried out by reacting compound (2) with a reactive carbamoyl derivative in a solvent and usually in the presence of a base, or when a —P(=O) (OH)$_2$ group is introduced as the $R^{\#}$ group, the reaction can be carried out by reacting compound (2) with a reactive phosphoryl derivative in a solvent and usually in the presence of a base.

Here, the reactive alkanoyl derivative represents a compound of formula $Z^2$—$R^{\#\#}$ (wherein, $R^{\#\#}$ represents the $C_1$-$C_6$ alkanoyl group (said $C_1$-$C_6$ alkanoyl group may optionally be substituted with 1 to 3 same or different group(s) selected from the group consisting of Substituent group β) in the definition of $R^{\#}$, and $Z^2$ represents a leaving group. Said leaving group, for example, can be a halogen atom such as a chlorine atom or a bromine atom; a cyano group; an acyloxy group such as a group of formula $R^{\#\#\#}$—O— or a pivaloyloxy group; or a sulfonyloxy group such as a methanesulfonyloxy, a toluenesulfonyloxy or a trifluoromethanesulfonyloxy group); and the reactive alkanoyl derivative can be prepared from a carboxylic acid compound of formula H—O—$R^{\#\#}$ by methods well known in the art. For example, when $Z^2$ is a chlorine atom, the reactive alkanoyl derivative can be prepared by reacting the carboxylic acid compound of formula H—O—$R^{\#\#}$ with oxalyl chloride.

The reactive carbamoyl derivative represents a compound of formula $Z^{2'}$—C(O)—$NR^2R^3$ (wherein, $R^2$ and $R^3$ are as defined above, and $Z^{2'}$ represents a leaving group such as halogen atom) or an isocyanate compound of formula O=C=N—$R^2$ (wherein, $R^2$ is as defined above); and the reactive carbamoyl derivative can be prepared using an amine compound, such as a compound of formula $HNR^2R^3$ or formula $H_2NR^2$, by methods well known in the art. For example, a carbamoyl chloride compound Cl—C(O)—$NR^2R^3$ can be prepared by reacting an amine compound of formula $HNR^2R^3$ with phosgene in an aprotic solvent, and an isocyanate compound of formula O=C=N—$R^2$ can be prepared by reacting an amine compound of formula $H_2NR^2$ with phosgene in an aprotic solvent.

The reactive phosphoryl derivative represents a compound of formula $Z^3$—P(=O)(O$Pg^2$)(O$Pg^3$) (wherein, $pg_2$ and $Pg^3$ represent a protecting group, and, for example, can be a $C_1$-$C_6$ alkyl group such as a methyl, an ethyl, a propyl, an isopropyl, a butyl, a pentyl, a hexyl group and the like; a $C_2$-$C_6$ alkenyl group such as an allyl, a 2-methylallyl, a 2-butenyl, a 2-propenyl, a prenyl group and the like; a $C_6$-$C_{10}$ aryl group which may optionally be substituted with 1 to 3 substituent(s) selected from the group consisting of $C_1$-$C_6$ alkyl groups, $C_1$-$C_6$ alkoxy groups and halogen atoms such as a phenyl, a methoxyphenyl, a tolyl, a naphthyl group and the like; a $C_7$-$C_{11}$ aralkyl group (the aryl moiety may optionally be substituted with 1 to 3 substituent(s) selected from the group consisting of $C_1$-$C_6$ alkyl groups, $C_1$-$C_6$ alkoxy groups and halogen atoms) such as a benzyl, a methoxybenzyl, a naphthylmethyl group and the like; or $Pg^2$ and $Pg^3$ together form a $C_2$-$C_6$ alkylene group such as an ethylene, a trimethylene, a tetramethylene group and the like; and $Z^3$ represents a leaving group, and, for example, can be a halogen atom such as a chlorine or a bromine atom; a cyano group; an acyloxy group such as a pivaloyloxy group; or a sulfonyloxy group such as a methanesulfonyloxy, a toluenesulfonyloxy or a trifluoromethanesulfonyloxy group), and the reactive phosphoryl derivative can be prepared using an alcohol compound of formula H—O—$Pg^2$ or H—O—$Pg^3$ (when $Pg^2$ and $Pg^3$ together form a $C_2$-$C_6$ alkylene group, the compound is a dihydric alcohol compound of formula H—O—($C_2$-$C_6$ alkylene)-O—H) by methods well known to those skilled in the art.

The amount of the reactive alkanoyl derivative, the reactive carbamoyl derivative and the reactive phosphoryl derivative to be used for the reaction is usually an amount of 1 to 3 molar equivalents relative to the amount of the compound (2).

The solvent to be employed, for example, can be a hydrocarbon such as hexane, cyclohexane, benzene, toluene and the like; a halogenated hydrocarbon such as dichloromethane, chloroform, 1,2-dichloroethane and the like; an ether such as diethyl ether, tetrahydrofuran and the like; a heteroaromatic compound having nitrogen atom(s), such as pyridine, picoline, lutidine and the like; an ester such as ethyl acetate and the like; a ketone such as acetone, 2-butanone and the like; or an amide such as N,N-dimethylformamide and the like.

The base to be used, for example, can be an amine such as triethylamine, diisopropylethylamine, dicyclohexylamine and the like; or a heteroaromatic compound having nitrogen atom(s), such as pyridine, picoline, lutidine, 4-(N,N-dimethylamino)pyridine and the like.

The amount of base to be used is usually an amount of 1 to 5 molar equivalents relative to the amount of the compound (2), however when basic compounds such as pyridine, picoline, lutidine and the like are used as the solvent, it is not necessary to add a base.

The reaction temperature is usually from −10° C. to the boiling point of the solvent employed, preferably from 0° C. to room temperature.

The time required for the reaction varies mainly depending on the reaction temperature, and is usually from 0.5 hours to 24 hours, preferably from 1 hour to 5 hours.

Alternatively, in the case of introducing a —P(=O)(OH)$_2$ group as the $R^{\#}$ group, the esterication can also be carried out using a reactive phosphinyl derivative instead of the reactive phosphoryl derivative, then oxidation of the resulting trivalent phosphorous ester compound can be carried out by methods well known in the art.

The reactive phosphinyl derivative represents a compound of formula $Z^3\text{—}P(OPg^2)(OPg^3)$ (wherein, $Pg^2$ and $Pg^3$ are protecting groups as defined above, and $Z^3$ represents a leaving group as defined above), and the reactive phosphinyl derivative can be prepared using an alcohol compound of formula $H\text{—}O\text{—}Pg^2$ or $H\text{—}O\text{—}Pg^3$ (when $Pg^2$ and $Pg^3$ together form a $C_2$-$C_6$ alkylene group, the compound is a dihydric alcohol compound of formula $H\text{—}O\text{—}(C_2\text{-}C_6$ alkylene group)$\text{-}O\text{—}H$) by methods well known to those skilled in the art.

The oxidizing agent to be used in the oxidation reaction of the trivalent phosphorous ester compound to the compound (3) is not particularly limited provided that it is one that is usually used in the field of synthetic organic chemistry, and, for example, can be a halogen such as iodine; oxygen molecule; a peroxide such as cumene hydroperperoxide, t-butyl hydroperoxide and hydrogen peroxide; a peroxy acid such as peracetic acid, trifluoroperoxyacetic acid and m-chloroperoxybenzoic acid; a halogenic acid salt such as hypochlorous acid salt, chlorous acid salt, chloric acid salt and perchloric acid; and is preferably a peroxide (especially t-butyl hydroperoxide).

After completion of the esterification reaction, the compound (3) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (3) can be further purified by conventional methods, for example, recrystallization, reprecipitation, chromatography or the like.

(Step A-3)

Step A-3 is a step to prepare compound (4) by deprotecting the protecting group of compound (3), and the reaction can be carried out by using methods well known in the art (examples of which are described in T. W. Greene et al., Protective Groups in Organic Synthesis, 2nd Edition, John Wiley & Sons, Inc. (1991)).

For example, when $Pg^1$ in compound (3) is a methoxybenzyl or dimethoxybenzyl group, compound (4) can be prepared by treating the compound (3) with an acid in the presence or absence of a solvent.

The solvent to be employed, for example, can be a hydrocarbon such as hexane, cyclohexane, benzene and toluene; a halogenated hydrocarbon such as dichloromethane, chloroform and 1,2-dichloroethane; or an ether such as anisole; and is preferably a hydrocarbon (especially toluene).

The acid, for example, can be a mineral acid such as hydrochloric acid and sulfuric acid; a carboxylic acid such as trifluoroacetic acid; or a sulfonic acid such as trifluoromethanesulfonic acid; and is preferably a carboxylic acid (especially trifluoroacetic acid).

There is no particular restriction on the amount of acid to be used, and the amount varies depending on the kind of the acid used and the kind of the solvent used. For example, when trifluoroacetic acid is used as the acid, the amount of acid is usually from an amount of 5 molar equivalents relative to the amount of compound (3) up to an amount used as a solvent, preferably from one-tenth up to half of the amount used as a solvent.

The reaction temperature of the acid treatment varies mainly depending on the solvent used, and is usually from 0° C. to room temperature.

The time required for the reaction varies mainly depending on the kind of protecting group to be removed and the kind and amount of acid used, and when the protecting group is a methoxybenzyl group and the acid is trifluoroacetic acid and the amount of the acid is a quarter of the solvent used, the time is usually from 0.1 hours to 24 hours (preferably from 0.1 hours to 2 hours).

After completion of the reaction, the compound (4) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (4) can be further purified by conventional methods, for example, recrystallization, reprecipitation, chromatography or the like.

Alternatively, compound (4) can be prepared by introducing a group $R^\#$ directly onto the alcoholic hydroxy group of compound (1) without Step A-1 to Step A-3. In this case, preferably, compound (1) can be treated using similar reaction conditions to Step A-2.

The compound (4) can also be obtained according to Method G and Method H described hereinafter.

(Step A-4)

Step A-4 is a step to prepare compound (Ia) of the present invention by esterifying compound (4) with an alcohol compound (5). Compound (4) is converted to a reactive derivative thereof, then the derivative is reacted with the alcohol compound (5) in a solvent in the presence of a base by methods well known in the art.

Here, the reactive derivative of compound (4) represents a compound of formula $Z^4\text{—}C(\!=\!O)\text{—}L^1\text{—}O\text{—}R^\#$, and it is prepared by methods well known in the art using a compound (4) of formula $HO\text{—}C(\!=\!O)\text{—}L^1\text{—}O\text{—}R^\#$. $R^\#$ and $L^1$ are as defined above and $Z^4$ represents a halogen atom or a leaving group.

The amount of the reactive derivative to be used is usually an amount of 1 to 3 molar equivalents relative to the amount of the alcohol compound (5).

The alcohol compound (5) is either a known compound or it can be easily prepared using similar methods for the preparation of known compounds.

The procedures are as follows.

For example, compounds wherein X represents general formula (III) can be synthesized according to the methods described in Japanese Patent Application Publication Number Hei 8-333350, Japanese Patent Application Publication Number Hei 10-279567, Japanese Patent Application Publication Number Hei 11-80135 and Japanese Patent Application Publication Number 2001-342187.

Particularly, compounds wherein X represents general formula (III), $Ar^2$ represents a phenyl group which may optionally be substituted with 1 to 5 same or different group(s) selected from the group consisting of Substituent group γ or a monocyclic heteroaryl group which may optionally be substituted with 1 to 5 same or different group(s) selected from the group consisting of Substituent group γ, E represents a group of formula $\text{—}S(O)_{n1}\text{—}$ (wherein, n1 is an integer from 0 to 2), $R^4$ represents a $C_1$-$C_4$ alkyl group, $R^5$ represents a hydrogen atom or a $C_1$-$C_4$ alkyl group, and G represents a group of formula (Ga') can be synthesized according to the methods described in Japanese Patent Application Publication Number Hei 8-333350.

Compounds wherein X represents general formula (III), E represents a methylene group, A¹ represents a group selected from

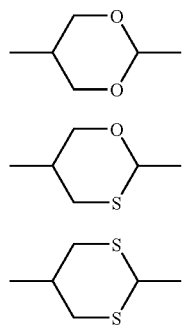

(B1)

(B2)

(B3)

and G represents a group of formula (Ga") can be synthesized according to the methods described in Japanese Patent Application Publication Number Hei 11-80135.

Compounds wherein X represents general formula (III), $Ar^2$ represents a naphthyl group which may optionally be substituted with 1 to 5 same or different group(s) selected from the group consisting of Substituent group γ or a fused bicyclic heteroaryl group which may optionally be substituted with 1 to 5 same or different group(s) selected from the group consisting of Substituent group γ, E represents a group of formula —S(O)$_{n1}$— (wherein, n1 is an integer from 0 to 2), $R^4$ represents a $C_1$-$C_6$ alkyl group, $R^5$ represents a hydrogen atom, and G represents a group of formula (Ga') can be synthesized according to the methods described in Japanese Patent Application Publication Number Hei 10-279567.

Compounds wherein X represents general formula (III), $Ar^2$ represents a phenyl group which may optionally be substituted with 1 to 5 same or different group(s) selected from the group consisting of Substituent group γ or a naphthyl group which may optionally be substituted with 1 to 5 same or different group(s) selected from the group consisting of Substituent group γ, E represents a methylene group or a sulfur atom, $R^5$ represents a hydrogen atom, and G represents a group of formula (Gb) can be synthesized according to the methods described in Japanese Patent Application Publication Number 2001-342187.

Compounds wherein X represents general formula (VI) can be synthesized according to the methods described in Japanese Patent Application Number Sho 62-12766.

Compounds wherein X represents general formula (VII) can be synthesized according to the methods described in Japanese Patent Application Publication Number Hei 8-53426.

Compounds wherein X represents general formula (VIII) can be synthesized according to the methods described in WO 99/45008.

Compounds wherein X represents general formula (IX) can be synthesized according to the methods described in Japanese Patent Number 2625584.

Compounds wherein X represents general formula (X) can be synthesized according to the methods described in Japanese Patent Application Publication Number Hei 9-183769.

Compounds wherein X represents general formula (XI) can be synthesized according to the methods described in Japanese Patent Application Publication Number Hei 11-240871.

Compounds wherein X represents general formula (XII) can be synthesized according to the methods described in WO 98/31675.

Compounds wherein X represents general formula (XIII) can be synthesized according to the methods described in WO 97/05130.

Compounds can also be synthesized according to the methods described in Japanese Patent Number 3050982, WO 95/25107, WO 00/27852, WO 01/66551 and WO 01/79196.

The base to be used for the esterification is not particularly limited provided that it can remove an alcoholic active proton from the alcohol compound (5), and for example, can be an organic amine such as triethylamine and the like; an aromatic compound having nitrogen atom(s), such as pyridine and the like; an alkali metal hydride such as lithium hydride, sodium hydride, potassium hydride and the like; an organolithium compound such as butyllithium, phenyllithium and the like; and is preferably a metal hydride (especially sodium hydride).

The amount of base to be used is usually an amount of 0.9 to 3.5 molar equivalents relative to the amount of the compound (5), and is preferably an amount of 1 to 2 molar equivalents relative to the amount of the compound (5).

There is no particular restriction on the nature of the solvent to be employed, provided that it has no adverse effect on the reaction and that it can dissolve the starting materials at least to some extent. Examples of suitable solvents which can be used include: an ether such as tetrahydrofuran, dioxane and dimethoxyethane; a hydrocarbon such as hexane, cyclohexane, benzene and toluene; a sulfoxide such as dimethyl sulfoxide; an amide such as N,N-dimethylformamide and hexamethylphosphoroamide; an urea such as 1,3-dimethyl-2-imidazolidinone; preferably an ether (particularly tetrahydrofuran) and an amide (particularly N,N-dimethylformamide).

The reaction temperature of the condensation reaction varies mainly depending on the kind of reagents used, and is usually from −78° C. to room temperature, preferably from 0° C. to room temperature.

The time required for the reaction varies mainly depending on the reaction temperature and solvent used, and is usually from 30 minutes to 24 hours, preferably from 30 minutes to 5 hours.

After completion of the reaction, the compound (Ia) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (Ia) can be further purified by conventional methods, for example, recrystallization, reprecipitation, chromatography or the like.

Further, $Pg^2$ and $Pg^3$, which are the protecting groups for the phosphoryl group, can be removed at a suitable time after completion of from Step A-2 to Step A-4. The reaction to remove the protecting groups from the compound varies depending on the kind of the protecting groups used, and can be carried out by the methods well known in the art. For example, when $Pg^2$ and $Pg^3$ are allyl groups, the reaction can be carried out by using a nucleophilic (reducing) reagent and a metal catalyst in an inert solvent.

The inert solvent to be employed, for example, can be water; an alcohol such as methanol, ethanol and the like; a hydrocarbon such as hexane and toluene; a halogenated hydrocarbon such as dichloromethane; a nitrile such as acetonitrile; an amide such as N,N-dimethylformamide; or an ether such as tetrahydrofuran; and is preferably an ether (particularly tetrahydrofuran), a halogenated hydrocarbon (particularly dichloromethane) or water. Alternatively, an amine used as the nucleophilic reagent can also be used as the solvent.

The nucleophilic (reducing) reagent, for example, can be an amine such as pyrrolidine and morpholine; a formic acid salt such as sodium formate; a carboxylic acid salt such as potassium 2-ethylhexanoate; a 1,3-dicarbonyl compound such as acetylacetone and dimedone; or a tin hydride such as tributyltin hydride; and is preferably pyrrolidine or tributyltin hydride.

The amount of the nucleophilic (reducing) reagent to be used is usually an amount of 1 to 1000 molar equivalents relative to the amount of the starting material. Preferably, when an amine such as pyrrolidine and the like is used as the nucleophilic (reducing) reagent, the amount of the nucleophilic (reducing) reagent is an amount of 1 to 5 molar equivalents for one protecting group of the starting material (when the starting material is a diallyl phosphoric ester compound, the amount of the nucleophilic (reducing) reagent is an amount of 2 to 10 molar equivalents), and when a tin hydride such as tributyltin hydride and the like is used as the nucleophilic (reducing) reagent, the amount of the nucleophilic (reducing) reagent is an amount of 1 to 3 molar equivalents for one protecting group of the starting material (when the starting material is a diallyl phosphoric ester compound, the amount of the nucleophilic (reducing) reagent is an amount of 2 to 6 molar equivalents).

The metal catalyst, for example, can be a palladium complex such as tetrakis(triphenylphosphine)palladium(O) and dichlorobis(triphenylphosphine)palladium(II) and the like.

The amount of the metal catalyst to be used is usually an amount of 0.0001 to 1 molar equivalents relative to the amount of the starting material, preferably an amount of 0.001 to 0.05 molar equivalents relative to the amount of the starting material.

To the reaction mixture, phosphine compounds such as triphenylphosphine and the like may be added. The maximum amount of the phosphine compound to be used is usually an amount of 5 molar equivalents relative to the amount of the metal catalyst.

The reaction temperature is usually from −20° C. to 60° C. (preferably from 0° C. to room temperature).

The time required for the reaction varies mainly depending on the reaction temperature and the kind of deprotecting agent, and is usually from 1 minute to 6 hours (preferably from 10 minutes to 2 hours).

[Method B]

Method B is a method to prepare compounds (Ib) [compounds (Ib) are compounds of general formula (I) of the present invention wherein $L^a$ represents a single bond, a $C_6$-$C_{10}$ aryl group which may optionally be substituted with 1 to 3 same or different group(s) selected from the group consisting of Substituent group α, a heterocyclic group which may optionally be substituted with 1 to 3 same or different group(s) selected from the group consisting of Substituent group α, or a $C_3$-$C_7$ cycloalkyl group which may optionally be substituted with 1 to 3 same or different group(s) selected from the group consisting of Substituent group α, and R represents a hydrogen atom], and the reaction scheme is shown below.

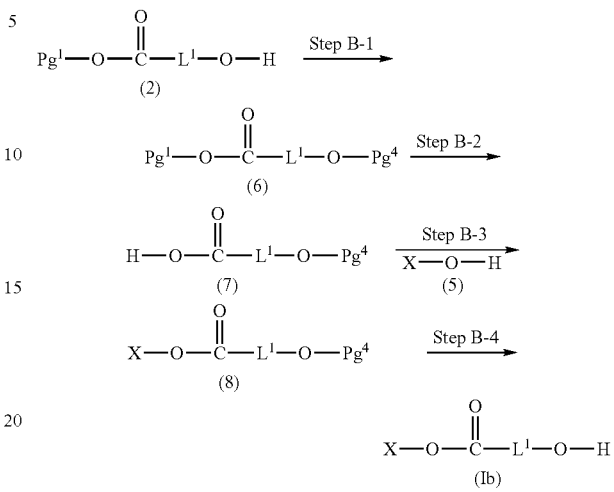

In the above reaction scheme, X, $L^1$ and $Pg^1$ are as defined above, and $Pg^4$ is a hydroxy protecting group.

Here, the protecting group $Pg^4$ is one which is conventionally used in organic synthesis for the protection of alcohols (examples of which are described in T. W. Greene et al., Protective Groups in Organic Synthesis, 2nd Edition, John Wiley & Sons, Inc. (1991)).

There is no particular restriction on the nature of this protecting group, provided that when the protecting group $Pg^1$ of compound (6) is removed in Step B-2, the protecting group $Pg^4$ is not removed, and when the carboxy group of compound (7) is esterified in Step B-3, the protecting group $Pg^4$ is not removed, but when the protecting group $Pg^4$ of compound (8) is removed in Step B-4, the deprotection can be carried out with no adverse effect on the compound (8). The protecting group, for example, can be a $C_1$-$C_6$ alkanoyl group which may optionally be substituted with 1 to 3 halogen atom(s) such as formyl, acetyl, chloroacetyl, dichloroacetyl, trichloroacetyl, fluoroacetyl, difluoroacetyl, trifluoroacetyl, propionyl, butyryl, isobutyryl, valeryl, pivaloyl, hexanoyl group and the like; a ($C_6$-$C_{10}$ aryl)carbonyl group which may optionally be substituted with 1 to 3 group(s) selected independently from $C_1$-$C_6$ alkyl groups, $C_1$-$C_6$ alkoxy groups and halogen atoms, such as benzoyl, chlorobenzoyl, methoxybenzoyl, dimethoxybenzoyl, methylbenzoyl, naphthoyl group and the like; a silyl group which is substituted with 3 groups selected independently from $C_1$-$C_6$ alkyl groups and phenyl groups, such as trimethylsilyl, triethylsilyl, triisopropylsilyl, t-butyldimethylsilyl, t-butyldiphenylsilyl group and the like; a $C_2$-$C_7$ alkoxycarbonyl group or a $C_3$-$C_7$ alkenyloxycarbonyl group which may optionally be substituted with 1 to 3 halogen atom(s), such as methoxycarbonyl, ethoxycarbonyl, trichloroethoxycarbonyl, propoxycarbonyl, allyloxycarbonyl, butoxycarbonyl, t-butoxycarbonyl, pentoxycarbonyl, hexyloxycarbonyl and the like; or a ($C_7$-$C_{11}$ aralkyl)oxycarbonyl group which may optionally be substituted with 1 to 3 group(s) selected independently from $C_1$-$C_6$ alkoxy groups and halogen atoms, such as benzyloxycarbonyl, methoxybenzyloxycarbonyl, dimethoxybenzyloxycarbonyl, chlorobenzyloxycarbonyl, naphthylmethyloxycarbonyl group and the like; and is preferably a $C_3$-$C_7$ alkenyloxycarbonyl group (particularly an allyloxycarbonyl group) or a silyl group which is substituted with 3 groups selected independently from $C_1$-$C_6$ alkyl groups and phenyl groups (particularly a t-butyldiphenylsilyl group).

The method is first to prepare compound (6) by protecting the hydroxy group of compound (2) which is a synthetic intermediate in Method A with $Pg^4$ (in Step B-1), then, to prepare compound (7) by removing the carboxyl protecting group $Pg^1$ selectively from compound (6)(in Step B-2), then, to prepare compound (8) by esterifying the carboxylic acid compound (7) with the alcohol compound (5) (in Step B-3), and finally to prepare compound (Ib) by deprotecting the alcohol protecting group $Pg^4$ (in Step B-4).

Each step is described in detail as follows.

(Step B-1)

Step B-1 is a step to prepare compound (6) by protecting the alcoholic hydroxy group of compound (2) which is a synthetic intermediate in Method A.

This step can be accomplished by protection reactions for an alcohol, and the reactions are well known in the field of synthetic organic chemistry (examples of which are described in T. W. Greene et al., Protective Groups in Organic Synthesis, 3rd Edition, John Wiley & Sons, Inc. (1999)).

For example, protected compound (6) is prepared by reacting compound (2) with a protecting agent in a solvent under basic conditions.

The protecting agent is a compound represented by the formula $Z^5$-$Pg^4$ (wherein, $Pg^4$ is as defined above, and $Z^5$ represents a halogen atom or a leaving group), and, for example, can be a halide such as chloride, bromide, iodide and the like; or a sulfonate such as methanesulfonate, trifluoromethanesulfonate, toluenesulfonate and the like; and is preferably a halide.

The solvent to be used, for example, can be a hydrocarbon such as hexane, cyclohexane, benzene, toluene and the like; a halogenated hydrocarbon such as dichloromethane, dichloroethane and the like; a ketone such as acetone, 2-butanone and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably an amide (particularly N,N-dimethylformamide), an ether (particularly tetrahydrofuran) or a halogenated hydrocarbon (particularly dichloromethane).

The base to be used is not particularly limited provided that it is one that is usually used in the field of synthetic organic chemistry, and examples thereof include alkali metal carbonates such as sodium carbonate, potassium carbonate, cesium carbonate, sodium hydrogen carbonate and the like; organic bases such as triethylamine, diisopropylethylamine, dicyclohexylamine, pyridine, lutidine, 4-(N,N-dimethylamino)pyridine, diazabicycloundecene, diazabicyclononene, imidazole and the like; and alkali metal alkoxides such as sodium methoxide and the like; preferably organic bases (particularly 4-(N,N-dimethylamino)pyridine and imidazole).

The reaction temperature is usually from 0° C. to the boiling point of the solvent (preferably from 0° C. to room temperature) The time required for the reaction varies mainly depending on the kind of protecting group, and is usually from 0.5 hours to 24 hours (preferably from 0.5 hours to 6 hours).

After completion of the reaction, the compound (6) can be isolated from the reaction mixture by conventional methods. For example, it can be obtained by neutralizing the reaction mixture, adding an organic solvent which is not miscible with water to the reaction mixture or to the residue obtained after distilling off the solvent from the reaction mixture, washing the mixture with water, and then distilling off the solvent.

If necessary, the obtained compound (6) can be further purified by conventional methods, for example, recrystallization, reprecipitation, chromatography or the like.

(Step B-2)

Step B-2 is a step to prepare carboxylic acid compound (7) by removing the protecting group $Pg^1$ from the compound (6), and this Step can be carried out in a manner similar to the reactions described in Step A-3.

Alternatively, compound (7) can be prepared directly by protecting the hydroxy group of compound (1) with a protecting group $Pg^4$ without Step A-1, Step B-1 and Step B-2. In this case, preferably compound (1) can be treated in a reaction similar to that described in Step B-1.

Compound (7) can also be obtained according to Method G and Method H described hereinafter.

(Step B-3)

Step B-3 is a step to prepare compound (8) by esterifying carboxylic acid compound (7) with the alcohol compound (5), and the reaction can be carried out according to a procedure similar to that described in Step A-4.

(Step B-4)

Step B-4 is a step to prepare compound (Ib) by removing the hydroxyl protecting group $Pg^4$ of compound (8).

This step can be accomplished by deprotection reactions for an alcohol, according to reactions well known in the field of synthetic organic chemistry (examples of which are described in T. W. Greene et al., Protective Groups in Organic Synthesis, 2nd Edition, John Wiley & Sons, Inc. (1999)).

For example, when the protecting group $Pg^4$ is an allyloxycarbonyl group, the reaction can be carried out by using a nucleophilic (reducing) reagent and a metal catalyst in an inert solvent.

The inert solvent, for example, can be water; an alcohol such as methanol, ethanol and the like; a hydrocarbon such as hexane and toluene; a halogenated hydrocarbon such as dichloromethane; a nitrile such as acetonitrile; an amide such as N,N-dimethylformamide; or an ether such as tetrahydrofuran; and is preferably an ether (particularly tetrahydrofuran) or a halogenated hydrocarbon (particularly dichloromethane).

The nucleophilic (reducing) reagent, for example, can be an amine such as pyrrolidine and morpholine; a formic acid salt such as sodium formate; a carboxylic acid salt such as potassium 2-ethylhexanoate; a 1,3-dicarbonyl compound such as acetylacetone and dimedone; or a tin hydride such as tributyltin hydride; and is preferably pyrrolidine or tributyltin hydride.

The amount of the nucleophilic (reducing) reagent to be used is usually an amount of 1 to 1000 molar equivalents relative to the amount of the compound (8), preferably an amount of 1 to 3 molar equivalents relative to the amount of the compound (8).

The metal catalyst, for example, can be a palladium complex such as tetrakis(triphenylphosphine)palladium(O) and dichlorobis(triphenylphosphine)palladium(II) and the like. The amount of the metal catalyst to be used is usually an amount of 0.0001 to 1 molar equivalents relative to the amount of the compound (8), preferably an amount of 0.001 to 0.05 molar equivalents relative to the amount of the compound (8).

To the reaction mixture, phosphine compounds such as triphenylphosphine and the like may be added. The maximum amount of the phosphine compound to be used is usually an amount of 5 molar equivalents relative to the amount of the metal catalyst.

The reaction temperature for the removal of the allyloxycarbonyl group is usually from −20° C. to 60° C. (preferably from 0° C. to room temperature). The time required for the reaction varies mainly depending on the reaction temperature and the kind of deprotecting agent, and is usually from 1 minute to 6 hours (preferably from 10 minutes to 2 hours).

Alternatively, for example, when the protecting group Pg is a silyl group which is substituted with 3 groups selected independently from $C_1$-$C_6$ alkyl groups and phenyl groups, such as a t-butyldiphenylsilyl group, the deprotecting reaction can be carried out by reacting compound (8) with a fluoride salt in a solvent.

The solvent to be used, for example, can be water; a hydrocarbon such as hexane, cyclohexane, benzene, toluene and the like; a halogenated hydrocarbon such as dichloromethane, dichloroethane and the like; an alcohol such as methanol, ethanol, t-butyl alcohol and the like; a ketone such as acetone, 2-butanone and the like; an ester such as ethyl acetate and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably a hydrocarbon, a halogenated hydrocarbon or an ether, more preferably an ether (particularly tetrahydrofuran).

The fluoride salt, for example, can be an alkali metal fluoride such as potassium fluoride and the like; or an organic ammonium fluoride such as tetrabutylammonium fluoride and the like.

The reaction may be carried out adjusting the reaction mixture to neutral by the addition of an acid such as acetic acid and the like.

The reaction temperature of desilylation is usually from 0° C. to room temperature.

The time required in the reaction for desilylation is usually from 1 hour to 4 hours.

After completion of the removal reaction of the protecting group $Pg^4$, the desired compound (Ib) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (6) can be further purified by conventional methods, for example, recrystallization, reprecipitation, chromatography or the like.

[Method C]

Method C is a method to prepare compounds (Ic) [compounds (Ic) are compounds of general formula (I) of the present invention wherein $L^a$ represents an oxygen atom, R represents a $C_1$-$C_6$ alkanoyl group which may optionally be substituted with 1 to 3 same or different group(s) selected from the group consisting of Substituent group β, a group of formula —C(O)—$NR^2R^3$ (wherein, $R^2$ and $R^3$ independently represent a hydrogen atom or a $C_1$-$C_6$ alkyl group, or $R^2$ and $R^3$, together with the nitrogen atom to which they are attached, form a 4- to 7-membered heterocyclic group containing nitrogen atom(s)) or a —P(=O)$(OH)_2$ group], and the reaction scheme is shown below.

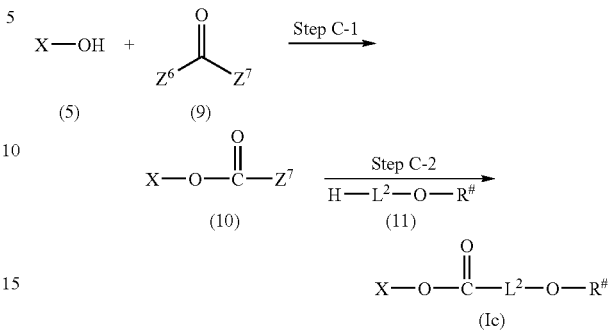

In the above reaction scheme, X and $R^\#$ are as defined above, $L^2$ has the same meaning as defined for L (provided that $L^a$ is an oxygen atom), and $Z^6$ and $Z^7$ independently represent a halogen atom or a leaving group. Examples of the leaving group include a halogen atom such as chlorine or bromine atom; a $C_1$-$C_6$ alkoxy group which may optionally be substituted with halogen atom(s) such as trichloromethoxy group; a $C_6$-$C_{10}$ aryloxy group such as phenoxy group; and a 5- to 7-membered heteroaryl group containing 1 to 4 nitrogen atom(s) such as imidazolyl, triazolyl or tetrazolyl group.

The method is first to prepare a reactive carbonate compound (10) by reacting alcohol compound (5) with compound (9) (in Step C-1), then, to prepare compound (Ic) by esterification of compound (10) with alcohol compound (11) (in Step C-2).

The compound (9) is a compound generally known as a "phosgene equivalent" in the art of synthetic organic chemistry, such as phosgene, trichloromethyl chloroformate, bis(trichloromethyl)carbonate, 1,1'-carbonyldiimidazole, phenyl chloroformate, and commercially available compounds can be used, of which 1,1'-carbonyldiimidazole is preferred.

The alcohol compound (11) can be prepared according to Method I.

(Step C-1)

Step C-1 is a step to prepare a reactive carbonate compound (10) by reacting alcohol compound (5) with compound (9) in an inert solvent and usually in the presence of a base.

There is no particular restriction on the nature of the inert solvent to be employed, provided that it has no adverse effect on the reaction and that it can dissolve the starting materials at least to some extent.

The solvent to be used, for example, can be a halogenated hydrocarbon such as dichloromethane; an ether such as tetrahydrofuran, dioxane and dimethoxyethane; a hydrocarbon such as hexane, cyclohexane, benzene and toluene; a sulfoxide such as dimethyl sulfoxide; or an amide such as N,N-dimethylformamide and hexamethylphosphoramide; and is preferably a halogenated hydrocarbon (particularly dichloromethane), an ether (particularly tetrahydrofuran) or an amide (particularly N,N-dimethylformamide).

The base to be used is not particularly limited provided that it can remove an alcoholic active proton from the alcohol compound (5), and, for example, can be an organic amine such as triethylamine and the like; an aromatic compound having nitrogen atom(s) such as pyridine and the like; an alkali metal hydride such as lithium hydride, sodium hydride, potassium hydride and the like; an organolithium compound such as butyllithium, phenyllithium and the like; or an alkali metal alkoxide such as potassium t-butoxide; and is preferably a metal hydride (particularly sodium hydride) or an alkali metal alkoxide (particularly potassium t-butoxide).

The amount of the base to be used is usually an amount of 0.01 to 5 molar equivalents relative to the amount of the compound (5), preferably an amount of 0.01 to 3 molar equivalents relative to the amount of the compound (5).

The reaction temperature varies mainly depending on the kind of compound (9) used, and is usually from −78° C. to 50° C., preferably from 0° C. to 40° C.

The time required for the reaction varies mainly depending on the reaction temperature and the kind of compound (9) used, and is usually from 30 minutes to 24 hours, preferably from 1 hour to 5 hours.

After completion of Step C-1, the reactive carbonate compound (10) can be used for the following Step C-2 without isolation. Namely, Step C-2 can be carried out by adding the alcohol compound (11) to the reaction mixture.

If necessary, the reactive carbonate compound (10) thus obtained can be isolated by conventional methods, for example, solvent extraction, recrystallization, reprecipitation, chromatography or the like.

(Step C-2)

Step C-2 is a step to prepare compound (Ic) by esterification of a reactive carbonate compound (10) with compound (11) in an inert solvent and usually in the presence of a base.

The kind of solvent and base to be employed in the reaction is the same kind of solvent and base as used in Step C-1. The amount of base to be used is the same amount of base as used in Step C-1.

The reaction temperature in Step C-2 varies mainly depending on the kind of compound (11) used, and is usually from −78° C. to the boiling point of the solvent employed, preferably from 0° C. to 40° C.

The time required for the reaction in Step C-2 varies mainly depending on the reaction temperature and the kind of compound (11) used, and is usually from 10 minutes to 24 hours, preferably from 10 minutes to 1 hour.

Alternatively, the Method can be carried out by changing the order of the reaction of the alcohol compound (5) and the reaction of the alcohol compound (11) with compound (9).

Namely, the Method can be accomplished by reacting the alcohol compound (11) with compound (9) in an inert solvent and usually in the presence of a base, followed by addition of the alcohol compound (5).

After completion of the reaction, the compound (Ic) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (Ic) can be further purified by conventional methods, for example, recrystallization, reprecipitation, chromatography or the like.

[Method D]

Method D is a method to prepare compounds (Id) [compounds (Id) are compounds of general formula (I) of the present invention wherein $L^a$ represents an oxygen atom, and R represents a hydrogen atom], and the reaction scheme is shown below.

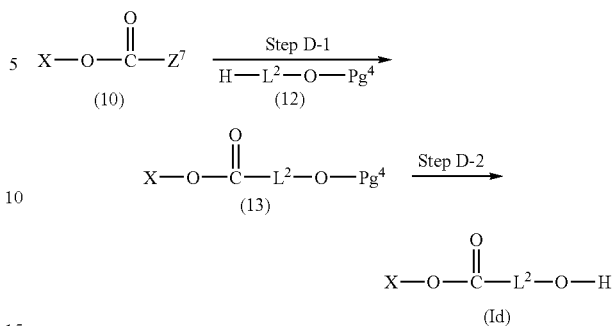

In the above reaction scheme, X, $Z^7$, $Pg^4$ and $L^2$ are as defined above.

The method is first to prepare compound (13) by esterification of the synthetic intermediate compound (10) in Method C with alcohol compound (12) (in Step D-1), then, to prepare compound (Id) by deprotecting the hydroxyl protecting group $Pg^4$ of compound (13) (in Step D-2)

(Step D-1)

Step D-1 is a step to prepare compound (13) by esterification of compound (10) with alcohol compound (12). This Step can be carried out in a manner similar to the reaction described in Step C-2. The compound (12) can also be prepared according to Method I described hereinafter.

Alternatively, compound (13) can be obtained by changing the order of the reaction of the alcohol compound (5) and the reaction of the alcohol compound (12) with compound (9), in a similar manner as described in Method C.

Namely, the Method can be accomplished by reacting the alcohol compound (12) with compound (9) in an inert solvent and usually in the presence of a base, followed by addition of the alcohol compound (5).

(Step D-2)

Step D-2 can be accomplished by deprotection reactions for an alcohol, and the reactions are well known in the field of synthetic organic chemistry (examples of which are described in T. W. Greene et al., Protective Groups in Organic Synthesis, 3rd Edition, John Wiley & Sons, Inc. (1999)).

The reaction can be carried out in a manner similar to the reactions described in Step B-4 as described hereinbefore.

[Method E]

Method E is a method to prepare compounds (If) [compounds (If) are compounds of general formula (I) of the present invention wherein R represents a $C_1$-$C_6$ alkanoyl group which may optionally be substituted with 1 to 3 same or different group(s) selected from the group consisting of Substituent group β, a group of formula —C(=O)—$NR^2R^3$ (wherein, $R^2$ and $R^3$ independently represent a hydrogen atom or a $C_1$-$C_6$ alkyl group, or $R^2$ and $R^3$, together with the nitrogen atom to which they are attached, form a 4- to 7-membered heterocyclic group containing nitrogen atom(s)) or a —P(=O) $(OH)_2$ group], and the reaction scheme is shown below.

83

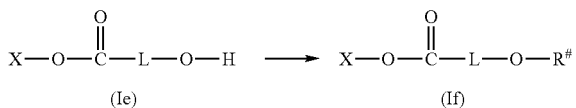

In the above reaction scheme, X, L and R# have the same meaning as defined above.

The starting compound (Ie) is a compound of general formula (I) of the present invention wherein R represents a hydrogen atom, namely this is compound (Ib) or compound (Id) and it can be obtained according to Method B or Method D as described above.

This method can be accomplished by esterification, carbamoylation or phosphorylation of compound (Ie) using procedures well known to those skilled in the art.

For example, this method can be accomplished in a manner similar to the reactions described in Step A-2, by reacting the compound (Ie) with a reactive alkanoyl derivative, a reactive carbamoyl derivative or a reactive phosphoryl derivative in a solvent and usually in the presence of a base.

After completion of the reaction, the compound (If) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (If) can be further purified by conventional methods, for example, recrystallization, reprecipitation, chromatography or the like.

[Method F]

Method F is a method to prepare hydroxycarboxylic acid compounds (1) or salts thereof which are starting materials in Method A, and the reaction scheme is shown below.

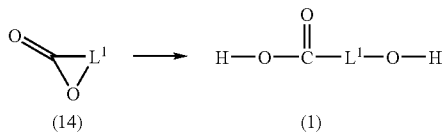

In the above reaction scheme, $L^1$ is as defined above.

The lactone compound (14) which is the starting material is commercially available, or it can be prepared by procedures well known to those skilled in the art or by known methods.

For example, said compound (14) can be prepared by subjecting the corresponding cyclic ketone to a Baeyer-Villiger reaction (see Matsumoto et al., Heterocycles, 24, 2443-2447 (1986)), the corresponding cyclic ether to an oxidation reaction (see H. Firouzabadi et al., Synthesis, 4, 285-288 (1986)), the corresponding cyclic anhydride to a reduction reaction (see D. M. Bailey et al., J. Org. Chem., 35, 3574-3576 (1970)), and similar methods.

This method can be accomplished by procedures well known to those skilled in the art. For example, the hydroxycarboxylic acid compound (1) or salt thereof can be prepared by reacting the lactone compound (14) with a basic compound in a solvent.

84

The salt of compound (1) is a metal salt where said metal is in the basic compound used, and examples include alkali metal salts such as sodium salts and potassium salts.

There is no particular restriction on the nature of the solvent to be employed, provided that it has no adverse effect on the reaction and that it can dissolve the starting material and the basic compound at least to some extent. The solvent to be used, for example, can be water; an alcohol such as methanol and ethanol; an ether such as tetrahydrofuran, dioxane and dimethoxyethane; a hydrocarbon such as hexane, cyclohexane, benzene and toluene; a sulfoxide such as dimethyl sulfoxide; a ketone such as acetone and 2-butanone; or a mixture thereof; and is preferably a mixture of water and an alcohol (particularly methanol) or a mixture of water and an ether (particularly tetrahydrofuran).

The basic compound to be used is not particularly limited provided that it is one that shows alkaline when added to the reaction mixture, and, for example, can be an alkali metal hydroxide such as lithium hydroxide, sodium hydroxide and potassium hydroxide; an alkaline earth metal hydroxide such as calcium hydroxide and barium hydroxide; an alkali metal carbonate such as lithium carbonate, sodium carbonate and potassium carbonate; an alkali metal alkoxide such as sodium methoxide and potassium t-butoxide; a metal thiolate such as sodium methanethiolate; or an alkali metal cyanide such as sodium cyanide and potassium cyanide; and is preferably an alkali metal hydroxide (particularly sodium hydroxide). The amount of the basic compound to be used is an amount of 1 to 5 molar equivalents relative to the amount of the starting material, preferably an amount of 1 to 1.5 molar equivalents relative to the amount of the starting material.

The reaction temperature varies depending on the kind and amount of basic compound used, and is usually from −10° C. to 70° C. (preferably from 0° C. to 50° C.)

The time required for the reaction varies depending on the kind and amount of basic compound used and the reaction temperature, and is usually from 0.3 hours to 24 hours, (preferably from 0.5 hours to 3 hours).

After completion of the reaction, the compound (1) or a salt thereof can be isolated from the reaction mixture by conventional methods. For example, the salt of compound (1) can be obtained by adding an organic solvent which is not miscible with water to the reaction mixture, separating the aqueous layer, and then distilling off the solvent. On the other hand, the compound (1) can be obtained by neutralizing the reaction mixture, adding an organic solvent which is not miscible with water, separating the aqueous layer, and then distilling off the solvent.

If necessary, the obtained compound (1) or salt thereof can be further purified by conventional methods, for example recrystallization, reprecipitation, chromatography or the like.

[Method G]

This method is an alternative method to prepare the intermediate compound (4) in Method A, and the reaction scheme is shown below.

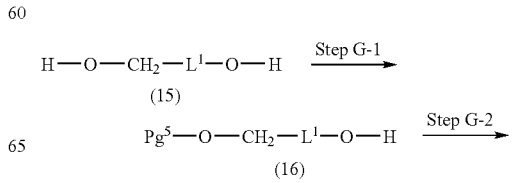

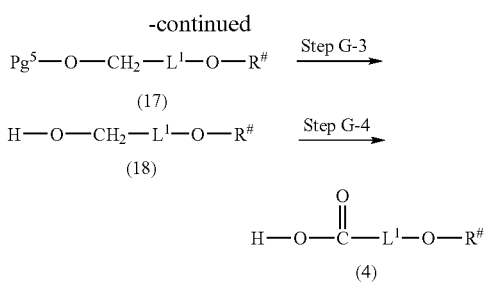

In the above reaction scheme, $L^1$ and $R^\#$ are as defined above, and $Pg^5$ represents a hydroxyl protecting group.

The protecting group $Pg^5$ is one which is conventionally used in organic synthesis for the protection of alcohols (examples of which are described in T. W. Greene et al., Protective Groups in Organic Synthesis, 3rd Edition, John Wiley & Sons, Inc. (1999)). There is no particular restriction on the nature of this protecting group, provided that when said protecting group is removed from compound (17) in Step G-3, the deprotection can be carried out with no adverse effect on the other parts of compound (17). Examples of the protecting group include: a 5- to 7-membered heterocyclyl group containing one oxygen atom, such as tetrahydropyranyl, oxolanyl group and the like; a ($C_1$-$C_6$ alkoxy)methyl group such as methoxymethyl group and the like; a ($C_6$-$C_{10}$ aryl)methyl group which may optionally be substituted with 1 to 3 group(s) selected independently from $C_1$-$C_6$ alkyl groups, $C_1$-$C_6$ alkoxy groups and halogen atoms, such as benzyl, methoxybenzyl, dimethoxybenzyl, chlorobenzyl, methylbenzyl group and the like; a $C_1$-$C_6$ alkanoyl group which may optionally be substituted with 1 to 3 halogen atom(s), such as formyl, acetyl, chloroacetyl, dichloroacetyl, trichloroacetyl, fluoroacetyl, difluoroacetyl, trifluoroacetyl, propionyl, butyryl, isobutyryl, valeryl, pivaloyl, hexanoyl group and the like; a ($C_6$-$C_{10}$ aryl)carbonyl group which may optionally be substituted with 1 to 3 group(s) selected independently from $C_1$-$C_6$ alkyl groups, $C_1$-$C_6$ alkoxy groups and halogen atoms, such as benzoyl, chlorobenzoyl, methoxybenzoyl, dimethoxybenzoyl, methylbenzoyl, naphthoyl group and the like; a silyl group which is substituted with 3 groups selected independently from $C_1$-$C_6$ alkyl groups and phenyl groups, such as trimethylsilyl, triethylsilyl, triisopropylsilyl, t-butyldimethylsilyl, t-butyldiphenylsilyl group and the like; a $C_2$-$C_7$ alkoxycarbonyl group or a $C_3$-$C_7$ alkenyloxycarbonyl group which may optionally be substituted with 1 to 3 halogen atom(s), such as methoxycarbonyl, ethoxycarbonyl, trichloroethoxycarbonyl, propoxycarbonyl, allyloxycarbonyl, butoxycarbonyl, t-butoxycarbonyl, pentoxycarbonyl, hexyloxycarbonyl and the like; and a ($C_7$-$C_{11}$ aralkyl)oxycarbonyl group which may optionally be substituted with 1 to 3 group(s) selected independently from $C_1$-$C_6$ alkoxy groups and halogen atoms, such as benzyloxycarbonyl, methoxybenzyloxycarbonyl, dimethoxybenzyloxycarbonyl, chlorobenzyloxycarbonyl, naphthylmethyloxycarbonyl group and the like; of these, preferred are silyl groups which are substituted with 3 groups selected independently from $C_1$-$C_6$ alkyl groups and phenyl groups (particularly t-butyldimethylsilyl group).

The method is first to prepare a mono-protected compound (16) by protecting one hydroxy group of dihydric alcohol compound (15) (in Step G-1), then, to prepare an ester, urethane or phosphoryl compound (17) by esterification, carbamoylation or phosphorylation of compound (16) (in Step G-2), and finally to prepare compound (18) by deprotecting the protecting group in compound (17) (in Step G-3).

Alternatively, compound (18) can be prepared by applying an esterification or carbamoylation reaction directly to compound (15) without protection. Then the desired compound (4) can be prepared by oxidation of compound (18).

Each step is described in detail as follows.

(Step G-1)

Step G-1 is a step to prepare compound (16) by protecting one of the hydroxy groups of dihydric alcohol compound (15).

The dihydric alcohol compound (15) which is the starting material is commercially available, or, if necessary, the compound can be prepared by procedures well known to those skilled in the art.

This step can be accomplished by protection reactions for alcohols, and the reactions are well known in the field of synthetic organic chemistry (examples of which are described in T. W. Greene et al., Protective Groups in Organic Synthesis, 3rd Edition, John Wiley & Sons, Inc. (1999)).

For example, the hydroxy-protected compound (16) can be prepared by reacting compound (15) with a protecting agent in a solvent under basic conditions.

The protecting agent is a compound represented by the formula $Pg^5$—$Z^8$ (wherein, $Pg^5$ is as defined above, and $Z^8$ represents a halogen atom or a leaving group) and, for example, can be a halide such as chloride, bromide, iodide and the like; or a sulfonate such as methanesulfonate, trifluoromethanesulfonate, toluenesulfonate and the like; and is preferably a halide.

The solvent to be used, for example, can be a hydrocarbon such as hexane, cyclohexane, benzene, toluene and the like; a halogenated hydrocarbon such as dichloromethane, dichloroethane and the like; a ketone such as acetone, 2-butanone and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably an ether, a halogenated hydrocarbon or an amide.

The base to be used is not particularly limited provided that it is one that is usually used in the field of synthetic organic chemistry, and, for example, can be an alkali metal carbonate such as sodium carbonate, potassium carbonate, cesium carbonate, sodium hydrogen carbonate and the like; an organic amine such as triethylamine, diisopropylethylamine, dicyclohexylamine, pyridine, lutidine, 4-(N,N-dimethylamino)pyridine, diazabicycloundecene, diazabicyclononene, imidazole and the like; or an alkali metal alkoxide such as sodium methoxide and the like; and is preferably an organic amine.

The reaction temperature is usually from 0° C. to the boiling point of the solvent employed (preferably from 0° C. to room temperature). The time required for the reaction varies mainly depending on the kind of protecting group to be introduced, and is usually from 0.5 hours to 24 hours (preferably from 0.5 hours to 6 hours).

After completion of the reaction, the compound (16) can be isolated from the reaction mixture by conventional methods. For example, it can be obtained by neutralizing the reaction mixture, adding an organic solvent which is not miscible with water to the reaction mixture or to the residue obtained after distilling off the solvent from the reaction mixture, washing the mixture with water, and then distilling off the solvent.

If necessary, the obtained compound (16) can be further purified by conventional methods, for example, recrystallization, reprecipitation, chromatography or the like.

Alternatively, in this Step a by-product where both hydroxy groups are protected may be obtained in addition to the desired compound (16). In this case, if desired, the compound (16) can be isolated from said by-product using a method such as recrystallization, reprecipitation or by chromatography.

(Step G-2)

Step G-2 is a step to prepare compound (17) by subjecting the hydroxy group of the mono-protected compound (16) to an esterification, carbamoylation or phosphorylation reaction.

This step can be carried out in a manner similar to the step described in Step A-2.

(Step G-3)

Step G-3 is a step to prepare alcohol compound (18) by deprotecting the protecting group in compound (17).

This step can be accomplished by deprotection reactions for an alcohol, according to reactions well known in the field of synthetic organic chemistry (examples of which are described in T. W. Greene et al., Protective Groups in Organic Synthesis, 3rd Edition, John Wiley & Sons, Inc. (1999)).

For example, when the protecting group $Pg^5$ is a silyl group which is substituted with 3 groups selected independently from $C_1$-$C_6$ alkyl groups and phenyl groups such as a t-butyldimethylsilyl group, the reaction can be carried out by treating compound (17) with a fluoride salt in a solvent.

The solvent to be employed, for example, can be water; a hydrocarbon such as hexane, cyclohexane, benzene, toluene and the like; a halogenated hydrocarbon such as dichloromethane, dichloroethane and the like; an alcohol such as methanol, ethanol, t-butyl alcohol and the like; a ketone such as acetone, 2-butanone and the like; an ester such as ethyl acetate and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably a hydrocarbon, a halogenated hydrocarbon or an ether, more preferably an ether.

The fluoride salt, for example, can be an alkali metal fluoride such as potassium fluoride and the like; or an organic ammonium fluoride such as tetrabutylammonium fluoride and the like.

The reaction may be carried out adjusting the reaction mixture to neutral by the addition of an acid such as acetic acid.

The reaction temperature is usually from 0° C. to room temperature. The time required for the reaction is usually from 1 hour to 4 hours.

After completion of the reaction, the compound (18) can be isolated from the reaction mixture by conventional methods. For example, it can be obtained by neutralizing the reaction mixture, adding an organic solvent which is not miscible with water to the reaction mixture or to the residue obtained after distilling off the solvent from the reaction mixture, washing the mixture with water, and then distilling off the solvent.

If necessary, the obtained compound (18) can be further purified by conventional methods, for example, recrystallization, reprecipitation, chromatography or the like.

Alternatively, the compound (18) can be prepared by introducing a group $R^\#$ directly onto one hydroxy group of compound (15) without Step G-1 to Step G-3. In this case, the compound (15) can be treated preferably under similar reaction conditions to Step G-2.

(Step G-4)

Step G-4 is a step to prepare the intermediate compound (4) in Method A by oxidizing the alcohol compound (18).

This step can be accomplished by treating compound (18) with an oxidizing agent in an inert solvent.

There is no particular restriction on the nature of the solvent to be employed, provided that it can dissolve the starting compound at least to some extent and it has no adverse effect on the reaction. The solvent to be used, for example, can be water; a hydrocarbon such as hexane, cyclohexane, benzene, toluene and the like; a halogenated hydrocarbon such as dichloromethane, dichloroethane and the like; an alcohol such as t-butyl alcohol and the like; a ketone such as acetone, 2-butanone and the like; an ester such as ethyl acetate and the like; a sulfoxide such as dimethyl sulfoxide and the like; an amide such as N,N-dimethylformamide and the like; a nitrile such as acetonitrile and the like; or an ether such as diethyl ether, tetrahydrofuran, 1,4-dioxane, 1,2-dimethoxyethane and the like; and is preferably water, a hydrocarbon, a halogenated hydrocarbon, a ketone, an amide or an ether, more preferably a halogenated hydrocarbon (particularly dichloromethane), a ketone (particularly acetone) or an amide (particularly N,N-dimethylformamide).

The oxidizing agent to be used in the oxidation reaction is not particularly limited provided that it is one that is usually used for converting an alcohol compound to a carboxylic acid compound by oxidation in the field of synthetic organic chemistry, and, for example, can be a salt, an oxide or a complex of chromium such as chromium trioxide, potassium dichromate, pyridinium chlorochromate, Jones reagent, Collins reagent and the like; a salt, an oxide or a complex of ruthenium such as ruthenium tetraoxide, tetrapropylammonium perruthenate and the like; a salt, an oxide or a complex of lead such as lead tetraacetate and the like; a salt, an oxide or a complex of manganese such as potassium permanganate, manganese dioxide and the like; a salt, an oxide or a complex of silver such as silver oxide and silver carbonate; a salt, an oxide or a complex of tungsten such as tungstic acid and the like; a salt, an oxide or a complex of molybdenum such as molybdic acid; a free radical such as 2,2,6,6-tetramethylpiperidinooxy radical and the like; a halogen such as chlorine, bromine, iodine and the like; a halogenic acid or salt thereof such as sodium hypochlorite, sodium chlorite, sodium perchlorate and the like; or an N-haloimide such as N-chlorosuccinimide, N-bromosuccinimide, N-iodosuccinimide and the like; and is preferably a salt, an oxide or a complex of chromium; a salt, an oxide or a complex of ruthenium; a salt, an oxide or a complex of manganese; a salt or a complex of silver; or a halogenic acid or salt thereof; and is more preferably a salt, an oxide or a complex of chromium.

The amount of the oxidizing agent to be used is usually an amount of 2 to 10 molar equivalents relative to the amount of the alcohol compound (18), preferably an amount of 2 to 3 molar equivalents of the amount of the compound (18).

The reaction temperature varies mainly depending on the oxidizing agent and the starting material used, and is usually from −78° C. to the boiling point of the solvent employed, preferably from −20° C. to room temperature.

The time required for the reaction varies mainly depending on the oxidizing agent, the starting material used, and the reaction temperature, and is usually from 0.1 hours to 24 hours, preferably from 0.5 hours to 2 hours.

After completion of the reaction, the desired compound (4) can be isolated from the reaction mixture by conventional methods. For example, it can be obtained by adding an organic solvent which is not miscible with water to the reaction mixture or to the residue obtained after distilling off the solvent from the reaction mixture, washing the mixture with water, and then distilling off the solvent.

If necessary, the obtained compound (4) can be further purified by conventional methods, for example, recrystallization, reprecipitation, chromatography or the like.

In a similar manner, the synthetic intermediate compound (7) in Method B can be obtained.

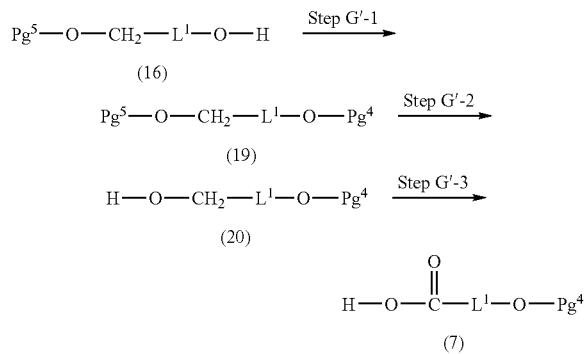

Compound (19) is prepared by protecting the mono-protected compound (16) with a protecting group $Pg^4$ in a manner similar to the Step G-2 (in Step G'-1), then compound (20) is prepared by deprotecting the protecting group $Pg^5$ (in Step G'-2), and finally compound (7) is prepared by oxidizing compound (20).

Alternatively, compound (20) can be prepared by protecting compound (15) with a protecting group $Pg^4$ directly without Step G-1, Step G'-1 and Step G'-2. In this case, compound (20) can be prepared preferably by treating compound (15) under similar reaction conditions to Step G'-1.

[Method H]

This method is an alternative method to prepare the intermediate compound (4) in Method A, and the reaction scheme is shown below.

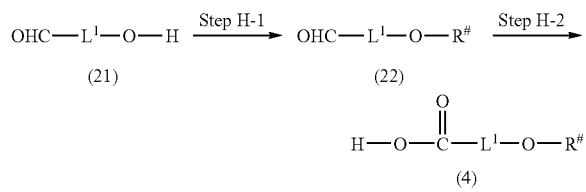

In the above reaction scheme, $L^1$ and $R^\#$ are as defined above.

The method is first to prepare compound (22) by esterification or carbamoylation of the hydroxy group of aldehyde compound (21) (in Step H-1), then, to prepare compound (4) by oxidizing compound (22).

Each step is described in detail as follows.

Step H-1 is a step to prepare compound (22) by esterification or carbamoylation of the hydroxy group of aldehyde compound (21).

The aldehyde compound (21) which is the starting material is commercially available, or can be prepared by procedures well known to those skilled in the art. For example, the corresponding lactone compound is subjected to reductive cleavage (examples of which are described in D. Johnston et al., Tetrahedron Lett., 40, 4913-4916, (1999)).

This step can be carried out in a manner similar to the step described in Step A-2.

Step H-2 is a step to prepare intermediate compound (4) in Method A by oxidizing the aldehyde compound (22).

This step can be accomplished by oxidation reactions of aldehyde compounds, according to reactions well known in the field of synthetic organic chemistry. For example, this step can be carried out in a manner similar to the step described in Step G-4.

In a similar manner, the synthetic intermediate compound (7) in Method B can be obtained.

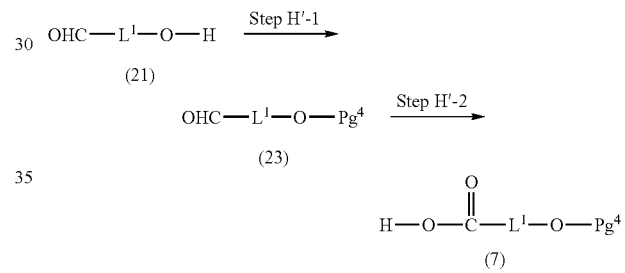

Compound (23) is prepared by protecting the hydroxy group of compound (21) with a protecting group $Pg^4$ in a manner similar to the Step B-1 (in Step H'-1), then compound (7) is prepared by oxidizing the aldehyde group of compound (23) (in Step H'-2)

[Method I]

Method I is a method to prepare the intermediate compound (11) in Method C, and the reaction scheme is shown below.

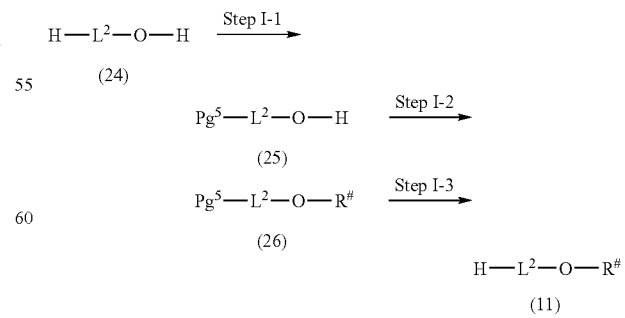

In the above reaction scheme, $R^\#$, $L^2$ and $Pg^5$ are as defined above.

The method is first to prepare mono-protected compound (25) by protecting one hydroxy group of dihydric alcohol compound (24) (in Step I-1), then, to prepare compound (26) by introducing the R# group into compound (25) (in Step I-2), and finally to prepare the desired compound (11) by deprotecting the protecting group from compound (26) (in Step I-3). The method can be carried out in a manner similar to the method described in Method G (Step G-1 to Step G-3).

Alternatively, the desired compound (11) can be prepared by introducing the R# group directly into compound (24) without protection.

In a similar manner, the intermediate compound (12) in Method D can be obtained.

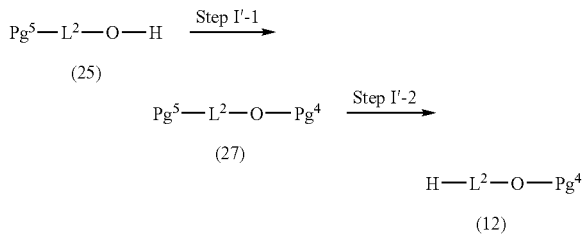

Compound (27) is prepared by protecting the hydroxy group of compound (25) with a protecting group $Pg^4$ (in Step I'-1), then compound (12) is prepared by removing the protecting group $Pg^5$ from compound (27) (in Step I'-2). The reactions can be carried out in a manner similar to the reactions described in Step G'-1 to Step G'-2.

Where the compounds (Ia), (Ib), (Ic), (Id) or (If) of the present invention prepared by Method A, Method B, Method C, Method D or Method E include protecting groups in group L or group R, the final desired compounds can be obtained by removing these protecting groups using procedures well known to those skilled in the art. Namely, a compound including a hydroxy group, a group of formula —NH—, carboxy group, a —P(=O) (OH)$_2$ group or a —SO$_3$H group can be prepared by using a starting compound wherein said groups are protected, and finally by removing these protecting groups.

The reactions for removing the protecting groups can be accomplished by reactions well known in the field of synthetic organic chemistry (examples of which are described in T. W. Greene et al., Protective Groups in Organic Synthesis, 3rd Edition, John Wiley & Sons, Inc. (1999)) and similar reactions. For example, in the case where a carboxy group or a —P(=O) (OH)$_2$ group is included in group L or group R, an allyl group can be used as the protecting group, and said protecting group can be removed in a similar manner to the procedures for removing $Pg^2$ and $Pg^3$ described in Method A and removing $Pg^4$ in Method B.

The triazole compounds and pharmacologically acceptable salts thereof of the present invention have high water solubility, therefore when they are administered as a medicament (especially for injection), they are capable of being cleaved in vivo and as a result they exhibit excellent antifungal activity against fungi of genera such as *Candida, Aspergillus, Cryptococcus, Mucor, Histoplasma, Blastomyces, Coccidioides, Paracoccidioides, Trichophyton, Epidermophyton, Microsporum, Malassezia, Pseudallescheria, Sporothrix, Rhinosporidium, Fonsecaea, Wangiella, Phialophora, Exophiala, Cladosporium, Alternaria, Aureobasidium, Chaetomium, Curvularia, Drechslera, Mycocentrospora, Phoma, Hendersonula, Scytalidium, Corynespora, Leptosphaeria, Madurella, Neotestudina, Sedosporium, Pyrenochaeta, Geotrichum, Trichosporon, Chrysosporium, Coprinus, Schizophyllum, Pneumocystis, Conidiobolus, Basidiobolus, Paecilomyces, Penicilliun, Acremonium, Fusarium, Scopulariopsis, Saccharomyces, Cephalosporium, Loboa, Rhizopus, Rhizomucor* and *Absidia*.

The usage amount varies depending on the symptoms of the patient (a warm-blooded animal, particularly a human being), age, administration route (intravenous administration, intramuscular administration, subcutaneous administration and the like) etc. and, in the case of intravenous administration, intramuscular administration and subcutaneous administration, it is desirable to administer 0.1 mg (preferably 0.5 mg) as a lower limit and 600 mg (preferably 500 mg) as an upper limit per one administration for an adult and one to six time(s) a day depending on the symptoms.

The above dosage ranges are based on a human adult. The dosage range for warm-blooded animals who differ in weight from a human adult would be proportional to the respective average weight of a human adult and a non-human, warm-blooded animal.

The compounds of the present invention can be administered in a form of composition comprising a pharmaceutically effective amount of the triazole compound or pharmaceutically acceptable salt in combination with a pharmaceutically acceptable carrier. Carriers include diluents such as water and alcohol, and excipients such as stabilizers, surfactants, solubilizers, buffering agents, antioxidants, aqueous vehicles, isotonicity agents, pH adjusting agents, bulking agents, preservatives, cosolvent solubilizers, and pharmaceutical solvents.

BRIEF DESCRIPTION OF THE DRAWING

The drawing is a graph showing the result of the Test Example 1. The abscissa represents an incubation time and the ordinate represents the percentage of persistence of the compound of Example 5 or the percentage of formation of compound A.

EXAMPLES

Figure 1:
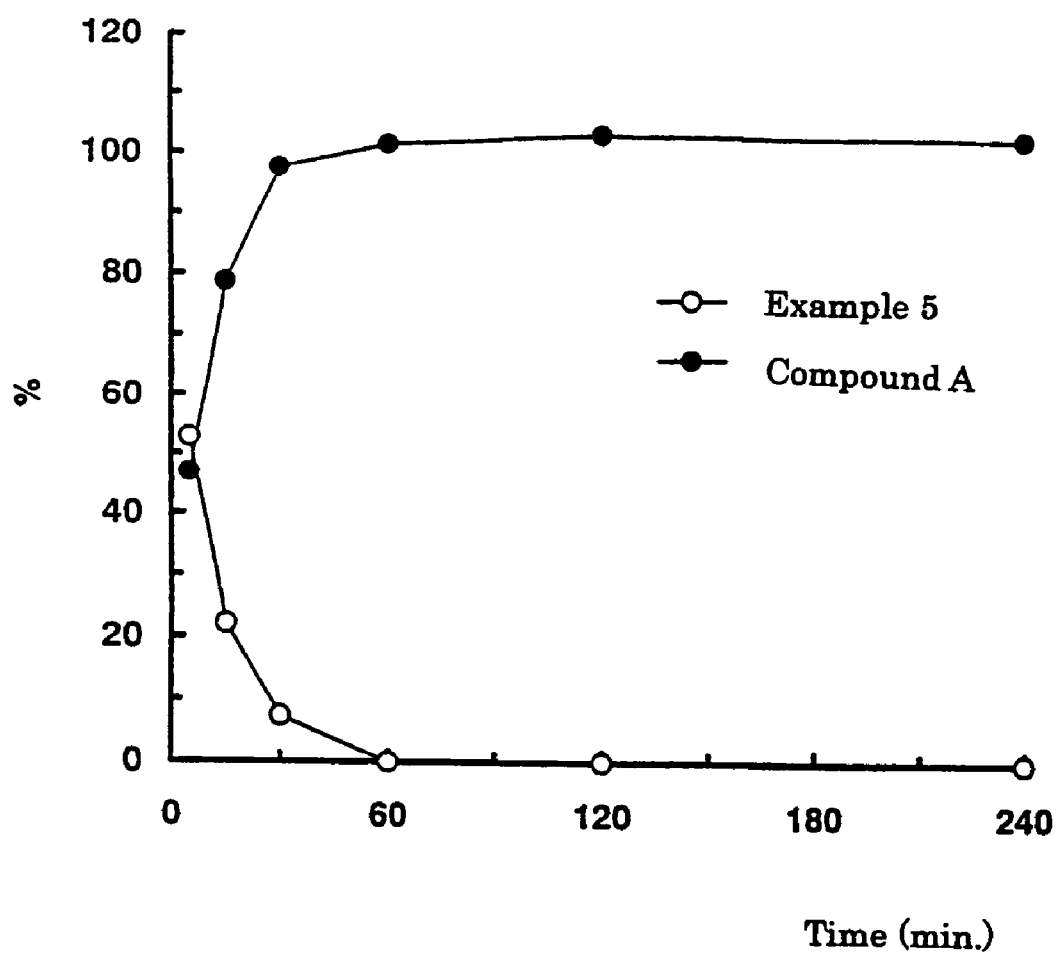

The following examples, reference examples, test examples and formulation examples are intended to further illustrate the present invention and are not intended to limit the scope of this invention in any manner.

Example 1

Sodium hydrogen 4-(acetoxymethyl)-3-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Mono Sodium Salt of Example Number 5-34)

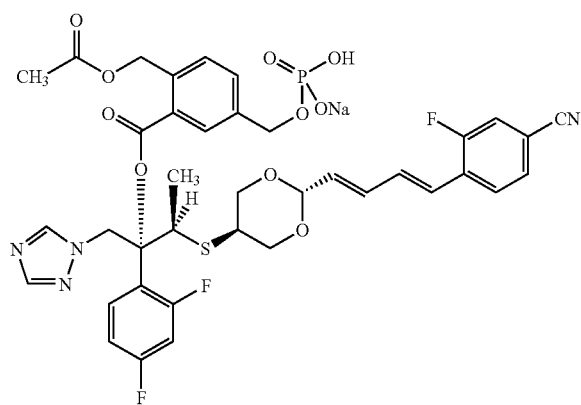

(1) 2-Bromo-1,4-benzenedimethanol

Crushed calcium chloride (14.55 g, 131.1 mmol) was added over a period of 20 minutes to a solution of sodium borohydride (6.61 g, 174.8 mmol) in ethanol (150 ml) with stirring at 0° C., and then a solution of dimethyl 2-bromoterephthalate (described in J. Med. Chem., 13, 1235 (1970); 11.94 g, 43.7 mmol) in ethanol (20 ml) was added thereto. After the mixture was stirred at the same temperature for 30 minutes, sodium borohydride (5.3 g, 140 mmol) and calcium chloride (1 g, 9.0 mmol) were further added thereto. The resulting mixture was stirred for 40 minutes, and a 2N aqueous solution of hydrochloric acid (250 ml) was added thereto. The product was extracted with ethyl acetate, and the organic layer was washed with a saturated aqueous solution of sodium chloride. The extract was concentrated under reduced pressure, and a solid residue was obtained. The residue was washed with a small amount of ethyl acetate to afford the title compound (7.98 g, 84% yield) as a colorless solid (mp. title compound (7.98 g, 84% yield) as a colorless solid (mp. 104° C.)

NMR spectrum (400 MHz, DMSO-$d_6$) δ ppm: 4.48 (2H, d, J=5 Hz), 4.49 (2H, d, J=6 Hz), 5.27 (1H, t, J=6 Hz), 5.37 (1H, t, J=5 Hz), 7.31 (1H, d, J=7 Hz), 7.46-7.50 (2H, m)

IR spectrum ν max KBr $cm^{-1}$: 3332, 3244, 1435, 1404, 1201, 1058, 1018, 825

Mass spectrum m/z (EI): 216, 218 ($M^+$).

(2) 2-Bromo-1,4-bis[(tetrahydropyran-2-yl)oxymethyl]benzene 3,4-Dihydro(2H)pyran (7.22 g, 84.9 mmol) was added dropwise to a solution of 2-bromo-1,4-benzenedimethanol (7.76 g, 35.8 mmol) obtained from Example 1-(1) and p-toluenesulfonic acid monohydrate (340.2 mg, 1.80 mmol) in dichloromethane (180 ml) with stirring at 0° C. The mixture was stirred for 1 hour, and then 3,4-dihydro(2H)pyran (0.8 g, 9.3 mmol) was further added thereto. After the mixture was stirred for 40 minutes, a saturated aqueous solution of sodium hydrogen carbonate (100 ml) was added thereto, then the resulting mixture was stirred for 5 minutes, and the product was extracted with ethyl acetate. The organic layer was washed with a saturated aqueous solution of sodium chloride, and the solvent was distilled off under reduced pressure. The obtained residue was subjected to chromatography on a silica gel (250 g) column (eluent; ethyl acetate:hexane=1:10) to give the title compound (12.07 g, 88% yield) as an oil.

NMR spectrum (400 MHz, $CDCl_3$) δ ppm: 1.52-1.91 (12H, m), 3.52-3.59 (2H, m), 3.85-3.93 (2H, m), 4.47 (1H, d, J=12 Hz), 4.57 (1H, d, J=13 Hz), 4.69 (1H, t, J=4 Hz), 4.74 (1H, d, J=12 Hz), 4.77 (1H, t, J=4 Hz), 4.81 (1H, d, J=13 Hz), 7.30 (1H, dd, J=8, 1 Hz), 7.48 (1H, d, J=8 Hz), 7.57 (1H, d, J=1 Hz)

IR spectrum ν max $CHCl_3$ $cm^{-1}$: 2947, 1608, 1562, 1388, 1345, 1075, 1032, 973, 906

Mass spectrum m/z (FAB): 385, 387 ($M^+$+1).

(3) 2,5-Bis[(tetrahydropyran-2-yl)oxymethyl]benzoic acid n-Butyllithium (1.57 M hexane solution; 8.33 ml, 13.1 mmol) was added dropwise to a solution of 2-bromo-1,4-bis[(tetrahydropyran-2-yl)oxymethyl]benzene (3.55 g, 9.22 mmol) obtained from Example 1-(2) in tetrahydrofuran (30 ml) with stirring at −78° C. After the mixture was stirred at the same temperature for 20 minutes, carbon dioxide gas was introduced thereto for 40 minutes. The resulting mixture was stirred at the same temperature for 1 hour, and then the reaction was stopped by addition of a saturated aqueous solution of ammonium chloride. The mixture was warmed to 0° C., and then the product was extracted with ethyl acetate. The organic layer was washed with a saturated aqueous solution of sodium chloride, and the solvent was distilled off under reduced pressure to afford the residue. The residue was subjected to chromatography on a silica gel (100 g) column (eluent; ethyl acetate:hexane=1:3) to give the title compound (1.63 g, 50% yield) as a colorless oil.

NMR spectrum (400 MHz, $CDCl_3$) δ ppm: 1.55-1.92 (12H, m), 3.56-3.60 (2H, m), 3.88-3.95 (2H, m), 4.55 (1H, d, J=12 Hz), 4.73 (1H, t, J=4 Hz), 4.81 (1H, t, J=4 Hz), 4.82 (1H, d, J=12 Hz), 4.96 (1H, d, J=15 Hz), 5.15 (1H, d, J=15 Hz), 7.59 (1H, dd, J=8, 1 Hz), 7.70 (1H, d, J=8 Hz), 8.06 (1H, d, J=1 Hz)

IR spectrum ν max $CHCl_3$ $cm^{-1}$: 2947, 1730, 1693, 1261, 1031, 908

Mass spectrum m/z (FAB): 351 ($M^+$+1).

(4) 6-(Hydroxymethyl)-1(3H)-isobenzofuranone

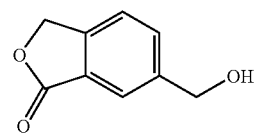

p-Toluenesulfonic acid monohydrate (103.0 mg, 0.54 mmol) was added to a solution of 2,5-bis[(tetrahydropyran-2-yl)oxymethyl]benzoic acid (1.62 g, 4.64 mmol) obtained from Example 1-(3) in methanol (30 ml), and the mixture was stirred at room temperature for 2 hours. The resulting solution was concentrated under reduced pressure to afford a solid residue. This residue was subjected to chromatography on a silica gel (50 g) column (eluent; ethyl acetate: hexane=1:1~1:0) to give the title compound (587.5 mg, 77% yield) as a colorless solid (mp. 107-108° C.).

NMR spectrum (400 MHz, $CDCl_3$) δ ppm: 1.91 (1H, t, J=5 Hz), 4.83 (2H, d, J=5 Hz), 5.33 (2H, s), 7.49 (1H, d, J=8 Hz), 7.72 (1H, d, J=8 Hz), 7.93 (1H, s)

IR spectrum ν max KBr $cm^{-1}$: 3461, 1735, 1048, 996, 771

Mass spectrum m/z (EI): 164 ($M^+$).

(5) Methyl 2,5-bis(acetoxymethyl)benzoate

Sodium acetate (10.4 g, 126.8 mmol) was added to a solution of methyl 2,5-bis(bromomethyl)benzoate (described in J. Am. Chem. Soc., 121, 1192 (1999); 12.65 g, 39.3 mmol) in dimethyl sulfoxide (80 ml), and the mixture was stirred at room temperature for 1 hour. After a saturated aqueous solution of ammonium chloride (150 ml) was added thereto, the product was extracted with ethyl acetate. The organic layer was washed with water and then with a saturated aqueous solution of sodium chloride, and the solvent was distilled off under reduced pressure. The obtained oily residue was subjected to chromatography on a silica gel (200 g) column (eluent; ethyl acetate:hexane=1: 5~1:2) to afford the title compound (7.72 g, 70% yield) as an oil.

NMR spectrum (400 MHz, $CDCl_3$) δ ppm: 2.12 (3H, s), 2.14 (3H, s), 3.92 (3H, s), 5.13 (2H, s), 5.51 (2H, s), 7.49 (1H, d, J=8 Hz), 7.53 (1H, dd, J=8, 1 Hz), 7.98 (1H, d, J=1 Hz)

IR spectrum ν max CHCl₃ cm⁻¹: 1737, 1255, 1037
Mass spectrum m/z (FAB): 281 (M⁺+1).

(6) 6-(Hydroxymethyl)-[(3H)-isobenzofuranone

Potassium carbonate (380.7 mg, 2.7 mmol) was added to a solution of methyl 2,5-bis(acetoxymethyl)benzoate (7.72 g, 27.5 mmol) obtained from Example 1-(5) in methanol (100 ml), and after the mixture was stirred at room temperature for 2 hours, 2N aqueous solution of hydrochloric acid (10 ml) was added thereto. The solvent was distilled off under reduced pressure, and the obtained solid residue was recrystallized from methanol to give the title compound (2.20 g) as a colorless solid. Further, the mother liquor was concentrated under reduced pressure to afford a solid residue. This residue was subjected to chromatography on a silica gel (100 g) column (eluent; ethyl acetate:hexane=2:1~3:1) to afford the title compound (1.05 g) as a colorless solid (total amount; 3.25 g, 76% yield). The data of the spectra of this compound coincided with those as described in Example 1-(4).

(7) 6-[(tert-Butyldimethylsilyl)oxymethyl]-1 (3H)-isobenzofuranone tert-Butylchlorodimethylsilane (647.3 mg, 4.30 mmol) and imidazole (292.3 mg, 4.30 mmol) were added to 6-(hydroxymethyl)-[(3H)-isobenzofuranone (587.5 mg, 3.58 mmol) obtained from Example 1-(4) or Example 1-(6) in N,N-dimethylformamide (10 ml). After the mixture was stirred at room temperature for 1 hour, water (20 ml) was added thereto, and then the product was extracted with a mixed solvent of ethyl acetate and hexane. The organic layer was washed with water and then with a saturated aqueous solution of sodium chloride, and the solvent was distilled off under reduced pressure to afford an oily residue. The residue was subjected to chromatography on a silica gel (25 g) column (eluent; ethyl acetate:hexane=1:10~1:1) to give the title compound (940.1 mg, 94% yield) as a colorless oil.

NMR spectrum (400 MHz, CDCl₃) δ ppm: 0.12 (6H, s), 0.95 (9H, s), 4.83 (2H, s), 5.31 (2H, s), 7.45 (1H, d, J=8 Hz), 7.67 (1H, d, J=8 Hz), 7.88 (1H, s)

IR spectrum ν max CHCl₃ cm⁻¹: 2956, 2931, 2958, 1766, 1156, 840

Mass spectrum m/z (FAB): 279 (M⁺1).

(8) 4-Methoxybenzyl 2-(acetoxymethyl)-5-[(tert-butyldimethylsilyl)oxymethyl]benzoate An aqueous solution (1.2 ml) of potassium hydroxide (188.0 mg, 3.35 mmol) was added to a solution of 6-[(tert-butyldimethylsilyl)oxymethyl]-[(3H)-isobenzofuranone (932.9 mg, 3.35 mmol) obtained from Example 1-(7) in tetrahydrofuran (3 ml). After the reaction mixture was stirred at room temperature for 4 hours, the solution was concentrated under reduced pressure, and the residue was dried using a vacuum pump to give an amorphous solid. The solid was dissolved in N,N-dimethylformamide (10 ml), and 4-methoxybenzyl chloride (577.3 mg, 3.69 mmol) was added thereto, and then the mixture was stirred at 80° C. for 1 hour. After cooling the mixture, a saturated aqueous solution of ammonium chloride was added thereto, and the product was extracted with ethyl acetate. The organic layer was washed with water and then with a saturated aqueous solution of sodium chloride, and the solvent was distilled off under reduced pressure to afford an oily residue. The residue was dissolved in dichloromethane (10 ml), and then 4-(N, N-dimethylamino)pyridine (450.3 mg, 3.69 mmol) and acetyl chloride (289.4 mg, 3.69 mmol) were added thereto at 0° C. The mixture was stirred at the same temperature for 30 minutes, and a saturated aqueous solution of sodium hydrogen carbonate was added thereto to stop the reaction. The product was extracted with ethyl acetate, and the extract was concentrated to afford an oily residue. The residue was subjected to chromatography on a silica gel (50 g) column (eluent; ethyl acetate:hexane=1:10~1:5) to give the title compound (905.6 mg, 59% yield) as a colorless oil.

NMR spectrum (400 MHz, CDCl₃) δ ppm: 0.08 (6H, s), 0.92 (9H, s), 2.08 (3H, s), 3.82 (3H, s), 4.74 (2H, s), 5.28 (2H, s), 5.49 (2H, s), 6.91 (2H, d, J=8 Hz), 7.38 (2H, d, J=8 Hz), 7.43 (1H, d, J=7 Hz), 7.48 (1H, dd, J=7, 1 Hz), 7.94 (1H, d, J=1 Hz)

IR spectrum ν max CHCl₃ cm⁻¹: 2957, 2931, 2858, 1721, 1257, 909, 839

Mass spectrum m/z (FAB): 457 (M⁺−1).

(9) 4-Methoxybenzyl 2-(acetoxymethyl)-5-(hydroxymethyl)benzoate

Tetrabutylammonium fluoride (1N tetrahydrofuran solution; 9.9 ml, 9.9 mmol) and acetic acid (592.9 mg, 9.87 mmol) were added to a solution of 4-methoxybenzyl 2-(acetoxymethyl)-5-[(tert-butyldimethylsilyl)oxymethyl]benzoate (905 mg, 1.97 mmol) obtained from Example 1-(8) in tetrahydrofuran (5 ml). The mixture was stirred at 50° C. for 1 hour, and then the solvent was distilled off under reduced pressure. The oily residue was subjected to chromatography on a silica gel (25 g) column (eluent; ethyl acetate:hexane=1:1) to give the title compound (500.1 mg, 74% yield) as a colorless amorphous solid.

NMR spectrum (400 MHz, CDCl₃) δ ppm: 2.09 (3H, s), 3.82 (3H, s), 4.72 (2H, s), 5.29 (2H, s), 5.50 (2H, s), 6.91 (2H, d, J=9 Hz), 7.39 (2H, d, J=9 Hz), 7.47 (1H, d, J=8 Hz), 7.53 (1H, dd, J=8, 1 Hz), 7.97 (1H, d, J=1 Hz)

IR spectrum ν max KBr cm⁻¹: 1737, 1714, 1519, 1253, 1039

Mass spectrum m/z (FAB): 345 (M⁺+1).

(10) 4-Methoxybenzyl 2-(acetoxymethyl)-5-[[bis (allyloxy)phosphoryl]oxymethyl]benzoate A solution of 4-methoxybenzyl 2-(acetoxymethyl)-5-(hydroxymethyl)benzoate (480.4 mg, 1.40 mmol) obtained from Example 1-(9) in dichloromethane (10 ml) was cooled to 0° C., and then tetrazole (195.4 mg, 2.79 mmol) and bis(allyloxy)(diisopropylamino)phosphine (Tetrahedron Lett., 30, 4219 (1989); 444.9 mg, 1.82 mmol) were added thereto with stirring, followed by stirring the mixture at the same temperature for 15 minutes. After the reaction mixture was warmed to room temperature and stirred for 1 hour, methanol (12 drops) was added thereto. The mixture was stirred for 5 minutes and then cooled to 0° C., and tert-butyl hydroperoxide (80% di-tert-butyl peroxide solution; Merck; 0.54 g, 4.8 mmol) was added thereto, then the mixture was warmed to room temperature and stirred for 15 minutes. A saturated aqueous solution of sodium hydrogen carbonate and an aqueous solution of sodium thiosulfate were added thereto, and the mixture was stirred for 10 minutes and partitioned between ethyl acetate and water. The obtained organic layers were combined and the solvent was distilled off under reduced pressure to give an oily residue. The residue was subjected to chromatography on a silica gel (25 g) column (eluent; ethyl acetate:hexane=1:2~1:1) to afford the title compound (598.3 mg, 85% yield) as a colorless oil.

NMR spectrum (400 MHz, CDCl$_3$) δ ppm: 2.10 (3H, s), 3.82 (3H, s), 4.50-4.53 (4H, m), 5.08 (2H, d, J=8 Hz), 5.23 (2H, dd, J=11, 1 Hz), 5.29 (2H, s), 5.33 (2H, dd, J=17, 1 Hz), 5.51 (2H, s), 5.90 (2H, ddt, J=17, 11, 5 Hz), 6.91 (2H, d, J=8 Hz), 7.39 (2H, d, J=8 Hz), 7.49 (1H, d, J=8 Hz), 7.55 (1H, dd, J=8, 2 Hz), 7.98 (1H, d, J=2 Hz)

IR spectrum ν max CHCl$_3$ cm$^{-1}$: 1721, 1516, 1256, 1031, 989

Mass spectrum m/z (FAB): 505 (M$^+$+1)

(11) 2-(Acetoxymethyl)-5-[[bis(allyloxy)phosphoryl]oxymethyl]benzoic acid

A mixture of 4-methoxybenzyl 2-(acetoxymethyl)-5-[[bis(allyloxy)phosphoryl]oxymethyl]benzoate (590.3 mg, 1.17 mmol) obtained from Example 1-(10) and anisole (600 mg, 5.55 mmol) was cooled to 0° C., and then trifluoroacetic acid (2 ml) was added thereto with stirring. The mixture was warmed to room temperature and allowed to stand for 20 minutes. The mixture was diluted with toluene and was concentrated under reduced pressure to eliminate the volatile components (repeated three times), and an aqueous solution of sodium hydrogen carbonate was added thereto, then the aqueous layer was washed with ethyl acetate. To the aqueous layer was added carefully a 2N aqueous solution of hydrochloric acid (10 ml), and the liberated carboxylic acid was extracted with ethyl acetate. The extract was washed with a saturated aqueous solution of sodium chloride, and the solvent was distilled off under reduced pressure to afford the title compound (477.5 mg, quantitative yield) as a colorless oil.

NMR spectrum (400 MHz, CDCl$_3$) δ ppm: 2.17 (3H, s), 4.57 (4H, m), 5.15 (2H, d, J=8 Hz), 5.27 (2H, d, J=10 Hz), 5.36 (2H, dd, J=17, 1 Hz), 5.57 (2H, s), 5.92 (2H, ddt, J=17, 10, 7 Hz), 7.55 (1H, d, J=8 Hz), 7.61 (1H, dd, J=8, 2 Hz), 8.13 (1H, br s)

IR spectrum ν max CHCl$_3$ cm$^{-1}$: 1738, 1700, 1256, 1167, 1028, 989

Mass spectrum m/z (FAB): 385 (M$^+$+1).

(12) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(acetoxymethyl)-5-[[bis(allyloxy)phosphoryl]oxymethyl]benzoate

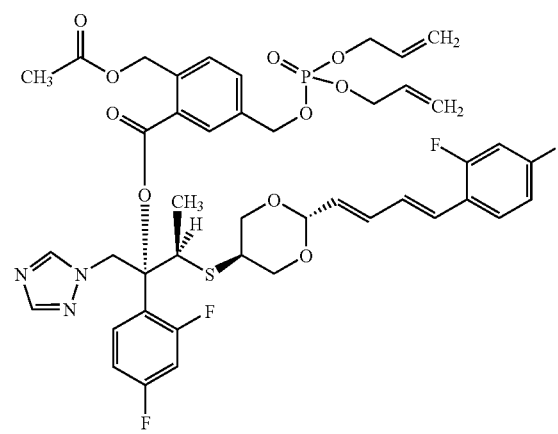

2-(Acetoxymethyl)-5-[[bis(allyloxy)phosphoryl]oxymethyl]benzoic acid (475.5 mg, 1.24 mmol) obtained from Example 1-(11) was dissolved in tetrahydrofuran (5 ml), and the solution was cooled to 0° C., then oxalyl chloride (189.2 mg, 1.49 mmol) and N,N-dimethylformamide (15 μl) were added thereto with stirring. The mixture was warmed to room temperature and then stirred for 40 minutes. The solvent was distilled off under reduced pressure to give the crude 2-(acetoxymethyl)-5-[[bis(allyloxy)phosphoryl]oxymethyl]benzoyl chloride.

To a mixture of 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (544.6 mg, 1.00 mmol) described below in Reference example 1 and tetrahydrofuran (5 ml) was added sodium hydride (55% dispersion in mineral oil; 56.9 mg, 1.31 mmol), and the mixture was irradiated with ultrasonic waves for 30 minutes using a commercially available ultrasonic cleaner. The mixture was taken out of the ultrasonic cleaner and cooled to 0° C., and all of the crude 2-(acetoxymethyl)-5-[[bis(allyloxy)phosphoryl]oxymethyl]benzoyl chloride obtained above was added thereto with stirring. The resulting mixture was stirred at room temperature for 40 minutes. After cooling, the reaction mixture was partitioned between ethyl acetate and an aqueous solution of ammonium chloride, and the organic layer was washed with a saturated aqueous solution of sodium chloride and the solvent was distilled off under reduced pressure. The oily residue was subjected to chromatography on a silica gel (30 g) column (eluent; ethyl acetate:hexane=2:1) to afford the title compound (368.3 mg, 41% yield) as a pale yellow amorphous solid.

NMR spectrum (400 MHz, CDCl$_3$) δ ppm: 1.46 (3H, dd, J=7, 2 Hz), 2.15 (3H, s), 3.04 (1H, tt, J=11, 5 Hz), 3.53 (1H, t, J=11 Hz), 3.54 (1H, t, J=11 Hz), 4.02 (1H, q, J=7 Hz), 4.11-4.20 (2H, m), 4.49-4.57 (4H, m), 5.01 (1H, d, J=4 Hz), 5.11 (2H, d, J=8 Hz), 5.23 (2H, dd, J=10, 5 Hz), 5.33 (2H, ddd, J=17, 6, 1 Hz), 5.43 (1H, d, J=14 Hz), 5.47-5.55 (3H, m), 5.83-5.96 (3H, m), 6.56 (1H, dd, J=15, 11 Hz), 6.73 (1H, d, J=16 Hz), 6.89-6.97 (3H, m), 7.33 (1H, dd, J=10, 1 Hz), 7.40 (1H, dd, J=8, 1 Hz), 7.42-7.46 (1H, m), 7.56-7.60 (2H, m), 7.62 (1H, dd, J=8, 1 Hz), 7.85 (1H, d, J=1 Hz), 7.89 (1H, s), 7.96 (1H, s)

IR spectrum ν max Liquid film cm$^{-1}$: 2232, 1731, 1504, 1276, 1258, 1026, 733

Mass spectrum m/z (FAB): 909 (M$^+$+1)

(13) Sodium hydrogen 4-(acetoxymethyl)-3-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (title target compound)

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(acetoxymethyl)-5-[[bis(allyloxy)phosphoryl]oxymethyl]benzoate (368.3 mg, 0.41 mmol) obtained from Example 1-(12) in dichloromethane (5 ml) were added bis(triphenylphosphine)dichloropalladium (14.7 mg, 0.02 mmol) and tributyltin hydride (240.1 mg, 0.83 mmol), and the mixture was stirred at room temperature for 1 hour. The mixture was concentrated under reduced pressure, and to the residue were added hexane (30 ml) and a saturated aqueous solution of sodium hydrogen carbonate (30 ml), then the resulting mixture was stirred at room temperature for 30 minutes. Methanol was added to the mixture, and then the aqueous methanol layer was separated out and the solvent was distilled off under reduced pressure to give a residue. Methanol (30 ml) was added to the residue to wash the solid, and then the combined washings were concentrated to give an oily residue. The residue was subjected to reverse phase column chromatography using Cosmosil 75 $C_{18}$-PREP (Nacalai Tesque, Inc.; 20 g) (eluent; water:methanol=4:6~3:7). The obtained fractions were concentrated, and the residue was lyophilized to afford the title target compound (85.6 mg, 25% yield) as a colorless solid.

NMR spectrum (400 MHz, $CD_3OD$) δ ppm: 1.44 (3H, dd, J=7, 2 Hz), 2.12 (3H, s), 2.97 (1H, tt, J=11, 5 Hz), 3.54 (1H, t, J=11 Hz), 3.55 (1H, t, J=11 Hz), 4.04 (1H, q, J=7 Hz), 4.08-4.16 (2H, m), 4.96 (2H, d, J=5 Hz), 5.03 (1H, d, J=5 Hz), 5.39 (1H, d, J=14 Hz), 5.48 (1H, d, J=14 Hz), 5.55 (1H, d, J=15 Hz), 5.61 (1H, dd, J=15, 2 Hz), 5.87 (1H, dd, J=15, 5 Hz), 6.57 (1H, dd, J=15, 11 Hz), 6.78 (1H, d, J=16 Hz), 7.02-7.09 (2H, m), 7.10 (1H, dd, J=16, 11 Hz), 7.49-7.66 (4H, m), 7.79 (1H, t, J=8 Hz), 7.86 (1H, dd, J=8, 1 Hz), 7.92 (1H, s), 7.94 (1H, d, J=1 Hz), 8.28 (1H, s)

IR spectrum ν max KBr $cm^{-1}$: 3433, 2231, 1733, 1503, 1384, 1141, 1120, 975, 543

Mass spectrum m/z (FAB): 851 ($M^+$+1).

Example 2

Sodium 2-acetoxy-5-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-5-oxopentanoate (Sodium Salt of Example Number 4-20)

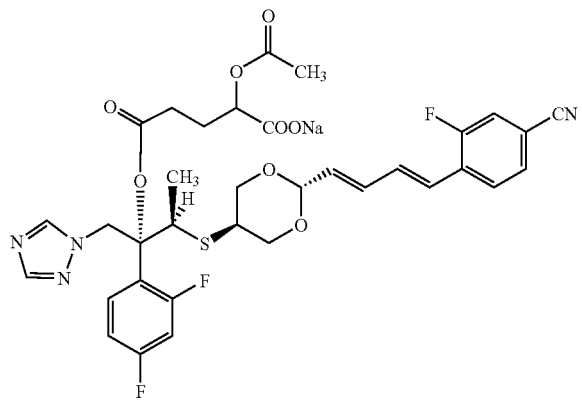

(1) Allyl 5-[4-methoxybenzyl)oxy]-2,5-dioxopentanoate

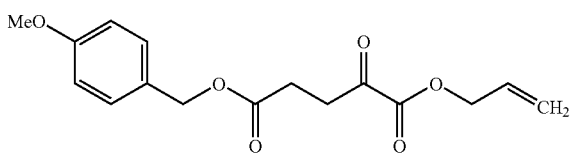

2-Oxoglutaric acid (2.92 g, 20.0 mmol), dicyclohexylamine (3.63 g, 20.0 mmol), and allyl iodide (2.01 ml, 22.0 mmol) were dissolved in N,N-dimethylformamide (30 ml), and the mixture was warmed to 60° C. and stirred for 30 minutes. Dicyclohexylamine (3.63 g, 20.0 mmol) and 4-methoxybenzyl chloride (3.13 g, 20.0 mmol) were added thereto, and the resulting mixture was stirred at the same temperature for 30 minutes. After cooling, the mixture was partitioned between water and ethyl acetate. The combined organic layers were washed with water and with a saturated aqueous solution of sodium chloride and the solvent was distilled off under reduced pressure to give an oily residue. The residue was subjected to chromatography on a silica gel (85 g) column (eluent; ethyl acetate:hexane=1:5~9:25) to afford the title compound (1.48 g, 24% yield) as a pale yellow oil. NMR spectrum (400 MHz, $CDCl_3$) δ ppm: 2.70 (2H, t, J=7 Hz), 3.17 (2H, t, J=7 Hz), 3.81 (3H, s), 4.75 (2H, dd, J=6, 1 Hz), 5.06 (2H, s), 5.33 (1H, dd, J=10, 1 Hz), 5.41 (1H, dd, J=17, 1 Hz), 5.95 (1H, ddt, J=17, 10, 6 Hz), 6.89 (2H, d, J=9 Hz), 7.28 (2H, d, J=9 Hz)

IR spectrum ν max $CHCl_3$ $cm^{-1}$: 1732, 1516, 1252, 1173, 1080, 1036

Mass spectrum m/z (EI): 306 ($M^+$).

(2) Allyl 2-hydroxy-5-[(4-methoxybenzyl)oxy]-5-oxopentanoate

Zinc chloride (1.0 M diethyl ether solution; 8.8 ml, 8.8 mmol) was added to tetrahydrofuran (5 ml), and sodium borohydride (605.3 mg, 16.0 mmol) was added thereto with stirring at 0° C. The mixture was irradiated with ultrasonic waves for 10 minutes using a commercially available ultrasonic cleaner. The mixture was taken out of the ultrasonic cleaner and cooled to −5° C., and a solution of allyl 5-[(4-methoxybenzyl)oxy]-2,5-dioxopentanoate (1.84 g, 6.0 mmol) obtained from Example 2-(1) in tetrahydrofuran (5 ml) was added thereto over a period of 10 minutes. The resulting mixture was stirred for 30 minutes, and then a saturated aqueous solution of ammonium chloride was added thereto to stop the reaction followed by extraction of the product with ethyl acetate. The organic layer was washed with a saturated aqueous solution of sodium chloride, and the solvent was distilled off under reduced pressure to afford an oily residue. The residue was subjected to chromatography on a silica gel (65 g) column (eluent; ethyl acetate:hexane=3:10~2:5) to afford the title compound (1.26 g, 68% yield) as a colorless oil.

NMR spectrum (400 MHz, $CDCl_3$) δ ppm: 1.91-2.05 (1H, m), 2.16-2.24 (1H, m), 2.43-3.58 (2H, m), 3.81 (3H, s), 4.23-4.27 (1H, m), 4.67 (2H, dt, J=6, 1 Hz), 5.06 (2H, s), 5.28 (1H, dt, J=10, 1 Hz), 5.34 (1H, dq, J=18, 1 Hz), 5.91 (1H, ddt, J=18, 10, 6 Hz), 6.89 (2H, d, J=9 Hz), 7.29 (2H, d, J=9 Hz)

IR spectrum ν max $CHCl_3$ $cm^{-1}$: 3322, 1743, 1252, 1171

Mass spectrum m/z (FAB): 309 ($M^+$+1).

(3) Allyl 2-acetoxy-5-[(4-methoxybenzyl)oxy]-5-oxopentanoate

Allyl 2-hydroxy-5-[(4-methoxybenzyl)oxy]-5-oxopentanoate (1.26 g, 4.09 mmol) obtained from Example 2-(2) was dissolved in pyridine (15 ml) at 0° C., and acetyl chloride (481.2 mg, 6.13 mmol) was added thereto. The mixture was warmed to room temperature and stirred for 30 minutes, and then, after cooling to 0° C., a saturated aqueous solution of sodium hydrogen carbonate was added thereto followed by extraction of the product with ethyl acetate. The organic layer was washed with a dilute aqueous solution of hydrochloric acid and with a saturated aqueous solution of sodium chloride, and the solvent was distilled off under reduced pressure to give an oily residue. The residue was subjected to chromatography on a silica gel (60 g) column (eluent; ethyl acetate:hexane=1:5) to afford the title compound (1.36 g, 95% yield) as a colorless oil.

NMR spectrum (400 MHz, CDCl$_3$) δ ppm: 2.11 (3H, s), 2.12-2.30 (2H, m), 2.41-2.52 (2H, m), 3.81 (3H, s), 4.63 (2H, d, J=6 Hz), 5.04-5.07 (1H, m), 5.06 (2H, s), 5.25 (1H, dd, J=10, 1 Hz), 5.33 (1H, dd, J=18, 1 Hz), 5.89 (1H, ddt, J=18, 10, 6 Hz), 6.89 (2H, d, J=9 Hz), 7.29 (2H, d, J=9 Hz)

IR spectrum ν max CHCl$_3$ cm$^{-1}$: 1742, 1614, 1516, 1252, 1170, 1036

Mass spectrum m/z (FAB): 351 (M$^+$+1).

(4) 4Acetoxy-5allyloxy-5-oxopentanoic acid

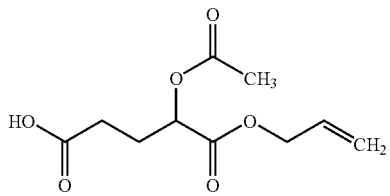

According to a similar procedure to that described in Example 1-(11), allyl 2-acetoxy-5-[(4-methoxybenzyl)oxy]-5-oxopentanoate (1.36 g, 3.88 mmol) obtained from Example 2-(3), anisole (1.50 g, 13.87 mmol), and trifluoroacetic acid (3 ml) were reacted, and the reaction mixture was worked up to afford the title compound (1.04 g, quantitative yield).

NMR spectrum (400 MHz, CDCl$_3$) δ ppm: 2.15 (3H, s), 2.18 (1H, ddd, J=16, 8, 1 Hz), 2.23-2.30 (1H, m), 2.45-2.59 (2H, m), 4.65 (2H, dt, J=6, 1 Hz), 5.09 (1H, dd, J=8, 5 Hz), 5.27 (1H, dt, J=17, 1 Hz), 5.35 (1H, dd, J=10, 1 Hz), 5.91 (1H, ddt, J=17, 10, 6 Hz)

IR spectrum ν max CHCl$_3$ cm$^{-1}$: 1746, 1714, 1375, 1276, 1248, 1184, 1077

Mass spectrum m/z (FAB): 231 (M$^+$+1).

(5) Allyl 2-acetoxy-5-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-5-oxopentanoate

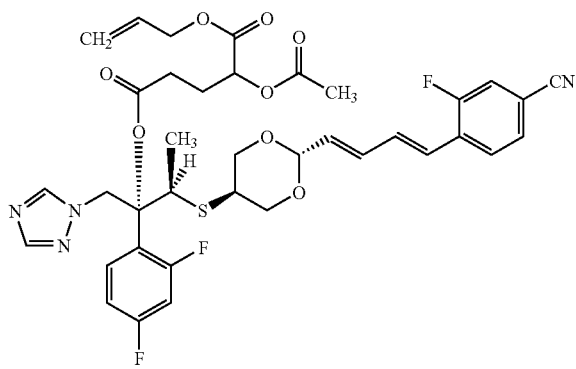

According to a similar procedure to that described in Example 1-(12), 4-acetoxy-5-allyloxy-5-oxopentanoic acid (345.3 mg, 1.50 mmol) obtained from Example 2-(4) and oxalyl chloride (209.4 mg, 1.65 mmol) were reacted, and the reaction mixture was worked up to afford 4-acetoxy-5-allyloxy-5-oxopentanoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (542.6 mg, 1.00 mmol) described in Reference example 1, sodium hydride (55% dispersion in mineral oil; 96.0 mg, 2.20 mmol), and the crude 4-acetoxy-5-allyloxy-5-oxo-pentanoyl chloride obtained above were reacted in tetrahydrofuran (7 ml), and the reaction mixture was worked up to afford, after extraction, the title compound as a crude oil. The crude oil was subjected to chromatography on a silica gel (50 g) column (eluent; ethyl acetate:hexane=1:1) to afford a mixture (567.4 mg, corresponding to 283 mg of the title compound) of the title compound and the starting material 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile.

(6) Sodium 2-acetoxy-5-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-5-oxopentanoate
(title target compound)

According to a similar procedure to that described in Example 1-(13), the mixture of allyl 2-acetoxy-5-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-5-oxopentanoate and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (all the amount obtained from Example 2-(5)), bis(triphenylphosphine)dichloropalladium (12.9 mg, 0.018 mmol), and tributyltin hydride (116.4 mg, 0.40 mmol) were reacted, and the reaction mixture was worked up to afford the title target compound as a crude oil. The crude oil was subjected to reverse phase column chromatography using Cosmosil 75 C$_{18}$-PREP (Nacalai Tesque, Inc.; 20 g) (eluent; water:methanol=4:6~3:7). The obtained fractions were concentrated, and the residue was lyophilized to afford the title target compound (86.0 mg, 12% total yield from Example 2-(5)) as a colorless solid.

NMR spectrum (400 MHz, CD$_3$OD) δ ppm: 1.31 (3H, dd, J=7, 1 Hz), 2.11 (3H, s), 2.04-2.27 (2H, m), 2.45-2.62 (2H, m), 3.01 (1H, tt, J=11, 5 Hz), 3.52 (1H, t, J=11 Hz), 3.53 (1H, t, J=11 Hz), 3.82 ((1/2)H, q, J=7 Hz), 3.84 ((1/2)H, q, J=7 Hz), 4.11-4.21 (2H, m), 4.86-4.91 (1H, m), 5.04 (1H, d, J=4 Hz), 5.41 (1H, d, J=15 Hz), 5.46 (1H, dd, J=15, 2 Hz), 5.87 (1H, dd, J=15, 4 Hz), 6.59 (1H, dd, J=15, 11 Hz), 6.79 (1H, d, J=15 Hz), 6.97-7.05 (2H, m), 7.09 (1H, dd, J=15, 11 Hz), 7.50-7.55 (3H, m), 7.78 (1H, t, J=8 Hz), 7.98 ((1/2)H, s), 7.99 ((1/2)H, s), 8.31 ((1/2)H, s), 8.33 ((1/2)H, s)

IR spectrum ν max KBr cm$^{-1}$: 3436, 2231, 1734, 1615, 1417, 1385, 1257, 1142, 1051

Mass spectrum m/z (FAB): 737 (M$^+$+1).

Example 3

Sodium [(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]trans-2-(acetoxymethyl)-1,1-cyclopropanedicarboxylate (Sodium Salt of Example Number 6-2)

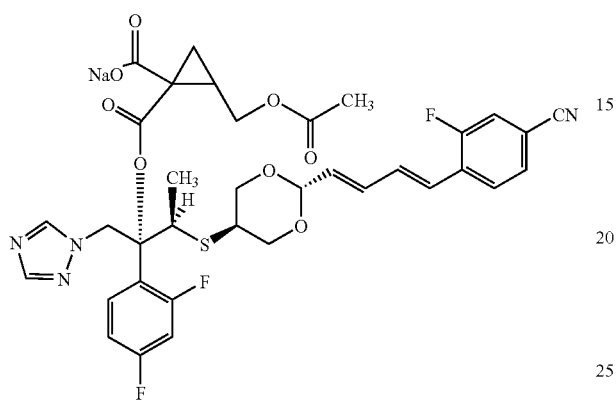

(1) Allyl 4-methoxybenzyl cis-2-(acetoxymethyl)-1,1-cyclopropanedicarboxylate

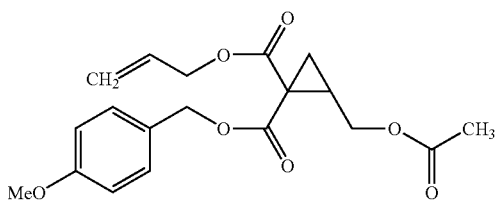

Allyl 2-oxo-3-oxabicyclo[3.1.0]hexane-1-carboxylate (described in J. Org. Chem., 54, 5684 (1989); 644.2 mg, 3.54 mmol) was dissolved in allyl alcohol, and potassium hydroxide (178.6 mg, 3.18 mmol) was added thereto followed by stirring the mixture at room temperature for 20 minutes. The solvent was distilled off under reduced pressure, and the residue was dried using a vacuum pump to give an amorphous solid. The solid was dissolved in N,N-dimethylformamide (3 ml), and 4-methoxybenzyl chloride (664.0 mg, 4.11 mmol) was added thereto followed by stirring the mixture at 80° C. for 20 minutes. After cooling the mixture, a saturated aqueous solution of ammonium chloride was added thereto, and the product was extracted with ethyl acetate. The organic layer was washed with water and with a saturated aqueous solution of sodium chloride, and the solvent was distilled off under reduced pressure to give an oily residue. The residue was dissolved in dichloromethane (10 ml), and 4-(N,N-dimethylamino)pyridine (432.0 mg, 3.54 mmol) and acetyl chloride (277.6 mg, 3.54 mmol) were added thereto at 0° C. The resulting mixture was stirred at the same temperature for 1 hour, and then water was added thereto to stop the reaction. The reaction product was extracted with dichloromethane, and the extract was concentrated under reduced pressure to give an oily residue. The residue was subjected to chromatography on a silica gel (35 g) column (eluent; ethyl acetate:hexane=1:4~1:2) to afford the title compound (521.9 mg, 41% yield) as a colorless oil.

NMR spectrum (400 MHz, CDCl$_3$) δ ppm: 1.48 (1H, dd, J=9, 5 Hz), 1.57 (1H, dd, J=8, 5 Hz), 1.95 (3H, s), 2.25-2.32 (1H, m), 3.81 (3H, s), 3.93 (1H, dd, J=12, 8 Hz), 4.19 (1H, dd, J=12, 6 Hz), 4.55-4.66 (2H, m), 5.11 (1H, d, J=12 Hz), 5.15 (1H, d, J=12 Hz), 5.21 (1H, d, J=11 Hz), 5.29 (1H, dt, J=17, 1 Hz), 5.83 (1H, ddt, J=17, 11, 5 Hz), 6.88 (2H, d, J=8 Hz), 7.30 (2H, d, J=8 Hz)

IR spectrum ν max CHCl$_3$ cm$^{-1}$: 1730, 1516, 1321, 1255, 1132, 1035, 909

Mass spectrum m/z (FAB): 363 (M$^+$+1).

(2) Allyl hydrogen trans-2-(acetoxymethyl)-1,1-cyclopropanedicarboxylate

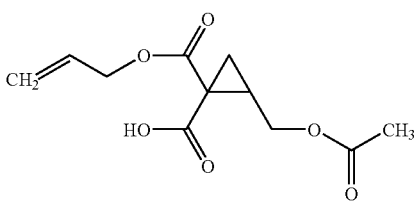

According to a similar procedure to that described in Example 1-(11), allyl 4-methoxybenzyl cis-2-(acetoxymethyl)-1,1-cyclopropanedicarboxylate (521.9 mg, 1.44 mmol) obtained from Example 3-(1), anisole (600 mg, 5.55 mmol), and trifluoroacetic acid (3 ml) were reacted, and the reaction mixture was worked up to afford the title compound (340.1 mg, 97% yield).

NMR spectrum (400 MHz, CDCl$_3$) δ ppm: 1.99 (1H, dd, J=9, 4 Hz), 2.02 (1H, dd, J=9, 5 Hz), 2.05 (3H, s), 2.40-2.48 (1H, m), 4.17 (1H, dd, J=12, 9 Hz), 4.58 (1H, dd, J=12, 5 Hz), 4.64-4.75 (2H, m), 5.34 (1H, d, J=10 Hz), 5.35 (1H, d, J=17 Hz), 5.88 (1H, ddt, J=17, 10, 5 Hz)

IR spectrum ν max CHCl$_3$ cm$^{-1}$: 1758, 1679, 1410, 1373, 1153, 1036

Mass spectrum m/z (FAB): 243 (M$^+$+1).

(3) Allyl (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl cis-2-(acetoxymethyl)-1,1-cyclopropanedicarboxylate

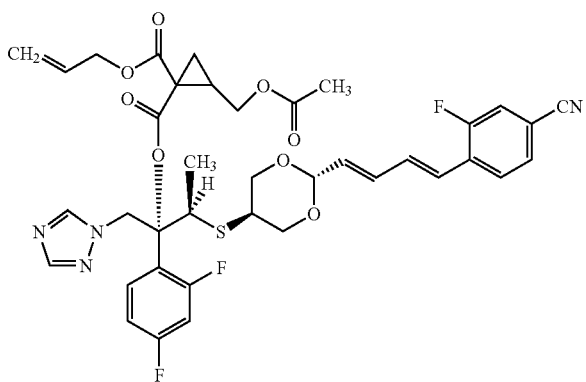

According to a similar procedure to that described in Example 1-(12), allyl hydrogen trans-2-(acetoxymethyl)-1,1-cyclopropanedicarboxylate (333.8 mg, 1.38 mmol) obtained from Example 3-(2) and oxalyl chloride (159.5 mg, 1.26 mmol) were reacted, and the reaction mixture was worked up to afford cis-2-(acetoxymethyl)-1-[(allyloxy)carbonyl]cyclopropanecarbonyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (547.0 mg, 1.01 mmol) described in Reference example 1, sodium hydride (55% dispersion in mineral oil; 57.2 mg, 1.31 mmol), and the crude cis-2-(acetoxymethyl)-1-[(allyloxy)carbonyl]cyclopropanecarbonyl chloride (all the amount obtained above) were reacted in tetrahydrofuran (5 ml), and the reaction mixture was worked up to afford, after extraction, the title compound as a crude oil. The crude oil was subjected to chromatography on a silica gel (50 g) column (eluent; ethyl acetate:hexane=1:1) to afford a mixture (669.3 mg, corresponding to 270.5 mg of the title compound) of the title compound and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile.

(4) Sodium [(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]trans-2-(acetoxymethyl)-1,1-cyclopropanedicarboxylate (title target compound)

According to a similar procedure to that described in Example 1-(13), the mixture of allyl (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]cis-2-(acetoxymethyl)-1,1-cyclopropanedicarboxylate and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (all the amount obtained from Example 3-(3)), bis(triphenylphosphine)dichloropalladium (12.4 mg, 0.018 mmol), and tributyltin hydride (112.9 mg, 0.39 mmol) were reacted, and the reaction mixture was worked up to afford the title compound as a crude oil. The crude oil was subjected to reverse phase column chromatography using Cosmosil 75 $C_{18}$-PREP (Nacalai Tesque, Inc.; 50 g) (eluent; water:methanol=1:1~3:7). The obtained fractions were concentrated, and the residue was lyophilized to afford the title target compound (100.1 mg, 38% yield) as a colorless solid.

NMR spectrum (400 MHz, $CD_3OD$) δ ppm: 1.06 ((1/2)H, dd, J=6, 4 Hz), 1.27-1.31 ((1/2)H, overlapped), 1.29 ((3/2)H, dd, J=7, 2 Hz), 1.32 ((3/2)H, J=7, 1 Hz), 1.43 ((1/2)H, dd, J=9, 4 Hz), 1.44 ((1/2)H, dd, J=9, 4 Hz), 1.86-1.94 ((1/2)H, m), 1.97-2.04 ((1/2)H, m), 2.03 ((3/2)H, s), 2.05 ((3/2)H, s), 2.99 ((1/2)H, tt, J=11, 5 Hz), 3.09 ((1/2)H, tt, J=11, 5 Hz), 3.51 ((1/2)H, t, J=11 Hz), 3.53 ((1/2)H, t, J=11 Hz), 3.54 ((1/2)H, t, J=11 Hz), 3.55 ((1/2)H, t, J=11 Hz), 3.68 ((1/2)H, q, J=7 Hz), 3.73 ((1/2)H, q, J=7 Hz), 4.04-4.30 (4H, m), 5.02 ((1/2)H, d, J=5 Hz), 5.04 ((1/2)H, d, J=5 Hz), 5.35 ((1/2)H, d, J=15 Hz), 5.41 ((1/2)H, d, J=15 Hz), 5.48 ((1/2)H, dd, J=15, 2 Hz), 5.53 ((1/2)H, d, J=15 Hz), 5.87 (1H, d, J=15, 5 Hz), 6.59 (1H, dd, J=15, 11 Hz), 6.76 (1H, d, J=16 Hz), 6.90-7.02 (2H, m), 7.09 (1H, dd, J=16, 11 Hz), 7.49-7.54 (2H, m), 7.78 (1H, t, J=8 Hz), 7.86 ((1/2)H, s), 7.93 ((1/2)H, dt, J=9, 7 Hz), 7.97 ((1/2)H, s), 8.39 ((1/2)H, dt, J=9, 7 Hz), 8.58 ((1/2)H, s), 8.68 ((1/2)H, s)

IR spectrum ν max KBr $cm^{-1}$: 3430, 2231, 1733, 1612, 1504, 1370, 1243, 1140, 1051, 972

Mass spectrum m/z (FAB): 749 ($M^+$+1).

Example 4

Disodium 5-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Disodium Salt of Example Number 5-17)

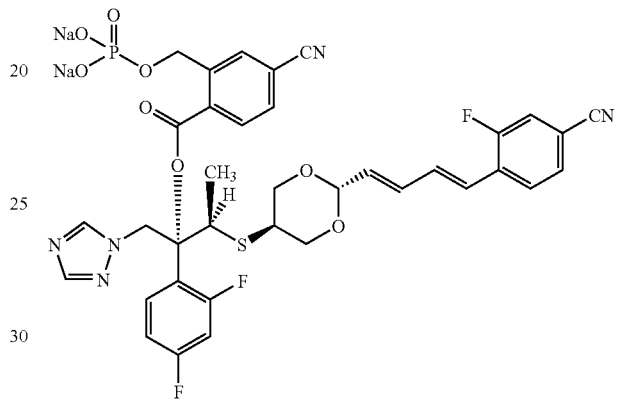

(1) Methyl 2,4-bis(acetoxymethyl)benzoate

According to a similar procedure to that described in Example 1-(5), methyl 2,4-bis(bromomethyl)benzoate (described in Chem. Ber., 127, 2081 (1994); 13.3 g, 41.3 mmol) and sodium acetate (16.4 g, 200 mmol) were reacted, and the reaction mixture was worked up to afford, after extraction, the title compound as a crude product. The crude product was subjected to chromatography on a silica gel (200 g) column (eluent; ethyl acetate:hexane=3:17~3:5) to afford the title compound (6.35 g, 55% yield) as an oil.

NMR spectrum (400 MHz, $CDCl_3$) δ ppm: 2.14 (3H, s), 2.16 (3H, s), 3.91 (3H, s), 5.15 (2H, s), 5.52 (2H, s), 7.37 (1H, d, J=8 Hz), 7.46 (1H, s), 7.99 (1H, d, J=8 Hz)

IR spectrum ν max $CHCl_3$ $cm^{-1}$: 1737, 1255, 1056

Mass spectrum m/z (FAB): 281 ($M^+$+1).

(2) 5-(Hydroxymethyl)-1 (3H)-isobenzofuranone

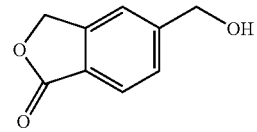

According to a similar procedure to that described in Example 1-(6), methyl 2,4-bis(acetoxymethyl)benzoate (6.35 g, 22.7 mmol) obtained from Example 4-(1) and potassium carbonate (373.2 mg, 2.7 mmol) were reacted, and the reaction mixture was worked up to afford, after extraction, the title compound as a crude product. The crude product was subjected to chromatography on a silica gel (200 g) column (eluent; ethyl acetate:dichloromethane=0:1~1:10) to afford the title compound (2.94 g, 79% yield) as a colorless solid (mp. 126° C.).

NMR spectrum (400 MHz, CDCl$_3$) δ ppm: 4.87 (2H, s), 5.33 (2H, s), 7.51 (1H, d, J=8 Hz), 7.55 (1H, s), 7.92 (1H, d, J=8 Hz)

IR spectrum ν max KBr cm$^{-1}$: 3422, 1738, 1138, 1076, 768

Mass spectrum m/z (EI): 164 (M$^+$).

(3) 1-Oxo-1,3-dihydroisobenzofuran-5-carbaldehyde 5-(Hydroxymethyl)-1 (3H)-isobenzofuranone (2.94 g, 17.9 mmol) obtained from Example 4-(2) was dissolved in tetrahydrofuran (100 ml), and activated manganese dioxide (31 g) was added thereto. The mixture was stirred at room temperature for 30 minutes, and an additional amount of activated manganese dioxide (3 g) was added thereto. The resulting mixture was stirred for a further 30 minutes and then filtered. The solid filtered off was washed with tetrahydrofuran, and the washings were combined with the previous filtrate, then the combined solution was concentrated under reduced pressure to give a solid residue. The residue was subjected to chromatography on a silica gel (150 g) column (eluent; ethyl acetate:dichloromethane=0:1~1:10). The eluate was concentrated under reduced pressure to afford a solid compound, which was washed with a mixed solvent of ethyl acetate-hexane (1:2) to afford the title compound (2.01 g, 69% yield) as a solid (mp. 160° C.)

NMR spectrum (400 MHz, CDCl$_3$) δ ppm: 5.43 (2H, s), 8.03 (1H, s), 8.06 (1H, d, J=8 Hz), 8.11 (1H, d, J=8 Hz), 10.18 (1H, s)

IR spectrum ν max KBr cm$^{-1}$: 1758, 1699, 1355, 1323, 1049, 993

Mass spectrum m/z (EI): 162 (M$^+$).

(4) 1-Oxo-1,3-dihydroisobenzofuran-5-carbonitrile

1-Oxo-1,3-dihydroisobenzofuran-5-carbaldehyde (2.01 g, 12.4 mmol) obtained from Example 4-(3) was suspended in tetrahydrofuran (50 ml), and after the suspension was cooled to 0° C., hydroxylamine hydrochloride (1.04 g, 14.9 mmol) in an aqueous solution of sodium hydroxide (1.0N; 14.8 ml, 14.8 mmol) was added thereto. The resulting mixture was stirred at room temperature for 1 hour, and then concentrated to one third of the volume under reduced pressure. To the concentrated solution was added water, and the product was extracted with ethyl acetate. The combined organic layers were washed with a saturated aqueous solution of sodium chloride, and the solvent was distilled off under reduced pressure to give crude 1-oxo-1,3-dihydroisobenzofuran-5-carbaldehyde oxime as a solid. The crude product was dissolved in tetrahydrofuran (50 ml), and the solution was cooled to 0° C., then triethylamine (3.04 g, 30 mmol) and anhydrous trifluoroacetic acid (3.13 g, 14.9 mmol) were added thereto. The resulting mixture was stirred at the same temperature for 30 minutes, and then warmed to room temperature followed by stirring for 30 minutes more. The reaction mixture was cooled again to 0° C., and a saturated aqueous solution of sodium hydrogen carbonate was added thereto. The reaction product was extracted with ethyl acetate, and the combined organic layers were washed with a saturated aqueous solution of sodium chloride. The extract was concentrated under reduced pressure to give a solid residue. The residue was subjected to chromatography on a silica gel (150 g) column (eluent; ethyl acetate:dichloromethane=0:1~1:10) to afford the title compound (1.57 g, 79% yield) as a solid (mp. 200-201° C.).

NMR spectrum (400 MHz, CDCl$_3$) δ ppm: 5.40 (2H, s), 7.84 (1H, s), 7.85 (1H, d, J=9 Hz), 8.12 (1H, d, J=9 Hz)

IR spectrum ν max KBr cm$^{-1}$: 1760, 1055, 1003, 681

Mass spectrum m/z (EI): 159 (M$^+$).

(5) 4-Methoxybenzyl 2-[[bis(allyloxy)phosphoryl]oxymethyl]-4-cyanobenzoate

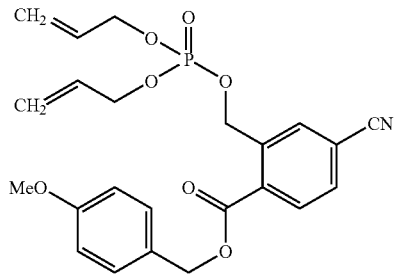

1-Oxo-1,3-dihydroisobenzofuran-5-carbonitrile (1.56 g, 9.78 mmol) obtained from in Example 4-(4) was suspended in tetrahydrofuran (15 ml), and an aqueous solution of sodium hydroxide (1.008N; 9.70 ml, 9.78 mmol) was added thereto. The mixture was stirred at room temperature for 15 minutes and the solvent was distilled off under reduced pressure. The residue was dried using a vacuum pump to give an amorphous solid. The solid was dissolved in N,N-dimethylformamide (30 ml), and 4-methoxybenzyl chloride (1.53 g, 9.78 mmol) was added thereto, and then the mixture was stirred at 80° C. for 5 minutes. After the mixture was cooled to 0° C., a saturated aqueous solution of ammonium chloride was added thereto, and the product was extracted with ethyl acetate. The organic layer was washed with water and with a saturated aqueous solution of sodium chloride, and the solvent was distilled off under reduced pressure to give an oily residue. The residue was dissolved in dichloromethane (50 ml), and tetrazole (1.40 g, 20 mmol) and bis(allyloxy)(diisopropylamino)phosphine (Tetrahedron Lett., 30, 4219 (1989); 3.43 g, 14 mmol) were added thereto at 0° C., and then the resulting mixture was stirred at the same temperature for 5 minutes. The mixture was warmed to room temperature and stirred for 20 minutes, and then methanol (0.5 ml) was added thereto. The mixture was stirred for 10 minutes and cooled to 0° C., and tert-butyl hydroperoxide (80% di-tert-butyl peroxide solution; Merck; 2.7 g, 24 mmol) was added thereto, and then the reaction mixture was warmed to room temperature followed by stirring 20 minutes. A saturated aqueous solution of sodium hydrogen carbonate and an aqueous solution of sodium thiosulfate were added to the reaction mixture, and the resulting mixture was stirred for 10 minutes and partitioned between ethyl acetate and water. The organic layers were combined and the solvent was distilled off under reduced pressure to give a residue. The residue was subjected to chromatography on a silica gel (120 g) column (eluent; ethyl acetate:hexane=2:3) to afford a mixture of a solid and an oily material. The mixture was washed with a mixed solvent of ethyl acetate-hexane, and the washings were concentrated to give a residue. The residue was subjected to chromatography on a silica gel (50 g) column (eluent; ethyl acetate:hexane=2:3) to afford the title compound (1.18 g, 26% yield) as a colorless oil.

NMR spectrum (400 MHz, CDCl$_3$) δ ppm: 3.82 (3H, s), 4.58-4.62 (4H, m), 5.29 (2H, dd, J=10, 1 Hz), 5.29 (2H, s), 5.39 (2H, dd, J=17, 1 Hz), 5.53 (2H, d, J=7 Hz), 5.96 (2H, ddt, J=17, 10, 5 Hz), 6.92 (2H, d, J=9 Hz), 7.37 (2H, d, J=9 Hz), 7.65 (1H, dd, J=8, 2 Hz), 8.00 (1H, br s), 8.09 (1H, d, J=8 Hz)

IR spectrum ν max CHCl$_3$ cm$^{-1}$: 2237, 1721, 1613, 1516, 1266, 1031, 990

Mass spectrum m/z (FAB): 458 (M$^+$+1).

(6) (1R,2R)-2-[[trans-2-[(1E,3E)-4-(4-Cyano-2-fluorophenyl)-1,3-butadienyl]-1,3-dioxan-5-yl]thio]1-(2,4-difluorophenyl)-1-[(1H-1,2,4-triazol-1-yl)methyl]propyl 2-[[bis(allyloxy)phosphoryl]oxymethyl]-4-cyanobenzoate robenzonitrile (759.6 mg, 1.40 mmol) described in Reference example 1, sodium hydride (55% dispersion in mineral oil; 73.3 mg, 1.68 mmol), and the crude 2-[[bis(allyloxy)phosphoryl]oxymethyl]-4-cyanobenzoyl chloride obtained above were reacted in tetrahydrofuran (8 ml) and the reaction mixture was worked up to afford, after extraction, the title compound as a crude oil. The crude oil was subjected to chromatography on a silica gel (60 g) column (eluent; ethyl acetate:hexane=2:1~5:1) to afford the title compound (656.9 mg, 54% yield) as a pale yellow amorphous solid.

NMR spectrum (400 MHz, CDCl$_3$) δ ppm: 1.43 (3H, dd, J=7, 2 Hz), 3.01 (1H, tt, J=11, 5 Hz), 3.48 (1H, t, J=11 Hz), 3.52 (1H, t, J=11 Hz), 4.01 (1H, q, J=7 Hz), 4.09 (1H, ddd, J=11, 5, 2 Hz), 4.17 (1H, ddd, J=11, 5, 2 Hz), 4.56-4.62 (4H, m), 4.99 (1H, d, J=4 Hz), 5.29 (2H, d, J=11 Hz), 5.38 (2H, dd, J=17, 1 Hz), 5.45-5.50 (4H, m), 5.83 (1H, dd, J=15, 4 Hz), 5.95 (2H, ddt, J=17, 11, 5 Hz), 6.56 (1H, dd, J=15, 10 Hz), 6.75 (1H, d, J=16 Hz), 6.93-6.96 (2H, m), 6.94 (1H, dd, J=16, 10 Hz), 7.33-7.39 (2H, m), 7.40 (1H, dd, J=8, 1 Hz),

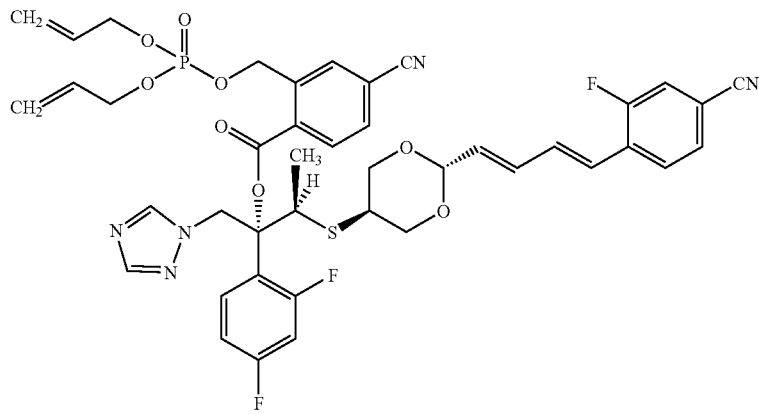

A mixture of 4-methoxybenzyl 2-[[bis(allyloxy)phosphoryl]oxymethyl]-4-cyanobenzoate (949.1 mg, 2.07 mmol) obtained from Example 4-(5) and anisole (1.0 g, 9.2 mmol) was cooled to 0° C., and trifluoroacetic acid (5 ml) was added thereto. The resulting mixture was warmed to room temperature and allowed to stand for 15 minutes, diluted with toluene, and concentrated under reduced pressure to eliminate the volatile components (repeated three times). Hexane was added to the residue, and then the supernatant solution was removed to give crude 2-[[bis(allyloxy)phosphoryl]oxymethyl]-4-cyanobenzoic acid. This crude product was dissolved in dichloromethane (20 ml), and oxalyl chloride (1.27 g, 10 mmol) and N,N-dimethylformamide (15 μl) were added thereto at 0° C. The mixture was warmed to room temperature and stirred for 30 minutes, and the solvent was distilled off under reduced pressure. The residue was diluted with toluene, and the solution was concentrated under reduced pressure to eliminate the volatile components (repeated three times), and crude 2-[[bis(allyloxy)phosphoryl]oxymethyl]-4-cyanobenzoyl chloride was obtained.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluo- 7.58 (1H, t, J=8 Hz), 7.69 (1H, dd, J=8, 1 Hz), 7.82 (1H, d, J=8 Hz), 7.87 (1H, s), 7.91 (1H, s), 8.03 (1H, s)

IR spectrum ν max CHCl$_3$ cm$^{-1}$: 2235, 1729, 1616, 1504, 1277, 1141, 1028, 991

Mass spectrum m/z (FAB): 862 (M$^+$+1)

(7) Disodium 5-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (title target compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-4-cyanobenzoate (643.1 mg, 0.75 mmol) obtained from Example 4-(6), bis(triphenylphosphine)dichloropalladium (26.2 mg, 0.037 mmol), and tributyltin hydride (534 mg, 1.83 mmol) were reacted, and the reaction mixture was worked up to afford the title target compound as a crude oil. The crude oil was subjected to reverse phase column chromatography using Cosmosil 75 $C_{18}$-PREP (Nacalai Tesque, Inc.; 25 g) (eluent; water:methanol=4:6~3:7). The obtained fractions were concentrated, and the residue was lyophilized to afford the title target compound (488.3 mg, 79% yield) as a colorless solid.

NMR spectrum (400 MHz, $CD_3OD$) δ ppm: 1.40 (3H, dd, J=7, 1 Hz), 3.02 (1H, tt, J=11, 5 Hz), 3.45 (1H, t, J=11 Hz), 3.53 (1H, t, J=11 Hz), 4.00 (1H, q, J=7 Hz), 4.02 (1H, ddd, J=11, 5, 2 Hz), 4.16 (1H, ddd, J=11, 5, 2 Hz), 5.01 (1H, d, J=4 Hz), 5.21 (1H, dd, J=17, 5 Hz), 5.36 (1H, dd, J=17, 6 Hz), 5.55 (2H, s), 5.86 (1H, dd, J=15, 4 Hz), 6.57 (1H, dd, J=15, 11 Hz), 6.80 (1H, d, J=15 Hz), 7.02-7.08 (2H, m), 7.10 (1H, dd, J=15, 11 Hz), 7.49-7.58 (3H, m), 7.66 (1H, dd, J=8, 1 Hz), 7.80 (1H, t, J=8 Hz), 7.83 (1H, d, J=8 Hz), 7.96 (1H, s), 8.37 (1H, s), 8.50 (1H, s)

IR spectrum ν max KBr $cm^{-1}$: 3422, 2232, 1731, 1615, 1503, 1276, 1257, 1140, 1053, 977

Mass spectrum m/z (FAB): 826 ($M^+$+1).

Specific rotation $[α]_D^{25}$ +31.7° (c=0.97, MeOH)

Example 5

Disodium 4-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Disodium Salt of Example Number 5-16)

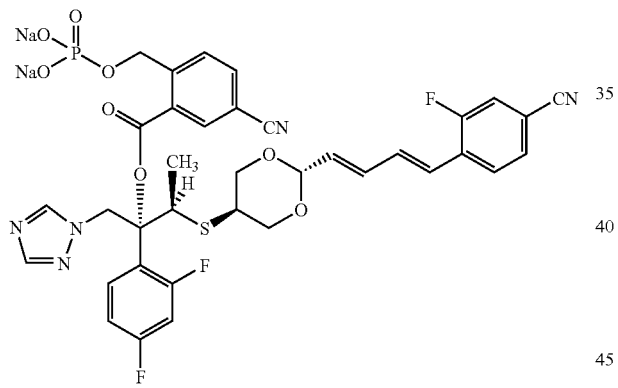

(1) 1-Oxo-1,3dihydroisobenzofuran-6-carbaldehyde

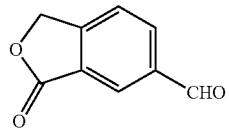

According to a similar procedure to that described in Example 4-(3), 6-(hydroxymethyl)-1 (3H)-isobenzofuranone (3.25 g, 20.8 mmol) obtained from Example 1-(4) or Example 1-(6) and activated manganese dioxide (33 g) were reacted, and the reaction mixture was worked up to afford the title compound as a crude solid. The crude solid was subjected to chromatography on a silica gel (40 g) column (eluent; ethyl acetate) to afford the title compound (2.45 g, 76% yield) as a solid (mp. 134° C.)

NMR spectrum (400 MHz, $CDCl_3$) δ ppm: 5.42 (2H, s), 7.69 (1H, d, J=8 Hz), 8.25 (1H, dd, J=8, 1 Hz), 8.42 (1H, s), 10.14 (1H, s)

IR spectrum ν max KBr $cm^{-1}$: 1764, 1707, 1154, 1120, 1000, 770

Mass spectrum m/z (EI): 162 ($M^+$).

(2) 1-Oxo-1,3-dihydroisobenzofuran-6-carbonitrile

According to a similar procedure to that described in Example 4-(4), 1-oxo-1,3-dihydroisobenzofuran-6-carbaldehyde (2.42 g, 14.9 mmol) obtained from Example 5-(1), hydroxylamine hydrochloride (1.35 g, 19.4 mmol), and an aqueous solution of sodium hydroxide (1.0N; 19.3 ml, 19.3 mmol) were reacted, and the reaction mixture was worked up to afford 1-oxo-1,3-dihydroisobenzofuran-6-carbaldehyde oxime as a crude solid. According to a similar procedure to that described in Example 4-(4), the crude product obtained above, triethylamine (3.92 g, 39 mmol), and anhydrous trifluoroacetic acid (4.08 g, 19.4 mmol) were reacted, and the reaction mixture was worked up to afford, after extraction and concentration, a solid residue. The residue was subjected to chromatography on a silica gel (50 g) column (eluent; ethyl acetate:dichloromethane=0:1~1:10) to afford the title compound (1.67 g, 70% yield) as a solid (mp. 195-196° C.).

NMR spectrum (400 MHz, $CDCl_3$) δ ppm: 5.42 (2H, s), 7.67 (1H, d, J=8 Hz), 7.97 (1H, dd, J=8, 1 Hz), 8.24 (1H, br s)

IR spectrum ν max KBr $cm^{-1}$: 2238, 1765, 1464, 1134, 1056, 1006, 771

Mass spectrum m/z (EI): 159 ($M^+$)

(3) 4-Methoxybenzyl 2-[[bis(allyloxy)phosphoryl]oxymethyl]-5-cyanobenzoate

According to a similar procedure to that described in Example 4-(5), 1-oxo-1,3-dihydroisobenzofuran-6-carbonitrile (1.66 g, 10.5 mmol) obtained from Example 5-(2) was reacted with an aqueous solution of sodium hydroxide (1.008N; 10.38 ml, 10.46 mmol), 4-methoxybenzyl chloride (1.64 g, 10.5 mmol), tetrazole (1.47 g, 20.9 mmol), bis(allyloxy)(diisopropylamino)phosphine (Tetrahedron Lett., 30, 4219 (1989); 3.68 g, 15 mmol), and tert-butyl hydroperoxide (80% di-tert-butyl peroxide solution; Merck; 2.7 g, 24 mmol), and the reaction mixture was worked up to afford, after extraction, a residue as a mixture of a solid (starting material) and an oil. The residue was washed with a mixed solvent of ethyl acetate-hexane, and the washings were concentrated to give a residue. The residue was subjected to chromatography on a silica gel (40 g) column (eluent; ethyl acetate:hexane=1:1~3:2) to afford a mixture of a solid and an oily material. The mixture was washed further with a mixed solvent of ethyl acetate-hexane, and the washings were concentrated to give a residue. The residue was subjected to chromatography on a silica gel (40 g) column (eluent; ethyl acetate:hexane=2:3) to afford the title compound (737.9 mg, 15% yield) as a colorless oil.

NMR spectrum (400 MHz, $CDCl_3$) δ ppm: 3.83 (3H, s), 4.57-4.61 (4H, m), 5.27 (2H, dd, J=11, 1 Hz), 5.29 (2H, s), 5.37 (2H, dd, J=17, 1 Hz), 5.58 (2H, d, J=7 Hz), 5.94 (2H, ddt, J=17, 11, 5 Hz), 6.94 (2H, d, J=9 Hz), 7.38 (2H, d, J=9 Hz), 7.83 (1H, dd, J=8, 1 Hz), 7.87 (1H, d, J=8 Hz), 8.30 (1H, d, J=1 Hz)

IR spectrum ν max $CHCl_3$ $cm^{-1}$: 2236, 1722, 1516, 1255, 1175, 1031

Mass spectrum m/z (FAB): 458 ($M^+$+1).

(4) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-cyanobenzoate

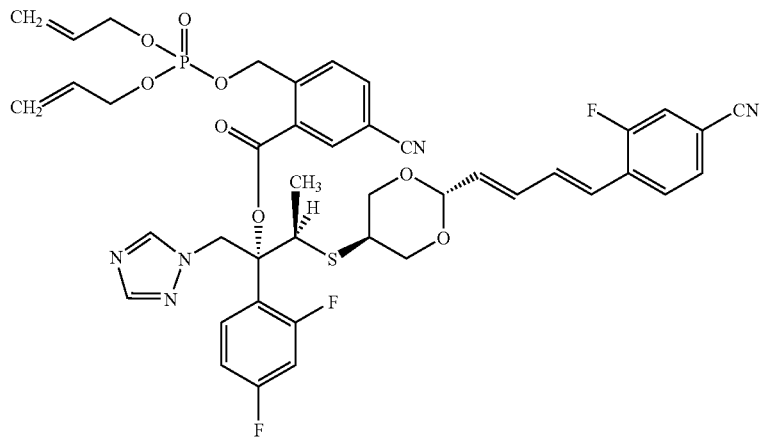

According to a similar procedure to that described in Example 4-(6), 4-methoxybenzyl 2-[[bis(allyloxy)phosphoryl]oxymethyl]-5-cyanobenzoate (737 mg, 1.61 mmol) obtained from Example 5-(3), anisole (1.0 g, 9.2 mmol), and trifluoroacetic acid (5 ml) were reacted, and the reaction mixture was worked up to afford 2-[[bis(allyloxy)phosphoryl]oxymethyl]-5-cyanobenzoic acid as a crude product. According to a similar procedure to that described in Example 4-(6), the crude product obtained above, oxalyl chloride (1.27 g, 10 mmol), and N,N-dimethylformamide (15 μl) were reacted, and the reaction mixture was worked up to afford 2-[[bis(allyloxy)phosphoryl]oxymethyl]-5-cyanobenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (651.1 mg, 1.20 mmol) described in Reference example 1, sodium hydride (55% dispersion in mineral oil; 62.8 mg, 1.44 mmol), and the crude 2-[[bis(allyloxy)phosphoryl]oxymethyl]-5-cyanobenzoyl chloride obtained above were reacted in tetrahydrofuran (8 ml), and the reaction mixture was worked up to afford, after extraction, the title compound as a crude oil. The crude oil was subjected to chromatography on a silica gel (60 g) column (eluent; ethyl acetate:hexane=2:1~3:1) to afford the title compound (237.5 mg, 23% yield) as a pale yellow amorphous solid.

NMR spectrum (400 MHz, CDCl$_3$) δ ppm: 1.45 (3H, dd, J=7, 2 Hz), 3.02 (1H, tt, J=12, 5 Hz), 3.54 (1H, t, J=12 Hz), 3.55 (1H, t, J=12 Hz), 4.00 (1H, q, J=7 Hz), 4.14-4.19 (2H, m), 4.58-4.61 (4H, m), 5.01 (1H, d, J=4 Hz), 5.26 (2H, dd, J=10, 1 Hz), 5.36 (2H, d, J=17 Hz), 5.47 (2H, s), 5.52 (2H, d, J=7 Hz), 5.87 (1H, dd, J=15, 4 Hz), 5.94 (2H, ddt, J=17, 10, 6 Hz), 6.58 (1H, dd, J=15, 11 Hz), 6.73 (1H, d, J=16 Hz), 6.90-7.00 (3H, m), 7.31-7.37 (2H, m), 7.40 (1H, dd, J=8, 1 Hz), 7.57 (1H, t, J=8 Hz), 7.88-7.92 (4H, m), 8.18 (1H, s)

IR spectrum ν max KBr cm$^{-1}$: 2232, 1731, 1615, 1504, 1276, 1142, 1027

Mass spectrum m/z (FAB): 862 (M$^+$+1)

(5) Disodium 4-cyano-2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-cyanobenzoate (230.5 mg, 0.27 mmol) obtained from Example 5-(4), bis(triphenylphosphine)dichloropalladium (9.4 mg, 0.013 mmol), and tributyltin hydride (155.4 mg, 0.53 mmol) were reacted, and the reaction mixture was worked up to afford the title target compound as an oil. The crude oil was subjected to reverse phase column chromatography using Cosmosil 75 C$_{18}$-PREP (Nacalai Tesque, Inc.; 25 g) (eluent; water:methanol=4:6~3:7). The obtained fractions were concentrated, and the residue was lyophilized to afford the title target compound (86.0 mg, 39% yield) as a colorless solid.

NMR spectrum (400 MHz, CD$_3$OD) δ ppm: 1.41 (3H, dd, J=7, 1 Hz), 3.04 (1H, tt, J=11, 5 Hz), 3.48 (1H, t, J=11 Hz), 3.54 (1H, t, J=11 Hz), 4.01 (1H, q, J=7 Hz), 4.05 (1H, ddd, J=11, 5, 2 Hz), 4.18 (1H, ddd, J=11, 5, 2 Hz), 5.01 (1H, d, J=4 Hz), 5.25 (1H, dd, J=18, 6 Hz), 5.39 (1H, dd, J=18, 5 Hz), 5.52 (1H, dd, J=15, 3 Hz), 5.58 (1H, d, J=15 Hz), 5.90 (1H, dd, J=15, 4 Hz), 6.58 (1H, dd, J=15, 11 Hz), 6.79 (1H, d, J=16 Hz), 7.02-7.12 (3H, m), 7.50-7.54 (3H, m), 7.78 (1H, t, J=8 Hz), 7.93 (1H, dd, J=8, 2 Hz), 8.01 (2H, s), 8.31 (1H, d, J=8 Hz), 8.40 (1H, s)

IR spectrum ν max KBr cm$^{-1}$: 3423, 2232, 1729, 1615, 1504, 1141, 1054, 976

Mass spectrum m/z (FAB): 826 (M$^+$+1).

Specific rotation [α]$_D^{25}$ +31.2° (c=0.73, MeOH).

Example 6

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-fluorobenzyl phosphate (Disodium Salt of Example Number 5-22)

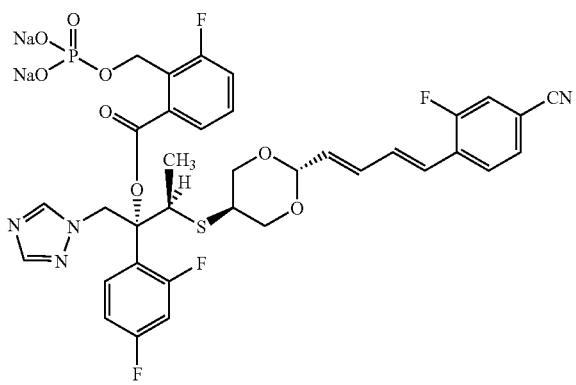

(1) 4-Methoxybenzyl 2-[[bis(allyloxy)phosphoryl]oxymethyl]-3-flourobenzoate

According to a similar procedure to that described in Example 4-(5), 4-fluoro-1(3H)-isobenzofuranone (described in Tetrahedron, 54, 7485 (1998); 1.52 g, 10 mmol) was reacted with an aqueous solution of sodium hydroxide (1.008N; 10 ml, 10 mmol), 4-methoxybenzyl chloride (1.57 g, 10 mmol), tetrazole (1.40 g, 20 mmol), bis(allyloxy)(diisopropylamino)phosphine (described in Tetrahedron Lett., 30, 4219 (1989); 3.43 g, 14 mmol), and tert-butyl hydroperoxide (80% di-tert-butyl peroxide solution; Merck; 2.7 g, 24 mmol), and the reaction mixture was worked up to afford, after extraction, an oily residue. The residue was subjected to chromatography on a silica gel (100 g) column (eluent; ethyl acetate:hexane=2:3) to afford an oily mixture. The mixture was further subjected to chromatography on a silica gel (50 g) column (eluent; ethyl acetate:hexane=1:2) to afford the title compound (1.40 g, 31% yield) as a colorless oil.

NMR spectrum (400 MHz, CDCl$_3$) δ ppm: 3.82 (3H, s), 4.49-4.53 (4H, m), 5.22 (2H, d, J=10, 1 Hz), 5.31 (2H, s), 5.33 (2H, d, J=17, 1 Hz), 5.52 (2H, dd, J=7, 1 Hz), 5.91 (2H, ddt, J=17, 10, 5 Hz), 6.91 (2H, d, J=8 Hz), 7.25 (1H, dt, J=1, 8 Hz), 7.37-7.42 (1H, m), 7.39 (2H, d, J=8 Hz), 7.72 (1H, d, J=8 Hz)

IR spectrum ν max CHCl$_3$ cm$^{-1}$: 1724, 1516, 1462, 1272, 1171, 1029

Mass spectrum m/z (FAB): 451 (M$^+$+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2[[bis(allyloxy)phosphoryl]oxymethyl]-3-fluorobenzoate

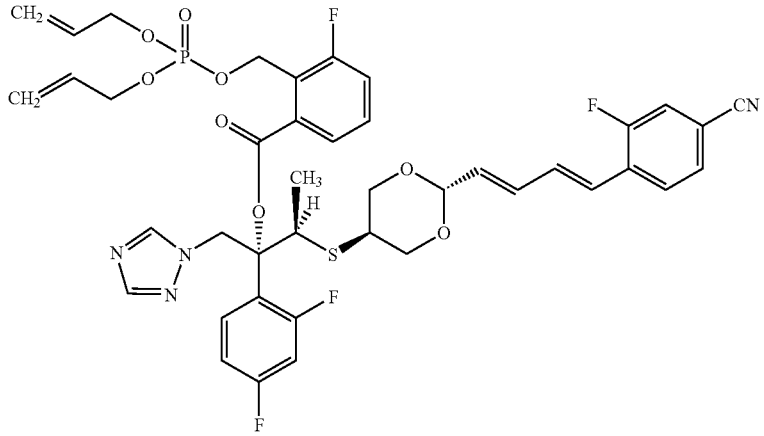

According to a similar procedure to that described in Example 4-(6), 4-methoxybenzyl 2-[[bis(allyloxy)phosphoryl]oxymethyl]-3-fluorobenzoate (1.40 g, 3.12 mmol) obtained in Example 6-(1) was reacted with anisole (1.4 g, 12.9 mmol) and trifluoroacetic acid (5 ml), and the reaction mixture was worked up to afford 2-[[bis(allyloxy)phosphoryl]oxymethyl]-3-fluorobenzoic acid as a crude product. According to a similar procedure to that described in Example 4-(6), the crude product obtained above, oxalyl chloride (1.98 g, 15.6 mmol), and N,N-dimethylformamide (15 µl) were reacted, and the reaction mixture was worked up to afford 2-[[bis(allyloxy)phosphoryl]oxymethyl]-3-fluorobenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.09 g, 2.0 mmol) described in Reference example 1, sodium hydride (55% dispersion in mineral oil; 104.7 mg, 2.4 mmol), and the crude 2-[[bis(allyloxy)phosphoryl]oxymethyl]-3-fluorobenzoyl chloride obtained above were reacted in tetrahydrofuran (10 ml), and the reaction mixture was worked up to afford, after extraction, the title compound as a crude oil. The crude oil was subjected to chromatography on a silica gel (75 g) column (eluent; ethyl acetate:hexane=2:1~3:1) to afford the title compound (876.0 mg, 51% yield) as a pale yellow amorphous solid.

NMR spectrum (400 MHz, CDCl$_3$) δ ppm: 1.44 (3H, dd, J=7, 2 Hz), 3.03 (1H, tt, J=12, 5 Hz), 3.46 (1H, t, J=12 Hz), 3.51 (1H, t, J=12 Hz), 3.99 (1H, q, J=7 Hz), 4.09 (1H, ddd, J=12, 5, 2 Hz), 4.18 (1H, ddd, J=12, 5, 2 Hz), 4.44-4.56 (4H, m), 4.97 (1H, d, J=4 Hz), 5.21 (2H, d, J=10 Hz), 5.31 (2H, d, J=17 Hz), 5.43-5.54 (4H, m), 5.83 (1H, dd, J=15, 4 Hz), 5.89 (2H, ddt, J=17, 10, 5 Hz), 6.55 (1H, dd, J=15, 11 Hz), 6.73 (1H, d, J=15 Hz), 6.87-6.93 (3H, m), 7.29-7.35 (2H, m), 7.39-7.49 (4H, m), 7.57 (1H, t, J=8 Hz), 7.93 (1H, s), 8.00 (1H, s)

IR spectrum ν max CHCl$_3$ cm$^{-1}$: 2233, 1732, 1504, 1462, 1276, 1141, 1023, 991.

Mass spectrum m/z (FAB): 855 (M$^+$+1).

(3) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-fluorobenzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-3-fluorobenzoate (860 mg, 1.0 mmol) obtained from Example 6-(2) was reacted with bis(triphenylphosphine)dichloropalladium (35.1 mg, 0.05 mmol), and tributyltin hydride (786.2 mg, 2.70 mmol), and the reaction mixture was worked up to afford the title target compound as a crude oil. The crude oil was subjected to reverse phase column chromatography using Cosmosil 75 C$_{18}$-PREP (Nacalai Tesque, Inc.; 40 g) (eluent; water:methanol=4:6~3:7). The obtained fractions were concentrated, and the residue was lyophilized to afford the title target compound (614.2 mg, 75% yield) as a colorless solid.

NMR spectrum (400 MHz, CD$_3$OD) δ ppm: 1.43 (3H, dd, J=7, 1 Hz), 2.98 (1H, tt, J=11, 5 Hz), 3.48 (1H, t, J=11 Hz), 3.53 (1H, t, J=11 Hz), 4.03 (1H, q, J=7 Hz), 4.05 (1H, ddd, J=11, 5, 2 Hz), 4.14 (1H, ddd, J=11, 5, 2 Hz), 5.00 (1H, d, J=4 Hz), 5.25 (1H, dd, J=12, 5 Hz), 5.32 (1H, ddd, J=12, 5, 2 Hz), 5.52 (1H, dd, J=15, 3 Hz), 5.69 (1H, d, J=15 Hz), 5.84 (1H, dd, J=15, 4 Hz), 6.56 (1H, dd, J=15, 10 Hz), 6.78 (1H, d, J=15 Hz), 7.00-7.13 (2H, m), 7.09 (1H, s, J=15, 10 Hz), 7.34 (1H, t, J=9 Hz), 7.42 (1H, td, J=8, 5 Hz), 7.49-7.54 (2H, m), 7.62-7.70 (2H, m), 7.78 (1H, t, J=8 Hz), 7.96 (1H, s), 8.70 (1H, s)

IR spectrum ν max KBr cm$^{-1}$: 2230, 1731, 1614, 1504, 1275, 1142, 1048, 975

Mass spectrum m/z (FAB): 819 (M$^+$+1)

Specific rotation [α]$_D^{25}$ +5.4° (c=0.91, MeOH)

Example 7

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-5-fluorobenzyl phosphate (Disodium Salt of Example Number 5-21)

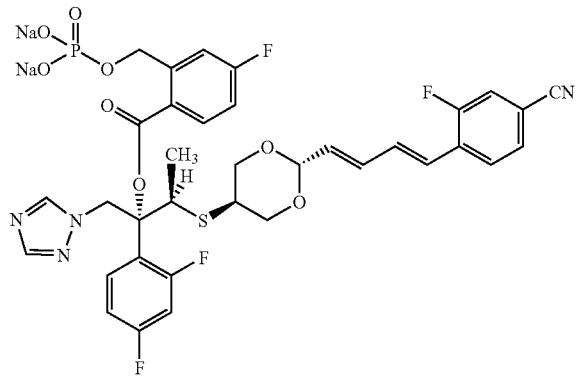

(1) 4-Methoxybenzyl 2-[[bis(allyloxy)phosphoryl]oxymethyl]-4-flourobenzoate

According to a similar procedure to that described in Example 4-(5), 5-fluoro-1(3H)-isobenzofuranone (described in Tetrahedron, 44, 4591 (1988); 1.52 g, 10 mmol) was reacted with an aqueous solution of sodium hydroxide (1.008N; 10 ml, 10 mmol), 4-methoxybenzyl chloride (1.57 g, 10 mmol), tetrazole (1.40 g, 20 mmol), bis(allyloxy)(diisopropylamino)phosphine (described in Tetrahedron Lett., 30, 4219 (1989); 3.05 g, 12.4 mmol), and tert-butyl hydroperoxide (80% di-tert-butyl peroxide solution; Merck; 2.7 g, 24 mmol), and the reaction mixture was worked up to afford, after extraction, an oily residue. The residue was subjected to chromatography on a silica gel (75 g) column (eluent; ethyl acetate:hexane=2:1~3:1) to afford an oily mixture. The mixture was further subjected to chromatography on a silica gel (50 g) column (eluent; ethyl acetate: hexane=1:4~1:2) to afford the title compound (2.07 g, 46% yield) as a colorless oil.

NMR spectrum (400 MHz, CDCl$_3$) δ ppm: 3.82 (3H, s), 4.58-4.61 (4H, m), 5.26 (2H, s), 5.26 (2H, dq, J=11, 1 Hz), 5.38 (2H, dq, J=17, 1 Hz), 5.54 (2H, d, J=7 Hz), 5.95 (2H, ddt, J=17, 11, 5 Hz), 6.91 (2H, d, J=9 Hz), 7.02 (1H, td, J=9.2 Hz), 7.37 (2H, d, J=9 Hz), 7.43 (1H, dd, J=10, 2 Hz), 8.06 (1H, dd, J=9, 6 Hz)

IR spectrum ν max CHCl$_3$ cm$^{-1}$: 1714, 1613, 1590, 1516, 1261, 1120, 1031

Mass spectrum m/z (FAB): 451 (M$^+$+1).

(2) (1R,2R)-2-[[trans-2-[(1E,3E)-4-(4-Cyano-2-fluorophenyl]-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-4-fluorobenzoate

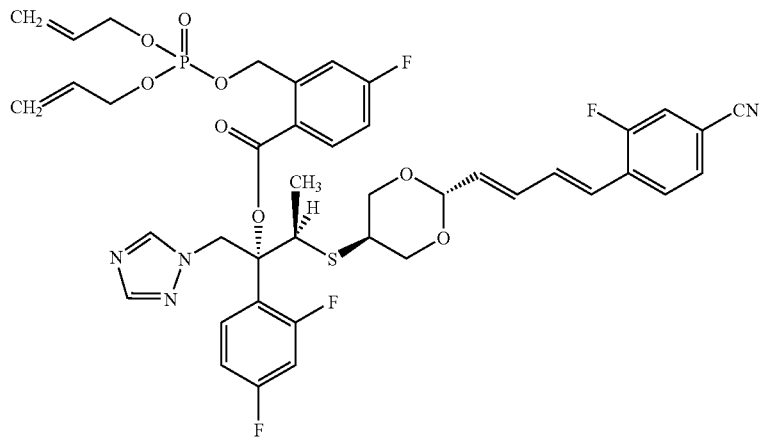

According to a similar procedure to that described in Example 4-(6), 4-methoxybenzyl 2-[[bis(allyloxy)phosphoryl]oxymethyl]-4-fluorobenzoate (1.41 g, 3.12 mmol) obtained from Example 7-(1) was reacted with anisole (2 g, 18.5 mmol) and trifluoroacetic acid (5 ml), and the reaction mixture was worked up to afford 2-[[bis(allyloxy)phosphoryl]oxymethyl]-4-fluorobenzoic acid as a crude product. According to a similar procedure to that described in Example 4-(6), the crude product obtained above was reacted with oxalyl chloride (1.98 g, 15.6 mmol) and N,N-dimethylformamide (15 μl), and the reaction mixture was worked up to afford 2-[[bis(allyloxy)phosphoryl]oxymethyl]-4-fluorobenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.09 g, 2.0 mmol) described in Reference example 1, sodium hydride (55% dispersion in mineral oil; 104.7 mg, 2.4 mmol), and the crude 2-[[bis(allyloxy)phosphoryl]oxymethyl]-4-fluorobenzoyl chloride obtained above were reacted in tetrahydrofuran (10 ml), and the reaction mixture was worked up to afford, after extraction, the title compound as a crude oil. The crude product was subjected to chromatography on a silica gel (60 g) column (eluent; ethyl acetate:hexane=2:1~3:1) to afford the title compound (948.1 mg, 55% yield) as a pale yellow amorphous solid.

NMR spectrum (400 MHz, CDCl$_3$) δ ppm: 1.45 (3H, dd, J=7, 2 Hz), 3.03 (1H, tt, J=11, 5 Hz), 3.50 (1H, t, J=11 Hz), 3.53 (1H, t, J=11 Hz), 4.01 (1H, q, J=7 Hz), 4.10-4.20 (2H, m), 4.57-5.61 (4H, m), 4.99 (1H, d, J=4 Hz), 5.26 (2H, dt, J=10, 1 Hz), 5.37 (2H, dt, J=17, 1 Hz) 5.41-5.52 (4H, m), 5.84 (1H, dd, J=15, 4 Hz), 5.95 (2H, ddt, J=17, 10, 5 Hz), 6.57 (1H, dd, J=15, 11 Hz), 6.74 (1H, d, J=15 Hz), 6.89-6.94 (2H, m), 6.94 (1H, dd, J=15, 11 Hz), 7.06 (1H, td, J=8, 3 Hz), 7.26-7.41 (3H, m), 7.46 (1H, dd, J=10, 3 Hz), 7.57 (1H, t, J=8 Hz), 7.81 (1H, dd, J=8, 6 Hz), 7.89 (1H, s), 7.89 (1H, s)

IR spectrum ν max CHCl$_3$ cm$^{-1}$: 2232, 1721, 1614, 1590, 1504, 1275, 1140, 1028

Mass spectrum m/z (FAB): 855 (M$^+$+1).

(3) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-5-fluorobenzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-4-fluorobenzoate (940 mg, 1.1 mmol) obtained from Example 7-(2) was reacted with bis(triphenylphosphine)dichloropalladium (38.6 mg, 0.055 mmol) and tributyltin hydride (640.1 mg, 2.20 mmol), and the reaction mixture was worked up to afford the title compound as a crude oil. The crude oil was subjected to reverse phase column chromatography using Cosmosil 75 C$_{18}$-PREP (Nacalai Tesque, Inc.; 75 g) (eluent; water:methanol=4:6~3:7). The obtained fractions were concentrated, and the residue was lyophilized to afford the title target compound (574.5 mg, 64% yield) as a colorless solid.

NMR spectrum (400 MHz, CD$_3$OD) δ ppm: 1.41 (3H, dd, J=7, 1 Hz), 3.04 (1H, tt, J=11, 4 Hz), 3.48 (1H, t, J=11 Hz), 3.54 (1H, t, J=11 Hz), 4.05 (1H, q, J=7 Hz), 4.08 (1H, ddd, J=11, 4, 2 Hz), 4.17 (1H, ddd, J=11, 4, 2 Hz), 5.03 (1H, d, J=5 Hz), 5.20 (1H, dd, J=17, 5 Hz), 5.34 (1H, dd, J=17, 5 Hz), 5.50 (1H, dd, J=15, 3 Hz), 5.58 (1H, d, J=15 Hz), 5.87 (1H, dd, J=15, 5 Hz), 6.58 (1H, dd, J=15, 11 Hz), 6.80 (1H, d, J=15 Hz), 6.98-7.05 (3H, m), 7.10 (1H, dd, J=15, 11 Hz), 7.48-7.54 (3H, m), 7.77-7.81 (2H, m), 7.87 (1H, dd, J=10, 3 Hz), 7.96 (1H, s), 8.31 (1H, s)

IR spectrum ν max KBr cm$^{-1}$: 2231, 1724, 1613, 1503, 1256, 1140, 1117, 1051, 977

Mass spectrum m/z (FAB): 819 (M$^+$+1)

Specific rotation [α]$_D^{25}$ +28.3° (c=0.86, MeOH)

Example 8

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-fluorobenzyl phosphate (Disodium Salt of Example Number 5-20)

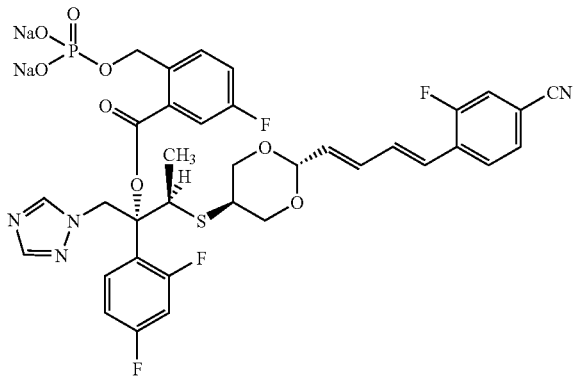

(1) 4-Methoxybenzyl 2-[[bis(allyloxy)phosphoryl]oxymethyl]-5-flourobenzoate

According to a similar procedure to that described in Example 4-(5), 6-fluoro-1(3H)-isobenzofuranone (described in Tetrahedron, 44, 4591 (1988); 1.52 g, 10 mmol) was reacted with an aqueous solution of sodium hydroxide (1.008N; 10 ml, 10 mmol), 4-methoxybenzyl chloride (1.57 g, 10 mmol), tetrazole (1.40 g, 20 mmol), bis(allyloxy)(diisopropylamino)phosphine (described in Tetrahedron Lett., 30, 4219 (1989); 3.0 g, 12.2 mmol), and tert-butyl hydroperoxide (80% di-tert-butyl peroxide solution); Merck; 2.7 g, 24 mmol), and the reaction mixture was worked up to afford, after extraction, an oily residue. The residue was subjected to chromatography on a silica gel (90 g) column (ethyl acetate:hexane=1:4~1:2) to give an oily mixture. The mixture was further subjected to chromatography on a silica gel (50 g) column (eluent; ethyl acetate:hexane=1:4~1:2) to afford the title compound (1.22 g, 27% yield) as a colorless oil.

NMR spectrum (400 MHz, CDCl$_3$) δ ppm: 3.82 (3H, s), 4.53-4.58 (4H, m), 5.25 (2H, dq, J=10, 1 Hz), 5.28 (2H, s), 5.35 (2H, dq, J=17, 1 Hz), 5.49 (2H, d, J=7 Hz), 5.93 (2H, ddt, J=17, 10, 5 Hz), 6.92 (2H, d, J=8 Hz), 7.25 (1H, td, J=8, 3 Hz), 7.38 (2H, d, J=8 Hz), 7.66 (1H, dd, J=8, 5 Hz), 7.69 (1H, dd, J=9, 3 Hz)

IR spectrum ν max CHCl$_3$ cm$^{-1}$: 1719, 1516, 1272, 1031, 989

Mass spectrum m/z (FAB): 451 (M$^+$+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-fluorobenzoate

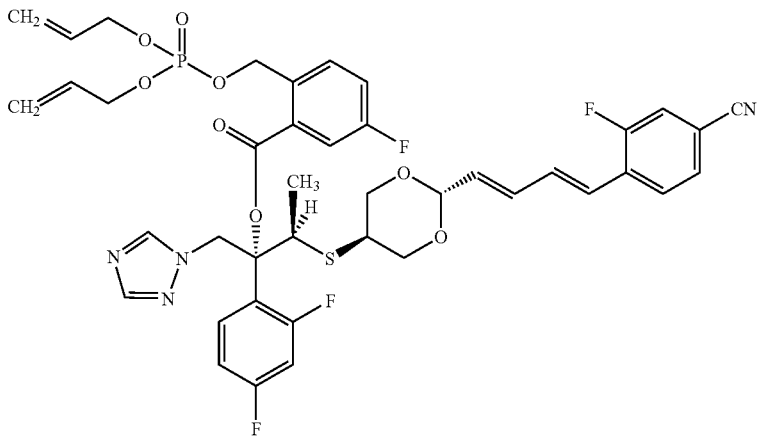

According to a similar procedure to that described in Example 4-(6), 4-methoxybenzyl 2-[[bis(allyloxy)phosphoryl]oxymethyl]-5-fluorobenzoate (1.19 g, 2.64 mmol) obtained from Example 8-(1) was reacted with anisole (1.5 g, 13.9 mmol) and trifluoroacetic acid (5 ml), and the reaction mixture was worked up to afford 2-[[bis(allyloxy)phosphoryl]oxymethyl]-5-fluorobenzoic acid as a crude product. According to a similar procedure to that described in Example 4-(6), the crude product obtained above was reacted with oxalyl chloride (1.68 g, 13.2 mmol) and N,N-dimethylformamide (15 μl), and the reaction mixture was-worked up to afford 2-[[bis(allyloxy)phosphoryl]oxymethyl]-5-fluorobenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (955.7 mg, 1.76 mmol) described in Reference example 1, sodium hydride (55% dispersion in mineral oil; 84.5 mg, 1.94 mmol), and the crude 2-[[bis(allyloxy)phosphoryl]oxymethyl]-5-fluorobenzoyl chloride obtained above were reacted in tetrahydrofuran (10 ml), and the reaction mixture was worked up to afford, after extraction, the title compound as a crude oil. The crude oil was subjected to chromatography on a silica gel (75 g) column (eluent; ethyl acetate:hexane=2:1~4:1) to afford the title compound (839.7 mg, 56% yield) as a pale yellow amorphous solid.

NMR spectrum (400 MHz, CDCl$_3$) δ ppm: 1.45 (3H, dd, J=7, 2 Hz), 3.03 (1H, tt, J=11, 4 Hz), 3.528 (1H, t, J=11 Hz), 3.532 (1H, t, J=11 Hz), 4.00 (1H, q, J=7 Hz), 4.15-4.20 (2H, m), 4.54-4.58 (4H, m), 5.00 (1H, d, J=4 Hz), 5.24 (2H, dd, J=10, 1 Hz), 5.35 (2H, dd, J=18, 1 Hz), 5.40-5.49 (4H, m), 5.85 (1H, dd, J=15, 4 Hz), 5.92 (2H, ddt, J=18, 10, 5 Hz), 6.58 (1H, dd, J=15, 11 Hz), 6.73 (1H, d, J=16 Hz), 6.90-7.00 (3H, m), 7.29-7.38 (3H, m), 7.40 (1H, dd, J=8, 1 Hz), 7.53-7.60 (2H, m), 7.69 (1H, dd, J=9, 6 Hz), 7.90 (1H, s), 7.93 (1H, s)

IR spectrum ν max CHCl$_3$ cm$^{-1}$: 2233, 1728, 1615, 1504, 1276, 1139, 1025

Mass spectrum m/z (FAB): 855 (M$^+$+1).

(3) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-fluorobenzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-fluorobenzoate (805.1 mg, 0.94 mmol) obtained from Example 8-(2) was reacted with bis(triphenylphosphine)dichloropalladium (19.8 mg, 0.028 mmol) and tributyltin hydride (903.1 mg, 3.10 mmol), and the reaction mixture was worked up to afford the title target compound as a crude oil. The crude oil was subjected to reverse phase column chromatography using Cosmosil 75 C$_{18}$-PREP (Nacalai Tesque, Inc.; 40 g) (eluent; water:methanol=4:6~3:7). The obtained fractions were concentrated, and the residue was lyophilized to afford the title target compound (103.1 mg, 13% yield) as a colorless solid.

NMR spectrum (400 MHz, CD$_3$OD) δ ppm: 1.41 (3H, dd, J=7, 1 Hz), 3.02 (1H, tt, J=11, 5 Hz), 3.49 (1H, t, J=11 Hz), 3.54 (1H, t, J=11 Hz), 4.04 (1H, q, J=7 Hz), 4.08 (1H, ddd, J=11, 5, 2 Hz), 4.17 (1H, ddd, J=11, 5, 2 Hz), 5.02 (1H, d, J=5 Hz), 5.18 (1H, dd, J=16, 6 Hz), 5.30 (1H, dd, J=16, 6 Hz), 5.51 (1H, dd, J=15, 3 Hz), 5.59 (1H, d, J=15 Hz), 5.86 (1H, dd, J=15, 5 Hz), 6.58 (1H, dd, J=15, 11 Hz), 6.79 (1H, d, J=15 Hz), 7.03-7.13 (3H, m), 7.33 (1H, td, J=9, 3 Hz), 7.43 (1H, dd, J=10, 3 Hz), 7.49-7.58 (3H, m), 7.79 (1H, t, J=8 Hz), 7.99 (1H, s), 8.10 (1H, dd, J=9, 6 Hz), 8.36 (1H, s)

IR spectrum ν max KBr cm$^{-1}$: 2231, 1727, 1614, 1503, 1275, 1199, 1140, 1052, 975

Mass spectrum m/z (FAB): 819 (M$^+$+1)

Specific rotation [α]$_D^{25}$ +22.8° (c=0.94, MeOH).

Example 9

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-fluorobenzyl phosphate (Disodium Salt of Example Number 5-19)

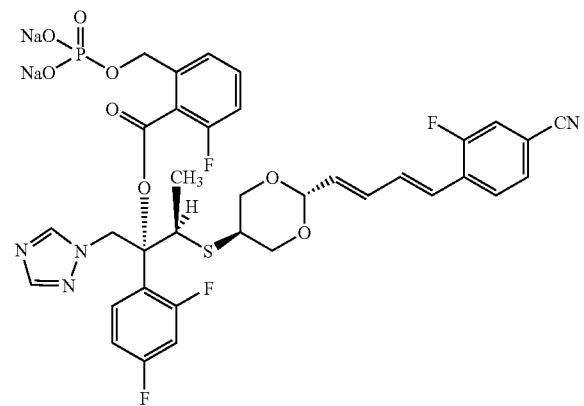

(1) 4-Methoxybenzyl 2-[[bis(allyloxy)phosphoryl]oxymethyl]-6-flourobenzoate

According to a similar procedure to that described in Example 4-(5), 7-fluoro-1(3H)-isobenzofuranone (described in Tetrahedron, 54, 7485 (1998); 1.67 g, 11 mmol) was reacted with an aqueous solution of sodium hydroxide (1.008N; 10.9 ml, 11 mmol), 4-methoxybenzyl chloride (1.57 g, 10 mmol), tetrazole (1.40 g, 20 mmol), bis(allyloxy)(diisopropylamino)phosphine (described in Tetrahedron Lett., 30, 4219 (1989); 3.1 g, 12.6 mmol), and tert-butyl hydroperoxide (80% di-tert-butyl peroxide solution; Merck; 2.7 g, 24 mmol), and the reaction mixture was worked up to afford, after extraction, an oily residue. The oily residue was subjected to chromatography on a silica gel (100 g) column (eluent; ethyl acetate:hexane=2:3) to afford a mixture of a solid and an oily material. The mixture was washed with a mixed solvent of ethyl acetate and hexane, the washings were concentrated under reduced pressure to give a residue. The residue was subjected to chromatography on a silica gel (50 g) column (eluent; ethyl acetate:hexane=1:4~1:2) to afford the title compound (1.08 g, 24% yield) as a colorless oil.

NMR spectrum (400 MHz, CDCl$_3$) δ ppm: 3.81 (3H, s), 4.49-4.54 (4H, m), 5.22-5.35 (6H, m), 5.33 (2H, dd, J=17, 1 Hz), 5.90 (2H, ddt, J=17, 11, 5 Hz), 6.91 (2H, d, J=9 Hz), 7.10 (1H, t, J=8 Hz), 7.32 (1H, d, J=8 Hz), 7.39 (2H, d, J=9 Hz), 7.43 (1H, td, J=8.6 Hz)

IR spectrum ν max CHCl$_3$ cm$^{-1}$: 1727, 1614, 1516, 1465, 1268, 1114, 1034

Mass spectrum m/z (FAB): 451 (M$^+$+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-6-fluorobenzoate

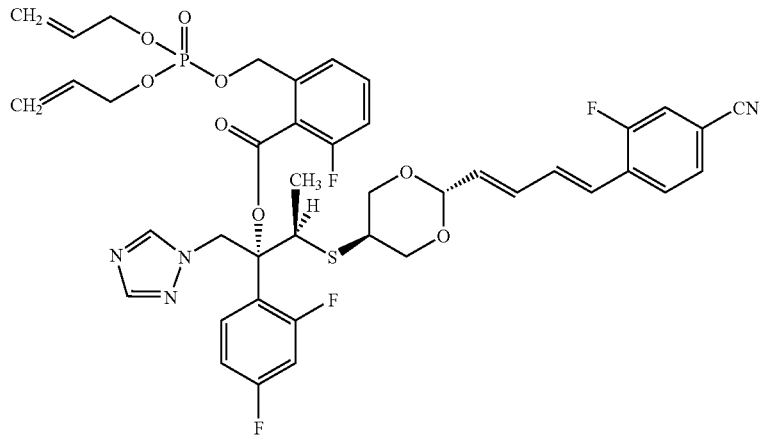

According to a similar procedure to that described in Example 4-(6), 4-methoxybenzyl 2-[[bis(allyloxy)phosphoryl]oxymethyl]-6-fluorobenzoate (1.07 g, 2.39 mmol) obtained from Example 9-(1) was reacted with anisole (1.8 g, 16.6 mmol) and trifluoroacetic acid (5 ml), and the reaction mixture was worked up to afford 2[[bis(allyloxy)phosphoryl]oxymethyl]-6-fluorobenzoic acid as a crude product.

According to a similar procedure to that described in Example 4-(6), the crude product obtained above was reacted with oxalyl chloride (1.52 g, 11.8 mmol) and N,N-dimethylformamide (15 µl), and the reaction mixture was worked up to afford 2-[[bis(allyloxy)phosphoryl]oxymethyl]-6-fluorobenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (864.1 mg, 1.59 mmol) described in Reference example 1, sodium hydride (55% dispersion in mineral oil; 83.4 mg, 1.91 mmol), and the crude 2-[[bis(allyloxy)phosphoryl]oxymethyl]-6-fluorobenzoyl chloride obtained above were reacted in tetrahydrofuran (8 ml), and the reaction mixture was worked up to afford, after extraction, the title compound as a crude oil. The crude oily product was subjected to chromatography on a silica gel (75 g) column (eluent; ethyl acetate:hexane=2:1~3:1) to afford the title compound (698.7 mg, 51% yield) as a pale yellow amorphous solid.

NMR spectrum (400 MHz, CDCl$_3$) δ ppm: 1.43 (3H, dd, J=7, 1 Hz), 3.05 (1H, tt, J=11, 5 Hz), 3.44 (1H, t, J=11 Hz), 3.51 (1H, t, J=11 Hz), 3.98 (1H, q, J=7 Hz), 4.08 (1H, ddd, J=11, 5, 2 Hz), 4.18 (1H, ddd, J=11, 5, 2 Hz), 4.53-4.59 (4H, m), 4.96 (1H, d, J=4 Hz), 5.24 (2H, dt, J=10, 1 Hz), 5.31-5.40 (4H, m), 5.44 (1H, d, J=15 Hz), 5.56 (1H, dd, J=15, 3 Hz), 5.83 (1H, dd, J=15, 4 Hz), 5.93 (2H, ddt, J=16, 10, 6 Hz), 6.55 (1H, dd, J=15, 11 Hz), 6.73 (1H, d, J=16 Hz), 6.88-6.98 (2H, m), 6.93 (1H, dd, J=16, 11 Hz), 7.11 (1H, td, J=8, 1 Hz), 7.34 (1H, dd, J=10, 1 Hz), 7.40 (1H, dd, J=8, 1 Hz), 7.48-7.59 (4H, m), 7.88 (1H, s), 7.89 (1H, s)

IR spectrum ν max CHCl$_3$ cm$^{-1}$: 2233, 1727, 1614, 1504, 1277, 1140, 1034

Mass spectrum m/z (FAB): 855 (M$^+$+1)

(3) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-fluorobenzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-6-fluorobenzoate (650 mg, 0.76 mmol) obtained from Example 9-(2), bis(triphenylphosphine)dichloropalladium (16.0 mg, 0.023 mmol), and tributyltin hydride (786.7 mg, 2.70 mmol) were reacted, and the reaction mixture was worked up to afford the title target compound as a crude oil. The crude compound was subjected to reverse phase column chromatography using Cosmosil 75 C$_{18}$-PREP (Nacalai Tesque, Inc.; 40 g) (eluent; water:methanol=4:6~3:7). The obtained fractions were concentrated, and the residue was lyophilized to afford the title target compound (440.5 mg, 71% yield) as a colorless solid.

NMR spectrum (400 MHz, CD$_3$OD) δ ppm: 1.39 (3H, dd, J=7, 1 Hz), 3.06 (1H, tt, J=11, 5 Hz), 3.25 (1H, t, J=11 Hz), 3.49 (1H, t, J=11 Hz), 3.94 (1H, ddd, J=11, 5, 2 Hz), 4.10 (1H, q, J=7 Hz), 4.15 (1H, ddd, J=11, 5, 2 Hz), 4.95 (1H, d, J=4 Hz), 5.03 (1H, dd, J=15, 5 Hz), 5.27 (1H, dd, J=15, 5 Hz), 5.52 (1H, dd, J=15, 3 Hz), 5.62 (1H, d, J=15 Hz), 5.83 (1H, dd, J=15, 4 Hz), 6.54 (1H, dd, J=15, 11 Hz), 6.79 (1H, d, J=16 Hz), 6.99-7.15 (4H, m), 7.50-7.58 (3H, m), 7.62 (1H, td, J=8, 6 Hz), 7.79 (1H, t, J=8 Hz), 7.88 (1H, d, J=8 Hz), 8.00 (1H, s), 8.33 (1H, s)

IR spectrum ν max KBr cm$^{-1}$: 2231, 1724, 1614, 1504, 1278, 1257, 1140, 1113, 1055, 975

Mass spectrum m/z (FAB): 819 (M$^+$+1)

Specific rotation [α]$_D^{25}$ +56.4° (c=1.02, MeOH).

Example 10

Disodium 4-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxo-3,3-dimethylbutyl phosphate (Disodium Salt of Example Number 4-18)

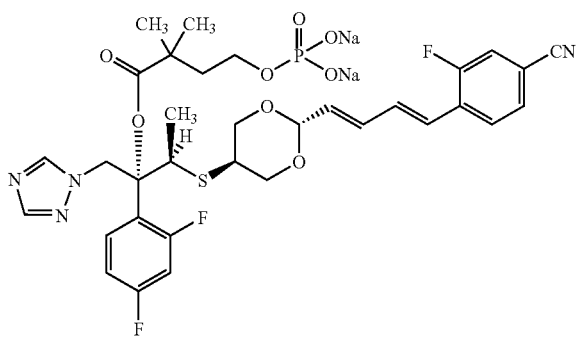

(1) 4-Methoxybenzyl 4-[[bis(allyloxy)phosphoryl]oxy]-2,2-dimethylbytyrate

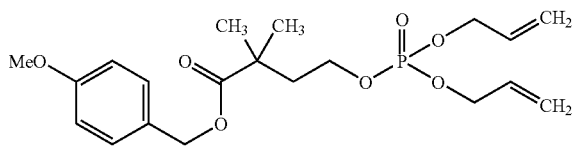

According to a similar procedure to that described in Example 4-(5), 2,2-dimethyl-5-pentanolide (described in Tetrahedron, 22, 285 (1966); 1.14 g, 10 mmol) was reacted with an aqueous solution of sodium hydroxide (1.008N; 10 ml, 10 mmol), 4-methoxybenzyl chloride (1.57 g, 10 mmol), tetrazole (1.40 g, 20 mmol), bis(allyloxy)(diisopropylamino)phosphine (described in Tetrahedron Lett., 30, 4219 (1989); 3.1 g, 12.6 mmol), and tert-butyl hydroperoxide (80% di-tert-butyl peroxide solution; Merck; 3.6 g, 32 mmol), and the reaction mixture was worked up to afford, after extraction, an oily residue. The oily residue was subjected to chromatography on a silica gel (60 g) column (eluent; ethyl acetate:hexane=1:2) to afford an oily mixture. The mixture was subjected to chromatography on a silica gel (75 g) column (eluent; ethyl acetate:hexane=1:3~3:1) to afford the title compound (1.86 g) as a colorless oil together with some impure fractions. The impure fractions were further subjected to chromatography on a silica gel (20 g) column (eluent; ethyl acetate:hexane=1:2~1:0) to afford the title compound (0.52 g, total amount 2.38 g, 58% yield).

NMR spectrum (400 MHz, CDCl$_3$) δ ppm: 1.22 (6H, s), 1.97 (2H, t, J=7 Hz), 3.81 (3H, s), 4.08 (2H, q, J=7 Hz), 4.50-4.53 (4H, m), 5.03 (2H, s), 5.24 (2H, dd, J=11, 1 Hz), 5.35 (2H, dq, J=17, 1 Hz), 5.92 (2H, ddt, J=17, 11, 5 Hz), 6.88 (2H, d, J=9 Hz), 7.27 (2H, d, J=9 Hz)

IR spectrum ν max CHCl$_3$ cm$^{-1}$: 1723, 1516, 1255, 1148, 1029, 990

Mass spectrum m/z (FAB): 413 (M$^+$+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[[bis(allyloxy)phosphoryl]oxy]-2,2-dimethylbutyrate

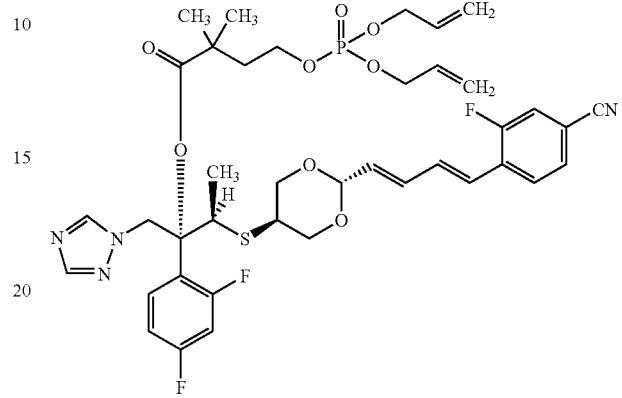

According to a similar procedure to that described in Example 4-(6), 4-methoxybenzyl 4-[[bis(allyloxy)phosphoryl]oxy]-2,2-dimethylbutyrate (1.24 g, 3.0 mmol) obtained from Example 10-(1) was reacted with anisole (1.8 g, 16.6 mmol) and trifluoroacetic acid (5 ml), and the reaction mixture was worked up to afford 4-[[bis(allyloxy)phosphoryl]oxy]-2,2-dimethylbutanoic acid as a crude product. According to a similar procedure to that described in Example 4-(6), the crude product obtained above was reacted with oxalyl chloride (1.98 g, 15.6 mmol) and N,N-dimethylformamide (15 µl), and the reaction mixture was worked up to afford 4-[bis(allyloxy)phosphoryl]oxy-2,2-dimethylbutyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.09 g, 2.0 mmol) described in Reference example 1, sodium hydride (55% dispersion in mineral oil; 104.7 mg, 2.4 mmol), and 4-[[bis(allyloxy)phosphoryl]oxy]-2,2-dimethylbutyl chloride were reacted in tetrahydrofuran (10 ml) and the reaction mixture was worked up to afford, after extraction, the title compound as a crude oil. The crude oily product was subjected to chromatography on a silica gel (75 g) column (eluent; ethyl acetate:hexane=2:1~3:1) to afford the title compound (238.8 mg, 15% yield) as a pale yellow amorphous solid.

NMR spectrum (400 MHz, CDCl$_3$) δ ppm: 1.17 (3H, s), 1.22 (3H, s), 1.38 (3H, dd, J=7, 2 Hz), 2.01 (2H, t, J=7 Hz), 3.03 (1H, tt, J=11, 5 Hz), 3.54 (2H, t, J=11 Hz), 4.04 (1H, q, J=7 Hz), 4.12-4.24 (4H, m), 4.51-4.56 (4H, m), 5.02 (1H, d, J=4 Hz), 5.26 (2H, d, J=10 Hz), 5.30-5.40 (4H, m), 5.86 (1H, dd, J=15, 4 Hz), 5.94 (2H, ddt, J=17, 10, 5 Hz), 6.59 (1H, dd, J=15, 10 Hz), 6.74 (1H, d, J=15 Hz), 6.86-6.97 (3H, m), 7.31-7.38 (2H, m), 7.40 (1H, dd, J=8, 2 Hz), 7.57 (1H, t, J=8 Hz), 7.87 (1H, s), 7.90 (1H, s)

IR spectrum ν max CHCl$_3$ cm$^{-1}$: 2233, 1734, 1504, 1275, 1139, 1027, 991

Mass spectrum m/z (FAB): 817 (M$^+$+1).

(3) Disodium 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxo-3,3-dimethylbutyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[[bis(allyloxy)phosphoryl]oxy]-2,2-dimethylbutyrate (230.7 mg, 0.28 mmol) obtained from Example 10-(2) was reacted with bis(triphenylphosphine)dichloropalladium (6.0 mg, 0.0085 mmol) and tributyltin hydride (280.9 mg, 0.97 mmol), and the reaction mixture was worked up to afford the title target compound as a crude oil. The crude oil was subjected to reverse phase column chromatography using Cosmosil 75 $C_{18}$-PREP (Nacalai Tesque, Inc.; 50 g) (eluent; water:methanol=4:6~3:7). The obtained fractions were concentrated, and the residue was lyophilized to afford the title target compound (84.0 mg, 38% yield) as a colorless solid.

NMR spectrum (400 MHz, $CD_3OD$) δ ppm: 1.17 (3H, s), 1.22 (3H, s), 1.37 (3H, dd, J=7, 2 Hz), 1.97 (2H, t, J=7 Hz), 3.00 (1H, tt, J=11, 5 Hz), 3.55 (1H, t, J=11 Hz), 3.56 (1H, t, J=11 Hz), 3.92-3.98 (2H, m), 4.08 (1H, q, J=7 Hz), 4.14-4.19 (2H, m), 5.06 (1H, d, J=4 Hz), 5.44 (2H, s), 5.88 (1H, dd, J=15, 4 Hz), 6.60 (1H, dd, J=15, 11 Hz), 6.80 (1H, d, J=16 Hz), 7.01-7.08 (2H, m), 7.10 (1H, dd, J=16, 11 Hz), 7.49-7.55 (3H, m), 7.79 (1H, t, J=8 Hz), 7.98 (1H, s), 8.25 (1H, s)

Mass spectrum m/z (FAB): 781 ($M^+$+1)

IR spectrum ν max KBr $cm^{-1}$: 2231, 1731, 1615, 1503, 1276, 1140, 1049, 974.

Example 11

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-hydroxybutyrate (Example Number 4-1)

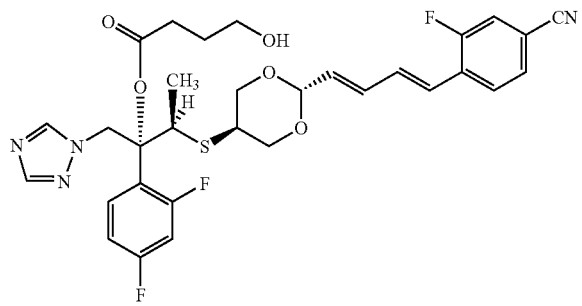

(1) 4-Methoxybenzyl 4-(allyloxycarbonyloxy)butyrate

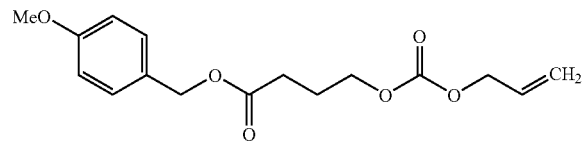

To a suspension of commercially available sodium 4-hydroxybutyrate (10.3 g, 81.7 mmol) in N,N-dimethylformamide (80 ml) was added 4-methoxybenzyl chloride (12.8 g, 81.7 mmol), and the mixture was heated at 100° C. for 1 hour. After cooling, the mixture was diluted with ethyl acetate, and the resulting solution was washed three times with water and once with an aqueous solution of sodium chloride, dried over anhydrous magnesium sulfate, and the solvent was distilled off under reduced pressure to give a colorless, oily residue. The residue was dissolved in dichloromethane (150 ml), and 4-(N,N-dimethylamino)pyridine (11.0 g, 90 mmol) and allyl chloroformate (9.85 g, 81.7 mmol) were added thereto at 0° C., and the resulting mixture was stirred at room temperature for 16 hours. The mixture was diluted with ethyl acetate, then washed successively with water, a saturated aqueous solution of sodium hydrogen carbonate, a saturated aqueous solution of ammonium chloride, and an aqueous solution of sodium chloride. The extract was dried over anhydrous magnesium sulfate, and the solvent was distilled off under reduced pressure to afford an oily residue. The residue was subjected to chromatography on a silica gel (600 g) column (eluent; ethyl acetate:hexane=4:1~2:1) to afford the title compound (15.61 g, 62% yield) as a colorless oil.

NMR spectrum (400 MHz, $CDCl_3$) δ ppm: 1.95-2.05 (2H, m), 2.45 (2H, t, J=7 Hz), 3.81 (3H, s), 4.18 (2H, t, J=6 Hz), 4.61 (2H, dt, J=6, 2 Hz), 5.06 (2H, s), 5.27 (1H, dt, J=10, 2 Hz), 5.36 (1H, dt, J=18, 2 Hz), 5.93 (1H, ddt, J=18, 10, 6 Hz), 6.89 (2H, d, J=9 Hz), 7.22 (2H, d, J=9 Hz)

IR spectrum ν max neat $cm^{-1}$: 1745, 1614, 1516, 1463, 1255

Mass spectrum m/z (FAB): 308 ($M^+$).

(2) 4-(Allyloxycarbonyloxy)butyryl chloride

Trifluoroacetic acid (30 ml) was added at room temperature to a mixture of 4-methoxybenzyl 4-(allyloxycarbonyloxy)butyrate (5.61 g, 18.2 mmol) obtained from Example 11-(1) and anisole (6 ml). The mixture was stirred at room temperature for 10 minutes, then diluted with toluene, and the resulting solution was concentrated under reduced pressure. The residue was redissolved in toluene, and then the solvent was evaporated under reduced pressure. The obtained oily residue was suspended in an aqueous solution of sodium hydrogen carbonate, and the suspension was washed with hexane. To the aqueous suspension was added slowly a 1N aqueous solution of hydrochloric acid to adjust the pH of the solution to about 2, and the liberated carboxylic acid was extracted three times with ethyl acetate. The combined organic layers were washed with an aqueous solution of sodium chloride, dried over anhydrous magnesium sulfate, and the solvent was distilled off under reduced pressure. The obtained colorless oil (3.50 g) was dissolved in dichloromethane (17 ml), and N,N-dimethylformamide (0.05 ml) and oxalyl chloride (3 g) were added thereto. The mixture was stirred at room temperature for 1 hour, then toluene was added thereto, and the resulting solution was concentrated under reduced pressure. The residue was purified by simple distillation under reduced pressure to afford the title compound (2.90 g, 77% yield) as a colorless oil.

NMR spectrum (400 MHz, $CDCl_3$) δ ppm: 2.08 (2H, m), 3.04 (2H, t, J=7 Hz), 4.20 (2H, t, J=6 Hz), 4.64 (2H, dt, J=6, 2 Hz), 5.29 (1H, dt, J=10, 2 Hz), 5.37 (1H, dt, J=18, 2 Hz), 5.94 (1H, ddt, J=18, 10, 6 Hz).

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-(allyloxycarbonyloxy)butyrate

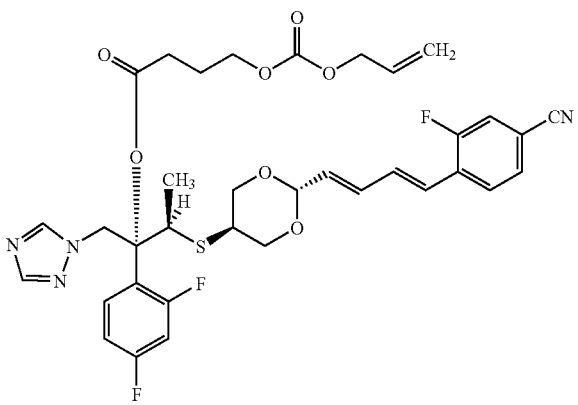

4-[(1E,3E)-4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (570 mg, 1.05 mmol) obtained from Example Reference example 1 was dissolved in N,N-dimethylformamide (3 ml), and sodium hydride (ca. 30 mg, 1.3 mmol) was added thereto at room temperature. The mixture was stirred for 1 hour, then 4-(allyloxycarbonyloxy)butyryl chloride (250 mg, 1.21 mmol) obtained from Example 11-(2) was added thereto, and the mixture was stirred further for 1 hour. The mixture was diluted with ethyl acetate, and a saturated aqueous solution of ammonium chloride was poured thereinto. The organic layer was separated, washed with an aqueous solution of sodium hydrogen carbonate and then with an aqueous solution of sodium chloride, dried over anhydrous magnesium sulfate, and the solvent was distilled off under reduced pressure. The residue was purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (562 mg, 75% yield) as a colorless amorphous solid.

NMR spectrum (400 MHz, CDCl$_3$) δ ppm: 1.35 (3H, dd, J=7, 2 Hz), 1.90-2.10 (2H, m), 2.40-2.60 (2H, m), 3.04 (1H, tt, J=11, 5 Hz), 3.52 (2H, t, J=11 Hz), 3.90 (1H, q, J=7 Hz), 4.15-4.25 (4H, m), 4.65 (2H, d, J=6 Hz), 5.00 (1H, d, J=4 Hz), 5.28 (1H, br d, J=18 Hz), 5.35 (2H, s), 5.37 (1H, br d, J=18 Hz), 5.86 (1H, dd, J=15, 4 Hz), 5.95 (1H, ddt, J=18, 10, 6 Hz), 6.59 (1H, dd, J=16, 11 Hz), 6.74 (1H, d, J=16 Hz), 6.85-6.95 (3H, m), 7.25-7.45 (3H, m), 7.57 (1H, t, J=8 Hz), 7.90 (1H, s), 7.91 (1H, s)

IR spectrum ν max KBr cm$^{-1}$: 2233, 1743, 1616, 1504
Mass spectrum m/z (FAB): 713 (M$^+$+1).

(4) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-hydroxybutyrate (Title Target Compound)

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-(allyloxycarbonyloxy)butyrate (352 mg, 4.94×10$^{-4}$ mol) obtained from Example 11-(3) and bis(triphenylphosphine) dichloropalladium (2 mg) were dissolved in dichloromethane (3 ml). Tributyltin hydride (215 mg, 7.39×10$^{-4}$ mol) was slowly added to the mixture at room temperature over a period of 5 minutes. After stirring at room temperature for 15 minutes further, hexane was added to the reaction mixture. The insoluble liberated oily material was separated by removing the supernatant liquid slowly. The insoluble residue was further washed twice with hexane. The oily residue was subjected to chromatography on a silica gel (15 g) column (eluent; ethyl acetate:hexane=3:1~1:0) to afford the title compound (289 mg, 93% yield) as a colorless amorphous solid.

NMR spectrum (400 MHz, CDCl$_3$) δ ppm: 1.34 (3H, dd, J=7, 2 Hz), 1.75-1.90 (2H, m), 1.90 (1H, t, J=6 Hz), 2.50 (2H, t, J=7 Hz), 3.10 (1H, tt, J=11, 5 Hz), 3.52 (1H, t, J=11 Hz), 3.53 (1H, t, J=11 Hz), 3.68 (2H, m), 3.96 (1H, q, J=7 Hz), 4.15-4.25 (2H, m), 5.01 (1H, d, J=5 Hz), 5.30-5.40 (2H, m), 5.85 (1H, dd, J=16, 4 Hz), 6.58 (1H, dd, J=16, 11 Hz), 6.74 (1H, d, J=16 Hz), 6.85-6.95 (3H, m), 7.25-7.45 (3H, m), 7.57 (1H, t, J=8 Hz), 7.94 (1H, s), 7.95 (1H, s)

IR spectrum ν max KBr cm$^{-1}$: 3403, 2231, 1741, 1616, 1504
Mass spectrum m/z (FAB): 629 (M$^+$+1).

Example 12

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-acetoxybutyrate (Example Number 4-2)

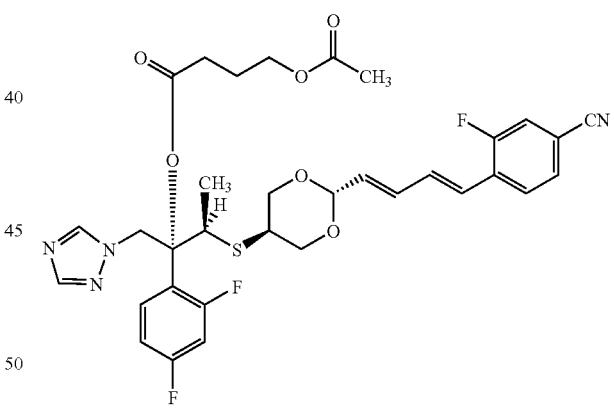

(1) 4-Cholro-4-oxobutyl acetate

4-Acetoxybutanoic acid (Tetrahedron, 0.45, 7783 (1989); 2.00 g, 13.7 mmol) was dissolved in dichloromethane (10 ml), and N,N-dimethylformamide (0.05 ml) and oxalyl chloride (2.5 g) were added thereto. The mixture was stirred at room temperature for 1 hour, then toluene was added thereto, and the resulting solution was concentrated under reduced pressure. The residue was purified by simple distillation under reduced pressure to afford the title compound (1.57 g, 70% yield) as a colorless oil.

NMR spectrum (400 MHz, CDCl$_3$) δ ppm: 2.05 (2H, m), 2.07 (3H, s), 3.00 (2H, t, J=7 Hz), 4.12 (2H, t, J=6 Hz).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-acetoxybutyrate (Title Target Compound)

4-[(1E,3E)-4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.10 g, 2.03 mmol) obtained from Reference example 1 was dissolved in N,N-dimethylformamide (5 ml), and then sodium hydride (ca. 50 mg, 2.1 mmol) was added thereto at room temperature. The mixture was stirred for 15 minutes, then 4-chloro-oxobutyl acetate (330 mg, 2.0 mmol) obtained from Example 12-(1) was added thereto, and the resulting mixture was stirred for another 1 hour. The mixture was diluted with ethyl acetate, and a saturated aqueous solution of ammonium chloride was poured thereinto. The organic layer was separated, then washed successively with an aqueous solution of sodium hydrogen carbonate and with an aqueous solution of sodium chloride, and dried over anhydrous magnesium sulfate, and then the solvent was distilled off under reduced pressure. The obtained crude compound was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title compound (662 mg, 49% yield) as a colorless amorphous solid.

NMR spectrum (400 MHz, CDCl$_3$) δ ppm: 1.35 (3H, dd, J=7, 2 Hz), 1.85-2.05 (2H, m), 2.08 (3H, s), 2.35-2.55 (2H, m), 3.06 (1H, tt, J=11, 5 Hz), 3.52 (1H, t, J=11 Hz), 3.53 (1H, t, J=11 Hz), 3.93 (1H, q, J=7 Hz), 4.12 (2H, t, J=7 Hz) 4.15-4.25 (2H, m), 5.00 (1H, d, J=4 Hz), 5.36 (2H, s), 5.86 (1H, dd, J=15, 4 Hz), 6.59 (1H, dd, J=15, 10 Hz), 6.73 (1H, d, J=15 Hz), 6.85-6.95 (3H, m), 7.30-7.45 (3H, m), 7.57 (1H, t, J=8 Hz), 7.90 (1H, s), 7.93 (1H, s)

IR spectrum ν max KBr cm$^{-1}$: 2231, 1739, 1616, 1504

Mass spectrum m/z (FAB): 671 (M$^+$+1).

Example 13

Disodium 4-[[(1R,2R)-2-[[trans-2-[(1E,3E)-4-(4-cyano-2-fluorophenyl)-1,3-butadienyl]-1,3-dioxan-5-yl]thio]1-(2,4-difluorophenyl)-1-[(1H-1,2,4-triazol-1-yl)methyl]propoxy]-4-oxobutyl phosphate (Disodium Salt of Example Number 4-16)

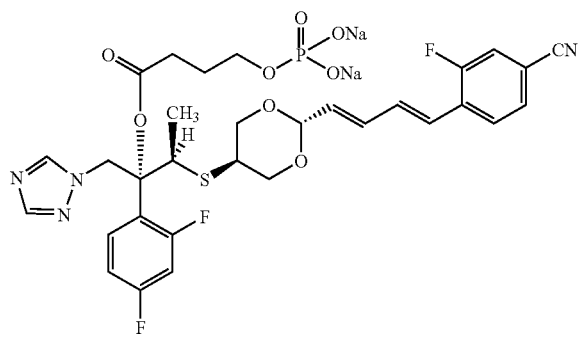

(1) 4-Methoxybenzyl 2-[[bis(allyloxy)phosphoryl]oxy]butyrate

To a suspension of a commercially available sodium 4-hydroxybutyrate (630 mg, 5.00 mmol) in N,N-dimethylformamide (3.5 ml) was added 4-methoxybenzyl chloride (783 mg, 5.00 mmol), and the mixture was heated at 100° C. for 3 hours. The mixture was cooled, diluted with ethyl acetate, and the diluted mixture was washed successively twice with water and twice with an aqueous solution of sodium chloride. The solution was dried over anhydrous magnesium sulfate, and the solvent was distilled off under reduced pressure to give a colorless oily residue. The residue was dissolved in dichloromethane (5 ml), and tetrazole (700 mg, 10 mmol) and bis(allyloxy)(diisopropylamino)phosphine (Tetrahedron Lett., 30, 4219 (1989); 1.5 g, 6.1 mmol) were added at 0° C., then the mixture was stirred at the same temperature for 5 minutes. The mixture was warmed to room temperature, then stirred for 30 minutes, and methanol (0.1 ml) was added thereto. The mixture was stirred for 5 minutes further, and tert-butyl hydroperoxide (ca. 5 M nonane solution, 1.5 ml, ca. 7.5 mmol) was added thereto at 0° C. followed by stirring the mixture at room temperature for 30 minutes. A saturated aqueous solution of sodium hydrogen carbonate and an aqueous solution of sodium thiosulfate were added thereto, and the mixture was stirred for 10 minutes and then partitioned between ethyl acetate and water. The organic layer was washed successively with a saturated aqueous solution of sodium hydrogen carbonate, a saturated aqueous solution of ammonium chloride, and an aqueous solution of sodium chloride, and then dried over anhydrous magnesium sulfate, and the solvent was distilled off under reduced pressure to give an oily residue. The residue was subjected to chromatography on a silica gel (30 g) column (eluent; ethyl acetate:hexane=2:3~1:1) to give the title compound (1.55 g, 81% yield) as a colorless oil.

NMR spectrum (400 MHz, CDCl$_3$) δ ppm: 2.01 (2H, quint, J=7 Hz), 2.47 (2H, t, J=7 Hz), 3.81 (3H, s), 4.10 (2H, q, J=7 Hz), 4.50-4.55 (4H, m), 5.06 (2H, s), 5.25 (2H, br d, J=10 Hz), 5.36 (2H, br d, J=17 Hz), 5.93 (2H, ddt, J=17, 10, 5 Hz), 6.84 (2H, d, J=9 Hz), 7.29 (2H, d, J=9 Hz)

IR spectrum ν max neat cm$^{-1}$: 1731, 1613, 1516, 1464, 1254

Mass spectrum m/z (FAB): 385 (M$^+$+1).

(2) Diallyl 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl phosphate

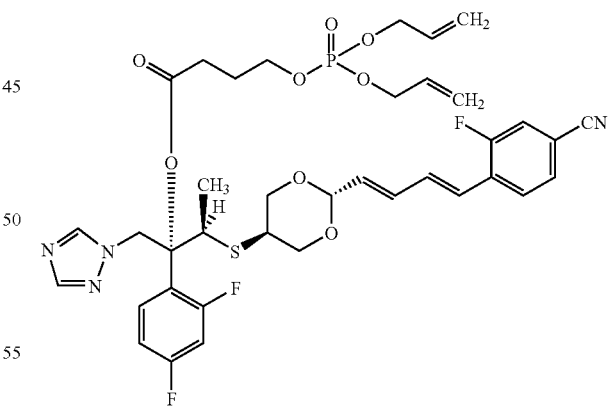

To a mixture of 4-methoxybenzyl 4-[[bis(allyloxy)phosphoryl]oxy]butyrate (700 mg, 1.82 mmol) obtained from Example 13-(1) and anisole (0.7 ml) was added trifluoroacetic acid (3 ml) at room temperature. The mixture was stirred at room temperature for 15 minutes, then diluted with toluene, and the solvent was distilled off under reduced pressure. The residue was redissolved in toluene, and the solvent was distilled off under reduced pressure to give crude 4-[[bis(allyloxy)phosphoryl]oxy]butanoic acid as a pale yellow oil.

NMR spectrum (400 MHz, CDCl$_3$) δ ppm: 2.03 (2H, quint, J=7 Hz), 2.51 (2H, t, J=7 Hz), 4.16 (2H, q, J=7 Hz), 4.55-4.60 (4H, m), 5.29 (1H, br d, J=10 Hz), 5.39 (2H, br d, J=17 Hz), 5.94 (2H, ddt, J=17, 10, 5 Hz), 11.29 (1H, br s).

The obtained crude 4-[[bis(allyloxy)phosphoryl]oxy]butanoic acid was dissolved in dichloromethane (3.5 ml), and N,N-dimethylformamide (0.05 ml) and oxalyl chloride (350 mg) were added thereto. The mixture was stirred at room temperature for 1 hour, then toluene was added thereto, and the resulting solution was concentrated under reduced pressure to afford crude 4-[[bis(allyloxy)phosphoryl]oxy]butylyl chloride.

4-[(1E,3E)-4-[trans-S-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (936 mg, 1.73 mmol) obtained from Reference example 1 was dissolved in tetrahydrofuran (10 ml), and sodium hydride (55% dispersion in mineral oil; 80 mg, 1.83 mmol) was added thereto at room temperature. The mixture was stirred for 3 hours. The obtained suspended mixture was cooled to 0° C., and the crude 4[[bis(allyloxy)phosphoryl]oxy]butylyl chloride obtained above was added thereto with stirring. The mixture was stirred at room temperature for 30 minutes. After cooling, the mixture was partitioned between ethyl acetate and an aqueous solution of ammonium chloride, and the organic layer was washed with a saturated aqueous solution of sodium chloride, dried over anhydrous magnesium sulfate and the solvent was distilled off under reduced pressure. The oily residue was subjected to chromatography on a silica gel (30 g) column (eluent; ethyl acetate:methanol=1:0~10:1) to afford the title compound (862 mg, 63% yield) as a pale yellow amorphous solid.

NMR spectrum (400 MHz, CDCl$_3$) δ ppm: 1.35 (3H, dd, J=7, 2 Hz), 1.90-2.10 (2H, m), 2.46 (1H, dt, J=17, 7 Hz), 2.57 (1H, dt, J=17, 7 Hz), 3.04 (1H, tt, J=11, 5 Hz), 3.52 (2H, t, J=11 Hz), 3.90 (1H, q, J=7 Hz), 4.12 (2H, q, J=7 Hz) 4.15-4.25 (2H, m), 4.55-4.60 (4H, m), 5.00 (1H, d, J=4 Hz), 5.27 (2H, d, J=11 Hz), 5.35 (2H, s), 5.38 (2H, d, J=17 Hz), 5.85 (1H, dd, J=15, 4 Hz), 5.90-6.00 (2H, m), 6.58 (1H, dd, J=16, 11 Hz), 6.74 (1H, d, J=15 Hz), 6.85-6.95 (3H, m), 7.30-7.45 (3H, m), 7.57 (1H, t, J=8 Hz), 7.90 (1H, s), 7.92 (1H, s)

IR spectrum ν max KBr cm$^{-1}$: 2233, 1741, 1615, 1600, 1504

Mass spectrum m/z (FAB): 789 (M$^+$+1).

(3) Disodium 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl phosphate (Title Target Compound)

Diallyl 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl phosphate (350 mg, 4.53×10$^{-4}$ mol) obtained from Example 13-(2), tetrakis(triphenylphosphine)palladium (5 mg), and triphenylphosphine (5 mg) were dissolved in dichloromethane (3 ml). To the mixture was added pyrrolidine (644 mg, 9.06×10$^{-3}$ mol) at room temperature, and the resulting mixture was stirred for 1 hour, then diluted with toluene and the solvent was distilled off under reduced pressure. The residue was subjected to reverse phase column chromatography using Cosmosil 75 C$_{18}$-PREP (Nacalai Tesque, Inc.; 15 g) (eluent; water:methanol=1:0~4:6). The obtained fractions were concentrated, and the residue was subjected to a cation exchange resin (Dowex 50W-8X, Na type preparated using 1N aqueous solution of sodium hydroxide; 5 ml) (eluent; water). The collected fractions were concentrated under reduced pressure and lyophilized to afford the title target compound (233 mg, 64% yield) as an amorphous colorless solid.

NMR spectrum (400 MHz, D$_2$O) δ ppm: 1.13 (3H, d, J=7 Hz), 1.68 (2H, quint, J=7 Hz), 2.35-2.50 (2H, m), 2.87 (1H, m), 3.43 (1H, t, J=12 Hz), 3.46 (1H, t, J=12 Hz), 3.55-3.65 (3H, m), 3.95-4.05 (2H, m), 4.97 (1H, d, J=4 Hz), 5.13 (1H, d, J=15 Hz), 5.26 (1H, d, J=15 Hz), 5.65 (1H, dd, J=15, 5 Hz), 6.42 (1H, dd, J=15, 10 Hz), 6.64 (1H, d, J=16 Hz), 6.80-6.90 (3H, m), 7.25-7.35 (3H, m), 7.51 (1H, t, J=7 Hz), 7.82 (1H, s), 8.13 (1H, s)

IR spectrum ν max KBr cm$^{-1}$: 3432, 2231, 1740, 1615, 1599, 1503, 1418, 1387, 1276, 1257, 1142

Mass spectrum m/z (FAB): 753 (M$^+$+1)

Elemental analysis for C$_{31}$H$_{30}$F$_3$N$_4$O$_8$PSNa$_2$.3H$_2$O:
Calculated: C:46.16; H:4.50; N:6.95; Na:5.70.
Found: C:46.41; H:4.83; N:7.04; Na:5.37.

Example 14

Sodium 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl succinate (Sodium Salt of Example Number 4-6)

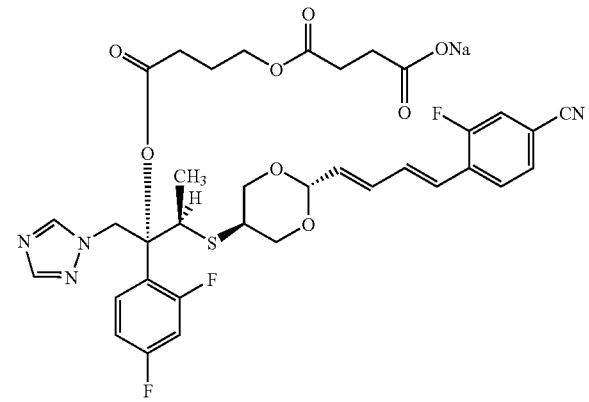

(1) Allyl 4-chloro-4-oxobutyrate

To a solution of commercially available succinic anhydride (2.00 g, 20.0 mmol) in dichloromethane (10 ml) were added allyl alcohol (1.75 g, 30.1 mmol), N,N-diisopropylethylamine (3.88 g, 30.1 mmol) and 4-(N,N-dimethylamino)pyridine (10 mg) at room temperature. The mixture was stirred for 1 hour, then 1N hydrochloric acid was added thereto, and the resulting solution was extracted with ethyl acetate. The extract was washed with an aqueous solution of sodium chloride, dried over anhydrous magnesium sulfate, and the solvent was distilled off under reduced pressure to afford crude allyl hydrogen succinate.

NMR spectrum (400 MHz, CDCl$_3$) δ ppm: 2.65-2.75 (4H, m), 4.61 (2H, d, J=6 Hz), 5.24 (1H, dd, J=10, 2 Hz), 5.33 (1H, dd, J=17, 1 Hz), 5.91 (1H, ddt, J=17, 10, 6 Hz), 11.05 (1H, br s).

The obtained crude allyl hydrogen succinate was dissolved in dichloromethane (10 ml), and N,N-dimethylformamide (0.05 ml) and oxalyl chloride (3.8 g) were added thereto. The mixture was stirred at room temperature for 2 hours, then toluene was added thereto, and the solvent was distilled off under reduced pressure. The residue was purified by simple distillation under reduced pressure to afford the title compound (2.89 g, 82% yield) as a pale yellow oil.

NMR spectrum (400 MHz, CDCl$_3$) δ ppm: 2.72 (2H, t, J=7 Hz), 3.23 (2H, t, J=7 Hz), 4.62 (2H, d, J=5 Hz), 5.26 (1H, dd, J=10, 1 Hz), 5.33 (1H, dd, J=17, 1 Hz), 5.90 (1H, ddt, J=17, 10, 5 Hz).

(2) Allyl 4-[(4-methoxybenzyl)oxy]-4-oxobutyl succinate

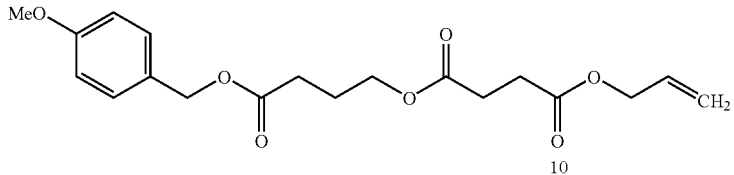

To a suspension of commercially available sodium 4-hydroxybutyrate (756 mg, 6.00 mmol) in N,N-dimethylformamide (10 ml) was added 4-methoxybenzyl chloride (987 mg, 6.30 mmol), and the mixture was heated at 100° C. for 3 hours. The reaction mixture was cooled, and allyl 4-chloro-4-oxobutyrate (1.06 g, 6.02 mmol) obtained from Example 14-(1), triethylamine (920 μl, 6.60 mmol), and 4-(N,N-dimethylamino)pyridine (10 mg) were added thereto at 0° C. The mixture was stirred at room temperature for 18 hours, and the obtained mixture was diluted with ethyl acetate, then the resulting solution was washed successively with water, a saturated aqueous solution of sodium hydrogen carbonate, a saturated aqueous solution of ammonium chloride, and an aqueous solution of sodium chloride. The solution was dried over anhydrous magnesium sulfate, and the solvent was distilled off under reduced pressure to give an oily residue. The residue was subjected to chromatography on a silica gel (50 g) column (eluent; hexane:ethyl acetate=3:1~2:1) to afford the title compound (1.52 g, 70% yield) as a colorless oil.

NMR spectrum (400 MHz, CDCl$_3$) δ ppm: 1.47 (2H, quint, J=7 Hz), 2.42 (2H, t, J=7 Hz), 2.55-2.70 (4H, m), 3.81 (3H, s), 4.13 (2H, t, J=7 Hz), 4.59 (2H, dt, J=6, 2 Hz), 5.06 (2H, s), 5.23 (1H, br d, J=11 Hz), 5.30 (1H, br d, J=18, 2 Hz), 5.89 (1H, ddt, J=18, 11, 6 Hz), 6.89 (2H, d, J=8 Hz), 7.29 (2H, d, J=8 Hz)

IR spectrum ν max neat cm$^{-1}$: 1735, 1614, 1516, 1249 1163

Mass spectrum m/z (EI): 364 (M$^+$).

(3) Allyl 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl succinate

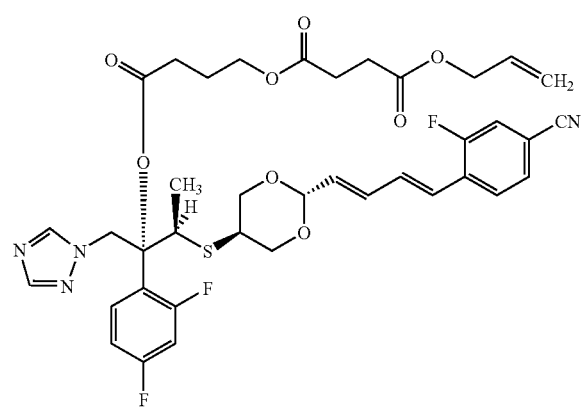

According to a similar procedure to that described in Example 13-(2), allyl 4-[(4-methoxybenzyl)oxy]-4-oxobutyl succinate (546 mg, 1.50 mmol) obtained from Example 14-(4) was treated with anisole (0.50 ml) and trifluoroacetic acid (5 ml), to afford 4-[4-(allyloxy)-4-oxobutyryloxy]butyric acid, and then treated with oxalyl chloride (290 mg) to give crude allyl 4-chloro-4-oxobutyl succinate.

The crude allyl 4-chloro-4-oxobutyl succinate was treated with 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (814 mg, 1.50 mmol) described in Reference example 1 and sodium hydride (55% dispersion in mineral oil; 70 mg, 1.6 mmol) according to a similar procedure to that described in Example 13-(2). The obtained crude title compound was purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (459 mg, 40% yield) as a colorless viscous material.

NMR spectrum (400 MHz, CDCl$_3$) δ ppm: 1.35 (3H, dd, J=7, 2 Hz), 1.85-2.05 (2H, m), 2.35-2.55 (2H, m), 2.60-2.75 (4H, m), 3.05 (1H, tt, J=12, 5 Hz), 3.52 (2H, t, J=11 Hz), 3.92 (1H, q, J=7 Hz), 4.15-4.25 (4H, m), 4.60 (2H, br d, J=6 Hz), 5.00 (1H, d, J=4 Hz), 5.23 (1H, br d, J=11 Hz), 5.31 (1H, br d, J=17 Hz), 5.35 (2H, s), 5.85 (1H, dd, J=15, 4 Hz), 5.90 (1H, ddt, J=17, 11, 6 Hz), 6.58 (1H, dd, J=16, 11 Hz), 6.74 (1H, d, J=16 Hz), 6.85-6.95 (3H, m), 7.30-7.45 (3H, m), 7.57 (1H, t, J=8 Hz), 7.90 (1H, s), 7.92 (1H, s)

IR spectrum ν max CHCl$_3$ cm$^{-1}$: 2233, 1737, 1616, 1598, 1504

Mass spectrum m/z (FAB): 769 (M$^+$+1).

(4) Sodium 4-[(1R,2R)-2-[[trans-2-[(1E,3E)-4-(4-cyano-2-fluorophenyl)-1,3-butadienyl]-1,3-dioxan-5-yl]thio]1-(2,4-difluorophenyl)-1-[(1H-1,2,4-triazol-1-yl)methyl]propoxy]-4-oxobutyl succinate (Title Target Compound)

According to a similar procedure to that described in Example 1-(13), allyl 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutyl succinate (180 mg, 2.35×10$^{-4}$ mmol) obtained from Example 14-(3), bis(triphenylphosphine)dichloropalladium (3 mg) and tributyltin hydride (100 mg, 3.44×10$^{-4}$ mmol) were reacted, and the reaction mixture was worked up to afford the title target compound as a crude oil. The crude oil was subjected to reverse phase column chromatography using Cosmosil 75 C$_{18}$-PREP (Nacalai Tesque, Inc.; 20 g) (eluent; water:methanol=4:6~3:7). The obtained fractions were concentrated, and the residue was lyophilized to afford the title target compound (64 mg, 36% yield) as a colorless solid.

NMR spectrum (400 MHz, CD$_3$OD) δ ppm: 1.31 (3H, dd, J=7, 2 Hz), 1.90-2.00 (2H, m), 2.40-2.65 (6H, m), 3.03 (1H, tt, J=12, 5 Hz), 3.52 (2H, t, J=11 Hz), 3.85 (1H, q, J=7 Hz), 4.05-4.25 (4H, m), 5.04 (1H, d, J=5 Hz), 5.44 (2H, m), 5.85 (1H, dd, J=15, 5 Hz), 6.59 (1H, dd, J=15, 10 Hz), 6.80 (1H, d, J=15 Hz), 6.95-7.05 (2H, m), 7.10 (1H, dd, J=15, 10 Hz), 7.45-7.55 (3H, m), 7.80 (1H, t, J=8 Hz), 8.00 (1H, s), 8.32 (1H, s)

IR spectrum ν max CHCl$_3$ cm$^{-1}$: 3438, 2231, 1737, 1614, 1595, 1504, 1419

Mass spectrum m/z (FAB): 751 (M$^+$+1)

Example 15

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl(2-hydroxyethyl) carbonate (Example Number 4-31)

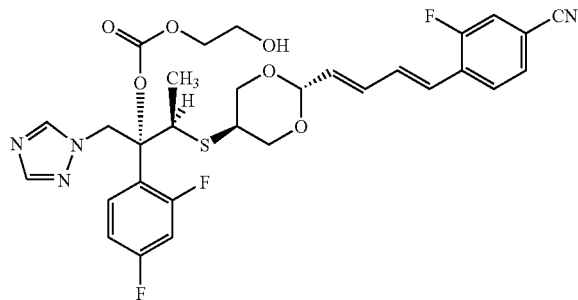

(1) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl imidazole-1-carboxylate

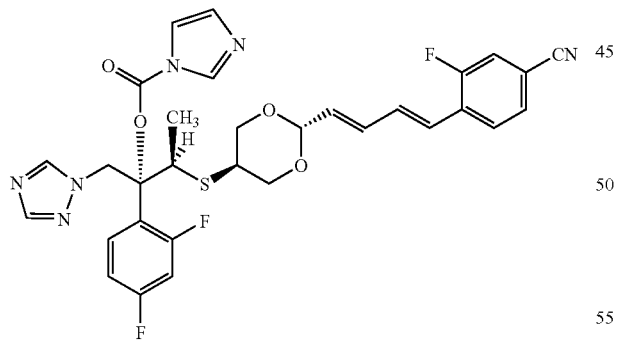

4-[(1E,3E)-4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (4.90 g, 9.03 mmol) described in Reference example 1 and 1,1'-carbonyldiimidazole (1.53 g, 9.44 mmol) were dissolved in dichloromethane (20 ml). To the mixture was added sodium hydride (55% dispersion in mineral oil; 10 mg, 2.3×10$^{-4}$ mol), and the reaction mixture was heated under reflux for 3 hours with stirring. After cooling, a phosphate buffer solution (pH 7.4) was added thereto, and the product was extracted with ethyl acetate. The organic layer was washed with an aqueous solution of sodium chloride, dried over anhydrous magnesium sulfate, and the solvent was distilled off under reduced pressure. The residue was subjected to chromatography on a silica gel (120 g) column (eluent; ethyl acetate:hexane=1:1~1:0) to afford the title compound (4.00 g, 70% yield) as a colorless amorphous solid.

NMR spectrum (400 MHz, CDCl$_3$) δ ppm: 1.46 (3H, dd, J=7, 2 Hz), 3.01 (1H, tt, J=11, 5 Hz), 3.51 (1H, t, J=12 Hz), 3.52 (1H, t, J=12 Hz), 4.01 (1H, q, J=7 Hz), 4.10-4.20 (2H, m), 5.00 (1H, d, J=5 Hz), 5.28 (1H, br d, J=18 Hz), 5.48 (2H, s), 5.85 (1H, dd, J=15, 4 Hz), 6.58 (1H, dd, J=15, 11 Hz), 6.90-7.00 (3H, m), 7.13 (1H, br s), 7.30-7.45 (4H, m), 7.57 (1H, t, J=8 Hz), 7.84 (1H, s), 7.97 (1H, s), 8.11 (1H, s)

IR spectrum ν max KBr cm$^{-1}$: 2230, 1763, 1615, 1504, 1418, 1390

Mass spectrum m/z (FAB): 637 (M$^+$+1).

(2) 2-[(tert-Butyldiphenylsilyl)oxy]ethanol

Commercially available 2-hydroxyethyl acetate (3.12 g, 30.0 mmol), triethylamine (4.6 ml, 33 mmol), and 4-(N,N-dimethylamino)pyridine (100 mg) were dissolved in dichloromethane (20 ml), then tert-butylchlorodiphenylsilane (8.65 g, 31.5 mmol) was added thereto at room temperature, and the mixture was stirred for 20 hours. The obtained solution was diluted with a mixed solvent of hexane-ethyl acetate (1:1), and then the resulting solution was washed with water and with an aqueous solution of sodium chloride. The solution was dried over anhydrous magnesium sulfate, and the solvent was distilled off under reduced pressure. The residue was dissolved in methanol (100 ml), and 28% sodium methoxide in methanol (3 ml) was added thereto at room temperature followed by stirring for 2 hours. The solvent was distilled off under reduced pressure, and the residue was partitioned between ethyl acetate and a phosphate buffer solution (pH 7), then the organic layer was washed with an aqueous solution of sodium chloride and dried over anhydrous magnesium sulfate. The solvent was distilled off under reduced pressure to afford the crude title compound (5.18 g, 57% gross yield) as a colorless oil.

NMR spectrum (400 MHz, CDCl$_3$) δ ppm: 1.07 (9H, s), 2.11 (1H, t, J=6 Hz), 3.65-3.70 (2H, m), 3.77 (2H, t, J=5 Hz), 7.35-7.50 (6H, m), 7.65-7.70 (4H, m).

(3) 2-[(tert-Butyldiphenylsilyl)oxy]ethyl(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl carbonate

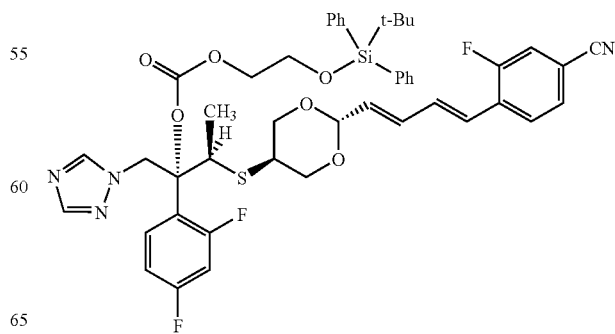

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl imidazole-1-carboxylate (637 mg, 1.00 mmol) obtained from Example 15-(1) and the crude 2-[(tert-butyldiphenylsilyl)oxy]ethanol (315 mg, ca. 1.05 mmol) obtained from Example 15-(2) were dissolved in dichloromethane (3 ml), and potassium tert-butoxide (5 mg) was added thereto. The mixture was heated under reflux for 15 minutes with stirring. After cooling, a phosphate buffer solution (pH 7) was poured into the mixture, and the reaction product was extracted with ethyl acetate. The organic layer was dried over anhydrous magnesium sulfate, and the solvent was distilled off under reduced pressure. The residue was purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (631.4 mg, 73% yield) as a colorless amorphous solid.

NMR spectrum (400 MHz, CDCl$_3$) δ ppm: 1.07 (9H, s), 1.35 (3H, dd, J=7, 2 Hz), 3.04 (1H, tt, J=11, 5 Hz), 3.48 (1H, t, J=11 Hz), 3.50 (1H, t, J=11 Hz), 3.80-3.95 (3H, m), 4.15-4.20 (2H, m), 4.30-4.35 (2H, m), 4.94 (1H, d, J=5 Hz), 5.36 (1H, dd, J=15, 3 Hz), 5.41 (1H, d, J=15 Hz), 5.84 (1H, dd, J=15, 4 Hz), 6.55 (1H, dd, J=15, 11 Hz), 6.71 (1H, d, J=16 Hz), 6.75-6.95 (3H, m), 7.30-7.50 (9H, m), 7.56 (1H, t, J=8 Hz), 7.65-7.75 (4H, m), 7.90 (1H, s), 7.95 (1H, s)

IR spectrum ν max KBr cm$^{-1}$: 2230, 1750, 1615, 1503
Mass spectrum m/z (FAB): 869 (M$^+$+1).

(4) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl(2-hydroxyethyl) carbonate (Title Target Compound)

To a solution of 2-[(tert-butyldiphenylsilyl)oxy]ethyl(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl carbonate (470 mg, 5.41×10$^{-4}$ mol) obtained from Example 15-(3) in tetrahydrofuran (1.5 ml) were added successively acetic acid (33 mg, 5.5×10$^{-4}$ mol) and tetrabutylammonium fluoride (1M solution in tetrahydrofuran; 0.55 ml, 5.5×10$^{-4}$ mol). The mixture was stirred at the same temperature for 1 hour, then ethyl acetate and a phosphate buffer solution (pH 7) were poured thereinto, and the organic layer was separated. The organic layer was washed with an aqueous solution of sodium chloride, dried over anhydrous magnesium sulfate, and the solvent was distilled off under reduced pressure. The residue was purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (186 mg, 55% yield) as a colorless amorphous solid.

NMR spectrum (400 MHz, CDCl$_3$) δ ppm: 1.34 (3H, dd, J=7, 3 Hz), 1.90 (1H, br s), 2.95-3.10 (1H, m), 3.49 (1H, t, J=11 Hz), 3.51 (1H, t, J=11 Hz), 3.80-3.90 (3H, m), 4.19 (1H, ddd, J=11, 5, 2 Hz), 4.25-4.40 (3H, m), 4.94 (1H, d, J=5 Hz), 5.39 (2H, m), 5.85 (1H, dd, J=15, 4 Hz), 6.58 (1H, dd, J=15, 11 Hz), 6.73 (1H, d, J=16 Hz), 6.85-7.00 (3H, m), 7.33 (1H, dd, J=10, 1 Hz), 7.40 (1H, dd, J=8, 1 Hz), 7.45 (1H, td, J=9, 6 Hz), 7.57 (1H, t, J=8 Hz), 7.96 (1H, s), 8.04 (1H, s).

Example 16

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyloxy]ethyl phosphate (Disodium Salt of Example Number 4-45)

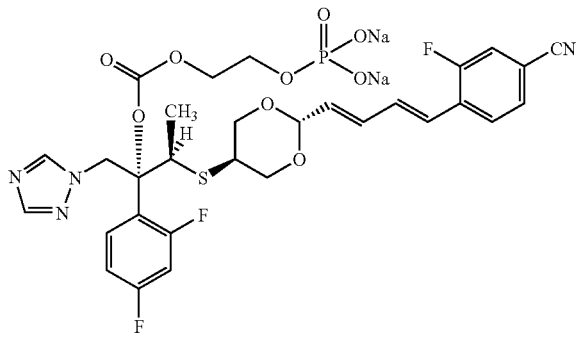

(1) 2-[[Bis(allyloxy)phosphoryl]oxy]ethyl(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl carbonate

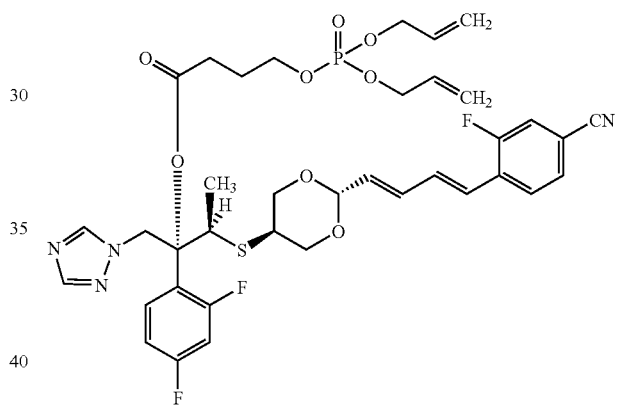

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl(2-hydroxyethyl)carbonate (180 mg, 2.85×10$^{-4}$ mol) obtained from Example 15 in dichloromethane (2 ml) were added tetrazole (40 mg, 5.7×10$^{-4}$ mol) and bis(allyloxy)(diisopropylamino)phosphine (Tetrahedron Lett., 30, 4219 (1989); 105 mg, 4.28×10$^{-4}$ mol) at room temperature, and the reaction mixture was stirred for 30 minutes. Allyl alcohol (0.1 ml) was added to the mixture at the same temperature, and the resulting mixture was stirred for 20 minutes further. The mixture was cooled to 0° C., and tert-butyl hydroperoxide (ca. 5M nonane solution; 1.5 ml, ca. 7.5 mmol) was added thereto, then the mixture was stirred at room temperature for 30 minutes. To the mixture were added a saturated aqueous solution of sodium hydrogen carbonate and an aqueous solution of sodium thiosulfate, then the resulting mixture was stirred for 10 minutes and partitioned between ethyl acetate and water. The organic layer was washed successively with a saturated aqueous solution of sodium hydrogen carbonate, a saturated aqueous solution of ammonium chloride, and an aqueous solution of sodium chloride, dried over anhydrous magnesium sulfate, and the solvent was distilled off under reduced pressure. The obtained residue was purified by recycle preparative HPLC

[LC-908; Japan Analytical Industry Co., Ltd.; GPC column JAIGEL-LH (20 mm i.d.×600 mm) and JAIGEL-2H (20 mm i.d.×600 mm) connected in series for use; solvent, chloroform] to afford the title compound (124 mg, 55% yield) as a colorless viscous material.

NMR spectrum (400 MHz, CDCl$_3$) δ ppm: 1.35 (3H, dd, J=7, 2 Hz), 3.01 (1H, tt, J=12, 5 Hz), 3.48 (1H, t, J=12 Hz), 3.50 (1H, t, J=12 Hz), 3.84 (1H, q, J=7 Hz), 4.17 (1H, ddd, J=12, 5, 2 Hz), 4.25-4.35 (4H, m), 4.40-4.50 (1H, m), 4.55-4.60 (4H, m), 4.97 (1H, d, J=4 Hz), 5.26 (2H, dt, J=12, 1 Hz), 5.35-5.40 (4H, m), 5.84 (1H, dd, J=15, 4 Hz), 5.85-6.00 (2H, m), 6.57 (1H, dd, J=15, 11 Hz), 6.73 (1H, d, J=15 Hz), 6.85-7.00 (3H, m), 7.33 (1H, dd, J=10, 1 Hz), 7.40 (1H, dd, J=8, 1 Hz), 7.46 (1H, td, J=9, 6 Hz), 7.57 (1H, t, J=8 Hz), 7.94 (1H, s), 7.98 (1H, s)

IR spectrum ν max CHCl$_3$ cm$^{-1}$: 2233, 1753, 1616, 1504, 1276, 1140

Mass spectrum m/z (FAB): 791 (M$^+$+1).

(2) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyloxy]ethyl phosphate (Title Target Compound)

2-[[Bis(allyloxy)phosphoryl]oxy]ethyl(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl carbonate (120 mg, 1.52×10$^{-4}$ mol) obtained from Example 16-(1) and tetrakis(triphenylphosphine)palladium (2 mg) were dissolved in dichloromethane (1.2 ml). To the mixture was added pyrrolidine (215 mg, 3.04 mmol) at room temperature, and the solution was stirred for 1 hour. And then according to a similar procedure to that described in Example 13-(3), the title target compound (87.5 mg, 76% yield) was obtained as an amorphous pale yellow solid.

NMR spectrum (400 MHz, D$_2$O) δ ppm: 1.18 (3H, d, J=7 Hz), 2.81 (1H, m), 3.43 (1H, br t, J=12 Hz), 3.46 (1H, br t, J=12 Hz), 3.59 (1H, m), 3.85 (2H, m), 3.95-4.15 (2H, m), 4.22 (2H, m), 4.97 (1H, br d, J=4 Hz), 5.21 (1H, br d, J=15 Hz), 5.34 (1H, br d, J=15 Hz), 5.65 (1H, br dd, J=15, 5 Hz), 6.41 (1H, m), 6.63 (1H, br d, J=16 Hz), 6.80-6.95 (3H, m), 7.25-7.60 (4H, m), 7.88 (1H, s), 8.26 (1H, s)

IR spectrum ν max KBr cm$^{-1}$: 3418, 2231, 1749, 1615, 1600, 1504, 1418, 1385, 1276, 1257, 1141.

Mass spectrum m/z (FAB): 755 (M$^+$+1).

Example 17

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (Example Number 5-1)

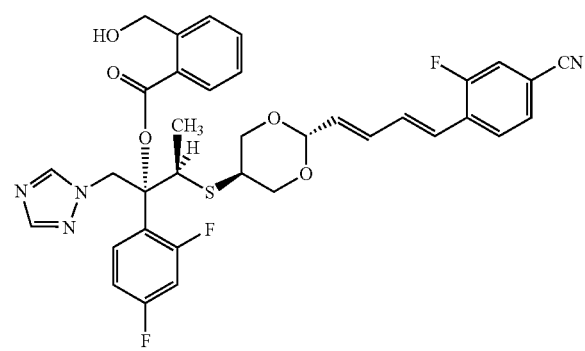

(1) 4-Methoxynenzyl 2-[(allyloxycarbonyl)oxymethyl]benzoate

Commercially available 1(3H)-isobenzofuranone (740 mg, 5.52 mmol) and potassium hydroxide (310 mg, 5.52 mmol) were suspended in a mixed solvent (10 ml) of methanol-water (2:1) followed by stirring for 3 hours while heating the suspension at 70° C. After cooling, the solvent was distilled off under reduced pressure. The residue was dried using a vaccum pump while heating the residue at 40° C. The obtained solid was suspended in N,N-dimethylformamide (10 ml), and 4-methoxybenzyl chloride (865 mg, 5.52 mmol) was added thereto. The mixture was stirred at 100° C. for 1 hour. The mixture was cooled, then diluted with ethyl acetate, and the resulting mixture was washed with water and then with an aqueous solution of sodium chloride. The solution was dried over anhydrous magnesium sulfate, and the solvent was distilled off under reduced pressure to give a colorless oily residue. The residue was dissolved in dichloromethane (10 ml), then 4-(N,N-dimethylamino)pyridine (673 mg, 5.51 mmol) and allyl chloroformate (644 mg, 5.51 mmol) were added thereto at 0° C. followed by stirring at room temperature for 1 hour. The mixture was diluted with ethyl acetate, and then washed successively with water and an aqueous solution of sodium chloride. The resulting solution was dried over anhydrous magnesium sulfate, and the solvent was distilled off under reduced pressure to give an oily residue. The residue was subjected to chromatography on a silica gel (60 g) column (eluent; hexane:ethyl acetate=5:1) to give the title compound (905 mg, 46% yield) as a colorless oil.

NMR spectrum (400 MHz, CDCl$_3$) δ ppm: 3.82 (3H, s), 4.66 (2H, dt, J=6, 1 Hz), 5.28 (1H, br d, J=10 Hz), 5.29 (2H, s), 5.38 (1H, br d, J=18 Hz), 5.61 (2H, s), 5.95 (1H, ddt, J=18, 10, 6 Hz), 6.91 (2H, d, J=9 Hz), 7.35-7.40 (1H, m), 7.39 (2H, d, J=9 Hz), 7.50-7.55 (2H, m), 8.02 (1H, d, J=7 Hz)

IR spectrum ν max neat cm$^{-1}$: 1750, 1716, 1614, 1516, 1248

Mass spectrum m/z (FAB): 356 (M$^+$).

(2) 2-[(Allyloxycarbonyl)oxymethyl]benzoic acid

A mixture of 4-methoxybenzyl 2-[(allyloxycarbonyl)oxymethyl]benzoate (6.80 g, 19.1 mmol) obtained from Example 17-(1) and anisole (5 g) was dissolved in trifluoroacetic acid (10 ml) at room temperature. The mixture was stirred for 15 minutes, then diluted with toluene, and the solvent was distilled off under reduced pressure. The residue was washed with hexane to afford the crude title compound (3.87 g, 86%) as a colorless solid.

NMR spectrum (400 MHz, CDCl$_3$) δ ppm: 4.68 (2H, dt, J=6, 1 Hz), 5.29 (1H, br d, J=10 Hz), 5.39 (1H, br d, J=17 Hz), 5.67 (2H, s), 5.94 (1H, ddt, J=17, 10, 6 Hz), 7.40-7.50 (1H, m), 7.60-7.65 (2H, m), 8.15 (1H, d, J=8 Hz), 11.5 (1H, br s).

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(allyloxycarbonyl)oxymethyl]benzoate

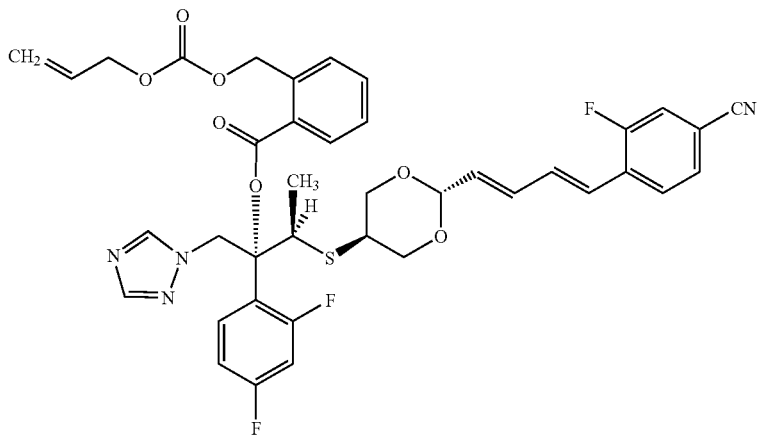

2-[(Allyloxycarbonyl)oxymethyl]benzoic acid (850 mg, 3.60 mmol) obtained from Example 17-(2) was dissolved in dichloromethane (5 ml), and N,N-dimethylformamide (0.05 ml) and oxalyl chloride (570 mg) were added thereto. The mixture was stirred at room temperature for 1 hour, then toluene was added thereto, and the solution was concentrated under reduced pressure to give crude 2-[(allyloxycarbonyl)oxymethyl]benzoyl chloride.

A chemical reaction was carried out according to a similar procedure to that described in Example 13-(2) using 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.63 g, 3.00 mmol) described in Reference example 1, sodium hydride (55% dispersion in mineral oil; 144 mg, 3.3 mmol) and the crude 2-[(allyloxycarbonyl)oxymethyl]benzoyl chloride obtained above. The obtained crude product was subjected to chromatography on a silica gel (50 g) column (eluent; ethyl acetate:hexane=1:1~4:1) to afford the title compound (1.68 g, 74% yield) as a pale yellow amorphous solid.

NMR spectrum (400 MHz, CDCl$_3$) δ ppm: 1.46 (3H, dd, J=7, 2 Hz), 3.05 (1H, tt, J=11, 5 Hz), 3.50 (1H, t, J=11 Hz), 3.52 (1H, t, J=11 Hz), 4.00 (1H, q, J=7 Hz), 4.10-4.20 (2H, m), 4.60-4.70 (2H, m), 4.98 (1H, d, J=4 Hz), 5.28 (1H, br d, J=10 Hz), 5.37 (1H, br d, J=18 Hz), 5.45-5.55 (4H, m), 5.84 (1H, dd, J=15, 4 Hz), 5.94 (1H, ddt, J=18, 10, 6 Hz), 6.57 (1H, dd, J=15, 11 Hz), 6.73 (1H, d, J=15 Hz), 6.85-6.95 (3H, m), 7.34 (1H, d, J=9 Hz), 7.35-7.45 (3H, m), 7.55-7.65 (3H, m), 7.76 (1H, t, J=7 Hz), 7.91 (1H, s), 7.98 (1H, s)

IR spectrum ν max KBr cm$^{-1}$: 2231, 1748, 1728, 1615, 1504

Mass spectrum m/z (FAB): 761 (M$^+$+1)

(4) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (Title Target Compound)

A chemical reaction was carried out according to a similar procedure to that described in Example 11-(4) using (1R,2R)-2-[[trans-2-[(1E,3E)-4-(4-cyano-2-fluorophenyl)-1,3-butadienyl]-1,3-dioxan-5-yl]thio]1-(2,4-difluorophenyl)-1-[(1H-1,2,4-triazol-1-yl)methyl]propyl 2-[(allyloxycarbonyl)oxymethyl]benzoate (1.52 g, 2.00 mmol), bis(triphenylphosphine)dichloropalladium (5 mg), and tributyltin hydride (620 mg, 2.13 mmol). The obtained crude product was subjected to chromatography on a silica gel (50 g) column (eluent; ethyl acetate:hexane=1:1~1:0) to afford the title compound (1.096 g, 81% yield) as a colorless amorphous solid.

NMR spectrum (400 MHz, CDCl$_3$) δ ppm: 1.46 (3H, dd, J=7, 2 Hz), 3.06 (1H, tt, J=12, 5 Hz), 3.31 (1H, t, J=7 Hz), 3.50 (1H, t, J=11 Hz), 3.53 (1H, t, J=11 Hz), 4.04 (1H, q, J=7 Hz), 4.10-4.25 (2H, m), 4.73 (1H, dd, J=13, 7 Hz), 4.80 (1H, dd, J=13, 7 Hz), 4.98 (1H, d, J=4 Hz), 5.52 (2H, m), 5.84 (1H, dd, J=16, 4 Hz), 6.57 (1H, dd, J=15, 11 Hz), 6.73 (1H, d, J=15 Hz), 6.85-7.00 (3H, m), 7.33 (1H, dd, J=10, 1 Hz), 7.35-7.45 (3H, m), 7.50-7.60 (3H, m), 7.79 (1H, dd, J=8, 1 Hz), 7.89 (1H, s), 7.94 (1H, s)

IR spectrum ν max KBr cm$^{-1}$: 3402, 2231, 1722, 1616, 1504

Mass spectrum m/z (FAB): 677 (M$^+$+1)

Example 18

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Disodium Salt of Example Number 5-15)

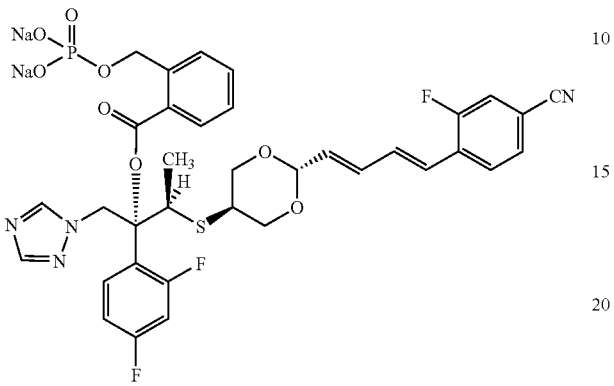

(1) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]benzoate

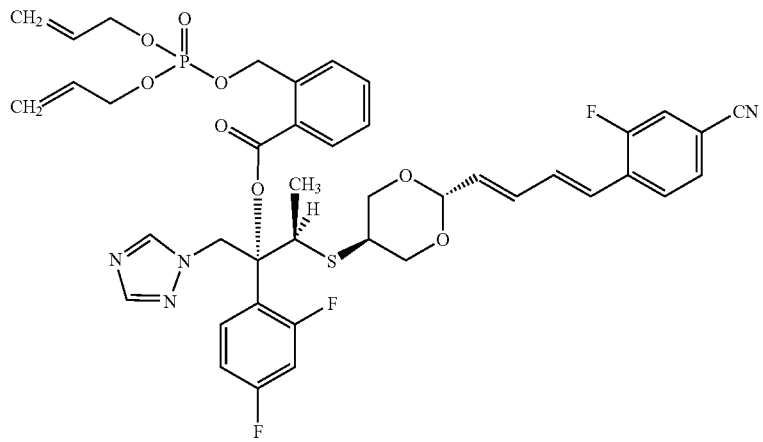

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (540 mg, $7.89 \times 10^{-4}$ mol) obtained from Example 17-(4) was dissolved in a mixed solvent (3 ml) of dichloromethane-acetonitrile (1:1). Tetrazole (112 mg, 1.6 mmol) and bis(allyloxy)(diisopropylamino)phosphine (Tetrahedron Lett., 30, 4219 (1989); 250 mg, $1.0 \times 10^{-3}$ mol) were added thereto at 0° C., and the mixture was stirred at the same temperature for 5 minutes. The mixture was warmed to room temperature, then stirred for 30 minutes, and allyl alcohol (0.1 ml) was added thereto. The mixture was stirred for another 5 minutes, then tert-butyl hydroperoxide (ca. 5M nonane solution, 1.5 ml, ca. 7.5 mmol) was added thereto at 0° C., and the resulting mixture was stirred at room temperature for 30 minutes. A saturated aqueous solution of sodium hydrogen carbonate and an aqueous solution of sodium thiosulfate were added thereto, then the mixture was stirred for 10 minutes and partitioned between ethyl acetate and water. The organic layer was washed successively with a saturated aqueous solution of sodium hydrogen carbonate, a saturated aqueous solution of ammonium chloride, and an aqueous solution of sodium chloride, dried over anhydrous magnesium sulfate, and the solvent was distilled off under reduced pressure to give an oily residue. The residue was subjected to chromatography on a silica gel (15 g) column (eluent; ethyl acetate:hexane=2: 1~1:0), and further purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (363 mg, 54% yield) as a colorless amorphous solid.

NMR spectrum (400 MHz, CDCl$_3$) δ ppm: 1.45 (3H, dd, J=7, 2 Hz), 3.05 (1H, tt, J=11, 5 Hz), 3.50 (1H, t, J=11 Hz), 3.53 (1H, t, J=11 Hz), 4.01 (1H, q, J=7 Hz), 4.10-4.20 (2H, m), 4.50-4.60 (4H, m), 4.99 (1H, d, J=4 Hz), 5.24 (2H, br d, J=10 Hz), 5.34 (2H, br d, J=18 Hz), 5.40-5.55 (4H, m), 5.71 (1H, dd, J=15, 4 Hz), 5.85-6.00 (2H, m), 6.57 (1H, dd, J=15, 11 Hz), 6.73 (1H, d, J=15 Hz), 6.85-6.95 (3H, m), 7.34 (1H, dd, J=10, 1 Hz), 7.35-7.45 (3H, m), 7.57 (1H, t, J=8 Hz), 7.62 (1H, td, J=7, 1 Hz), 7.72 (1H, d, J=8 Hz), 7.76 (1H, d, J=9 Hz), 7.90 (1H, s), 7.91 (1H, s)

IR spectrum ν max KBr cm$^{-1}$: 2231, 1724, 1615, 1504

Mass spectrum m/z (FAB): 837 (M$^+$+1).

(2) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate
(Title Target Compound)

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]benzoate (1.55 g, 1.85 mmol) obtained from Example 18-(1) and tetrakis(triphenylphosphine)palladium (20 mg) were dissolved in dichloromethane (13 ml). To the mixture was added pyrrolidine (2.63 g, 37.0 mmol) followed by stirring for 0.5 hours. The title compound (1.22 g, 76% yield) was obtained as an amorphous colorless solid according to a similar procedure to that described in Example 13-(3).

NMR spectrum (400 MHz, D$_2$O) δ ppm: 1.27 (3H, d, J=7 Hz), 2.95 (1H, m), 3.40 (1H, t, J=11 Hz), 3.45 (1H, t, J=11 Hz), 3.79 (1H, q, J=7 Hz), 3.93 (1H, m), 4.05 (1H, m), 4.90 (1H, dd, J=16, 7 Hz), 4.95 (1H, d, J=5 Hz), 5.03 (1H, dd, J=16, 7 Hz), 5.35 (1H, d, J=15 Hz), 5.44 (1H, br d, J=15 Hz), 5.67 (1H, m), 6.34 (1H, m), 6.68 (1H, br d, J=15 Hz), 6.85-7.00 (3H, m), 7.20-7.30 (1H, m), 7.30-7.45 (3H, m), 7.50-7.65 (3H, m), 7.76 (1H, d, J=8 Hz), 7.84 (1H, s), 8.23 (1H, s)

IR spectrum ν max KBr cm$^{-1}$: 3414, 2231, 1722, 1615, 1503, 1418, 1387, 1275, 1257, 1205, 1139

Mass spectrum m/z (FAB): 801 (M$^+$+1)

Elemental analysis for C$_{35}$H$_{30}$F$_3$N$_4$O$_8$PSNa$_2$·4H$_2$O: Calculated: C, 48.17; H, 4.39; N, 6.24; Na, 5.27. Found: C, 47.94; H, 4.31; N, 6.39; Na, 5.07.

Example 19

2-[[(1R,2R)-2-[[trans-2-[(1E,3E)-4-(4-Cyano-2-fluorophenyl)-1,3-butadienyl]-1,3-dioxan-5-yl]thio]1-(2,4-difluorophenyl)-1-[(1H-1,2,4-triazol-1-yl)methyl]propoxy]carbonyl]benzyl hydrogen succinate
(Example Number 5-5)

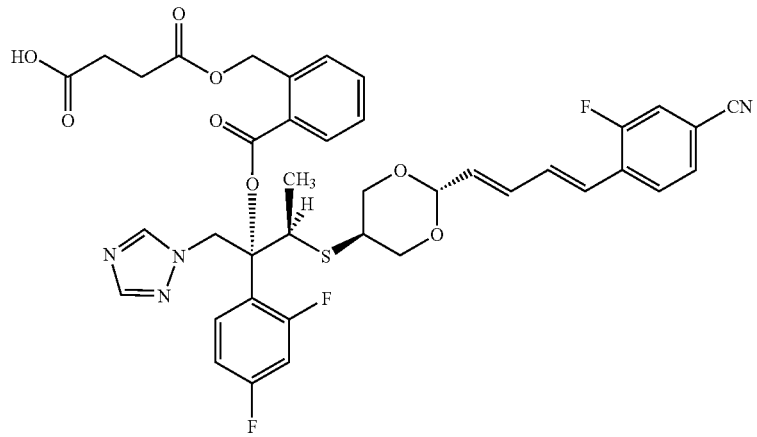

(1) Allyl [2-(methoxybenzyloxy)carbonyl]benzyl succcinate

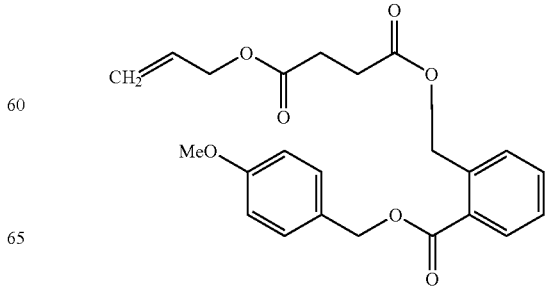

Commercially available 1(3H)-isobenzofuranone (805 mg, 6.00 mmol) and potassium hydroxide (0.34 g, 5.9 mmol) were suspended in a mixed solvent of methanol-water (2:1), and the suspension was stirred at 70° C. for 3 hours. After cooling the reaction mixture, the solvent was evaporated under reduced pressure. The residue was dried using a vaccum pump while heating the residue at 40° C. The obtained solid was suspended in N,N-dimethylformamide (10 ml), and 4-methoxybenzyl chloride (987 mg, 6.30 mmol) was added thereto. The mixture was stirred at 100° C. for 1 hour. The obtained mixture was cooled, diluted with ethyl acetate, washed with water and then with an aqueous solution of sodium chloride, dried over anhydrous magnesium sulfate, and the solvent was distilled off under reduced pressure to give a colorless oily residue. The residue was dissolved in dichloromethane (10 ml), and triethylamine (976 μl, 7.00 mmol), 4-(N,N-dimethylamino)pyridine (10 mg), and allyl 4-chloro-4-oxobutyrate (1.06 g, 6.00 mmol) obtained from Example 14-(1) were successively added thereto at 0° C., and the resulting mixture was stirred at room temperature for 1 hour. The mixture was diluted with ethyl acetate, then washed successively with water and an aqueous solution of sodium chloride, and the solution was dried over anhydrous magnesium sulfate and the solvent was distilled off under reduced pressure. The residue was subjected to chromatography on a silica gel (60 g) column (eluent; hexane:ethyl acetate=4:1~3:1) to give the title compound (1.00 g, 40% yield) as a pale yellow oil.

NMR spectrum (400 MHz, CDCl$_3$) δ ppm: 2.68 (4H, m), 3.82 (3H, s), 4.59 (2H, br d, J=6 Hz), 5.23 (1H, br d, J=10 Hz), 5.28 (2H, s), 5.31 (1H, br d, J=18 Hz), 5.54 (2H, s), 5.90 (1H, ddt, J=18, 10, 6 Hz), 6.91 (2H, d, J=9 Hz), 7.35-7.40 (1H, m), 7.39 (2H, d, J=9 Hz), 7.45-7.55 (2H, m), 8.00 (1H, dd, J=8, 1 Hz)

IR spectrum ν max neat cm$^{-1}$: 1737, 1614, 1516, 1249

Mass spectrum m/z (FAB): 413 (M$^+$+1).

(2) Allyl 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl succinate mixture was diluted with toluene, and the solvent was distilled off under reduced pressure. The obtained residue was dissolved in dichloromethane (3 ml), and N,N-dimethylformamide (0.02 ml) and oxalyl chloride (300 mg) were added thereto. The mixture was stirred at room temperature for 1 hour, then toluene was added thereto, and the solvent was distilled off under reduced pressure to give crude allyl 2-(chlorocarbonyl)benzyl succinate.

A chemical reaction was carried out according to a similar procedure to that described in Example 13-(2) using 4-[(1E, 3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (814 mg, 1.50 mmol) described in Reference example 1, sodium hydride (55% dispersion in mineral oil; 74 mg, 1.7 mmol), and the crude allyl 2-(chlorocarbonyl)benzyl succinate obtained above. The obtained crude product was subjected to chromatography on a silica gel (35 g) column (eluent; ethyl acetate:hexane=1:1~4:1) to afford the title compound (368 mg, 30% yield) as a pale yellow amorphous solid.

NMR spectrum (400 MHz, CDCl$_3$) δ ppm: 1.46 (3H, dd, J=7, 2 Hz), 2.60-2.80 (4H, m), 3.05 (1H, tt, J=11, 5 Hz), 3.51 (1H, t, J=11 Hz), 3.53 (1H, t, J=11 Hz), 4.02 (1H, q, J=7 Hz), 4.10-4.20 (2H, m), 4.59 (2H, d, J=6 Hz), 4.99 (1H, d, J=4 Hz), 5.23 (1H, dd, J=10, 1 Hz), 5.31 (1H, dd, J=18, 1 Hz), 5.45-5.55 (4H, m), 5.85 (1H, dd, J=15, 4 Hz), 5.90 (1H, ddt, J=18, 10, 6 Hz), 6.57 (1H, dd, J=15, 10 Hz), 6.74 (1H, d, J=15 Hz), 6.85-6.95 (3H, m), 7.34 (1H, d, J=9 Hz), 7.35-7.45 (3H, m), 7.55-7.65 (3H, m), 7.79 (1H, t, J=7 Hz), 7.90 (1H, s), 7.95 (1H, s)

IR spectrum ν max KBr cm$^{-1}$: 2231, 1734, 1615, 1504

Mass spectrum m/z (FAB): 817 (M$^+$+1).

(3) 2-[[(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl hydrogen succinate (Title Target Compound)

Allyl 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]

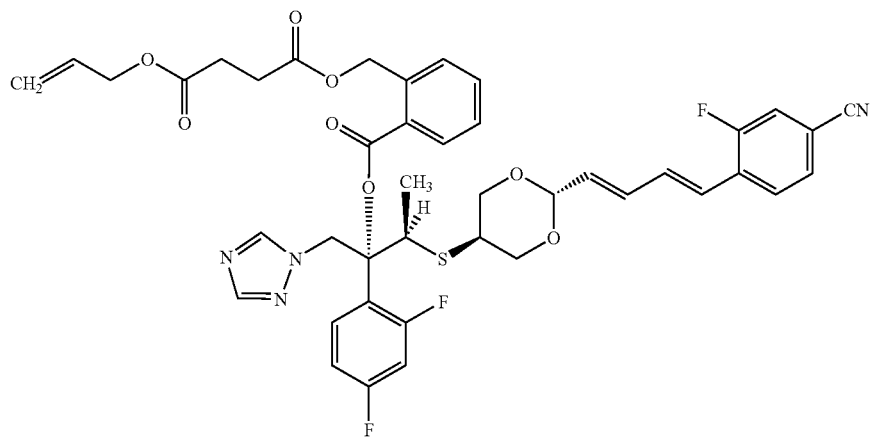

Allyl [2-(4-methoxybenzyloxy)carbonyl]benzyl succinate (620 mg, 1.50 mmol) obtained from Example 19-(1) and anisole (600 mg) were dissolved in trifluoroacetic acid followed by stirring at room temperature for 30 minutes. The carbonyl]benzyl succinate (150 mg, 1.84×10-4 mol) obtained from Example 19-(2) and bis(triphenylphosphine) dichloropalladium (2 mg) were dissolved in dichloromethane (1.5 ml). To the mixture was added water (0.1 ml), and tributyltin hydride (80 mg, 2.7×10$^{-4}$ mol) was slowly added thereto over a period of 5 minutes at room temperature. The resulting mixture was stirred at room temperature for 15 minutes further, and then hexane was added thereto. The liberated oily insoluble material was separated by removing the supernatant liquid slowly. The insoluble residue was further washed twice with hexane. The oily residue was subjected to chromatography on a silica gel (8 g) column (eluent; ethyl acetate), and then purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title compound (123.9 mg, 87% yield) as a colorless amorphous solid.

NMR spectrum (400 MHz, CDCl$_3$) δ ppm: 1.47 (3H, dd, J=7, 2 Hz), 2.65-2.75 (4H, m), 3.06 (1H, tt, J=11, 5 Hz), 3.52 (1H, t, J=11 Hz), 3.54 (1H, t, J=11 Hz), 4.05 (1H, q, J=7 Hz), 4.10-4.20 (2H, m), 4.99 (1H, d, J=4 Hz), 5.43 (1H, d, J=13 Hz), 5.49 (1H, br dd, J=15, 3 Hz), 5.56 (1H, d, J=15 Hz), 5.59 (1H, d, J=13 Hz), 5.84 (1H, dd, J=15, 4 Hz), 6.57 (1H, dd, J=15, 10 Hz), 6.73 (1H, d, J=15 Hz), 6.85-7.00 (3H, m), 7.33 (1H, d, J=10, 1 Hz), 7.35-7.45 (3H, m), 7.55-7.60 (3H, m), 7.89 (1H, t, J=7 Hz), 7.90 (1H, s), 8.09 (1H, s)

IR spectrum ν max KBr cm$^{-1}$: 2232, 1729, 1616, 1504

Mass spectrum m/z (FAB): 777 (M$^+$+1).

Example 20

Sodium (S)-3-amino-4-[4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutoxy]-4-oxobutyrate (Sodium Salt of Example Number 4-12)

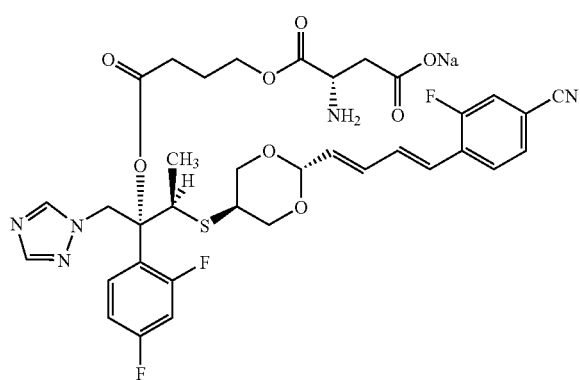

(1) tert-Butyl (S)-3-[(tert-butyl)oxycarbonylamino]-4-oxo-4-(2,2,2-trichloroethoxy)butyrate

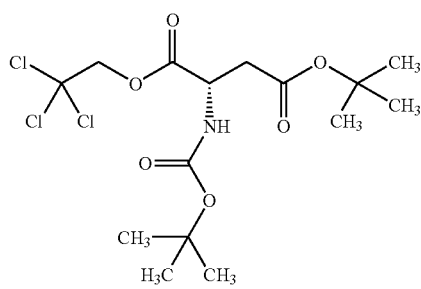

Commercially available N-(t-butoxycarbonyl)-L-aspartic acid β-t-butylester dicyclohexylammonium salt (1.00 g, 2.12 mmol) was subjected to column chromatography using an ion exchange resin (Dowex 50W-8X, Na type prepared using 1N aqueous solution of sodium hydroxide; 5 ml) (eluent; methanol). The collected fractions were concentrated under reduced pressure, and the residue was dissolved in water (50 ml). To the aqueous solution was added a 1N aqueous solution of hydrochloric acid (22 ml) to adjust the pH of the solution to about 4, and the liberated carboxylic acid was extracted with ethyl acetate. The organic layer was dried over anhydrous magnesium sulfate and the solvent was distilled off under reduced pressure. The obtained colorless oil was dissolved in dichloromethane (10 ml), and triethylamine (420 μl, 3.0 mmol) and 2,2,2-trichloroethyl formate (466 mg, 2.20 mmol) were added thereto at room temperature followed by stirring for 1 hour. The mixture was concentrated under reduced pressure, then the obtained residue was dissolved in ethyl acetate, and the organic layer was washed successively with an aqueous solution of sodium hydrogen carbonate, an aqueous solution of ammonium chloride, and an aqueous solution of sodium chloride. The solution was dried over anhydrous magnesium sulfate and then the solvent was distilled off under reduced pressure. The residue was subjected to chromatography on a silica gel (15 g) column (eluent; hexane:ethyl acetate=2:1) to afford the title compound (627 mg, 73% yield) as a colorless oil.

NMR spectrum (400 MHz, CDCl$_3$) δ ppm: 1.44 (9H, s), 1.46 (9H, s), 2.79 (1H, dd, J=17, 4 Hz), 3.01 (1H, dd, J=17, 5 Hz), 4.68 (1H, m), 4.86 (2H, s), 5.54 (1H, br d, J=9 Hz)

IR spectrum ν max CHCl$_3$ cm$^{-1}$: 3439, 2982, 2934, 1769, 1717, 1498

Mass spectrum m/z (FAB): 420 (M$^+$+1).

(2) Allyl (S)-3-(allyloxycarbonylamino)-4-oxo-4-(2,2,2-trichloroethoxy)butyrate tert-Butyl (S)-3-[(tert-butyl)oxycarbonylamino]-4-oxo-4-(2,2,2-trichloroethoxy)butyrate (605 mg, 1.48 mmol) obtained from Example 20-(1) was dissolved in trifluoroacetic acid (2.5 ml) followed by stirring for 1 hour. The mixture was diluted with toluene, and the solvent was distilled off under reduced pressure. The obtained white powder was suspended in dichloromethane (5 ml), and diisopropylethylamine (1.8 ml, 10 mmol) and allyl chloroformate (624 mg, 5.18 mmol) were added thereto at room temperature. The mixture was stirred for 1 hour, then a saturated aqueous solution of ammonium chloride was added thereto, and the product was extracted with ethyl acetate. The organic layer was washed successively with water and an aqueous solution of sodium chloride, dried over anhydrous magnesium sulfate, and the solvent was distilled off under reduced pressure. The residue was subjected to chromatography on a silica gel (25 g) column (eluent; hexane:ethyl acetate=4:1) to afford the title compound (384 mg, 67% yield) as a colorless oil.

NMR spectrum (400 MHz, CDCl$_3$) δ ppm: 2.95 (1H, dd, J=18, 4 Hz), 3.16 (1H, dd, J=18, 4 Hz), 4.55-4.65 (4H, m), 4.73 (1H, d, J=12 Hz), 4.79 (1H, m), 4.82 (1H, d, J=12 Hz), 5.23 (1H, br d, J=10 Hz), 5.26 (1H, br d, J=10 Hz), 5.32 (2H, br d, J=18 Hz), 5.77 (1H, br d, J=9 Hz), 5.85-6.00 (2H, m)

IR spectrum ν max CHCl$_3$ cm$^{-1}$: 3356, 1767, 1732, 1512

Mass spectrum m/z (FAB): 388 (M$^+$+1).

(3) (S)-4-Allyloxy-2-(allyloxycarbonylamino)-4-oxobutyric acid

Allyl(S)-3-(allyloxycarbonylamino)-4-oxo-4-(2,2,2-trichloroethoxy)butyrate (350 mg, 9.02×10$^{-4}$ mol) obtained from Example 20-(2) was dissolved in acetic acid (1.8 ml), then zinc powder (350 mg) was added thereto, and the resulting mixture was stirred at room temperature for 1 hour. The insoluble material was filtered off and washed with ethyl acetate. The filtrates were combined, and the solvent was distilled off under reduced pressure. The residue was dissolved in ethyl acetate, and the solution was washed successively with a 0.2N aqueous solution of hydrochloric acid and a saturated aqueous solution of sodium chloride. The resulting solution was dried over anhydrous magnesium sulfate, and the solvent was distilled off under reduced pressure to afford the crude title compound (180 mg, 78% yield) as a pale yellow oil.

NMR spectrum (400 MHz, CDCl$_3$) δ ppm: 2.91 (1H, dd, J=17, 5 Hz), 3.10 (1H, dd, J=17, 4 Hz), 4.55-4.65 (4H, m), 4.68 (1H, m), 5.23 (1H, dd, J=11, 1 Hz), 5.27 (1H, d, J=10 Hz), 5.32 (2H, br d, J=17 Hz), 5.79 (1H, br d, J=9 Hz), 5.85-6.00 (2H, m).

(4) Allyl (S)-3-(allyloxycarbonylamino)-4-[4-(1R, 2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutoxy]-4-oxobutyrate

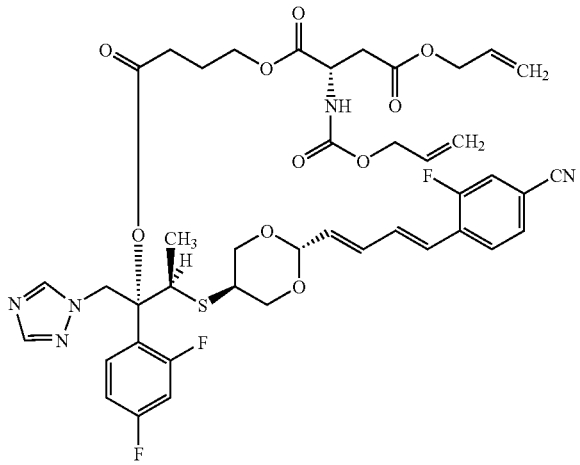

The crude (S)-4-allyloxy-2-(allyloxycarbonylamino)-4-oxobutyric acid (180 mg, 7.0×10$^{-4}$ mol) obtained from Example 20-(3), (1R,2R)-2-[[trans-2-[(1E,3E)-4-(4-cyano-2-fluorophenyl)-1,3-butadienyl]-1,3-dioxan-5-yl]thio]-1-(2, 4-difluorophenyl)-1-[(1H-1,2,4-triazol-1-yl)methyl]propyl 4-hydroxybutyrate (364 mg, 5.79×10-4 mol) obtained from Example 11, and 4-(N,N-dimethylamino)pyridine (183 mg, 1.50×10$^{-3}$ mol) were dissolved in dichloromethane (2 ml), and 2-chloro-1,3-dimethylimidazolium chloride (118 mg, 6.98×10$^{-4}$ mol) was added thereto at room temperature followed by stirring for 30 minutes. The mixture was diluted with ethyl acetate, then washed successively with an aqueous solution of sodium hydrogen carbonate and an aqueous solution of sodium chloride, dried over anhydrous magnesium sulfate, and the solvent was distilled off under reduced pressure. The residue was subjected to chromatography on a silica gel (10 g) column (eluent; ethyl acetate:hexane=2: 1~1:0) to afford the title compound (386 mg, 77% yield) as a pale yellow amorphous solid.

NMR spectrum (400 MHz, CDCl$_3$) δ ppm: 1.35 (3H, dd, J=7, 2 Hz), 1.90-2.00 (2H, m), 2.35-2.55 (2H, m), 2.90 (1H, dd, J=17, 5 Hz), 3.00-3.10 (2H, m), 3.52 (2H, t, J=11 Hz), 3.92 (1H, q, J=7 Hz), 4.10-4.25 (4H, m), 4.55-4.65 (4H, m), 4.65 (1H, m), 5.00 (1H, d, J=4 Hz), 5.20-5.35 (6H, m), 5.80-5.95 (4H, m), 6.58 (1H, dd, J=15, 10 Hz), 6.74 (1H, d, J=15 Hz), 6.85-7.00 (3H, m), 7.30-7.35 (2H, m), 7.40 (1H,dd, J=8, 1 Hz), 7.57 (1H, t, J=8 Hz), 7.90 (1H, s), 7.92 (1H, s)

IR spectrum ν max KBr cm$^{-1}$: 3359, 2231, 1737, 1615, 1503

Mass spectrum m/z (FAB): 868 (M$^+$+1).

(5) Sodium (S)-3-amino-4-[4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutoxy]-4-oxobutyrate (title target compound)

Allyl (S)-3-(allyloxycarbonylamino)-4-[4-(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-4-oxobutoxy]-4-oxobutyrate (200 mg, 2.30×10$^{-4}$ mol) obtained from Example 20-(4) and bis(triphenylphosphine)dichloropalladium (5 mg) were dissolved in dichloromethane (1 ml). To the mixture were added pyrrolidine (65 mg, 9.4×10$^{-4}$ mol) and tributyltin hydride (67 mg, 2.3×10$^{-4}$ mol), and the resulting mixture was stirred at room temperature for 10 minutes. The mixture was diluted with toluene and then the solvent was distilled off under reduced pressure. The residue was suspended in a mixed solvent of methanol-water (3:1), and the suspension was subjected to a cation exchange resin (Dowex 5W-8X, Na type preparated using 1N aqueous solution of sodium hydroxide; 10 ml) (eluent; water). The collected fractions were concentrated under reduced pressure, and the obtained residue was subjected to reverse phase column chromatography using Cosmosil 75 C$_{18}$-PREP (Nacalai Tesque, Inc.; 10 g) (eluent; water:methanol=1:1~3:7). The obtained fractions were concentrated, and the residue was lyophilized to afford the title target compound (96.3 mg, 55% yield) as an amorphous colorless solid.

NMR spectrum (400 MHz, DMSO-d$_6$) δ ppm: 1.24 (3H, d, J=7 Hz), 1.82 (2H, quint, J=7 Hz), 2.12 (1H, dd, J=15, 8 Hz), 2.22 (1H, dd, J=15, 4 Hz), 2.30-2.50 (2H, m), 2.98 (1H, tt, J=11, 5 Hz), 3.40-3.50 (3H, m), 3.59 (1H, q, J=7 Hz), 4.00-4.10 (4H, m), 5.06 (1H, d, J=5 Hz), 5.24 (1H, d, J=15 Hz), 5.40 (1H, br d, J=15 Hz), 5.90 (1H, dd, J=15, 4 Hz), 6.59 (1H, dd, J=15, 10 Hz), 6.83 (1H, d, J=15 Hz), 7.10-7.20 (1H, m), 7.20 (1H, dd, J=15, 11 Hz), 7.25-7.35 (1H, m), 7.45-7.55 (1H, m), 7.67 (1H, dd, J=10, 1 Hz), 7.84 (1H, dd, J=11, 1 Hz), 7.89 (1H, t, J=7 Hz), 8.05 (1H, s), 8.42 (1H, s)

Mass spectrum m/z (FAB): 766 (M$^+$+1)

Example 21

Disodium 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methoxybenzyl phosphate (Disodium Salt of Example Number 5-24)

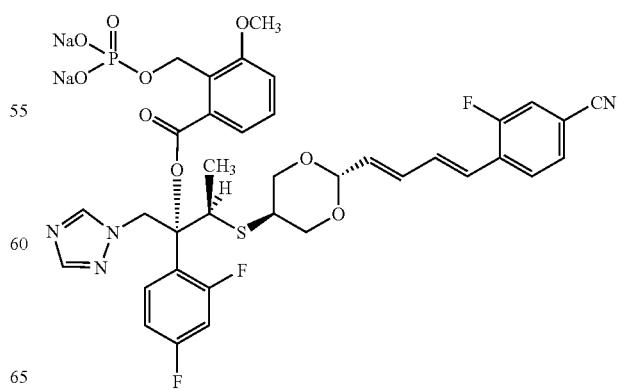

(1) 3-Methoxy-1,2-benzenedimethanol

To a solution of 4-methoxy-1-(3H)-isobenzofuranone (described in J. Org. Chem., 52, 129 (1987); 1.64 g, 10.0 mmol) in tetrahydrofuran (30 ml) was added lithium borohydride (652.2 mg, 30 mmol) with stirring at 0° C., and the mixture was heated under reflux for 2.5 hours with stirring. After cooling the mixture to room temperature, a 2N aqueous solution of hydrochloric acid (20 ml) was added thereto. The product was extracted with ethyl acetate, and the organic layer was washed with a saturated aqueous solution of sodium chloride. The filtrate was concentrated under reduced pressure to give a solid residue. The residue was subjected to chromatography on a silica gel (30 g) column (eluent; ethyl acetate:hexane=2:1~4:1) to afford the title compound (1.31 g, 78% yield) as a colorless solid (mp. 95° C.).

NMR spectrum (400 MHz, CDCl$_3$) δ ppm: 2.6 (2H, br s), 3.87 (3H, s), 4.75 (2H, s), 4.86 (2H, s), 6.91 (1H, d, J=8 Hz), 6.98 (1H, d, J=8 Hz), 7.28 (1H, t, J=8 Hz)

IR spectrum ν max KBr cm$^{-1}$: 3275, 1588, 1262, 1043, 1010, 787

Mass spectrum m/z (EI): 168 (M$^+$).

(2) 2-[(tert-Butyldimethylsilyl)oxymethyl]-6-methoxybenzyl alcohol

3-Methoxy-1,2-benzenedimethanol (1.30 g, 7.73 mmol) obtained from Example 21-(1) was dissolved in tetrahydrofuran (15 ml), and imidazole (526.2 mg, 7.73 mmol) and tert-butylchlorodimethylsilane (1.165 g, 7.73 mmol) were added thereto at 0° C. with stirring. The mixture was stirred at room temperature for 2 hours, then water was added thereto, and the product was extracted with ethyl acetate. The organic layer was washed with a saturated aqueous solution of sodium chloride, and the solvent was distilled off under reduced pressure. The residue was subjected to chromatography on a silica gel (60 g) column (eluent; ethyl acetate:hexane=1:4) to afford the title compound (1.156 g, 53% yield) as an oil.

NMR spectrum (400 MHz, CDCl$_3$) δ ppm: 0.11 (6H, s), 0.91 (9H, s), 3.03 (1H, br t-like), 3.86 (3H, s), 4.77 (2H, br d-like), 4.79 (2H, s), 6.88 (1H, d, J=8 Hz), 6.94 (1H, d, J=8 Hz), 7.24 (1H, t, J=8 Hz)

IR spectrum ν max CHCl$_3$ cm$^{-1}$: 2957, 2931, 1588, 1472, 1463, 1264

Mass spectrum m/z (FAB): 283 (M$^+$+1)

(3) Diallyl 2-[(tert-butyldimethylsilyl)oxymethyl]-6-methoxybenzyl phosphate According to a similar procedure to that described in Example 1-(10), 2-[(tert-butyldimethylsilyl)oxymethyl]-6-methoxybenzyl alcohol (1.13 g, 4.00 mmol) obtained from Example 21-(2), tetrazole (672.3 mg, 9.6 mmol), bis(allyloxy)(diisopropylamino)phosphine (described in Tetrahedron Lett., 30, 4219 (1989); 1.37 g, 5.6 mmol), and tert-butyl hydroperoxide (80% di-tert-butyl peroxide solution; Merck; 0.9 g, 8 mmol) were reacted, and the reaction mixture was worked up to afford, after extraction, an oily residue. The residue was subjected to chromatography on a silica gel (60 g) column (eluent; ethyl acetate:hexane=1:6~1:2) to give the title compound (1.07 g, 60% yield) as a colorless oil.

NMR spectrum (400 MHz, CDCl$_3$) δ ppm: 0.10 (6H, s), 0.93 (9H, s), 3.84 (3H, s), 4.49-4.52 (4H, m), 4.86 (2H, s), 5.22 (2H, dd, J=10, 1 Hz), 5.25 (2H, d, J=6 Hz), 5.33 (2H, dd, J=17, 1 Hz), 5.91 (2H, ddt, J=17, 10, 5 Hz), 6.83 (1H, d, J=8 Hz), 7.12 (1H, d, J=8 Hz), 7.33 (1H, t, J=8 Hz)

IR spectrum ν max CHCl$_3$ cm$^{-1}$: 2956, 2931, 1591, 1472, 1270, 1015

Mass spectrum m/z (FAB): 443 (M$^+$+1).

(4) Diallyl 2-(hydroxymethyl)-6-methoxybenzyl phosphate

To a solution of diallyl 2-[(tert-butyldimethylsilyl)oxymethyl]-6-methoxybenzyl phosphate (1.03 g, 2.33 mmol) obtained from Example 21(3) in tetrahydrofuran (10 ml) was added tetrabutylammonium fluoride (1N tetrahydrofuran solution; 2.5 ml, 2.5 mmol), and the mixture was stirred at room temperature for 1 hour. Water was added to the reaction mixture, then the product was extracted with ethyl acetate, and the solvent was evaporated under reduced pressure to give an oily residue. The residue was subjected to chromatography on a silica gel (50 g) column (eluent; ethyl acetate:hexane=3:1~1:0) to afford the title compound (715.0 mg, 93% yield) as a colorless oil.

NMR spectrum (400 MHz, CDCl$_3$) δ ppm: 3.3 (1H, br s), 3.86 (3H, s), 4.42-4.50 (4H, m), 4.75 (2H, s), 5.22 (2H, d-like, J=10 Hz), 5.32 (2H, d-like, J=17 Hz), 5.34 (2H, d, J=10 Hz), 5.89 (2H, ddt, J=17, 10, 6 Hz), 6.88 (1H, d, J=8 Hz), 7.06 (1H, d, J=8 Hz), 7.35 (1H, t, J=8 Hz)

IR spectrum ν max CHCl$_3$ cm$^{-1}$: 3385, 1473, 1463, 1271, 1021, 989

Mass spectrum m/z (FAB): 329 (M$^+$+1).

(5) 2-[[Bis(allyloxy)phosphoryl]oxymethyl]-3-methoxybenzoic acid

Diallyl 2-(hydroxymethyl)-6-methoxybenzyl phosphate (715.0 mg, 2.18 mmol) obtained from Example 21-(4) was dissolved in N,N-dimethylformamide (8 ml), and pyridinium dichromate (2.87 g, 7.63 mmol) was added thereto. After the mixture was stirred at room temperature for 12 hours, water (60 ml) was added thereto, and the product was extracted with diethyl ether. The organic layer was washed successively with water, a 2N aqueous solution of hydrochloric acid, and a saturated aqueous solution of sodium chloride, and then the solvent was distilled off under reduced pressure to give an oily residue. The residue was dissolved in acetone (5 ml), and Jones reagent (a mixture of chromic anhydride (5.34 g, 4 mmol) and concentrated sulfuric acid (4.6 ml) diluted with water to 20 ml total volume; 1.5 ml) was added thereto. The reaction mixture was stirred at room temperature for 1.5 hours, and then 2-propanol (1 ml) was added thereto to stop the reaction. The solid insoluble material was filtered off, and the filtrate was concentrated under reduced pressure to give an oily residue. The residue was dried using a vaccum pump, and then subjected to chromatography on a silica gel (25 g) column (eluent; ethyl acetate:dichloromethane=1:1) to afford the title compound (447.0 mg, 60% yield) as a colorless oil.

NMR spectrum (400 MHz, CDCl$_3$) δ ppm: 3.89 (3H, s), 4.47-4.57 (4H, m), 5.21 (2H, d-like, J=10 Hz), 5.32 (2H, d-like, J=17 Hz), 5.53 (2H, d, J=8 Hz), 5.90 (2H, ddt, J=17, 10, 6 Hz), 7.07 (1H, dd, J=8, 1 Hz), 7.41 (1H, t, J=8 Hz), 7.48 (1H, d, J=8 Hz)

IR spectrum ν max CHCl$_3$ cm$^{-1}$: 1725, 1587, 1461, 1272, 1021, 989

Mass spectrum m/z (FAB): 343 (M$^+$+1).

(6) (1R,2R)-2-[[trans-2-[(1E,3E)-4-(4-Cyano-2-fluorophenyl]-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-3-methoxybenzoate

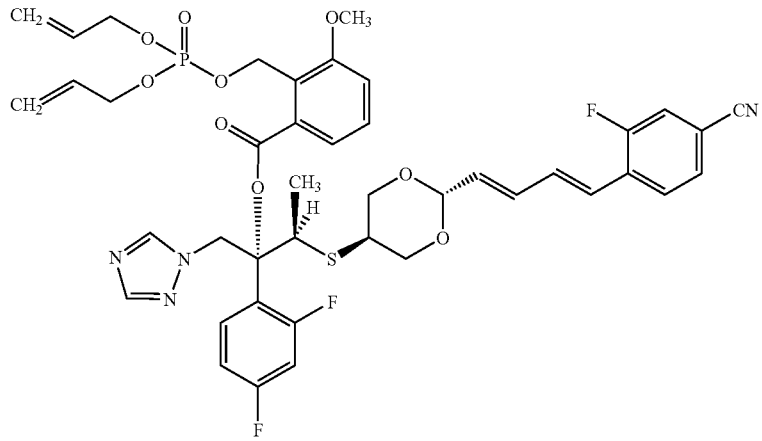

According to a similar procedure to that described in Example 1-(12), 2-[[bis(allyloxy)phosphoryl]oxymethyl]-3-methoxybenzoic acid (440 mg, 1.29 mmol) obtained from 21-(5) and oxalyl chloride (815.8 mg, 6.4 mmol) were reacted, and the reaction mixture was worked up to afford 2-[[bis(allyloxy)phosphoryl]oxymethyl]-3-methoxybenzoyl chloride as a crude product.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (542.6 mg, 1.00 mmol) described in Reference example 1, sodium hydride (55% dispersion in mineral oil; 52.4 mg, 1.20 mmol), and the crude 2-[[bis(allyloxy)phosphoryl]oxymethyl]-3-methoxybenzoyl chloride were reacted in tetrahydrofuran (7 ml), and the reaction mixture was worked up to afford, after extraction, the title compound as a crude oil. The crude oil was subjected to chromatography on a silica gel (30 g) column (eluent; ethyl acetate:hexane=2:1~4:1) to afford the title compound (425.5 mg, 49% yield).

NMR spectrum (400 MHz, CDCl$_3$) δ ppm: 1.44 (3H, dd, J=7, 2 Hz), 3.04 (1H, tt, J=12, 5 Hz), 3.45 (1H, t, J=12 Hz), 3.51 (1H, t, J=12 Hz), 3.89 (3H, s), 3.98 (1H, q, J=7 Hz), 4.09 (1H, ddd, J=12, 5, 2 Hz), 4.18 (1H, ddd, J=12, 5, 2 Hz), 4.43-4.55 (4H, m), 4.96 (1H, d, J=4 Hz), 5.19 (2H, dd, J=10, 1 Hz), 5.31 (2H, dq, J=17, 1 Hz), 5.43-5.55 (4H, m), 5.83 (1H, dd, J=15, 4 Hz), 5.84-5.94 (2H, m), 6.56 (1H, dd, J=15, 10 Hz), 6.73 (1H, d, J=16 Hz), 6.93 (1H, dd, J=16, 10 Hz), 6.86-7.00 (2H, m), 7.12 (1H, d, J=8 Hz), 7.16 (1H, d, J=8 Hz), 7.34 (1H, dd, J=9, 1 Hz), 7.39 (2H, t, J=8 Hz), 7.48 (1H, td, J=9, 6 Hz), 7.57 (1H, t, J=8 Hz), 7.93 (1H, s), 8.00 (1H, s)

IR spectrum ν max CHCl$_3$ cm$^{-1}$: 2233, 1731, 1504, 1462, 1277, 1141, 1059, 1018, 991

Mass spectrum m/z (FAB): 867 (M$^+$+1).

(7) Disodium 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methoxybenzyl phosphate (title target compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-3-methoxybenzoate (400 mg, 0.46 mmol) obtained from Example 21-(6) was reacted with bis(triphenylphosphine)dichloropalladium (16.2 mg, 0.023 mmol) and tributyltin hydride (308.9 mg, 1.06 mmol), and the reaction mixture was worked up to afford the title target compound as a crude oil. The crude oil was subjected to reverse phase column chromatography using Cosmosil 75 C$_{18}$-PREP (Nacalai Tesque, Inc.; 30 g) (eluent; water:methanol=4:6~3:7). The obtained fractions were concentrated, and the residue was lyophilized to afford the title target compound (93.5 mg, 24% yield) as a colorless solid.

NMR spectrum (400 MHz, CD$_3$OD) δ ppm: 1.42 (3H, dd, J=7, 2 Hz), 3.00 (1H, tt, J=11, 5 Hz), 3.46 (1H, t, J=11 Hz), 3.52 (1H, t, J=11 Hz), 3.88 (3H, s), 4.01-4.77 (2H, m), 4.15 (1H, ddd, J=11, 5, 2 Hz), 5.00 (1H, d, J=4 Hz), 5.28 (1H, dd, J=10, 4 Hz), 5.32 (1H, dd, J=10, 4 Hz), 5.58 (1H, dd, J=15, 3 Hz), 5.68 (1H, d, J=15 Hz), 5.84 (1H, dd, J=15, 4 Hz), 6.56 (1H, dd, J=11, 15 Hz), 6.78 (1H, d, J=15 Hz), 6.99-7.13 (2H, m), 7.08 (1H, dd, J=15, 11 Hz), 7.21 (1H, d, J=7 Hz), 7.30 (1H, d, J=7 Hz), 7.36 (1H, t, J=8 Hz), 7.51 (1H, t, J=8 Hz), 7.52 (1H, t, J=8 Hz), 7.62-7.70 (1H, m), 7.78 (1H, t, J=8 Hz), 7.97 (1H, s), 8.62 (1H, s)

IR spectrum ν max KBr cm$^{-1}$: 2231, 1730, 1615, 1503, 1278, 1142, 1054

Mass spectrum m/z (FAB): 831 (M$^+$+1)

Specific rotation [α]$_D^{25}$ +15.4° (c=0.84, MeOH)

Example 22

Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methylbenzyl phosphate (Disodium Salt of Example Number 5-23)

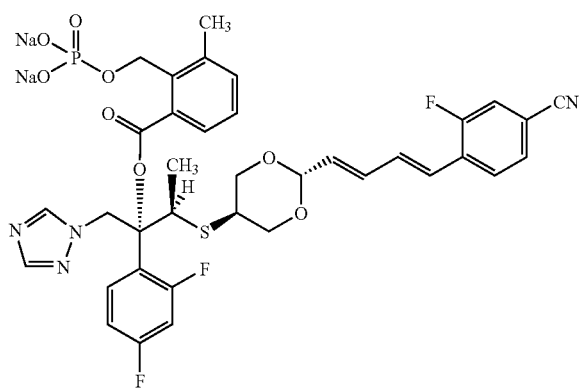

(1) 3-Methyl-1,2-benzenedimethanol

To a solution of methyl 2,6-dimethylbenzoate (described in J. Am. Chem. Soc., 99, 6405 (1977); 23.4 g, 143 mmol) in dichloroethane (200 ml) were added N-bromosuccinimide (25.46 g, 143 mmol) and α,α'-azobisisobutyronitrile (234.8 mg, 1.43 mmol), and the mixture was irradiated with visible light (tungsten lamp, 375 W) for 1 hour. After cooling the reaction mixture, the precipitated material was filtered off, and the solvent was distilled off under reduced pressure. The obtained oily residue was subjected to chromatography on a silica gel (200 g) column (eluent; ethyl acetate:hexane=1:10) to give an oily mixture containing ca. 50% methyl 2-(bromomethyl)-6-methylbenzoate. The mixture was dissolved in dimethyl sulfoxide (150 ml), and sodium acetate (16.4 g, 0.2 mol) was added thereto. The resulting mixture was stirred at room temperature for 2 hours, then a saturated aqueous solution of ammonium chloride was added thereto, and the product was extracted with ethyl acetate. The organic layer was washed with a saturated aqueous solution of sodium chloride, and the solvent was distilled off under reduced pressure to give an oily residue. The residue was subjected to chromatography on a silica gel (200 g) column (eluent; ethyl acetate:hexane=1:10~1:3) to give methyl 2-(acetoxymethyl)-6-methylbenzoate (8.09 g, more than 80% content) as a colorless oil. The obtained methyl 2-(acetoxymethyl)-6-methylbenzoate was used for the following reaction without further purification.

NMR spectrum (400 MHz, CDCl$_3$) δ ppm: 2.07 (3H, s), 2.38 (3H, s), 3.92 (3H, s), 5.15 (2H, s), 6.99-7.12 (3H, m).

Methyl 2-(acetoxymethyl)-6-methylbenzoate obtained above was dissolved in methanol (80 ml), and potassium carbonate (251.5 mg, 1.8 mmol) was added thereto. The mixture was stirred at room temperature for 2 hours, then a 2N aqueous solution of hydrochloric acid (3 ml) was added thereto, and the solvent was distilled off under reduced pressure. The obtained solid residue was dissolved in ethyl acetate, and the solution was washed with a saturated aqueous solution of sodium chloride and then the solvent was distilled off under reduced pressure. The solid residue was subjected to chromatography on a silica gel (100 g) column (eluent; ethyl acetate:hexane=1:2) to afford 7-methyl-[(3H)-isobenzofuranone (5.18 g, more than 80% content). The obtained 7-methyl-1(3H)-isobenzofuranone was used for the following reaction without further purification.

NMR spectrum (400 MHz, CDCl$_3$) δ ppm: 2.71 (3H, s), 5.23 (2H, s), 7.25-7.30 (2H, m), 7.56 (1H, t, J=8 Hz).

A solution of the 7-methyl-1(3H)-isobenzofuranone obtained above in tetrahydrofuran (80 ml) was cooled to 0° C., and lithium borohydride (1.90 g, 87.2 mmol) was added thereto. The mixture was stirred at 60° C. for 2 hours, then cooled to 0° C., and a 2N aqueous solution of hydrochloric acid (50 ml) was added dropwise. The product was extracted with ethyl acetate, and the solvent was evaporated under reduced pressure to give an oily residue. The residue was subjected to chromatography on a silica gel (75 g) column (eluent; ethyl acetate:hexane=2:1~1:0) to afford the title compound (4.17 g, 19% total yield from methyl 2,6-dimethylbenzoate) as an oil.

NMR spectrum (400 MHz, CDCl$_3$) δ ppm: 2.45 (3H, s), 4.76 (2H, s), 4.79 (2H, s), 7.17-7.22 (3H, m)

IR spectrum ν max CHCl$_3$ cm$^{-1}$: 3605, 1469, 1380, 1002

Mass spectrum m/z (EI): 152 (M$^+$).

(2) 2-[(tert-Butyldimethylsilyl)oxymethyl]-6-methylbenzyl alcohol

A solution of 3-methyl-1,2-benzenedimethanol (4.16 g, 27.3 mmol) obtained from Example 22-(1) in tetrahydrofuran (50 ml) was cooled to 0° C., and imidazole (1.86 g, 27.3 mmol) and tert-butylchlorodimethylsilane (4.12 g, 27.3 mmol) were added thereto. The mixture was stirred at room temperature for 3 hours, and then after adding water, the product was extracted with ethyl acetate. The organic layer was washed with a saturated aqueous solution of sodium chloride, then the solvent was distilled off under reduced pressure, and the residue was subjected to chromatography on a silica gel (120 g) column (eluent; ethyl acetate:hexane=1:4) to afford the title compound (4.93 g, 68% yield) as a colorless oil.

NMR spectrum (400 MHz, CDCl$_3$) δ ppm: 0.13 (6H, s), 0.92 (9H, s), 2.46 (3H, s), 3.04 (1H, t, J=6 Hz), 4.72 (2H, d, J=6 Hz), 4.80 (2H, s), 7.11 (1H, dd, J=6, 2 Hz), 7.15-7.19 (2H, m)

IR spectrum ν max CHCl$_3$ cm$^{-1}$: 3459, 1732, 1599, 1471, 1257, 1061, 1038, 1005, 840

Mass spectrum m/z (FAB): 267 (M$^+$+1).

(3) Diallyl 2-[(tert-butyldimethylsilyl)oxymethyl]-6-methylbenzyl phosphate

According to a similar procedure to that described in Example 1-(10), 2-[(tert-butyldimethylsilyl)oxymethyl]-6-methylbenzylalcohol (4.92 g, 18.5 mmol) obtained from Example 22-(2), tetrazole (3.23 g, 46.2 mmol), bis(allyloxy)(diisopropylamino)phosphine (described in Tetrahedron Lett., 30, 4219 (1989); 5.43 g, 22.2 mmol), and tert-butyl hydroperoxide (80% di-tert-butyl peroxide solution; Merck; 1.8 g, 16 mmol) were reacted, and the reaction mixture was worked up to afford, after extraction, an oily residue. The residue was subjected to chromatography on a silica gel (200 g) column (eluent; ethyl acetate:hexane=1:4~2:3) to afford the title compound (6.03 g, 74% yield) as a colorless oil.

NMR spectrum (400 MHz, CDCl$_3$) δ ppm: 0.09 (6H, s), 0.93 (9H, s), 2.44 (3H, s), 4.45-4.51 (4H, m), 4.86 (2H, s), 5.20-5.25 (4H, m), 5.32 (2H, dq, J=17, 1 Hz), 5.89 (2H, ddt, J=17, 10, 6 Hz), 7.13 (1H, d, J=7 Hz), 7.25 (1H, t, J=7 Hz), 7.32 (1H, d, J=7 Hz)

IR spectrum ν max CHCl$_3$ cm$^{-1}$: 1598, 1732, 1471, 1464, 1258, 1005

Mass spectrum m/z (FAB): 427 (M$^+$+1)

(4) Diallyl 2-(hydroxymethyl)-6-methylbenzyl phosphate

To a solution of diallyl 2-[(tert-butyldimethylsilyl)oxymethyl]-6-methylbenzyl phosphate (6.02 g, 14.1 mmol) obtained from Example 22-(3) in tetrahydrofuran (50 ml) was added tetrabutylammonium fluoride (1 mol/l tetrahydrofuran solution; 17.6 ml, 17.6 mmol), and the mixture was stirred at room temperature for 3 hours. Water was added thereto, and the product was extracted with ethyl acetate. The solvent was distilled off under reduced pressure to give an oily residue. The residue was subjected to chromatography on a silica gel (75 g) column (eluent; ethyl acetate: hexane=3:1) to afford the title compound (3.84 g, 87% yield) as a colorless oil.

NMR spectrum (400 MHz, CDCl$_3$) δ ppm: 2.46 (3H, s), 3.33 (1H, t, J=6 Hz), 4.36-4.49 (4H, m), 4.75 (2H, d, J=6 Hz), 5.22 (2H, br d, J=11 Hz), 5.30 (2H, dq, J=17, 1 Hz), 5.32 (2H, d, J=10 Hz), 5.86 (2H, ddt, J=17, 11, 5 Hz), 7.18 (1H, t, J=4 Hz), 7.26-7.28 (2H, m)

IR spectrum ν max CHCl$_3$ cm$^{-1}$: 3607, 1732, 1598, 1466, 1266, 1006

Mass spectrum m/z (FAB): 313 (M$^+$+1).

(5) 2-[[Bis(allyloxy)phosphoryl]oxymethyl]-3-methylbenzoic acid

A solution of diallyl 2-(hydroxymethyl)-6-methylbenzyl phosphate (1.22 g, 4.02 mmol) obtained from Example 22-(4) in acetone (25 ml) was cooled to 0° C., and Jones reagent (a mixture of chromic anhydride (5.34 g) and concentrated sulfuric acid (4.6 ml) diluted with water to 20 ml total volume; 6 ml, ca. 16 mmol) was added thereto. The reaction mixture was stirred at room temperature for 2 hours, and then 2-propanol (1 ml) was added thereto to stop the reaction. The insoluble material was filtered off, and the filtrate was concentrated under reduced pressure to give an oily residue. The residue was dried using a vaccum pump, and then subjected to chromatography on a silica gel (50 g) column (eluent; ethyl acetate:dichloromethane=1:1) to afford the title compound (905.3 mg, 71% yield) as a colorless oil.

NMR spectrum (400 MHz, CDCl$_3$) δ ppm: 2.49 (3H, s), 4.43-4.55 (4H, m), 5.22 (2H, dd, J=10, 1 Hz), 5.32 (2H, dq, J=17, 1 Hz), 5.53 (2H, d, J=8 Hz), 5.88 (2H, ddt, J=17, 10, 6 Hz), 7.34 (1H, t, J=7 Hz), 7.38 (1H, dd, J=8, 1 Hz), 7.72 (1H, d, J=8 Hz)

IR spectrum ν max CHCl$_3$ cm$^{-1}$: 2960, 1725, 1271, 1012

Mass spectrum m/z (FAB): 327 (M$^+$+1).

(6) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-3-methylbenzoate A solution of 2-[[bis(allyloxy)phosphoryl]oxymethyl]-3-methylbenzoic acid (880 mg, 2.70 mmol) obtained from Example 22-(5) in dichloromethane (15 ml) was cooled to 0° C., and then N,N-dimethylformamide (15 μl) and oxalyl chloride (1.71 g, 13.5 mmol) were added thereto. After the mixture was stirred at room temperature for 30 minutes, crude 2-[[bis(allyloxy)phosphoryl]oxymethyl]-3-methylbenzoyl chloride was obtained according to a similar procedure to that described in Example 1-(12).

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (976.6 mg, 1.80 mmol) described in Reference example 1, sodium hydride (55% dispersion in mineral oil; 94.2 mg, 1.96 mmol), and 2-[[bis(allyloxy)phosphoryl]oxymethyl]-3-methylbenzoyl chloride obtained above were reacted in tetrahydrofuran (10 ml), and the reaction mixture was worked up to afford, after extraction, the title compound as a crude oil. The crude oil was subjected to chromatography on a silica gel (100 g) column (eluent; ethyl acetate:hexane=3:2~4:1) to afford the title compound (1.0641 g, 69% yield) as a pale yellow amorphous solid.

NMR spectrum (400 MHz, CDCl$_3$) δ ppm: 1.44 (3H, dd, J=7, 2 Hz), 2.51 (3H, s), 3.04 (1H, tt, J=11, 5 Hz), 3.45 (1H, t, J=11 Hz), 3.51 (1H, t, J=11 Hz), 4.00 (1H, q, J=7 Hz), 4.09 (1H, ddd, J=11, 5, 2 Hz), 4.19 (1H, ddd, J=11, 5, 2 Hz), 4.42-4.55 (4H, m), 4.96 (1H, d, J=5 Hz), 5.19 (2H, br d, J=10 Hz), 5.30 (2H, br d, J=18 Hz), 5.43-5.56 (4H, m), 5.83 (1H, dd, J=16, 5 Hz), 5.82-5.92 (2H, m), 6.55 (1H, dd, J=16, 11 Hz), 6.73 (1H, d, J=16 Hz), 6.86-6.99 (3H, m), 7.30-7.35 (2H, m), 7.39-7.43 (3H, m), 7.48 (1H, td, J=9, 6 Hz), 7.57 (1H, t, J=8 Hz), 7.94 (1H, s), 8.00 (1H, s)

IR spectrum ν max CHCl$_3$ cm$^{-1}$: 2233, 1727, 1616, 1504, 1419, 1387, 1276, 1141, 1211

Mass spectrum m/z (FAB): 851 (M$^+$+1).

(7) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methylbenzyl phosphate (title target compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2, 4-difluorophenyl)-1-[(1H-1,2,4-triazol-1-yl)methyl]propyl 2-[[bis(allyloxy)phosphoryl]oxymethyl]-3-methylbenzoate (592.2 mg, 0.70 mmol) obtained from Example 22-(6) was reacted with bis(triphenylphosphine)dichloropalladium (24.4 mg, 0.035 mmol) and tributyltin hydride (706 mg, 2.43 mmol), and the reaction mixture was worked up to afford the title target compound as a crude oil. The crude oil was subjected to reverse phase column chromatography using Cosmosil 75 C$_{18}$-PREP (Nacalai Tesque, Inc.; 30 g) (eluent; water:methanol=4:6~3:7). The obtained fractions were concentrated, and the residue was lyophilized to afford the title target compound (323.2 mg, 57% yield) as a colorless solid.

NMR spectrum (400 MHz, CD$_3$OD) δ ppm: 1.41 (3H, dd, J=7, 2 Hz), 2.58 (3H, s), 2.99 (1H, tt, J=11, 5 Hz), 3.45 (1H, t, J=11 Hz), 3.52 (1H, t, J=11 Hz), 4.03 (1H, ddd, J=11, 5, 2 Hz), 4.08 (1H, q, J=7 Hz), 4.14 (1H, ddd, J=11, 5, 2 Hz), 4.99 (1H, d, J=5 Hz), 5.15 (1H, dd, J=11, 4 Hz), 5.30 (1H, dd, J=11, 4 Hz), 5.51 (1H, dd, J=15, 4 Hz), 5.69 (1H, d, J=15 Hz), 5.83 (1H, dd, J=16, 5 Hz), 6.55 (1H, dd, J=15, 11 Hz), 6.77 (1H, d, J=15 Hz), 7.01-7.11 (3H, m), 7.27 (1H, t, J=8 Hz), 7.41 (1H, d, J=7 Hz), 7.49-7.54 (3H, m), 7.64 (1H, td, J=9, 6 Hz), 7.77 (1H, t, J=8 Hz), 7.98 (1H, s), 8.60 (1H, s)

IR spectrum ν max KBr cm⁻¹: 2231, 1725, 1615, 1503, 1276, 1141, 1048, 974

Mass spectrum m/z (FAB): 815 (M⁺+1)

Specific rotation $[\alpha]_D^{25}$ +16.3° (c=1.01, MeOH)

Example 23

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-(N,N-diethylamino)-4-hydroxyvalerate
(Example Number 4-48)

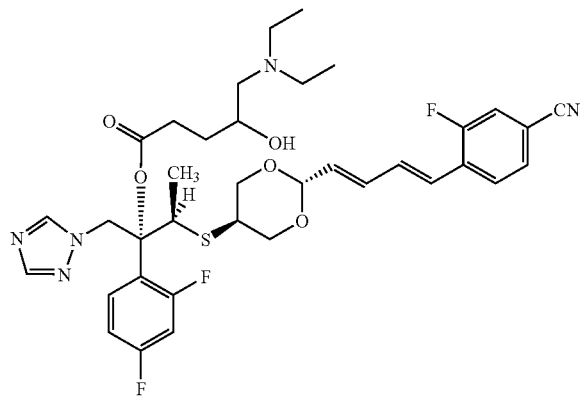

4-Methoxybenzyl 4-(allyloxycarbonyloxy)-5-(N,N-diethylamino)valerate 5-(N,N-Dimethylaminomethyl)-tetrahydrofuran-2-one (described in Bull. Soc. Chim. Fr., p. 401 (1953); 500 mg, 2.94 mmol) was dissolved in a 1N aqueous solution of potassium hydroxide (3 ml) followed by stirring at room temperature for 30 minutes. The mixture was dried under reduced pressure, and the residue (670 mg) was obtained as a colorless oil. A part of the obtained oil (139 mg, 6.11×10⁻⁴ mol) was dissolved in dimethylformamide (0.8 ml), then 4-methoxybenzylchloride (100 mg, 6.49×10⁻⁴ mol) was added thereto followed by stirring at 100° C. for 30 minutes. The mixture was cooled to 0° C., and then allyl chloroformate (80 mg, 6.6×10⁻⁴ mol) and 4-(N,N-dimethylamino) pyridine (5 mg) were added thereto. The obtained mixture was stirred at room temperature for 2 hours, then diluted with ethyl acetate, and washed successively with a saturated aqueous solution of sodium hydrogen carbonate and an aqueous solution of sodium chloride. The organic layer was dried over anhydrous magnesium sulfate and the solvent was distilled off under reduced pressure. The obtained residue was subjected to chromatography on a silica gel (5 g) column (eluent; ethyl acetate:hexane=3:2) to give the title compound (125 mg, 52% yield) as a colorless oil.

NMR spectrum (400 MHz, CDCl₃) δ ppm: 0.98 (6H, t, J=7 Hz), 1.80-1.90 (1H, m), 2.05-2.15 (1H, m), 2.40-2.60 (8H, m), 3.81 (3H, s), 4.55-4.65 (2H, m), 4.75-4.85 (1H, m), 5.05 (2H, s), 5.25 (1H, d-like, J=10 Hz), 5.34 (1H, d-like, J=18 Hz), 5.92 (1H, ddt, J=18, 10, 6 Hz), 6.88 (2H, d, J=9 Hz), 7.29 (2H, d, J=9 Hz)

IR spectrum ν max neat cm⁻¹: 1743, 1614, 1516, 1257

Mass spectrum m/z (FAB): 394 (M⁺+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl] 4-(allyloxycarbonyloxy)-5-(N,N-diethylamino)valerate To a mixture of 4-methoxybenzyl 4-(allyloxycarbonyloxy)-5-(N,N-diethylamino)valerate (120 mg, 3.05×10⁻⁴ mol) obtained from Example 23-(1) and anisole (0.1 ml) was added trifluoroacetic acid (1.2 ml) at room temperature. The mixture was stirred at room temperature for 1 hour, then diluted with toluene, and the solvent was distilled off under reduced pressure. The residue was dissolved in dichloromethane (0.6 ml), and then N,N-dimethylformamide (0.02 ml) and oxalyl chloride (100 mg) were added thereto. The mixture was stirred at room temperature for 1 hour, then toluene was added thereto, and the resulting solution was concentrated under reduced pressure to give crude 4-(allyloxycarbonyloxy)-5-(N,N-diethylamino)valeryl chloride.

4-[(1E,3E)-4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (346 mg, 6.38×10⁻⁴ mol) described in Reference example 1 was dissolved in N,N-dimethylformamide (2 ml), and sodium hydride (55% dispersion in mineral oil; 30 mg, 6.9×10⁻⁴ mol) was added thereto at room temperature followed by stirring for 1 hour. The obtained suspension mixture was cooled to 0° C., and then the total amount of the crude 4-(allyloxycarbonyloxy)-5-(N,N-diethylamino)valeryl chloride obtained above was added thereto with stirring. The mixture was stirred at room temperature for 30 minutes. After cooling, the mixture was partitioned between ethyl acetate and an aqueous solution of ammonium chloride, and then the organic layer was washed with a saturated aqueous solution of sodium chloride, dried over anhydrous magnesium sulfate, and the solvent was distilled off under reduced pressure to give an oily residue. The residue was subjected to chromatography on a silica gel (6 g) column (eluent; ethyl acetate:methanol=1:0~9:1) to afford the title compound (101 mg, 20% yield) as a pale yellow amorphous solid.

NMR spectrum (400 MHz, CDCl₃) δ ppm: 0.98 (3H, t, J=7 Hz), 0.99 (3H, t, J=7 Hz), 1.35 (3H, br d, J=7 Hz), 1.75-1.90 (1H, m), 2.00-2.20 (1H, m), 2.40-2.65 (8H, m), 3.03 (1H, tt, J=11, 5 Hz), 3.45-3.55 (2H, m), 3.85-3.95 (1H, m), 4.15-4.25 (2H, m), 4.60-4.70 (2H, m), 4.70-4.85 (1H, m), 4.99 (1H, d, J=4 Hz), 5.26 (1H, d-like, J=10 Hz), 5.35 (2H,s), 5.37 (1H, d-like, J=18 Hz), 5.85 (1H, dd, J=15, 4 Hz), 5.94 (1H, ddt, J=18, 10, 6 Hz), 6.58 (1H, dd, J=16, 11 Hz), 6.74 (1H, d, J=16 Hz), 6.80-6.95 (3H, m), 7.30-7.45 (3H, m), 7.57 (1H, t, J=7 Hz), 7.90 (1/2H, s), 7.906 (1/2H, s), 7.91 (1/2H, s), 7.92 (1/2H, s)

IR spectrum ν max KBr cm⁻¹: 2232, 1744, 1616, 1504

Mass spectrum m/z (FAB): 798 (M⁺+1).

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl5-(N,N-diethylamino)-4-hydroxyvalerate
(Title Target Compound)

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]4-(allyloxycarbonyloxy)-5-(N,N-diethylamino)valerate (95 mg, 1.2×10⁻⁴ mol) obtained from Example 23-(2) and bis(triphenylphosphine)dichloropalladium (1 mg) were dissolved in dichloromethane (1.5 ml). To the mixture was slowly added tributyltin hydride (52 mg, 1.8×10⁻⁴ mol) at room temperature over a period of 5 minutes. The mixture was stirred at room temperature for 10 minutes further, and hexane was added thereto. The liberated oily insoluble material was separated by removing the supernatant solution slowly. The insoluble residue was washed twice with hexane. The obtained oily residue was subjected to chromatography on a silica gel (3 g) column (eluent; ethyl acetate:methanol=1:0~7:3), and further purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title compound (78 mg, 92% yield) as a colorless amorphous solid.

NMR spectrum (400 MHz, CDCl$_3$) δ ppm: 1.03 (6H, t, J=7 Hz), 1.35 (3H, br d, J=7 Hz), 1.50-1.80 (2H, m), 2.25-2.70 (8H, m), 3.06 (1H, tt, J=12, 4 Hz), 3.35-3.50 (1H, m), 3.52 (2H, t, J=12 Hz), 3.55-3.65 (1H, m), 3.80-3.95 (1H, m), 4.10-4.30 (2H, m), 4.99 (1H, d, J=4 Hz), 5.30-5.40 (2H, m), 5.85 (1H, dd, J=16, 4 Hz), 6.58 (1H, dd, J=16, 10 Hz), 6.74 (1H, d, J=16 Hz), 6.80-7.00 (3H, m), 7.30-7.45 (3H, m), 7.57 (1H, t, J=8 Hz), 7.91-7.96 (2H, m)

IR spectrum ν max KBr cm⁻¹: 3430, 2232, 1742, 1616, 1504

Mass spectrum m/z (FAB): 714 (M⁺+1).

Example 24

Sodium hydrogen 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-1-(N,N-diethylaminomethyl)-4-oxobutyl phosphate
(Example Number 4-50)

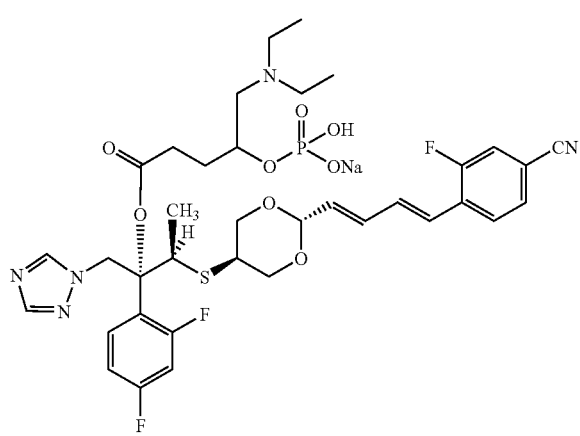

(1) 4-Methoxybenzyl 4-[[bis(allyloxy)phosphoryl]oxy]-5-(N,N-diethylamino)valerate According to a similar procedure to that described in Example 23-(1), 5-(N,N-dimetylaminomethyl)-tetrahydrofuran-2-one (described in Bull. Soc. Chim. Fr., p. 401 (1953); 200 mg, 1,17 mmo) was dissolved in a 1N aqueous solution of potassium hydroxide (1.17 mmol) followed by stirring at room temperature for 30 minutes. The mixture was dried under reduced pressure, then the obtained oily residue was dissolved in dimethylformamide (1 ml), and 4-methoxybenzyl chloride (200 mg, 1.28 mmol) was added thereto followed by stirring at 90° C. for 30 minutes. The mixture was cooled to 0° C., and then tetrazole (420 mg, 6.0 mmol) and bis(allyloxy)(diisopropylamino)phosphine (Tetrahedron Lett., 30, 4219 (1989); 368 mg, 1.5 mmol) were added thereto at room temperature followed by stirring for 30 minutes. To the obtained mixture was added allyl alcohol (0.1 ml). The resulting mixture was stirred for another 1 hour, then tert-butyl hydroperoxide (ca. 5M nonane solution, 0.4 ml, ca. 2 mmol) was added thereto at 0° C., and the mixture was stirred at room temperature for 30 minutes. A saturated aqueous solution of sodium hydrogen carbonate and an aqueous solution of sodium thiosulfate were added to the reaction mixture, and the mixture was stirred for 10 minutes and then partitioned between the organic layer and the aqueous layer. The organic layer was washed successively with a saturated aqueous solution of sodium hydrogen carbonate and an aqueous solution of sodium chloride, dried over anhydrous magnesium sulfate, and the solvent was distilled off under reduced pressure. The residue was subjected to chromatography on a silica gel (6 g) column (eluent; ethyl acetate:methanol=1:0~9:1), and further purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title compound (286 mg, 61% yield) as a colorless oil.

NMR spectrum (400 MHz, CDCl$_3$) δ ppm: 0.98 (6H, t, J=7 Hz), 1.80-1.95 (1H, m), 2.10-2.25 (1H, m), 2.40-2.55 (7H, m), 2.67 (1H, dd, J=13, 6 Hz), 3.81 (3H, s), 4.40-4.60 (5H, m), 5.00-5.10 (2H, m), 5.22 (2H, d-like, J=10 Hz), 5.34 (2H, d-like, J=18 Hz), 5.92 (2H, ddt, J=18, 10, 6 Hz), 6.88 (2H, d, J=9 Hz), 7.29 (2H, d, J=9 Hz)

IR spectrum ν max CHCl$_3$ cm⁻¹: 1730, 1613, 1516, 1254

Mass spectrum m/z (FAB): 470 (M⁺+1).

(2) Diallyl 4-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-1-(N,N-diethylaminomethyl)-4-oxobutyl phosphate To a mixture of 4-methoxybenzyl 4-[[bis(allyloxy)phosphoryl]oxy]-5-(N,N-diethylamino)valerate (275 mg, 5.75×10⁻⁴ mol) and anisole (0.2 ml) was added trifluoroacetic acid (2.7 ml) at room temperature. The mixture was stirred at room temperature for 30 minutes, diluted with toluene, and the solvent was distilled off under reduced pressure. The residue was dissolved in dichloromethane (2 ml), and then N,N-dimethylformamide (0.02 ml) and oxalyl chloride (200 mg) were added thereto. The mixture was stirred at room temperature for 1 hour, then toluene was added thereto, and the solvent was distilled off under reduced pressure to give crude 4-[[bis(allyloxy)phosphoryl]oxy]-5-(N,N-diethylamino)valeryl chloride.

4-[(1E,3E)-4-[trans-5-[[(1R,2R)-2-(2,4-Difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (624 mg, 1.15 mmol) obtained from Reference example 1 was dissolved in N,N-dimethylformamide (4 ml), then sodium hydride (55% dispersion in mineral oil; 52 mg, 1.2 mmol) was added thereto, and the mixture was stirred for 1 hour. The obtained suspension mixture was cooled to 0° C., and all of the crude 4-[[bis(allyloxy)phosphoryl]oxy]-5-(N,N-diethylamino)valeryl chloride obtained above was added thereto with stirring. The resulting mixture was stirred at room temperature for 30 minutes. After cooling, the reaction mixture was partitioned between ethyl acetate and an aqueous solution of ammonium chloride, then the organic layer was washed with a saturated aqueous solution of sodium chloride, dried over anhydrous magnesium sulfate, and the solvent was distilled off under reduced pressure. The oily residue was subjected to chromatography on a silica gel (12 g) column (eluent; ethyl acetate:methanol=1:0~9:1), and further purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title compound (210 mg, 21% yield) as a colorless amorphous solid.

NMR spectrum (400 MHz, CDCl$_3$) δ ppm: 0.99 (3H, t, J=7 Hz), 1.00 (3H, t, J=7 Hz), 1.35 (3H, dd, J=7, 2 Hz), 1.75-1.95 (1H, m), 2.05-2.15 (1H, m), 2.40-2.75 (8H, m), 2.95-3.10 (1H, m), 3.45-3.55 (2H, m), 3.85-3.95 (1H, m), 4.10-4.30 (2H, m), 4.35-4.50 (1H, m), 4.50-4.65 (4H, m), 4.99 (1H, d, J=4 Hz), 5.26 (2H, d-like, J=10 Hz), 5.25-5.45 (4H, m), 5.85 (1H, dd, J=15, 4 Hz), 5.95 (2H, ddt, J=18, 10, 6 Hz), 6.58 (1H, dd, J=15, 11 Hz), 6.74 (1H, d, J=16 Hz), 6.80-6.95 (3H, m), 7.30-7.50 (3H, m), 7.57 (1H, t, J=7 Hz), 7.90-7.92 (2H, m)

IR spectrum ν max CHCl$_3$ cm$^{-1}$: 2233, 1742, 1616, 1504

Mass spectrum m/z (FAB): 874 (M$^+$+1)

(3) Sodium hydrogen 4-[(1R,2R)-2-[[trans-2-[(1E, 3E)-4-(4-cyano-2-fluorophenyl)-1,3-butadienyl]-1,3-dioxan-5-yl]thio]-1-(2,4-difluorophenyl)-1-[(1H-1,2, 4-triazol-1-yl)methyl]propoxy]-1-(N,N-diethylaminomethyl)-4-oxobutyl phosphate (Title Target Compound)

Diallyl 4-[(1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propoxy]-1-(N,N-diethylaminomethyl)-4-oxobutyl phosphate (175 mg, 2.00×10$^{-4}$ mol) obtained from Example 24-(2) and bis(triphenylphosphine)dichloropalladium (2 mg) were dissolved in dichloromethane (2 ml). Tributyltin hydride (145 mg, 5.0×10$^{-4}$ mol) was slowly added to the mixture at room temperature over a period of 15 minutes. After stirring at room temperature for another 10 minutes, hexane was added to the reaction mixture. The insoluble liberated oily material was separated by removing the supernatant liquid slowly. The insoluble residue was further washed twice with hexane. The oily residue was dissolved in methanol (2 ml), then a saturated aqueous solution of sodium hydrogen carbonate (0.5 ml) was added thereto, and the resulting suspension was stirred at room temperature for 15 hours. The resulting homogeneous mixture was concentrated under reduced pressure. The residue was dissolved in methanol, and the insoluble material was removed. The solvent was evaporated under reduced pressure, and the residue was subjected to reverse phase column chromatography using Cosmosil 75 C$_{18}$-PREP (Nacalai Tesque, Inc.; 10 g) (eluent; water:methanol=1:1~3:7). The obtained fractions were concentrated, and the residue was lyophilized to afford the title target compound (80.2 mg, 46% yield) as a colorless solid.

NMR spectrum (400 MHz, CDCl$_3$) δ ppm: 0.95-1.20 (9H, m), 1.50-1.70 (2H, m), 2.05-2.30 (1H, m), 2.35-2.50 (1H, m), 2.50-3.45 (9H, m), 3.45-3.60 (1H, m), 3.80-4.05 (2H, m), 4.15-4.40 (1H, m), 4.95-5.50 (4H, m), 6.05-6.20 (1H, m), 6.20-6.35 (1H, m), 6.50-6.90 (3H, m), 7.05-7.50 (4H, m), 7.85-7.95 (1H, m), 8.00-8.15 (1, m)

IR spectrum ν max KBr cm$^{-1}$: 3411, 2232, 1741, 1616, 1504

Mass spectrum m/z (FAB): 816 (M$^+$+1).

Example 25

Disodium [8-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-1-naphthyl]methyl phosphate (Disodium Salt of Example Number 5-41)

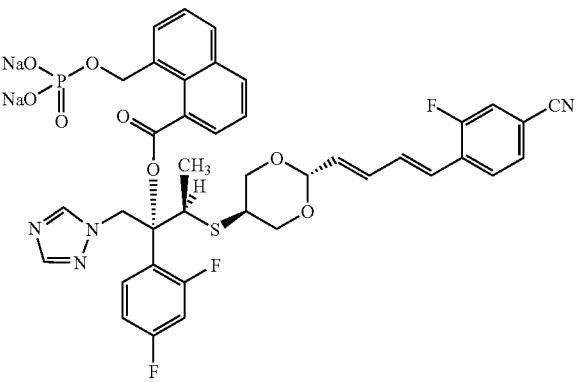

(1) Diallyl [8-[(tert-butyldimethylsilyl)oxymethyl]-1-naphthyl]methyl phosphate

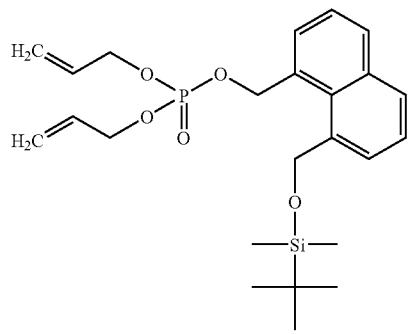

According to a similar procedure to that described in Example 1-(10), [8-[(tert-butyldimethylsilyl)oxymethyl]-1-naphthyl]methanol (described in Aust. J. Chem., 49, 793 (1996); 4.04 g, 13.4 mmol), tetrazole (2.34 g, 33.4 mmol), bis(allyloxy)(diisopropylamino)phosphine (described in Tetrahedron Lett., 30, 4219 (1989); 3.93 g, 16.0 mmol), and tert-butyl hydroperoxide (80% di-tert-butyl peroxide solution; Merck; 1.8 g, 16 mmol) were reacted, and the reaction mixture was worked up to afford, after extraction, an oily residue. The residue was subjected to chromatography on a silica gel (120 g) column (eluent; ethyl acetate:hexane=1:5~1:2) to afford the title compound (5.02 g, 81% yield) as a colorless oil.

NMR spectrum (400 MHz, CDCl$_3$) δ ppm: 0.03 (6H, s), 0.87 (9H, s), 4.37-4.45 (4H, m), 5.16 (2H, br d, J=10 Hz), 5.24 (2H, dq, J=18, 1 Hz), 5.25 (2H, s), 5.80 (2H, d, J=10 Hz), 5.77-5.86 (2H, m), 7.44-7.48 (2H, m), 7.61 (1H, dd, J=7, 1 Hz), 7.69 (1H, dd, J=7, 1 Hz), 7.84 (1H, dd, J=8, 1 Hz), 7.89 (1H, dd, J=7, 1 Hz)

IR spectrum ν max CHCl$_3$ cm$^{-1}$: 1732, 1471, 1464, 1259, 1027, 999

Mass spectrum m/z (FAB): 463 (M$^+$+1).

(2) Diallyl [8-(hydroxymethyl)-1-naphthyl]methyl phosphate

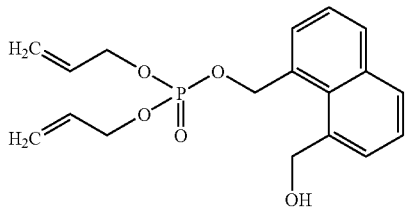

To a solution of diallyl [8-[(tert-butyldimethylsilyl)oxymethyl]-1-naphthyl]methyl phosphate (5.01 g, 10.8 mmol) obtained from Example 25-(1) in tetrahydrofuran (50 ml) was added tetrabutylammonium fluoride (1 mol/l tetrahydrofuran solution; 13.5 ml, 13.5 mmol), and the mixture was stirred at room temperature for 1 hour. Water was added and the product was extracted with ethyl acetate. The organic layer was concentrated under reduced pressure to give an oily residue. The residue was subjected to chromatography on a silica gel (75 g) column (eluent; ethyl acetate:hexane=3:1~4:1) to afford the title compound (2.22 g, 59% yield) as a colorless oil.

NMR spectrum (400 MHz, CDCl$_3$) δ ppm: 4.41-4.46 (4H, m), 5.18 (2H, br d, J=10 Hz), 5.19 (2H, s), 5.26 (2H, br d, J=17 Hz), 5.82 (2H, d, J=9 Hz), 5.84 (2H, ddt, J=17, 10, 6 Hz), 7.47 (1H, t, J=7 Hz), 7.49 (1H, t, J=7 Hz), 7.61 (1H, dd, J=7, 1 Hz), 7.71 (1H, dd, J=7, 1 Hz), 7.88 (1H, d, J=7 Hz), 7.92 (1H, d, J=7 Hz)

IR spectrum ν max CHCl$_3$ cm$^{-1}$: 3603, 1732, 1270, 1028, 990

Mass spectrum m/z (FAB): 349 (M$^+$+1).

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 8-[[bis(allyloxy)phosphoryl]oxymethyl]-1-naphthoate mixture of chromic anhydride (5.34 g) and concentrated sulfuric acid (4.6 ml) diluted with water to 20 ml total volume; 5 ml, ca. 13.2 mmol). The reaction mixture was stirred at room temperature for 90 minutes, then cooled to 0° C., and then 2-propanol (0.5 ml) was added thereto to stop the reaction. The insoluble material was filtered off, and the solvent was distilled off under reduced pressure to give an oily residue. The residue was dried using a vaccum pump, and then subjected to chromatography on a silica gel (30 g) column (eluent; ethyl acetate:dichloromethane=1:10~3:10) to afford crude 8-[[bis(allyloxy)phosphoryl]oxymethyl]-1-naphthoic acid as an oil. The product was dissolved in dichloromethane (10 ml), and then oxalyl chloride (1 g, 7.88 mmol) and N,N-dimethylformamide (15 μl) were added thereto. After the mixture was stirred at room temperature for 30 minutes, crude 8-[[bis(allyloxy)phosphoryl]oxymethyl]-1-naphthoyl chloride was obtained according to a similar procedure to that described in Example 1-(12). According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (542.7 mg, 1.0 mmol) described in Reference example 1, sodium hydride (55% dispersion in mineral oil; 43 mg, 1.0 mmol), and the crude 8-[[bis(allyloxy)phosphoryl]oxymethyl]-1-naphthoyl chloride obtained above were reacted in tetrahydrofuran (5 ml) and the reaction mixture was worked up to afford, after extraction, the title compound as a crude oil. The crude oil was subjected to chromatography on a silica gel (50 g) column (eluent; ethyl acetate:hexane=1:1~5:1) to afford the title compound (459.2 mg, 52% yield) as a pale yellow amorphous solid.

NMR spectrum (400 MHz, CDCl$_3$) δ ppm: 1.47 (3H, dd, J=7, 2 Hz), 3.18 (1H, tt, J=11, 5 Hz), 3.46 (1H, t, J=11 Hz), 3.55 (1H, t, J=11 Hz), 4.20 (1H, ddd, J=11, 5, 2 Hz), 4.22-4.42 (6H, m), 4.94 (1H, d, J=4 Hz), 5.13 (2H, br d, J=11 Hz), 5.20 (2H, br d, J=18 Hz), 5.34 (1H, dd, J=14, 10 Hz), 5.43-5.56 (3H, m), 5.70-5.82 (3H, m), 6.50 (1H, dd, J=15, 11 Hz), 6.70 (1H, d, J=15 Hz), 6.90 (1H, dd, J=15, 11 Hz), 6.90-6.95 (1H, m), 7.14 (1H, td, J=8, 3 Hz), 7.33 (1H, dd, J=10, 1 Hz), 7.38-7.44 (3H, m), 7.56 (1H, t, J=8 Hz), 7.58 (1H, t, J=8 Hz), 7.79 (1H, s), 7.83-7.89 (3H, m), 8.01 (1H, s), 8.05 (1H, dd, J=6, 3 Hz)

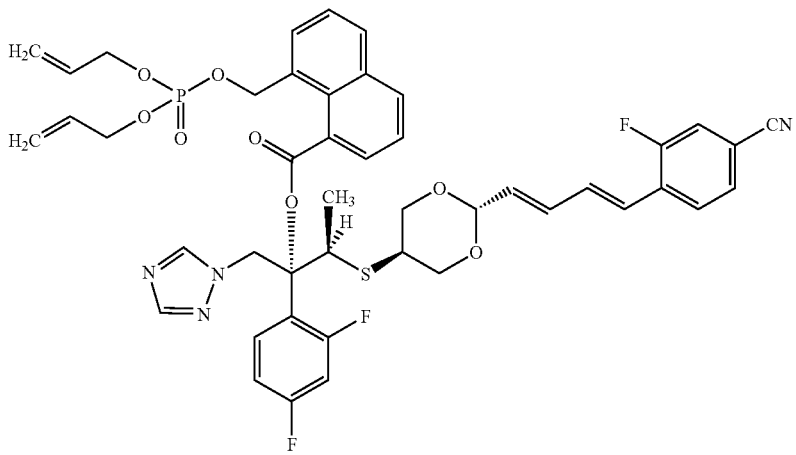

To a solution of diallyl [8-(hydroxymethyl)-1-naphthyl]methyl phosphate (1.1492 g, 3.30 mmol) in acetone (20 ml) obtained from Example 25-(2) was added Jones reagent (a IR spectrum ν max KBr cm$^{-1}$: 3431, 2230, 1718, 1615, 1503, 1274, 1143, 1039, 1011

Mass spectrum m/z (FAB): 887 (M$^+$+1).

(4) Disodium [8-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-1-naphthyl]methyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 8-[[bis(allyloxy)phosphoryl]oxymethyl]-1-naphthoate (450.3 mg, 0.51 mmol) obtained from Example 25-(3) was reacted with bis(triphenylphosphine)dichloropalladium (17.9 mg, 0.026 mmol) and tributyltin hydride (443 mg, 1.52 mmol) and the reaction mixture was worked up to afford the title target compound as a crude oil. The crude product was subjected to reverse phase column chromatography using Cosmosil 75 $C_{18}$-PREP (Nacalai Tesque, Inc.; 30 g) (eluent; water:methanol=4:6~3:7). The obtained fractions were concentrated, and the residue was lyophilized to afford the title target compound (117.7 mg, 27% yield) as a colorless solid.

NMR spectrum (400 MHz, $CD_3OD$) δ ppm: 1.48 (3H, dd, J=7, 2 Hz), 3.15 (1H, tt, J=11, 5 Hz), 3.49 (1H, t, J=11 Hz), 3.58 (1H, t, J=11 Hz), 4.17 (1H, ddd, J=11, 5, 2 Hz), 4.24 (1H, ddd, J=11, 5, 2 Hz), 4.34 (1H, q, J=7 Hz), 5.00 (1H, d, J=4 Hz), 5.21 (1H, dd, J=15, 8 Hz), 5.26 (1H, dd, J=15, 8 Hz), 5.59 (1H, dd, J=15, 3 Hz), 5.69 (1H, d, J=15 Hz), 5.82 (1H, dd, J=16, 4 Hz), 6.54 (1H, dd, J=16, 11 Hz), 6.77 (1H, d, J=16 Hz), 7.02 (1H, ddd, J=13, 9, 3 Hz), 7.07 (1H, dd, J=16, 11 Hz), 7.30 (1H, td, J=8, 3 Hz), 7.42 (1H, t, J=8 Hz), 7.49-7.54 (2H, m), 7.58 (1H, t, J=8 Hz), 7.70 (1H, d, J=7 Hz), 7.77 (1H, t, J=7 Hz), 7.84 (1H, d, J=8 Hz), 7.96 (1H, td, J=9, 6 Hz), 8.05 (1H, s), 8.09 (1H, dd, J=8, 1 Hz), 8.19 (1H, d, J=7 Hz), 8.39 (1H, s)

Mass spectrum m/z (FAB): 851 ($M^+$+1)

Specific rotation $[α]_D^{25}$ +63.0° (c=0.61, MeOH).

Example 26

Disodium 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-methylbenzyl phosphate (Disodium Salt of Example Number 5B-92)

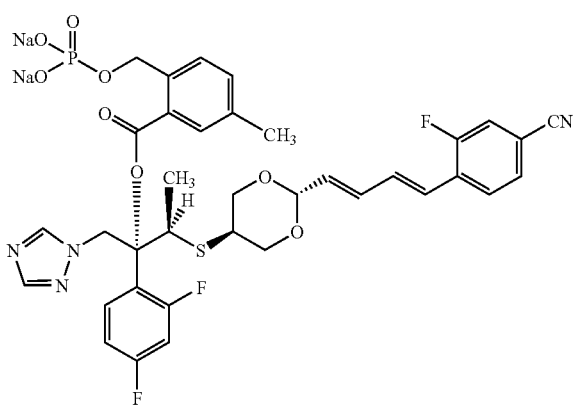

(1) 6-Amino-1(3H)-isobenzofuranone

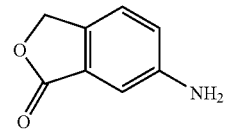

Commercially available 6-nitro-1(3H)-isobenzofuranone (9.9 g, 55 mmol) was dissolved in a mixed solvent of tetrahydrofuran (20 ml)-methanol (60 ml), then 5% palladium-charcoal catalyst (1.5 g) was added thereto, and the mixture was stirred at room temperature for 20 hours under an atmosphere of hydrogen gas. The reaction mixture was filtered, and the solid was washed successively with ethyl acetate and methanol. The filtrate and washings were combined, and the resulting solution was concentrated under reduced pressure. The obtained solid was washed with ethyl acetate to give the title compound (6.21 g) as a crystalline solid. The washings were concentrated, and the residue was crystallized from a mixed solvent of ethyl acetate-hexane to give an additional amount of the title compound (0.95 g, total yield 87%).

NMR spectrum (400 MHz, $CD_3OD$) δ ppm: 5.225 (2H, s), 7.060 (1H, d-like, J=2 Hz), 7.071 (1H, dd-like, J=9, 2 Hz), 7.288 (1H, d, J=9 Hz)

IR spectrum ν max KBr $cm^{-1}$: 3473, 3372, 3278, 1735, 1631, 1504, 1330, 1059, 992.

(2) 6-Bromo-1(3H)-isobenzofuranone

6-Amino-1(3H)-isobenzofuranone (3.0 g, 20 mmol) obtained from Example 26-(1) was dissolved in a mixture of 47% aqueous hydrobromic acid solution (15 ml) and water (15 ml), then the mixture was cooled to 0° C., and a solution of sodium nitrite (1.45 g, 21 mmol) in water (7 ml) was slowly added thereto. Further, a solution of copper (I) bromide (3.6 g, 25 mmol) dissolved in 47% aqueous hydrobromic acid solution (10 ml) was added to the reaction mixture, and the resulting mixture was stirred at 80° C. for 20 minutes. After cooling the mixture, the liberated product was collected by filtration and then washed with water. The obtained pale brown solid was dissolved in ethyl acetate, then the insoluble material was removed by filtration, and the filtrate was washed successively with a 1N aqueous solution of hydrochloric acid, an aqueous solution of sodium hydrogen carbonate, and an aqueous solution of sodium chloride, and then dried over anhydrous magnesium sulfate. After filtration, the filtrate was concentrated to afford the title compound (3.57 g, 84% yield) as a crystalline solid.

NMR spectrum (400 MHz, $CDCl_3$) δ ppm: 5.289 (2H, s), 7.391 (1H, d, J=8 Hz), 7.808 (1H, dd, J=8, 2 Hz), 8.068 (1H, d, J=2 Hz)

IR spectrum ν max KBr $cm^{-1}$: 1778, 1458, 1359, 1191, 1046, 998, 768

Mass spectrum m/z (EI): 214, 212 ($M^+$), 185, 183, 157, 155.

(3) 6-Methyl-1(3H)-isobenzofuranone

Tris(dibenzylideneacetone)dipalladium (0) (30 mg, 0.033 mmol), tri-o-tolylphosphine (40 mg, 0.13 mmol), and tetramethyltin (600 mg, 3.35 mmol) were dissolved in hexamethylphosphoramide (0.6 ml), and 6-bromo-1(3H)-isobenzofuranone (144 mg, 0.676 mmol) obtained from Example 26-(2) was added thereto, then the mixture was heated at 50° C. for 2 hours. After cooling the reaction mixture, the mixture was diluted with ethyl acetate, and washed successively twice with water and twice with an aqueous solution of sodium chloride. The organic layer was dried over anhydrous magnesium sulfate, filtered and concentrated. The residue was subjected to chromatography on a silica gel (5 g) column (eluent; hexane:ethyl acetate=3:1). The fractions containing the target compound were concentrated, and the obtained solid was recrystallized to afford the title compound (88.3 mg, 88% yield) as a crystalline solid.

NMR spectrum (400 MHz, CDCl$_3$) δ ppm: 2.472 (3H, s), 5.284 (2H, s), 7.376 (1H, d, J=8 Hz), 7.497 (1H, d, J=8 Hz), 7.721 (1H, s).

(4) 2-[[Bis(allyloxy)phosphoryl]oxymethyl]-5-methylbenzoic acid

According to a similar procedure to that described in Example 4-(5), 6-methyl-1(3H)-isobenzofuranone (2.22 g, 14.98 mmol) obtained from Example 26-(3) was successively treated with sodium hydroxide (a 1N aqueous solution; 14 ml, 14 mmol), 4-methoxybenzyl chloride (2.58 g, 16.5 mmol), tetrazole (2.10 g, 30 mmol), bis(allyloxy) (diisopropylamino)phosphine (5.52 g, 22.5 mmol), and tert-butyl hydroperoxide to afford, after purification by column chromatography (eluent; ethyl acetate:hexane=1:2~2:1), 4-methoxybenzyl 2-[[bis(allyloxy)phosphoryl]oxymethyl]-5-methylbenzoate. Further, the product was treated with trifluoroacetic acid according to a similar procedure to that described in Example 4-(6) to afford, after washing with hexane, the title compound (2.37 g, 48% yield) as a colorless oil.

NMR spectrum (400 MHz, CDCl$_3$) δ ppm: 2.396 (3H, s), 4.69 (4H, dd-like, J=7, 6 Hz), 5.246 (2H, dd-like, J=10, 1.5 Hz), 5.364 (2H, dd-like, J=17, 1.5 Hz), 5.590 (2H, d, J=6.6 Hz), 5.938 (2H, ddt, J=17, 10, 7 Hz), 7.391 (1H, d, J=8 Hz), 7.545 (1H, d, J=8 Hz), 7.803 (1H, brs)

IR spectrum ν max CHCl$_3$ cm$^{-1}$: 1695, 1267, 1167, 1030

Mass spectrum m/z (FAB): 327 (M$^+$+1)

(5) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-methylbenzoate According to a similar procedure to that described in Example 4-(6), 4-methoxybenzyl 2-[[bis(allyloxy)phosphoryl]oxymethyl]-5-methylbenzoate (690 mg, 1.54 mmol) was treated with trifluoroacetic acid to afford 2-[[bis(allyloxy) phosphoryl]oxymethyl]-5-methylbenzoic acid as a crude product. According to a similar procedure to that described in Example 4-(6), the above product was treated with oxalyl chloride and N,N-dimethylformamide to afford 2-[[bis(allyloxy)phosphoryl]oxymethyl]-5-methylbenzoyl chloride as a crude product. According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (670 mg, 1.23 mmol) described in Reference example 1 was treated with sodium hydride and then reacted with the crude 2-[[bis(allyloxy)phosphoryl] oxymethyl]-5-methylbenzoyl chloride (the whole amount) obtained above to afford, after purification by column chromatography, the title compound (448 mg, 43% yield) as a pale yellow, candy-like material.

NMR spectrum (400 MHz, CDCl$_3$) δ ppm: 1.452 (3H, dd, J=7, 2 Hz), 2.382 (3H, s), 3.092 (1H, tt, J=11, 5 Hz), 3.481 (1H, t, J=11 Hz), 3.537 (1H, t, J=11 Hz), 4.016 (1H, q, J=7 Hz), 4.132 (1H, ddd, J=11, 5, 2 Hz), 4.221 (1H, ddd, J=11, 5, 2 Hz), 4.47-4.6 (4H, m), 4.981 (1H, d, J=4 Hz), 5.208 (2H, dq-like, J=11, 1 Hz), 5.26-5.46 (5H, m), 5.543 (1H, d, J=15 Hz), 5.836 (1H, dd, J=15, 4 Hz), 5.912 (1H, ddt, J=16, 11, 5 Hz), 5.917 (1H, ddt, J=16, 11, 5 Hz), 6.559 (1H, dd, J=15, 11 Hz), 6.728 (1H, d, J=16 Hz), 6.86-6.97 (3H, m), 7.335 (1H, dd, J=10, 1.5 Hz), 7.34-7.44 (1H, m), 7.402 (2H, d, J=8 Hz), 7.513 (1H, br s), 7.561 (1H, d, J=8 Hz), 7.571 (1H, t, J=10 Hz), 7.925 (1H, s), 7.932 (1H, s)

IR spectrum ν max CHCl$_3$ cm$^{-1}$: 2233, 1764, 1721, 1616, 1504, 1276

Mass spectrum m/z (FAB): 851 (M$^+$+1).

(6) Disodium 2-[[[(1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propoxy]carbonyl]-4-methylbenzyl phosphate (Title Target Compound)

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-5-methylbenzoate (420 mg, 0.494 mmol) obtained from Example 26-(5) was treated with tetrakis(triphenylphosphine)palladium, triphenylphosphine, and pyrrolidine in dichloromethane according to a similar procedure to that described in Example 18-(2). The reaction mixture was worked up according to a similar procedure to that described in Example 18-(2), and the residue obtained by extraction was subjected to reverse phase column chromatography using Cosmosil 75 C$_{18}$-PREP (Nacalai Tesque, Inc.) (eluent; water:methanol=1: 0~7:3). The obtained fractions were concentrated, and the residue was subjected to a cation exchange resin (Dowex 50W-8X, Na type) (eluent; water). The collected fractions were concentrated under reduced pressure and lyophilized to afford the title target compound (298 mg, 74% yield) as an amorphous colorless solid.

NMR spectrum (400 MHz, D$_2$O) δ ppm: 1.404 (3H, d, J=7 Hz), 2.327 (3H, s), 3.150 (1H, tt, J=11, 5 Hz), 3.446 (1H, t, J=11 Hz), 3.565 (1H, t, J=11 Hz), 4.06 (1H, ddd, J=11, 5, 2 Hz), 4.120 (1H, q, J=7 Hz), 4.22 (1H, ddd, J=11, 5, 2 Hz), 5.015 (1H, d, J=4 Hz), 5.100 (1H, dd, J=16, 5 Hz), 5.302 (1H, dd, J=16, 5 Hz), 5.45 (1H, dd, J=14, 2 Hz), 5.625 (1H, d, J=14 Hz), 5.850 (1H, dd, J=15, 4 Hz), 6.565 (1H, dd, J=15, 11 Hz), 6.788 (1H, d, J=15 Hz), 7.024 (2H, t-like, J=ca.9 Hz), 7.092 (1H, dd, J=15, 11 Hz), 7.35-7.40 (2H, m), 7.45-7.6 (3H, m), 7.785 (1H, t, J=8 Hz), 7.955 (1H, d, J=8 Hz), 8.028 (1H, s), 8.330 (1H, s)

IR spectrum ν max KBr cm$^{-1}$: 3422, 2231, 1721, 1615, 1503, 1276, 1141, 1053, 975

Mass spectrum m/z (FAB): 815 (M$^+$+1)

High resolution mass spectrum m/z (FAB): Calculated for C$_{36}$H$_{33}$F$_3$N$_4$O$_8$PSNa$_2$ (M$^+$+1): 815.1504. Found: 815.1506.

Example 27

Disodium 2-chloro-6-[[(1R,2R)-2-[[trans-2-[(1E, 3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Disodium Salt of Example Number 5-45)

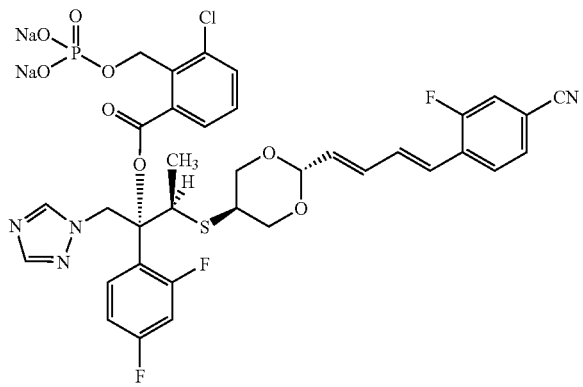

(1) 2-[(tert-Butyldimethylsilyl)oxymethyl]-6-chlorobenzyl alcohol

A solution of 3-chloro-1,2-benzenedimethanol (described in J. Chem. Soc., p. 5050 (1952); 3.02 g, 17.5 mmol) in tetrahydrofuran (40 ml) was cooled to 0° C., and then imidazole (1.19 g, 17.5 mmol) and tert-butylchlorodimethylsilane (2.64 g, 17.5 mmol) were added thereto. The mixture was stirred at room temperature for 1 hour, then water was added thereto, and the product was extracted with ethyl acetate. The organic layer was washed with a saturated aqueous solution of sodium chloride, and the solvent was distilled off under reduced pressure to give a residue. The residue was subjected to chromatography on a silica gel (100 g) column (eluent; ethyl acetate:hexane=1:5) to afford the title compound (3.69 g, 73% yield) as a colorless oil.

NMR spectrum (400 MHz, CDCl$_3$) δ ppm: 0.13 (6H, s), 0.92 (9H, s), 2.93 (1H, t, J=7 Hz), 4.83 (2H, s), 4.86 (2H, d, J=7 Hz), 7.19-7.25 (2H, m), 7.37 (1H, dd, J=8, 2 Hz)

IR spectrum ν max CHCl$_3$ cm$^{-1}$: 2959, 2931, 1732, 1257, 1049, 839

Mass spectrum m/z (FAB): 287 (M$^+$+1).

(2) Diallyl 2-[(tert-butyldimethylsilyl)oxymethyl]-6-chlorobenzyl phosphate

According to a similar procedure to that described in Example 1-(10), 2-[(tert-butyldimethylsilyl)oxymethyl]-6-chlorobenzyl alcohol (3.66 g, 12.8 mmol) obtained from Example 27-(1), tetrazole (2.23 g, 31.9 mmol), bis(allyloxy)(diisopropylamino)phosphine (described in Tetrahedron Lett., 30, 4219 (1989); 3.91 g, 16.0 mmol), and tert-butyl hydroperoxide (ca. 80% di-tert-butyl peroxide solution; Merck; 1.8 g, ca. 16 mmol) were reacted, and the reaction mixture was worked up to afford, after extraction, an oily residue. The residue was subjected to chromatography on a silica gel (200 g) column (eluent; ethyl acetate:hexane=1:5~2:3) to afford the title compound (4.52 g, 79% yield) as a colorless oil.

NMR spectrum (400 MHz, CDCl$_3$) δ ppm: 0.11 (6H, s), 0.94 (9H, s), 4.51-4.55 (4H, m), 4.88 (2H, s), 5.23 (2H, br d, J=10 Hz), 5.30 (2H, d, J=7 Hz), 5.34 (2H, dq, J=17, 1 Hz), 5.91 (2H, ddt, J=17, 10, 5 Hz), 7.28-7.34 (2H, m), 7.44 (1H, d, J=7 Hz)

IR spectrum ν max CHCl$_3$ cm$^{-1}$: 2956, 2931, 1259, 1018, 989, 839

Mass spectrum m/z (FAB): 447 (M$^+$+1).

(3) Diallyl 2-chloro-6-(hydroxymethyl)benzyl phosphate

To a solution of diallyl 2-[(tert-butyldimethylsilyl)oxymethyl]-6-chlorobenzyl phosphate (4.41 g, 9.87 mmol) obtained from Example 27-(2) in tetrahydrofuran (50 ml) was added tetrabutylammonium fluoride (1N tetrahydrofuran solution; 10 ml, 10 mmol), and the mixture was stirred at room temperature for 40 minutes. Water was added to the mixture, then the product was extracted with ethyl acetate, and the solvent was distilled off under reduced pressure to give an oily residue. The residue was subjected to chromatography on a silica gel (50 g) column (eluent; ethyl acetate:hexane=1:1~3:1) to afford the title compound (2.71 g, 83% yield) as a colorless oil.

NMR spectrum (400 MHz, CDCl$_3$) δ ppm: 3.49 (1H, t, J=6 Hz), 4.47-4.51 (4H, m), 4.78 (2H, d, J=6 Hz), 5.23 (2H, br d, J=10 Hz), 5.33 (2H, br d, J=18 Hz), 5.40 (2H, d, J=9 Hz), 5.89 (2H, ddt, J=18, 10, 6 Hz), 7.32 (1H, t, J=8 Hz), 7.37-7.40 (2H, m)

IR spectrum ν max CHCl$_3$ cm$^{-1}$: 3608, 1732, 1268, 1028, 987

Mass spectrum m/z (FAB): 333 (M$^+$+1).

(4) 2-[[Bis(allyloxy)phosphoryl]oxymethyl]-3-chlorobenzoic acid

A solution of diallyl 2-chloro-6-(hydroxymethyl)benzyl phosphate (2.62 g, 7.88 mmol) obtained from Example 27-(3) in acetone (25 ml) was cooled to 0° C., and Jones reagent (a mixture of chromic anhydride (5.34 g) and concentrated sulfuric acid (4.6 ml) diluted with water to 20 ml total volume; 12 ml, ca. 32 mmol) was added thereto. The reaction mixture was stirred at room temperature for 1 hour, and then 2-propanol (1 ml) was added thereto to stop the reaction. The insoluble material was filtered off, and then the filtrate was concentrated under reduced pressure to give an oily residue. The residue was thoroughly dried using a vaccum pump, and then subjected to chromatography on a silica gel (40 g) column (eluent; ethyl acetate:dichloromethane=1:10~1:1) to afford the title compound (2.065 g, 76% yield) as a pale brown oil.

NMR spectrum (400 MHz, CDCl$_3$) δ ppm: 4.50-4.62 (4H, m), 5.23 (2H, br d, J=10 Hz), 5.34 (2H, dq, J=17, 1 Hz), 5.64 (2H, dd, J=7, 2 Hz), 5.91 (2H, ddt, J=17, 10, 6 Hz), 7.39 (1H, t, J=8 Hz), 7.57 (1H, d, J=8 Hz), 7.81 (1H, d, J=8 Hz)

IR spectrum ν max CHCl$_3$ cm$^{-1}$: 2951, 1727, 1267, 1025

Mass spectrum m/z (FAB): 347 (M$^+$+1).

(5) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl2-[[bis(allyloxy)phosphoryl]oxymethyl]-3-chlorobenzoate

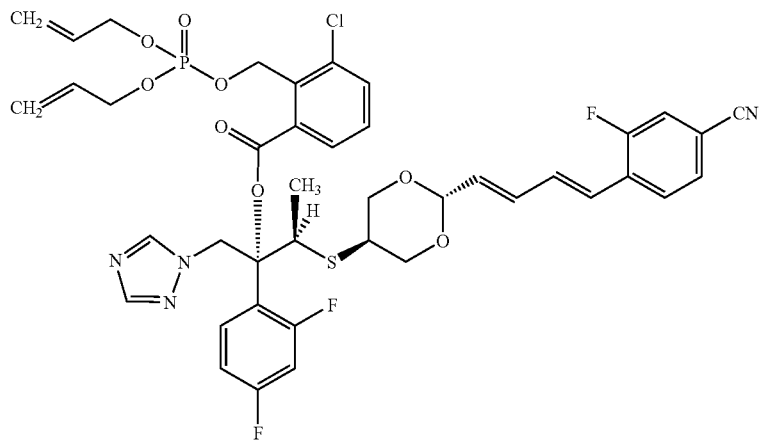

A solution of 2-[[bis(allyloxy)phosphoryl]oxymethyl]-3-chlorobenzoic acid (936.1 mg, 2.7 mmol) obtained from Example 27-(4) in dichloromethane (15 ml) was cooled to 0° C., and then N,N-dimethylformamide (15 μl) and oxalyl chloride (1.71 g, 13.5 mmol) were added thereto. After the mixture was stirred at room temperature for 30 minutes, it was worked up according to a similar procedure to that described in Example 1-(12) to afford crude 2-[[bis(allyloxy)phosphoryl]oxymethyl]-3-chlorobenzoyl chloride.

According to a similar procedure to that described in Example 1-(12), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (976.7 mg, 1.80 mmol) described in Reference example 1, sodium hydride (55% dispersion in mineral oil; 78.5 mg, 1.8 mmol), and the crude 2-[[bis(allyloxy)phosphoryl]oxymethyl]-3-chlorobenzoyl chloride obtained above were reacted in tetrahydrofuran (10 ml), and the reaction mixture was worked up to afford, after extraction, the title compound as a crude oil. The crude oil was subjected to chromatography on a silica gel (100 g) column (eluent; ethyl acetate:hexane=1:1~5:1) to afford the title compound (1136 mg, 72% yield) as a pale yellow amorphous solid.

NMR spectrum (400 MHz, CDCl$_3$) δ ppm: 1.44 (3H, dd, J=7, 2 Hz), 3.02 (1H, tt, J=11, 5 Hz), 3.45 (1H, t, J=11 Hz), 3.51 (1H, t, J=11 Hz), 4.00 (1H, q, J=7 Hz), 4.07 (1H, ddd, J=11, 5, 2 Hz), 4.18 (1H, ddd, J=11, 5, 2 Hz), 4.45-4.58 (4H, m), 4.96 (1H, d, J=4 Hz), 5.20 (2H, br d, J=10 Hz), 5.31 (2H, br d, J=17 Hz), 5.45 (1H, dd, J=15, 3 Hz), 5.51 (1H, d, J=15 Hz), 5.56 (1H, dd, J=10, 6 Hz), 5.59 (1H, dd, J=10, 6 Hz), 5.82 (1H, dd, J=15, 4 Hz), 5.85-5.94 (2H, m), 6.55 (1H, dd, J=15, 11 Hz), 6.73 (1H, d, J=16 Hz), 6.95 (1H, dd, J=16, 11 Hz), 6.87-7.03 (2H, m), 7.32-7.50 (5H, m), 7.57 (1H, t, J=8 Hz), 7.63 (1H, dd, J=8, 1 Hz), 7.94 (1H, s), 8.00 (1H, s)

IR spectrum ν max CHCl$_3$ cm$^{-1}$: 2233, 1732, 1504, 1276, 1140, 1019, 991

Mass spectrum m/z (FAB): 871 (M$^+$+1).

(6) Disodium 6-chloro-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate (Title Target Compound)

According to a similar procedure to that described in Example 1-(13), (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[bis(allyloxy)phosphoryl]oxymethyl]-3-chlorobenzoate (598.8 mg, 0.69 mmol) obtained from Example 27-(5) was reacted with bis(triphenylphosphine)dichloropalladium (24.1 mg, 0.034 mmol) and tributyltin hydride (429.9 mg, 1.51 mmol), and the reaction mixture was worked up to afford, after extraction, the title target compound as a crude oil. The crude oil was subjected to reverse phase column chromatography using Cosmosil 75 C$_{18}$-PREP (Nacalai Tesque, Inc.; 30 g) (eluent; water:methanol=4:6~3:7). The obtained fractions were concentrated, and the residue was lyophilized to afford the title target compound (174.8 mg, 30% yield) as a colorless solid.

NMR spectrum (400 MHz, CD$_3$OD) δ ppm: 1.42 (3H, dd, J=7, 2 Hz), 2.98 (1H, tt, J=11, 5 Hz), 3.46 (1H, t, J=11 Hz), 3.52 (1H, t, J=11 Hz), 4.00-4.06 (2H, m), 4.14 (1H, ddd, J=11, 5, 2 Hz), 5.00 (1H, d, J=4 Hz), 5.35 (1H, dd, J=11, 4 Hz), 5.42 (1H, dd, J=11, 4 Hz), 5.53 (1H, dd, J=15, 3 Hz), 5.67 (1H, d, J=15 Hz), 5.83 (1H, dd, J=15, 4 Hz), 6.55 (1H, dd, J=15, 11 Hz), 6.78 (1H, d, J=15 Hz), 7.00-7.16 (3H, m), 7.38 (1H, t, J=8 Hz), 7.49-7.54 (2H, m), 7.62-7.71 (3H, m), 7.78 (1H, t, J=8 Hz), 7.98 (1H, s), 8.63 (1H, s)

IR spectrum ν max KBr cm$^{-1}$: 2231, 1732, 1615, 1503, 1275, 1257, 1142, 1105, 1048, 974

Mass spectrum m/z (FAB): 835 (M$^+$+1)

Specific rotation [α]$_D^{25}$ +7.7° (c=1.20, MeOH).

Example 28

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(2-aminoacetoxy)methyl]benzoate
(Example Number 5-2)

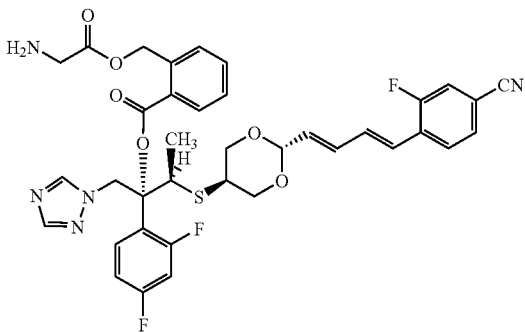

(1) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[(2-allyloxycarbonylamino)acetoxy]methyl]benzoate

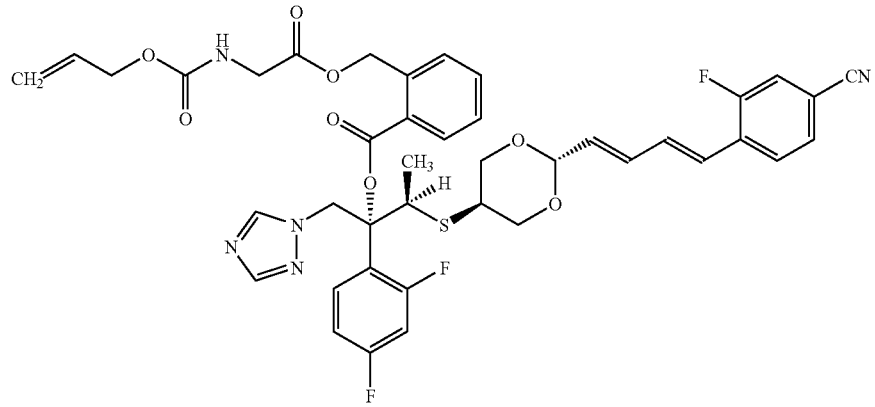

A solution of N-(allyloxycarbonyl)glycine (described in Chem. Pharm. Bull., 48, 716 (2000); 600 mg, 3.77 mmol) in dichloromethane (15 ml) was cooled to 0° C., and N,N-dimethylformamide (0.03 ml) and oxalyl chloride (0.6 g, 4.7 mmol) were added thereto. The mixture was stirred at room temperature for 1 hour, then toluene was added thereto, and the solvent was distilled off under reduced pressure to give crude 2-(allyloxycarbonylamino)acetyl chloride.

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (800 mg, 1.18 mmol) obtained Example 17-(4) in dichloromethane (20 ml) was cooled to 0° C., and 4-(N,N-dimethylamino)pyridine (366.5 mg, 3 mmol) and the crude 2-(allyloxycarbonylamino)acetyl chloride obtained above were added thereto. The mixture was stirred at the same temperature for 1 hour, diluted with dichloromethane, and then the organic layer was washed successively with a saturated aqueous solution of sodium hydrogen carbonate and water. The solvent was evaporated under reduced pressure, and the residue was subjected to chromatography on a silica gel (40 g) column (eluent; ethyl acetate: hexane=3:2) to afford the title compound (777.0 mg, 80% yield) as a pale yellow amorphous solid.

NMR spectrum (400 MHz, CDCl$_3$) δ ppm: 1.47 (3H, dd, J=7, 2 Hz), 3.06 (1H, tt, J=11, 5 Hz), 3.50 (1H, t, J=11 Hz), 3.53 (1H, t, J=11 Hz), 4.03-4.10 (3H, m), 4.13-4.21 (2H, m), 4.59 (2H, d, J=5 Hz), 4.99 (1H, d, J=4 Hz), 5.21 (1H, dd, J=10, 1 Hz), 5.30 (1H, dd, J=18, 1 Hz), 5.46-5.56 (3H, m), 5.60 (1H, d, J=14 Hz), 5.84 (1H, dd, J=16, 4 Hz), 5.87-5.96 (1H, m), 6.57 (1H, dd, J=16, 11 Hz), 6.73 (1H, d, J=16 Hz), 6.88-7.00 (3H, m), 7.33 (1H, dd, J=10, 1 Hz), 7.39-7.46 (3H, m), 7.54-7.62 (3H, m), 7.84 (1H, d, J=7 Hz), 7.89 (1H, s), 7.96 (1H, s)

IR spectrum ν max KBr cm$^{-1}$: 2230, 1724, 1504, 1274, 1258, 1140, 1051

Mass spectrum m/z (ESI): 818 (M$^+$+1).

(2) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(2-aminoacetoxy)methyl]benzoate
(Title Target Compound)

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(allyloxycarbonylamino)acetoxy]methyl]benzoate (366.9 mg, 0.449 mmol) obtained from Example 28-(1) in dichloromethane (10 ml) was added bis(triphenylphosphine)dichloropalladium (15.7 mg, 0.022 mmol) at room temperature, and then tributyltin hydride (156.8 mg, 0.54 mmol) was added dropwise thereto. The reaction solution was stirred at room temperature for 30 minutes, concentrated, and then the obtained oily residue was subjected to chromatography on a silica gel (10 g) column (eluent; ethyl acetate:methanol=4:1) to afford the title target compound (282.5 mg, 86% yield) as a colorless amorphous solid.

NMR spectrum (400 MHz, CDCl$_3$) δ ppm: 1.46 (3H, dd, J=7, 1 Hz), 3.05 (1H, tt, J=11, 5 Hz), 3.51 (1H, t, J=11 Hz), 3.53 (1H, t, J=11 Hz), 3.53 (2H, s), 4.02 (1H, q, J=7 Hz), 4.10-4.21 (2H, m), 4.99 (1H, d, J=4 Hz), 5.47-5.57 (4H, m), 5.85 (1H, dd, J=15, 4 Hz), 6.57 (1H, dd, J=15, 11 Hz), 6.73 (1H, d, J=16 Hz), 6.89-6.96 (3H, m), 7.34 (1H, d, J=10 Hz), 7.39-7.46 (3H, m), 7.53-7.59 (3H, m), 7.81 (1H, d, J=8 Hz), 7.89 (1H,s), 7.95 (1H, s)

IR spectrum ν max KBr cm$^{-1}$: 2230, 1726, 1503, 1274, 1257, 1140, 1051, 973

Mass spectrum m/z (ESI): 734 (M$^+$+1)

Specific rotation [α]$_D^{25}$ −5.2° (c=1.11, CHCl$_3$).

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(2-aminoacetoxy)methyl]benzoate (219.0 mg, 0.299 mmol) obtained above in ethyl acetate (5 ml) was added hydrogen chloride (4N ethyl acetate solution; 67 μl, 0.27 mmol), and the mixture was stirred at 0° C. for 5 minutes. The solvent was distilled off under reduced pressure to afford the hydrochloric acid salt of the title target compound (230 mg, quantitative yield) as a pale yellow amorphous solid.

NMR spectrum (400 MHz, CDCl$_3$) δ ppm: 1.45 (3H, d, J=7 Hz), 3.03 (1H, tt, J=12, 5 Hz), 3.51 (1H, t, J=12 Hz), 3.52 (1H, t, J=12 Hz), 3.93 (2H, s), 4.05 (1H, q, J=7 Hz), 4.10-4.18 (2H, m), 4.99 (1H, d, J=4 Hz), 5.38 (1H, d, J=14 Hz), 5.42 (1H, d, J=14 Hz), 5.51 (1H, d, J=14 Hz), 5.67 (1H, d, J=14 Hz), 5.84 (1H, dd, J=15, 4 Hz), 6.56 (1H, dd, J=15, 10 Hz), 6.72 (1H, d, J=16 Hz), 6.86-7.00 (3H, m), 7.32 (1H, dd, J=10, 1 Hz), 7.37-7.43 (3H, m), 7.52-7.58 (3H, m), 7.85 (1H, s), 7.91 (1H, d, J=7 Hz), 8.09 (1H, s)

IR spectrum ν max KBr cm$^{-1}$: 2231, 1724, 1503, 1274, 1257, 1140, 1051, 973

Mass spectrum m/z (FAB): 734 [M$^+$ (free base)+1]

Specific rotation [α]$_D^{25}$ −16.1° (c=1.13, CHCl$_3$).

Example 29

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N,N-dimethylamino)acetoxy]methyl]benzoate (Example Number 5A-2)

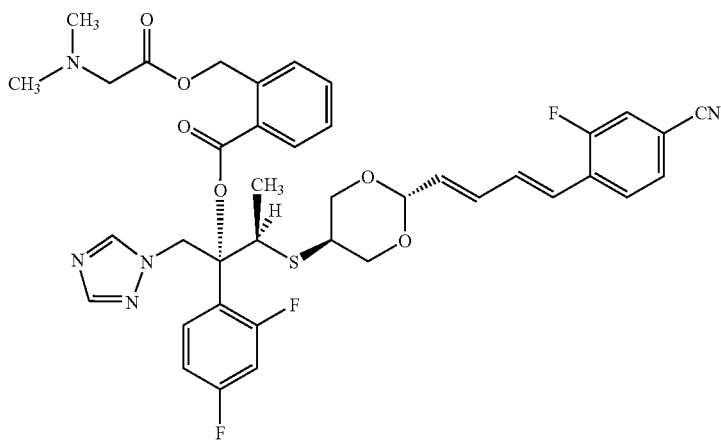

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (640.7 mg, 0.95 mmol) obtained from Example 17-(4) in dichloromethane (20 ml) was cooled to 0° C., and then 4-(N,N-dimethylamino)pyridine (254.5 mg, 2.1 mmol), N,N-dimethylglycine (117.2 mg, 1.14 mmol), and 2-chloro-1,3-dimethylimidazolinium chloride (256.1 mg, 1.52 mmol) were added thereto. The reaction mixture was stirred at room temperature for 3 hours, diluted with ethyl acetate, and then the organic layer was washed successively with a saturated aqueous solution of ammonium chloride and with a saturated aqueous solution of sodium chloride. The solvent was evaporated under reduced pressure, and then the residue was subjected to chromatography on a silica gel (40 g) column (eluent; ethyl acetate:methanol=100:3) to give a mixture of the title compound and 1,3-dimethyl-2-imidazolidinone. The mixture was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title target compound (368.1 mg, 51% yield) as a colorless amorphous solid.

NMR spectrum (400 MHz, CDCl$_3$) δ ppm: 1.46 (3H, dd, J=7, 2 Hz), 2.79 (6H, s), 3.05 (1H, tt, J=11, 5 Hz), 3.27 (2H, s), 3.51 (1H, t, J=11 Hz), 3.53 (1H, t, J=11 Hz), 4.02 (1H, q, J=7 Hz), 4.12-4.21 (2H, m), 4.99 (1H, d, J=5 Hz), 5.48 (1H, dd, J=15, 3 Hz), 5.51 (2H, s), 5.54 (1H, d, J=15 Hz), 5.85 (1H, dd, J=15, 4 Hz), 6.57 (1H, dd, J=15, 11 Hz), 6.73 (1H, d, J=16 Hz), 6.89-6.96 (3H, m), 7.34 (1H, dd, J=10, 1 Hz), 7.38-7.42 (2H, m), 7.44 (1H, td, J=9, 7 Hz), 7.52-7.61 (3H, m), 7.79 (1H, d, J=7 Hz), 7.90 (1H, s), 7.96 (1H, s)

IR spectrum ν max KBr cm$^{-1}$: 2230, 1726, 1503, 1275, 1257, 1140, 1052, 973

Mass spectrum m/z (ESI): 762 (M$^+$+1).

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N,N-dimethylamino)acetoxy]methyl]benzoate (215.0 mg, 0.28 mmol) obtained above in ethyl acetate (5 ml) was added hydrogen chloride (4N ethyl acetate solution; 66 μl, 0.27 mmol), and the mixture was stirred at 0° C. for 5 minutes. The solvent was distilled off under reduced pressure and the residue was dried in vacuo to afford the hydrochloric acid salt of the title target compound (230 mg, quantitative yield) as a pale yellow amorphous solid.

NMR spectrum (400 MHz, CDCl$_3$) δ ppm: 1.46 (3H, dd, J=7, 2 Hz), 2.60 (6H, s), 3.05 (1H, tt, J=11, 5 Hz), 3.48-3.57

(4H, m), 4.03 (1H, q, J=7 Hz), 4.13-4.22 (2H, m), 4.99 (1H, d, J=4 Hz), 5.45-5.53 (3H, m), 5.58 (1H, d, J=14 Hz), 5.85 (1H, dd, J=15, 4 Hz), 6.57 (1H, dd, J=15, 10 Hz), 6.74 (1H, d, J=16 Hz), 6.89-7.00 (3H, m), 7.34 (1H, dd, J=10, 1 Hz), 7.39-7.47 (3H, m), 7.52-7.63 (3H, m), 7.84 (1H, d, J=9 Hz), 7.90 (1H, s), 7.96 (1H, s)

IR spectrum ν max KBr cm$^{-1}$: 2230, 1726, 1503, 1275, 1257, 1140, 1051, 973

Mass spectrum m/z (ESI): 762 [M$^+$ (free base)+1]

Specific rotation $[\alpha]_D^{25}$ −1.1° (c=1.07, CHCl$_3$).

Example 30

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(4-methyl-1-piperazinyl)acetoxy]methyl]benzoate (Example Number 5A-9)

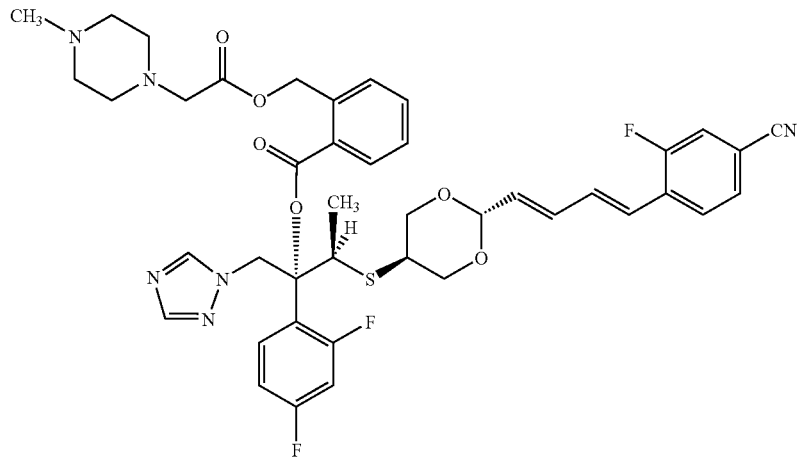

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (1.104 g, 1.63 mmol) obtained from Example 17-(4) in dichloromethane (25 ml) was cooled to 0° C., and then 4-(N,N-dimethylamino)pyridine (299.1 mg, 2.45 mmol), 2-(4-methyl-1-piperazinyl)acetic acid (described in J. Med. Chem., 43, 1493 (2000); 387.3 mg, 2.45 mmol), and 1-ethyl-3-[3-(N,N-dimethylamino)propyl]carbodiimide (625.5 mg, 3.26 mmol) were added thereto. The reaction solution was stirred at room temperature for 4 hours, diluted with dichloromethane, and then the organic layer was washed successively with water and a saturated aqueous solution of sodium chloride. The solvent was evaporated under reduced pressure, and the residue was subjected to chromatography on a silica gel (40 g) column (eluent; ethyl acetate:methanol=4:1) to give a mixture of the title target compound and 4-(N,N-dimethylamino)pyridine. The mixture was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title target compound (865.2 mg, 65% yield) as a colorless amorphous solid.

NMR spectrum (400 MHz, CDCl$_3$) δ ppm: 1.46 (3H, dd, J=7, 2 Hz), 2.29 (3H, s), 2.4-2.5 (4H, br s), 2.6-2.7 (4H, br s), 3.05 (1H, tt, J=12, 5 Hz), 3.31 (2H, s), 3.50 (1H, t, J=12 Hz), 3.53 (1H, t, J=12 Hz), 4.01 (1H, q, J=7 Hz), 4.12-4.21 (2H, m), 4 99 (1H, d, J=4 Hz), 5.45-5.55 (4H, m), 5.84 (1H, dd, J=15, 4 Hz), 6.57 (1H, dd, J=15, 10 Hz), 6.73 (1H, d, J=16 Hz), 6.93 (1H, dd, J=16, 10 Hz), 6.88-7.00 (2H, m), 7.34 (1H, dd, J=11, 1 Hz), 7.27-7.46 (3H, m), 7.53-7.60 (3H, m), 7.79 (1H, dd, J=8, 1 Hz), 7.90 (1H, s), 7.95 (1H, s)

IR spectrum ν max KBr cm$^{-1}$: 2230, 1726, 1503, 1275, 1257, 1051, 1140, 973

Mass spectrum m/z (FAB): 817 (M$^+$+1)

Specific rotation $[\alpha]_D^{25}$ +0.4° (c=0.99, CHCl$_3$).

A solution of (1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propyl 2-[[2-(4-methylpiperazin-1-yl)acetoxy]methyl]benzoate (280 mg, 0.343 mmol) obtained above in ethyl acetate (5 ml) was cooled to 0° C., and hydrogen chloride (4N ethyl acetate solution; 95 μl, 0.38 mmol) was added thereto, and the mixture was stirred at 0° C. for 5 minutes. The solvent was evaporated under reduced pressure, and the residue was dried in vacuo to afford the mono hydrochloric acid salt of the title compound (298 mg, quantitative yield) as a pale yellow amorphous solid.

NMR spectrum (400 MHz, CD$_3$OD) δ ppm: 1.43 (3H, dd, J=7, 1 Hz), 2.87 (3H, s), 2.8-3.4 (8H, m), 3.04 (1H, tt, J=11, 5 Hz), 3.48 (1H, t, J=11 Hz), 3.53 (2H, s), 3.54 (1H, t, J=11 Hz), 4.06 (1H, q, J=7 Hz), 4.04-4.08 (2H, m), 4.17 (1H, ddd, J=11, 5, 2 Hz), 5.20 (1H, d, J=4 Hz), 5.46 (1H, d, J=14 Hz), 5.53 (1H, d, J=14 Hz), 5.58 (2H, s), 5.85 (1H, dd, J=15, 4 Hz), 6.57 (1H, dd, J=15, 10 Hz), 6.79 (1H, d, J=16 Hz), 7.01-7.11 (2H, m), 7.09 (1H, dd, J=16, 10 Hz), 7.46 (1H, td, J=8, 1 Hz), 7.50-7.61 (3H, m), 7.63 (1H, qd, J=7, 1 Hz), 7.78 (1H, t, J=8 Hz), 7.86 (1H, dd, J=7, 1 Hz), 7.95 (1H, s), 8.34 (1H, s)

IR spectrum ν max KBr cm$^{-1}$: 2230, 1726, 1503, 1274, 1257, 1140, 1050, 973

Mass spectrum m/z (FAB): 817 [M$^+$ (free base)+1]

Specific rotation $[\alpha]_D^{25}$ −1.9° (c=0.97, CHCl$_3$).

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-([2-(4-methylpiperazin-1-yl)acetoxy]methyl]benzoate (338.5 mg, 0.41 mmol) obtained above in ethyl acetate (5 ml) was cooled to 0° C., and hydrogen chloride (4N ethyl acetate solution; 207 μl, 0.83 mmol) was added thereto, and the mixture was stirred at 0° C. for 5 minutes. The solvent was evaporated under reduced pressure, and the residue was dried in vacuo to afford the bis hydrochloric acid salt of the title compound (354 mg, quantitative yield) as a pale yellow amorphous solid.

NMR spectrum (400 MHz, DMSO-$d_6$) δ ppm: 1.35 (3H, dd, J=7, 2 Hz), 2.76 (3H, s), 2.82-2.92 (2H, m), 2.99 (1H, tt, J=11, 5 Hz), 3.06-3.16 (4H, m), 3.41 (2H, br d, J=15 Hz), 3.46 (1H, t, J=11 Hz), 3.47 (1H, t, J=11 Hz), 3.65-3.75 (2H, m), 3.79 (1H, q, J=7 Hz), 3.96 (1H, ddd, J=11, 5, 2 Hz), 4.07 (1H, ddd, J=11, 5, 2 Hz), 5.05 (1H, d, J=5 Hz), 5.39 (1H, d, J=13 Hz), 5.40 (1H, d, J=14 Hz), 5.49 (1H, d, J=13 Hz), 5.56 (1H, d, J=14 Hz), 5.88 (1H, dd, J=15, 5 Hz), 6.56 (1H, dd, J=15, 11 Hz), 6.82 (1H, d, J=16 Hz), 7.16-7.20 (1H, m), 7.19 (1H, dd, J=16, 11 Hz), 7.31-7.37 (1H, m), 7.49-7.55 (1H, m), 7.55 (1H, td, J=9, 6 Hz), 7.60 (1H, d, J=7 Hz), 7.67-7.71 (2H, m), 7.84-7.89 (3H, m), 7.96 (1H, s), 8.44 (1H, s)

Mass spectrum m/z (FAB): 817 [M$^+$ (free base)+1]

Specific rotation [α]$_D^{25}$ −3.1° (c=1.87, CHCl$_3$)

Example 31

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl] 2-[[3-(4-methyl-1-piperazinyl)propioriyl]oxymethyl]benzoate (Example Number 5A-19)

silica gel (50 g) column (eluent; ethyl acetate:methanol=4:1) to give a mixture of the title target compound and 4-(N,N-dimethylamino)pyridine. The mixture was subjected to chromatography on a silica gel (50 g) column (eluent; ethyl acetate:methanol=4:1) to afford the title target compound (576.1 mg, 47% yield) as a pale yellow amorphous solid.

NMR spectrum (400 MHz, CDCl$_3$) δ ppm: 1.46 (3H, dd, J=7, 2 Hz), 2.3-2.5 (4H, m), 2.28 (3H, s), 2.4-2.6 (4H, m), 2.61 (2H, t, J=7 Hz), 2.75 (2H, t, J=7 Hz), 3.05 (1H, tt, J=11, 5 Hz), 3.50 (1H, t, J=11 Hz), 3.53 (1H, t, J=11 Hz), 4.01 (1H, q, J=7 Hz), 4.04-4.20 (2H, m), 4.98 (1H, d, J=4 Hz), 5.43-5.56 (4H, m), 5.84 (1H, dd, J=15, 4 Hz), 6.57 (1H, dd, J=15, 11 Hz), 6.73 (1H, d, J=15 Hz), 6.88-7.00 (3H, m), 7.32-7.46 (4H, m), 7.52-7.61 (3H, m), 7.79 (1H, d, J=8 Hz), 7.90 (1H, s), 7.94 (1H, s)

IR spectrum ν max KBr cm$^{-1}$: 2230, 1729, 1615, 1503, 1275, 1257, 1140, 1051, 973

Mass spectrum m/z (ESI): 831 (M$^+$+1)

Specific rotation [α]$_D^{25}$ −1.4° (c=0.91, CHCl$_3$).

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]2-[[3-(4-methyl-1-piperazinyl)propionyl]oxymethyl]benzoate (288.9 mg, 0.35 mmol) obtained above in ethyl acetate (5 ml) was cooled to 0° C., and hydrogen chloride (4N ethyl acetate solution; 87 μl, 0.35 mmol) was added thereto, and the mixture was stirred at 0° C. for 5 minutes. The solvent was evaporated under reduced pressure, and the residue was

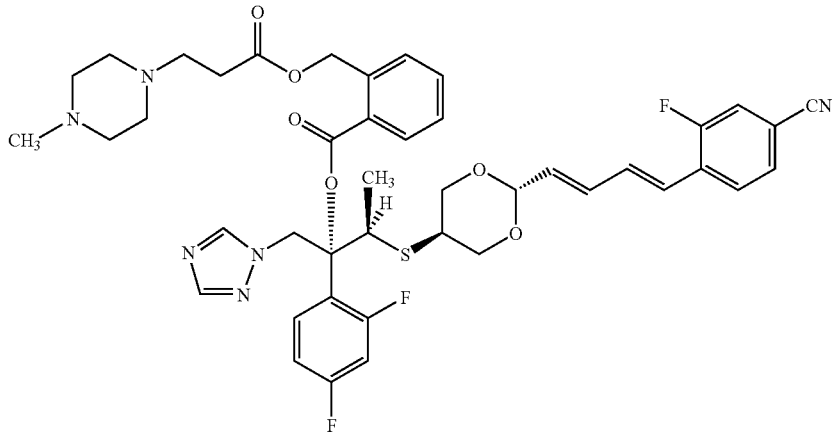

A solution of (1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propyl 2-(hydroxymethyl)benzoate (993.3 mg, 1.47 mmol) obtained from Example 17-(4) in dichloromethane (20 ml) was cooled to 0° C., and then 4-(N,N-dimethylamino) pyridine (358.7 mg, 2.94 mmol), 3-(4-methyl-1-piperazinyl) propionic acid (described in J. Med. Chem., 43, 1493 (2000); 454.8 mg, 2.64 mmol), and 1-ethyl-3-[3-(N,N-dimethylamino)propyl]carbodiimide (619.0 mg, 3.23 mmol) were added thereto. The reaction solution was stirred at room temperature for 2 hours and diluted with dichloromethane, and then the organic layer was washed successively with water and a saturated aqueous solution of sodium chloride. The solvent was evaporated under reduced pressure, and the residue was subjected to chromatography on a dried in vacuo to afford the mono hydrochloric acid salt of the title compound (289.5 mg, 95% yield) as a pale yellow amorphous solid.

NMR spectrum (400 MHz, CDCl$_3$) δ ppm: 1.47 (3H, dd, J=7, 2 Hz), 2.68 (6H, m), 2.90 (9H, m), 3.05 (1H, tt, J=11, 5 Hz), 3.51 (1H, t, J=11 Hz), 3.54 (1H, t, J=11 Hz), 4.03 (1H, q, J=7 Hz), 4.15 (1H, ddd, J=11, 5, 2 Hz), 4.19 (1H, ddd, J=11, 5, 2 Hz), 4.99 (1H, d, J=4 Hz), 5.44-5.57 (4H, m), 5.84 (1H, dd, J=16, 4 Hz), 6.57 (1H, dd, J=16, 11 Hz), 6.74 (1H, d, J=16 Hz), 6.89-6.95 (2H, m), 6.94 (1H, dd, J=16, 11 Hz), 7.34 (1H, dd, J=10, 1 Hz), 7.39-7.47 (3H, m), 7.55-7.62 (3H, m), 7.85 (1H, d, J=8 Hz), 7.89 (1H, s), 7.97 (1H, s)

IR spectrum ν max KBr cm$^{-1}$: 2230, 1729, 1614, 1503, 1273, 1257, 1139, 1050, 973

Mass spectrum m/z (ESI): 831 [M$^+$ (free base)+1]

Specific rotation [α]$_D^{25}$ −4.2° (c=1.08, CHCl$_3$).

A solution of (1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propyl]2-[[3-(4-methyl-1-piperazinyl)propionyl]oxymethyl]benzoate (260 mg, 0.31 mmol) obtained above in ethyl acetate (5 ml) was cooled to 0° C., and hydrogen chloride (4N ethyl acetate solution; 156 µl, 0.63 mmol) was added thereto, and the mixture was stirred at 0° C. for 5 minutes. The solvent was evaporated under reduced pressure, and the residue was dried in vacuo to afford the bis hydrochloric acid salt of the title compound (277 mg, 98% yield) as a pale yellow amorphous solid.

NMR spectrum (400 MHz, DMSO-$d_6$) δ ppm: 1.35 (3H, dd, J=7, 1 Hz), 2.76 (4H, m), 2.98 (1H, tt, J=11, 5 Hz), 3.38 (12H, br s-like), 3.43 (1H, t, J=11 Hz), 3.47 (1H, t, J=11 Hz), 3.80 (1H, q, J=7 Hz), 3.95 (1H, ddd, J=11, 5, 2 Hz), 4.08 (1H, ddd, J=11, 5, 2 Hz), 5.05 (1H, d, J=5 Hz), 5.37 (1H, d, J=15 Hz), 5.40 (1H, d, J=14 Hz), 5.46 (1H, d, J=14 Hz), 5.55 (1H, d, J=15 Hz), 5.88 (1H, dd, J=15, 5 Hz), 6.56 (1H, dd, J=15, 11 Hz), 6.82 (1H, d, J=16 Hz), 7.16-7.20 (1H, m), 7.19 (1H, dd, J=16, 11 Hz), 7.33-7.39 (1H, m), 7.50-7.59 (2H, m), 7.60 (1H, d, J=8 Hz), 7.67-7.71 (2H, m), 7.83-7.89 (3H, m), 7.96 (1H, s), 8.43 (1H, s)

IR spectrum ν max KBr $cm^{-1}$: 2230, 1729, 1615, 1503, 1273, 1257, 1139, 1050, 972

Mass spectrum m/z (ESI): 831 [M(free base)$^+$+1]

Specific rotation $[α]_D^{25}$ −5.3° (c=1.07, $CHCl_3$).

Example 32

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]2-[[4-(4-methyl-1-piperazinyl)butyryl]oxymethyl]benzoate (Example Number 5A-29)

The reaction solution was stirred at room temperature for 2 hours, diluted with dichloromethane, and then the organic layer was washed successively with water and a saturated aqueous solution of sodium chloride. The solvent was evaporated under reduced pressure, and the residue was subjected to chromatography on a silica gel (50 g) column (eluent; ethyl acetate:methanol=4:1) to give a mixture of the title target compound and 4-(N,N-dimethylamino)pyridine. The mixture was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title target compound (901.1 mg, 67% yield) as a colorless amorphous solid.

NMR spectrum (400 MHz, $CDCl_3$) δ ppm: 1.46 (3H, dd, J=7, 2 Hz), 1.85 (2H, quint., J=7 Hz), 2.27 (3H, s), 2.3-2.6 (8H, m), 2.37 (2H, t, J=7 Hz), 2.45 (2H, t, J=7 Hz), 3.05 (1H, tt, J=11, 5 Hz), 3.51 (1H, t, J=11 Hz), 3.53 (1H, t, J=11 Hz), 4.01 (1H, q, J=7 Hz), 4.10-4.20 (2H, m), 4.99 (1H, d, J=4 Hz), 5.30-5.56 (4H, m), 5.85 (1H, dd, J=15, 4 Hz), 6.57 (1H, dd, J=15, 10 Hz), 6.73 (1H, d, J=15 Hz), 6.88-7.00 (3H, m), 7.34 (1H, dd, J=10, 1 Hz), 7.37-7.46 (3H, m), 7.52-7.60 (3H, m), 7.79 (1H, d, J=8 Hz), 7.90 (1H, s), 7.95 (1H, s)

IR spectrum ν max KBr $cm^{-1}$: 2230, 1729, 1503, 1357, 1257, 1139, 1051, 973

Mass spectrum m/z (ESI): 845 ($M^+$+1)

Specific rotation $[α]_D^{25}$ −1.8° (c=1.06, $CHCl_3$).

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]2-[[4-(4-methyl-1-piperazinyl)butyryl]oxymethyl]benzoate (290.5 mg, 0.34 mmol) obtained above in ethyl acetate (5 ml) was cooled to 0° C., and hydrogen chloride (4N-ethyl acetate solution; 86 µl, 0.35 mmol) was added thereto, and

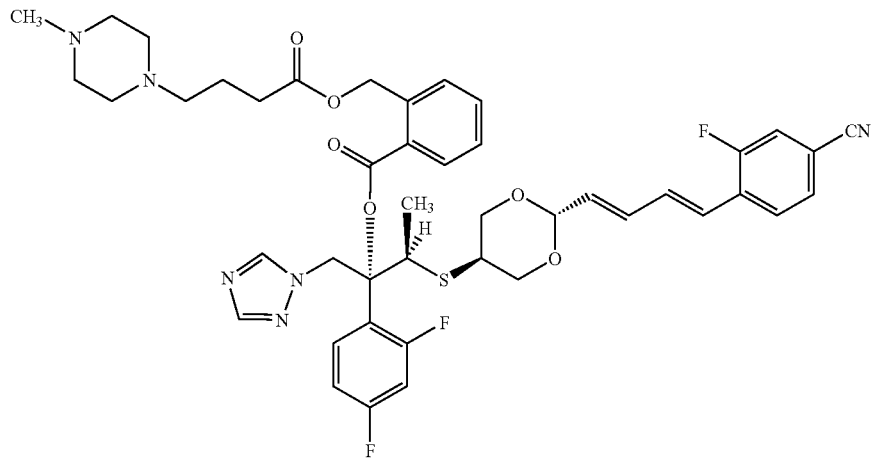

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (1.07 g, 1.58 mmol) obtained from Example 17-(4) in dichloromethane (20 ml) was cooled to 0° C., and 4-(N,N-dimethylamino)pyridine (386.1 mg, 3.16 mmol), 4-(4-methyl-1-piperazinyl)butanoic acid (described in J. Med. Chem., 43, 1493 (2000); 529.5 mg, 2.84 mmol), and 1-ethyl-3-[3-(N,N-dimethylamino)propyl] carbodiimide (666.8 mg, 3.48 mmol) were added thereto.

then the mixture was stirred at 0° C. for 5 minutes. The solvent was distilled off under reduced pressure to afford the mono hydrochloric acid salt of the title compound (305.1 mg, quantitative yield) as a pale yellow amorphous solid.

NMR spectrum (400 MHz, $CDCl_3$) δ ppm: 1.46 (3H, dd, J=7, 2 Hz), 1.90 (2H, m), 2.47 (2H, t, J=7 Hz), 2.6-2.8 (13H, m), 3.05 (1H, tt, J=11, 5 Hz), 3.51 (1H, t, J=11 Hz), 3.53 (1H, t, J=11 Hz), 4.01 (1H, q, J=7 Hz), 4.10-4.15 (1H, m), 4.18 (1H, ddd, J=11, 5, 2 Hz), 4.99 (1H, d, J=4 Hz), 5.44 (1H, d, J=14 Hz), 5.46-5.53 (2H, m), 5.55 (1H, d, J=15 Hz), 5.85 (1H, dd, J=15, 4 Hz), 6.57 (1H, dd, J=15, 11 Hz), 6.74 (1H, d, J=15 Hz), 6.89-6.93 (2H, m), 6.94 (1H, dd, J=15, 11 Hz), 7.34 (1H, dd, J=10, 1 Hz), 7.40-7.47 (3H, m), 7.54-7.62 (3H, m), 7.84 (1H, d, J=7 Hz), 7.89 (1H, s), 7.97 (1H, s)

IR spectrum ν max KBr cm$^{-1}$: 2230, 1729, 1503, 1274, 1256, 1139, 1051, 973

Mass spectrum m/z (ESI): 845 [M(free base)$^+$+1]

Specific rotation $[α]_D^{25}$ −4.50 (c=0.89, CHCl$_3$).

Example 33

(1R, 2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]5-cyano-2-(hydroxymethyl)benzoate (example number 5A-75)

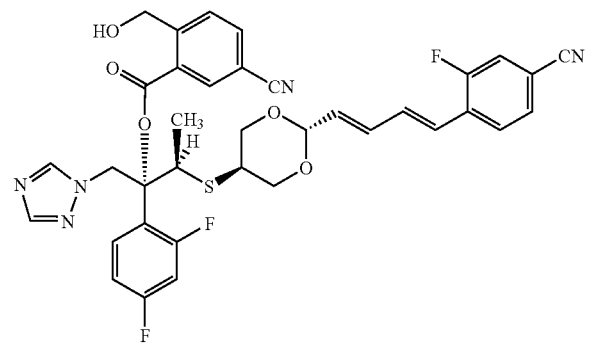

(1) 4-Methoxybenzyl 2-[(allyloxycarbonyl)oxymethyl]-5-cyanobenzoate

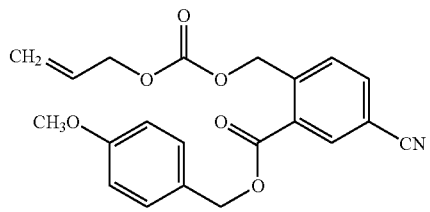

1-Oxo-1,3-dihydroisobenzofuran-6-carbonitrile (3.01 g, 18.9 mmol) obtained from Example 5-(2) was dissolved in a mixed solvent (200 ml) of tetrahydrofuran-methanol (3:1), and an aqueous solution of sodium hydroxide (1.004N; 17.4 ml, 17.4 mmol) was added thereto over a period of 10 minutes. The mixture was stirred at room temperature for 30 minutes, and the solvent was distilled off under reduced pressure. The resulting residue was dried using a vacuum pump. The obtained solid was dissolved in N,N-dimethylformamide (40 ml), and 4-methoxybenzyl chloride (2.96 g, 18.9 mmol) was added thereto. The mixture was heated at 70-80° C. for 1 hour. After cooling the mixture to 0° C., dichloromethane (40 ml) was added thereto, and 4-(N,N-dimethylamino)pyridine (5.78 g, 47.3 mmol) and allyl chloroformate (4.56 g, 37.9 mmol) were added thereto, then the mixture was stirred at the same temperature for 30 minutes. The mixture was diluted with ethyl acetate and then washed successively with water and an aqueous solution of sodium chloride. The resulting mixture was dried over anhydrous magnesium sulfate, and the solvent was distilled off under reduced pressure to give an oily residue. The residue was subjected to chromatography on a silica gel (100 g) column (eluent; hexane:ethyl acetate=3:1) to afford the title compound (3.11 g, 43% yield) as a colorless oil.

NMR spectrum (400 MHz, CDCl$_3$) δ ppm: 3.83 (3H, s), 4.67 (2H, br d, J=6 Hz), 5.31 (2H, s), 5.31 (1H, d, J=10 Hz), 5.39 (1H, dd, J=17, 1 Hz)., 5.66 (2H, s), 5.96 (1H, ddt, J=17, 10, 6 Hz), 6.93 (2H, d, J=9 Hz), 7.39 (2H, d, J=9 Hz), 7.70 (1H, d, J=8 Hz), 7.81 (1H, dd, J=8, 1 Hz), 8.30 (1H, d, J=1 Hz)

IR spectrum ν max CHCl$_3$ cm$^{-1}$: 2236, 1725, 1296, 1256

Mass spectrum m/z (FAB): 381 (M$^+$).

(2) 2-[(Allyloxycarbonyl)oxymethyl]-5-cyanobenzoic acid

A mixture of 4-methoxybenzyl 2-[(allyloxycarbonyl)oxymethyl]-5-cyanobenzoate (3 g, 7.9 mmol) and anisole (3.5 g) was cooled to 0° C., and trifluoroacetic acid (10 ml) was added thereto. The mixture was stirred at room temperature for 15 minutes, diluted with toluene, and the solvent was distilled off under reduced pressure. The residue was subjected to chromatography on a silica gel (35 g) column (eluent; dichloromethane:ethyl acetate=1:1) to afford the title compound (1.95 g, 95% yield) as a colorless solid (mp. 81-83° C.)

NMR spectrum (400 MHz, CDCl$_3$) δ ppm: 4.70 (2H, dt, J=6, 1 Hz), 5.32 (1H, dd, J=10, 1 Hz), 5.41 (1H, dd, J=17, 1 Hz), 5.71 (2H, s), 5.97 (1H, ddt, J=17, 10, 6 Hz), 7.89 (1H, d, J=8 Hz), 7.90 (1H, dd, J=8, 1 Hz), 8.44 (1H, d, J=1 Hz)

IR spectrum ν max KBr cm$^{-1}$: 2236, 1754, 1700, 1278, 1251

Mass spectrum m/z (FAB): 262 (M$^+$+1).

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]2-[(allyloxycarbonyl)oxymethyl]-5-cyanobenzoate 2-[(Allyloxycarbonyl)oxymethyl]-5-cyanobenzoic acid (1.6 g, 6.12 mmol) obtained from Example 33-(2) was dissolved in dichloromethane (40 ml), and N,N-dimethylformamide (0.05 ml) and oxalyl chloride (2 g) were added thereto. The mixture was stirred at room temperature for 1 hour, then diluted with toluene, and the solvent was distilled off under reduced pressure to give crude 2-[(allyloxycarbonyl)oxymethyl]-5-cyanobenzoyl chloride.

A reaction was carried out according to a similar procedure to that described in Example 13-(2) using 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2- yl]-1,3-butadienyl]-3-fluorobenzonitrile (2.56 g, 4.7 mmol) described in Reference example 1, sodium hydride (55% dispersion in mineral oil; 246.7 mg, 5.65 mmol), and 2-[(allyloxycarbonyl)oxymethyl]-5-cyanobenzoyl chloride obtained above. The obtained crude product was subjected to chromatography on a silica gel (50 g) column (eluent; ethyl acetate:hexane=1:1~4:1) to give a mixture (2.67 g) of the title compound and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (starting material). The proportion of the title compound was ca. 80%.

NMR spectrum (400 MHz, CDCl$_3$, selected signals related to the target compound) δ ppm: 1.45 (3H, dd, J=7, 2 Hz), 3.02 (1H, tt, J=11, 5 Hz), 3.54 (1H, t, J=11 Hz), 4.00 (1H, q, J=7 Hz), 4.10-4.19 (2H, m), 4.67 (2H, m), 5.01 (1H, d, J=4 Hz), 5.31 (1H, br d, J=10 Hz), 5.29 (1H, dd, J=17, 1 Hz), 5.49 (2H, s), 5.55 (1H, d, J=14 Hz), 5.62 (1H, d, J=14 Hz), 5.87 (1H, dd, J=15, 4 Hz), 5.95 (1H, ddt, J=17, 10, 6 Hz), 6.58 (1H, d, J=15, 11 Hz), 6.73 (1H, d, J=15 Hz), 6.90-6.96 (3H, m), 7.32-7.60 (3H, m), 7.77 (1H, t, J=9 Hz), 7.87 (1H, dd, J=8, 2 Hz), 7.90 (1H, s), 7.98 (1H, s), 8.18 (1H, d, J=1 Hz)

Mass spectrum m/z (FAB): 786 (M$^+$+1).

(4) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]5-cyano-2-(hydroxymethyl)benzoate (title target compound)

A similar procedure to that described in Example 11-(4) was carried out using a mixture (583.2 mg, component ratio ca. 8:2) of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]2-[[allyloxycarbonyl)oxymethyl]-5-cyanobenzoate and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile obtained from Example 33-(3), bis(triphenylphosphine)dichloropalladium (13 mg), and tributyltin hydride (184 mg, 0.63 mmol). The crude product was subjected to chromatography on a silica gel (50 g) column (eluent; ethyl acetate: hexane=1:1~4:0) to afford the title target compound (293.6 mg, 56% yield) as a colorless amorphous solid.

NMR spectrum (400 MHz, CDCl$_3$) δ ppm: 1.46 (3H, dd, J=7, 2 Hz), 3.03 (1H, tt, J=12, 5 Hz), 3.09 (1H, t, J=7 Hz), 3.55 (2H, t, J=12 Hz), 4.02 (1H, q, J=7 Hz), 4.14-4.21 (2H, m), 4.91 (2H, t, J=7 Hz), 5.01 (1H, d, J=5 Hz), 5.50 (1H, d, J=14 Hz), 5.51 (1H, d, J=14 Hz), 5.86 (1H, dd, J=15, 5 Hz), 6.58 (1H, dd, J=15, 11 Hz), 6.73 (1H, d, J=16 Hz), 6.90-6.97 (3H, m), 7.33 (1H, dd, J=7, 1 Hz), 7.37 (1H, td, J=9, 6 Hz), 7.57 (1H, t, J=8 Hz), 7.77 (1H, d, J=8 Hz), 7.86-7.88 (2H, m), 7.96 (1H, s), 8.18 (1H, s)

IR spectrum ν max KBr cm$^{-1}$: 2232, 1730, 1504, 1276, 1142, 1049

Mass spectrum m/z (FAB): 702 (M$^+$+1).

Specific rotation [α]$_D^{25}$ −21.9° (c=0.98, CHCl$_3$).

Example 34

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(4-methyl-1-piperazinyl)acetoxy] ethyl carbonate (example number 4A-13)

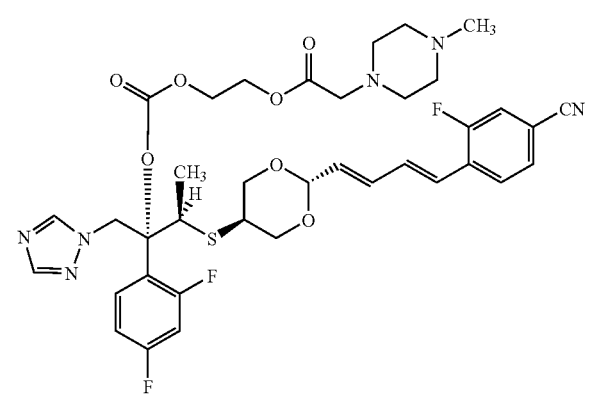

(1) 2-Chloroethyl (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl carbonate

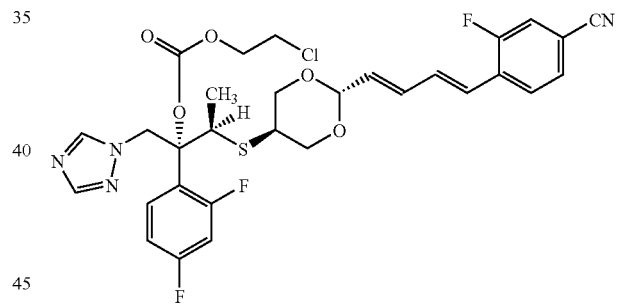

A mixture of potassium hydride (30% dispersion in mineral oil; 739 mg, 5.53 mmol) and tetrahydrofuran (8 ml) was cooled to 0° C., and 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (1.00 g, 1.84 mmol) described in Reference example 1 was added thereto with stirring, then the mixture was stirred at room temperature for 30 minutes. The mixture was cooled to 0° C., and then a mixture of 2-chloroethyl chloroformate (315 mg, 2.21 mmol) and tetrahydrofuran (1.5 ml) was added thereto with stirring. The resulting mixture was stirred at room temperature for 18 hours. After cooling, the mixture was partitioned between ethyl acetate and water, and the organic layer was washed successively with water and a saturated aqueous solution of sodium chloride, and the solvent was distilled off under reduced pressure to give an oily residue. The residue was subjected to column chromatography (eluent; ethyl acetate:hexane=1:1) to afford the title compound (1.06 g, 88% yield) as a colorless oil.

NMR spectrum (400 MHz, CDCl$_3$) δ ppm: 1.35 (3H, dd, J=7, 2 Hz), 3.04 (1H, m), 3.50 (1H, t, J=11 Hz), 3.51 (1H, t, J=11 Hz), 3.73 (2H, t, J=6 Hz), 3.88 (1H, q, J=7 Hz), 4.19 (1H, ddd, J=11, 4, 2 Hz), 4.32 (1H, ddd, J=11, 4, 2 Hz), 4.33-4.81 (2H, m), 4.98 (1H, d, J=5 Hz), 5.36 (1H, d, J=15 Hz), 5.40 (1H, d, J=15 Hz), 5.86 (1H, dd, J=15, 4 Hz), 6.58 (1H, dd, J=15, 11 Hz), 6.72 (1H, d, J=15 Hz), 6.76-6.96 (3H, m), 7.33 (1H, dd, J=11, 2 Hz), 7.39 (1H, d, J=8 Hz), 7.44-7.50 (1H, m), 7.57 (1H, t, J=8 Hz), 7.95 (1H, s), 7.97 (1H, s)

Mass spectrum m/z (FAB): 649 (M$^+$+1).

High resolution mass spectrum m/z (FAB; addition of an aqueous solution of sodium iodide): Calculated for C$_{30}$H$_{28}$O$_5$N$_4$ClF$_3$SNa (M$^+$+Na): 671.1318. Found: 671.1329.

(2) Cesium 2-(4-methyl-1-piperazinyl)acetate

A solution of 2-(4-methyl-1-piperazinyl)acetic acid (described in J. Med. Chem., 43, 1493 (2000); 2.5 g, 16 mmol) in water (30 ml) was cooled to 0° C., and cesium carbonate (2.6 g, 7.9 mmol) was added thereto with stirring, then the mixture was stirred at room temperature for 1 hour. The mixture was concentrated under reduced pressure to give the title compound (4.49 g, 98% yield) as a pale yellow solid.

(3) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[(4-methyl-1-piperazinyl)acetoxy] ethyl carbonate (title target compound)

A solution of cesium 2-(4-methyl-1-piperazinyl)acetate (939 mg, 6.0 mmol) obtained from Example 34-(2) in N,N-dimethylformamide (5 ml) was cooled to 0° C., and a solution of 2-chloroethyl(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl]carbonate (700 mg, 1.1 mmol) obtained from 34-(1) in N,N-dimethylformamide (5 ml) and 18-crown-6 (910 mg, 3.2 mmol) were added thereto with stirring. The mixture was stirred at room temperature for 1 hour, and then warmed to 40° C. and stirred for 3 hours. According to a similar procedure to that described in Example 34-(1), the reaction mixture was worked up to afford an oily residue. The residue was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title compound (568 mg, 68% yield) as a pale yellow oil.

NMR spectrum (400 MHz, CDCl$_3$) δ ppm: 1.34 (3H, dd, J=7, 2 Hz), 2.28 (3H, s), 2.48 (4H, bs), 2.61 (4H, bs), 3.02 (1H, m), 3.24 (1H, d, J=16 Hz), 3.27 (1H, d, J=16 Hz), 3.48 (1H, t, J=11 Hz), 3.49 (1H, t, J=11 Hz), 3.85 (1H, q, J=7 Hz), 4.17 (1H, ddd, J=11, 5, 2 Hz), 4.27-4.44 (5H, m), 4.97 (1H, d, J=5 Hz), 5.36 (1H, d, J=15 Hz), 5.39 (1H, d, J=15 Hz), 5.84 (1H, dd, J=15, 4 Hz), 6.57 (1H, dd, J=16, 11 Hz), 6.74 (1H, d, J=17 Hz), 6.86-7.00 (3H, m), 7.33 (1H, dd, J=10, 2 Hz), 7.39-7.48 (2H, m), 7.57 (1H, t, J=7 Hz), 7.95 (1H, s), 7.99 (1H, s)

Mass spectrum m/z (FAB): 771 (M$^+$+1)

High resolution mass spectrum m/z (FAB): Calculated for C$_{37}$H$_{42}$O$_7$N$_6$F$_3$S (M$^+$+1): 771.2788. Found: 771.2751.

The compound (565 mg, 0.73 mmol) obtained above was dissolved in ethyl acetate (12 ml), and the solution was cooled to 0° C., then hydrogen chloride (4N ethyl acetate solution; 183 μl, 0.73 mmol) was added thereto with stirring. The solvent was distilled off under reduced pressure to give an oily residue. The residue was dissolved in water (18 ml) at 0° C., and the solution was lyophilized to afford the hydrochloric acid salt of the title target compound (590 mg, 92% yield) as a pale yellow solid.

NMR spectrum (400 MHz, DMSO-d$_6$) δ ppm: 1.24 (3H, d, J=7 Hz), 2.25-3.20 (11H, m), 2.91 (1H, m), 3.28-3.36 (2H, m), 3.42 (1H, t, J=11 Hz), 3.44 (1H, t, J=11 Hz), 3.57 (1H, q, J=7 Hz), 4.04 (1H, ddd, J=11, 5, 2 Hz), 4.13 (1H, ddd, J=11, 5, 2 Hz), 4.28 (2H, t, J=3 Hz), 4.35 (2H, t, J=3 Hz), 5.03 (1H, d, J=4 Hz), 5.27 (1H, d, J=14 Hz), 5.45 (1H, d, J=14 Hz), 5.87 (1H, dd, J=15, 4 Hz), 6.57 (1H, dd, J=15, 10 Hz), 6.82 (1H, d, J=16 Hz), 7.16-7.22 (2H, m), 7.33 (1H, ddd, J=13, 6, 2 Hz), 7.45-7.51 (1H, m), 7.68 (1H, dd, J=8, 2 Hz), 7.84-7.90 (2H, m), 8.05 (1H, s), 8.45 (1H, s), 9.71 (1H, bs)

IR spectrum ν max KBr cm$^{-1}$: 2230, 1751, 1615, 1504

Mass spectrum m/z (FAB): 771 (M$^+$+1).

Example 35

Disodium [4-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-furyl]methyl phosphate (disodium salt of example number 5C-18)

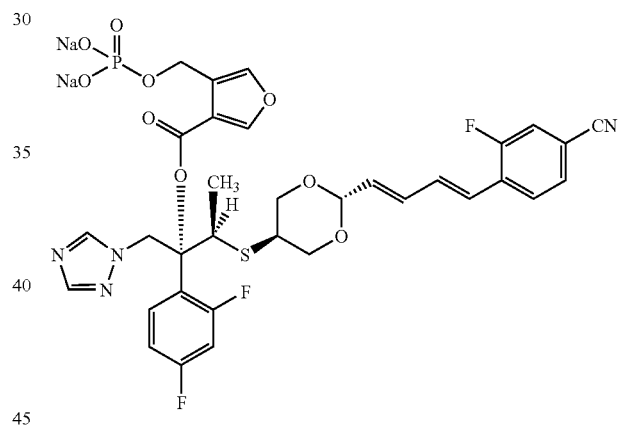

(1) [4-[(tert-Butyldimethylsilyl)oxymethyl]3-furyl]methanol

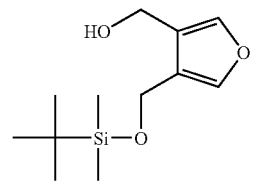

According to a similar procedure to that described in Example 21-(2), 3,4-furandimethanol (described in J. Org. Chem., 65, 6153 (2000); 3.4 g, 26.5 mmol) was reacted with imidazole (1.80 g, 26.4 mmol) and tert-butylchlorodimethylsilane (4.00 g, 26.5 mmol) in tetrahydrofuran (50 ml), and the reaction mixture was worked up to afford a mixture of the title compound, 3,4-furandimethanol and 3,4-bis[(tert-butyldimethylsilyl)oxymethyl]furan. The mixture was subjected to chromatography on a silica gel (50 g) column (eluent; ethyl acetate:hexane=3:17~4:16) to afford the title compound (3.20 g, 50% yield) as a colorless oil.

NMR spectrum (400 MHz, CDCl₃) δ ppm: 0.125 (6H, s), 0.916 (9H, s), 3.177 (1H, t, J=6 Hz), 4.522 (2H, d, J=6 Hz), 4.640 (2H, s), 7.317 (1H, s), 7.371 (1H, s)

IR spectrum ν max CHCl₃ cm⁻¹: 3449, 2956, 2931, 2859, 1471, 1258, 1040

Mass spectrum m/z (FAB): 243 (M⁺+1).

(2) Diallyl [4-[(tert-butyldimethylsilyl)oxymethyl]-3-furyl]methyl phosphate

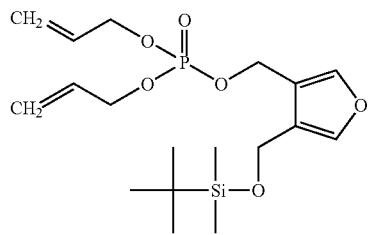

[4-[(tert-Butyldimethylsilyl)oxymethyl]-3-furyl]methanol (174 mg, 0.72 mmol) obtained from Example 35-(1) was reacted in dichloromethane (3 ml) with tetrazole (61 mg, 0.87 mmol), bis(allyloxy)(diisopropylamino)phosphine (265 mg, 1.08 mmol), and tert-butyl hydroperoxide (80% di-tert-butyl peroxide solution; Merck; 135 mg, 1.2 mmol) according to a similar procedure to that described in Example 1-(10). The oily residue obtained by extraction was subjected to chromatography on a silica gel (5 g) column (eluent; ethyl acetate:hexane=1:4) to afford the title compound (273 mg, 93% yield) as a colorless oil.

NMR spectrum (400 MHz, CDCl₃) δ ppm: 0.083 (6H, s), 0.908 (9H, s), 4.55-4.55 (4H, m), 4.627 (2H, s), 5.003 (2H, d, J=8, 2 Hz), 5.328 (2H, dd, J=10.4, 1.2 Hz), 5.340 (1H, dddd, J=17, 1.5, 1.5, 1.2 Hz), 5.912 (2H, ddt, J=17, 10, 5 Hz), 7.328 (1H, s), 7.447 (1H, s)

IR spectrum ν max CHCl₃ cm⁻¹: 2956, 2931, 1258, 1010

Mass spectrum m/z (FAB): 403 (M⁺+1).

(3) Diallyl [4[(hydroxymethyl)-3-furyl]methyl phospate

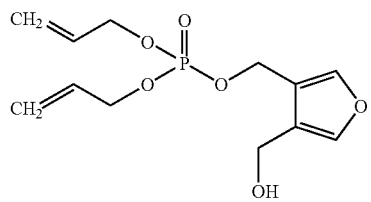

Diallyl [4-[(tert-butyldimethylsilyl)oxymethyl]-3-furyl] methyl phosphate obtained from Example 35-(2) was dissolved in tetrahydrofuran (3 ml), and a mixture of tetrabutylammonium fluoride (1N tetrahydrofuran solution; 1.34 ml, 1.34 mmol) and acetic acid (48 mg, 0.80 mmol) was added thereto with stirring in an ice bath. The reaction mixture was stirred at room temperature for 2 hours, and then partitioned between ethyl acetate and an aqueous solution of sodium hydrogen carbonate. The organic layer was washed with a saturated aqueous solution of sodium chloride, dried over anhydrous magnesium sulfate, and the solvent was distilled off under reduced pressure to give a residue. The residue was subjected to chromatography on a silica gel (5 g) column (eluent; ethyl acetate:hexane=3:2~1:0) to afford the title compound (148 mg, 76% yield) as a colorless oil.

NMR spectrum (400 MHz, CDCl₃) δ ppm: 3.168 (1H, t-like, J=ca. 6 Hz), 4.523 (4H, td, J=7, 1.2 Hz), 4.580 (2H, d, J=6 Hz), 5.050 (2H, d, J=9.5 Hz), 5.255 (2H, dd-like, J=10, ca. 1.2 Hz), 5.350 (2H, dt-like, J=17, ca. 1.2 Hz), 5.917 (2H, ddt, J=17, 10, 6 Hz), 7.414 (1H, s), 7.483 (1H, s)

IR spectrum ν max CHCl₃ cm⁻¹: 3401, 1602, 1554, 1462, 1424, 1267, 1022

Mass spectrum m/z (FAB): 289 (M⁺+1).

(4) Diallyl (4-formyl-3-furyl)methyl phosphate

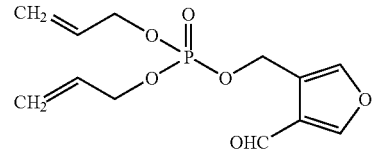

Diallyl [4-[(hydroxymethyl)-3-furyl]methyl phosphate (113 mg, 0.39 mmol) obtained from Example 35-(3) was dissolved in dichloromethane (2 ml), and activated manganese dioxide (0.52 g, 6.0 mmol) was added thereto with ice cooling, then the mixture was stirred at room temperature for 8 hours. The resulting mixture was allowed to stand overnight (14 hours), and then activated manganese dioxide (40 mg, 0.46 mmol) was further added thereto. The mixture was stirred at room temperature for 1.5 hours, diluted with ethyl acetate, and filtered with suction to remove solids. The filtrate was concentrated under reduced pressure, and the obtained residue was subjected to chromatography on a silica gel (3 g) column (eluent; ethyl acetate:hexane=3:2~1:0) to afford the title compound (101 mg, 90% yield) as a colorless oil.

NMR spectrum (400 MHz, CDCl₃) δ ppm: 4.569 (4H, dd-like, J=7, 6 Hz), 5.245 (2H, dd-like, J=6, 1 Hz), 5.259 (2H, dd-like, J=11, 1 Hz), 5.369 (2H, dd-like, J=17, 1 Hz), 5.943 (2H, d, J=17, 11, 6 Hz), 7.569 (1H, br s), 8.046 (1H, d, J=1.6 Hz), 9.971 (1H, s)

IR spectrum ν max CHCl₃ cm⁻¹: 1689, 1544, 1273, 1147, 1027

Mass spectrum m/z (EI): 287 (M⁺+1).

(5) 4-[[Bis(allyloxy) phosphoryl]oxymethyl]furoic acid

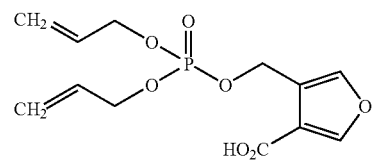

Diallyl (4-formyl-3-furyl)methyl phosphate (97 mg, 0.34 mmol) obtained from Example 35-(4) and 2-methyl-2-butene (1.18 g, 19.9 mmol) were dissolved in tert-butyl alcohol (2.70 ml), and then a solution of sodium chlorite (122 mg, 1.35 mmol) and sodium dihydrogen phosphate dihydrate (1.034 g, 6.76 mmol) dissolved in water (1.2 ml) was added thereto with stirring in an ice bath. The mixture was stirred for 2 hours while warming spontaneously to room temperature, and partitioned between ethyl acetate and an aqueous solution of sodium chloride, then the organic layer was dried over anhydrous magnesium sulfate and the solvent was distilled off under reduced pressure. The residue was subjected to chromatography on a silica gel (2 g) column (eluent; ethyl acetate) to afford the title compound (74 mg, 72% yield) as a colorless oil.

NMR spectrum (400 MHz, CDCl$_3$) δ ppm: 4.572 (4H, dd-like, J=7, 6 Hz), 5.25 (4H, d-like, J=9 Hz), 5.367 (2H, dd-like, J=17, 1.4 Hz), 5.940 (2H, ddt, J=17, 10, 6 Hz), 7.533 (1H, d, J=ca. 1.4 Hz), 8.059 (1H, d, J=ca. 1.7 Hz)

IR spectrum ν max CHCl$_3$ cm$^{-1}$: 1736, 1697, 1549, 1269, 1149, 1029

Mass spectrum m/z (EI): 303 (M$^+$+1).

(6) (1R,2R)-2-[[trans-2-[(1E,3E)-4-(4-Cyano-2-fluorophenyl)-1,3-butadienyl]1,3-dioxan-5-yl]thio]1-(2,4-difluorophenyl)-1-[(1H-1,2,4-triazol-1-yl)methyl]propyl 4-[[bis(allyloxy)phosphoryl]oxymethyl]-3-furoate

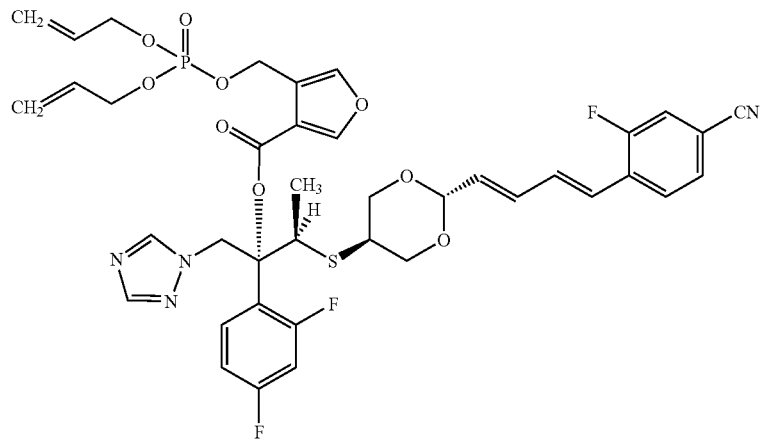

4-[[Bis(allyloxy)phosphoryl]oxymethyl]-3-furoic acid (500 mg, 1.65 mmol) obtained from Example 35-(5) was dissolved in dichloromethane (10 ml), and N,N-dimethylformamide (0.03 ml) and oxalyl chloride (0.7 g, 5.5 mmol) were added thereto. The mixture was stirred at room temperature for 1 hour, and toluene was added thereto, then the solvent was distilled off under reduced pressure to give crude 4-[[bis(allyloxy)phosphoryl]oxymethyl]-3-furoyl chloride.

According to a similar procedure to that described in Example 13-(2), 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (690.5 mg, 1.27 mmol) described in Reference example 1, sodium hydride (55% dispersion in mineral oil; 66.5 mg, 1.52 mmol), and crude 4-[[bis(allyloxy)phosphoryl]oxymethyl]-3-furoyl chloride were reacted, and the reaction mixture was worked up to afford, after extraction, the title compound as a crude oil. The crude product was subjected to chromatography on a silica gel (30 g) column (eluent; ethyl acetate:hexane=2:1~9:1) to afford the title compound (740.8 mg, 70% yield) as a colorless amorphous solid.

NMR spectrum (400 MHz, CDCl$_3$) δ ppm: 1.43 (3H, dd, J=7, 2 Hz), 3.05 (1H, tt, J=11, 5 Hz), 3.53 (2H, t, J=11 Hz), 3.96 (1H, q, J=7 Hz), 4.14-4.22 (2H, m), 4.53 (4H, br t, J=7 Hz), 5.01 (1H, d, J=5 Hz), 5.10-5.18 (2H, m), 5.25 (2H, d, J=10 Hz), 5.35 (2H, dd, J=17, 1 Hz), 5.40 (1H, dd, J=15, 3 Hz), 5.47 (1H, d, J=15 Hz), 5.85 (1H, dd, J=15, 5 Hz), 5.92 (2H, ddt, J=17, 10, 5 Hz), 6.58 (1H, dd, J=15, 11 Hz), 6.74 (1H, d, J=16 Hz), 6.88-6.93 (2H, m), 6.93 (1H, dd, J=16, 11 Hz), 7.32-7.37 (2H, m), 7.40 (1H, dd, J=8, 1 Hz), 7.56-7.59 (2H, m), 7.89 (1H, s), 7.92 (2H, s)

IR spectrum ν max KBr cm$^{-1}$: 2230, 1727, 1615, 1504, 1276, 1258, 1143, 1051, 1021, 973

Mass spectrum m/z (FAB): 827 (M$^+$+1).

(7) Disodium [4-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-furyl] methyl phosphate (title target compound)

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[[bis(allyloxy)phosphoryl]oxymethyl]-3-furoate (740 mg, 0.895 mmol) obtained from Example 35-(6) was dissolved in dichloromethane (20 ml), and, while stirring, tetrakis(triphenylphosphine)palladium (31 mg, 0.027 mmol) and pyrrolidine (1.27 g, 17.9 mmol) were added thereto at 0° C. under an atmosphere of nitrogen gas. The mixture was warmed to room temperature, stirred for 1 hour, diluted with toluene, and the solvent was distilled off under reduced pressure. The residue was subjected to reverse phase column chromatography using Cosmosil 75 C$_{18}$-PREP (Nacalai Tesque, Inc.; 30 g) (eluent; water:acetonitrile=3:1~7:3). The obtained fractions were concentrated, and the residue was subjected to a cation exchange resin (Dowex 50W-8X, Na type preparated using 1N aqueous solution of sodium hydroxide; 5 ml) (eluent; water). The collected fractions were concentrated under reduced pressure and lyophilized to afford the title target compound (618.5 mg, 87% yield) as an amorphous colorless solid.

NMR spectrum (400 MHz, CD$_3$OD) δ ppm: 1.38 (3H, dd, J=7, 2 Hz), 3.07 (1H, tt, J=11, 5 Hz), 3.54 (1H, t, J=11 Hz), 3.55 (1H, t, J=11 Hz), 4.00 (1H, q, J=7 Hz), 4.16 (2H, dd, J=11, 5 Hz), 4.98 (1H, ddd, J=15, 6, 1 Hz), 5.03 (1H, ddd, J=15, 6, 1 Hz), 5.05 (1H, d, J=4 Hz), 5.51 (2H, s), 5.88 (1H, dd, J=15, 4 Hz), 6.59 (1H, dd, J=15, 11 Hz), 6.79 (1H, d, J=15 Hz), 6.97-7.06 (2H, m), 7.01 (1H, dd, J=15, 11 Hz), 7.48-7.54 (3H, m), 7.69 (1H, q, J=2 Hz), 7.78 (1H, t, J=8 Hz), 7.92 (1H, s), 7.99 (1H, d, J=1 Hz), 8.27 (1H, s)

IR spectrum ν max KBr cm$^{-1}$: 2231, 1726, 1615, 1503, 1143, 1101, 1052, 975

Mass spectrum m/z (ESI): 745 [M(non sodium part)+1]$^-$.

Example 36

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(4-methyl-1-piperazinyl)-4-oxobutyryl]oxymethyl]benzoate (example number 5A-20)

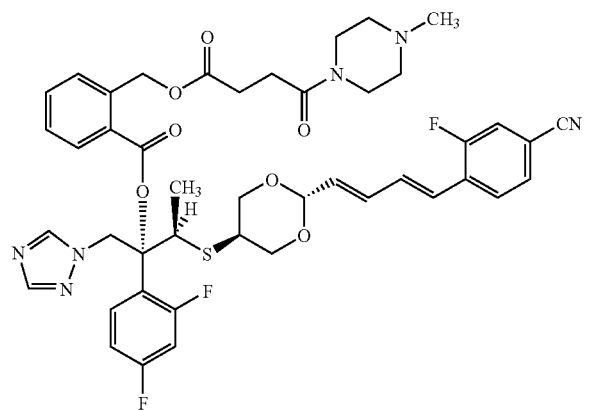

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(hydroxymethyl)benzoate (1.11 g, 1.64 mmol) obtained from Example 17 in dichloromethane (20 ml) was cooled to 0° C., and then 4-(N,N-dimethylamino)pyridine (400.7 mg, 3.28 mmol), 4-(4-methyl-1-piperazinyl)-4-oxobutanoic acid (described in Bioorg. Med. Chem., 8, 2693 (2000); 590.4 mg, 2.95 mmol), and 1-ethyl-3-(3-dimethylaminopropyl) carbodiimide hydrochloride (691.8 mg, 3.61 mmol) were added thereto. The reaction mixture was stirred at room temperature for 1 hour, diluted with dichloromethane, and the organic layer was washed successively with water and a saturated aqueous solution of sodium chloride, and then the solvent was distilled off under reduced pressure. The residue was subjected to chromatography on a silica gel (25 g) column (eluent; ethyl acetate:methanol=4:1) to give a mixture (ca. 1.4 g) of the title target compound and 4-(N,N-dimethylamino)pyridine. A part (0.95 g) of the mixture was purified by recycle preparative HPLC [LC-908; Japan Analytical Industry Co., Ltd.; GPC column JAIGEL-1H (20 mm i.d.×600 mm) and JAIGEL-2H (20 mm i.d.×600 mm) connected in series for use; solvent, chloroform] to afford the title target compound (796.0 mg, 55% yield) as a colorless amorphous solid.

NMR spectrum (400 MHz, CDCl$_3$) δ ppm: 1.46 (3H, dd, J=7, 2 Hz), 2.31 (3H, s), 2.36 (2H, t, J=5 Hz), 2.40 (2H, t, J=5 Hz), 2.65-2.68 (2H, m), 2.76-2.78 (2H, m), 3.05 (1H, tt, J=11, 5, Hz), 3.48-3.56 (4H, m), 3.63 (2H, t, J=5 Hz), 4.01 (1H, q, J=7 Hz), 4.15 (1H, ddd, J=11, 5, 2 Hz), 4.18 (1H, ddd, J=11, 5, 2, Hz), 4.99 (1H, d, J=4 Hz), 5.46 (1H, d, J=15 Hz), 5.47 (1H, dd, J=15, 3 Hz), 5.54 (1H, d, J=15 Hz), 5.55 (1H, d, J=15 Hz), 5.85 (1H, dd, J=15, 4 Hz), 6.57 (1H, dd, J=15, 11 Hz), 6.73 (1H, d, J=16 Hz), 6.88-6.93 (2H, m), 6.93 (1H, dd, J=16, 11 Hz), 7.34 (1H, dd, J=10, 1 Hz), 7.36-7.45 (3H, m), 7.56 (1H, d, J=8 Hz), 7.57-7.60 (2H, m), 7.79 (1H, d, J=8 Hz), 7.90 (1H, s), 7.97 (1H, s)

IR spectrum ν max KBr cm$^{-1}$: 2230, 1729, 1645, 1503, 1274, 1257, 1141, 1051

Mass spectrum m/z (FAB): 859 (M$^+$+1)

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(4-methyl-1-piperazinyl)-4-oxobutyryl]oxymethyl] benzoate (288.6 mg, 0.34 mmol) obtained above in ethyl acetate (5 ml) was cooled to 0° C., and hydrogen chloride (4 mol/l ethyl acetate solution; 74 μl, 0.30 mmol) was added thereto followed by stirring at 0° C. for 5 minutes. The solvent was evaporated under reduced pressure, and the residue was dried in vacuo to afford the mono hydrochloric acid salt of the title compound (296.6 mg, 99% yield) as a pale yellow amorphous solid.

NMR spectrum (400 MHz, CDCl$_3$) δ ppm: 1.46 (3H, dd, J=7, 2 Hz), 2.6-3.1 (13H, m), 3.05 (1H, tt, J=11, 5 Hz), 3.51 (1H, t, J=11 Hz), 3.53 (1H, t, J=11 Hz), 3.9-4.0 (2H, m), 4.00 (1H, q, J=7 Hz), 4.14-4.21 (2H, m), 4.99 (1H, d, J=4 Hz), 5.41 (1H, d, J=14 Hz), 5.48 (1H, dd, J=15, 3 Hz), 5.55 (1H, d, J=15 Hz), 5.57 (1H, d, J=14 Hz), 5.84 (1H, dd, J=16, 4 Hz), 6.57 (1H, dd, J=16, 11 Hz), 6.74 (1H, d, J=15 Hz), 6.88-6.94 (2H, m), 6.94 (1H, dd, J=16, 11 Hz), 7.34 (1H, dd, J=10, 1 Hz), 7.39-7.46 (3H, m), 7.56-7.62 (3H, m), 7.86 (1H, d, J=7 Hz), 7.88 (1H, s), 7.99 (1H, s)

IR spectrum ν max KBr cm$^{-1}$: 2230, 1729, 1652, 1503, 1419, 1274, 1257, 1140, 1051, 974

Mass spectrum m/z (FAB): 859 [M$^+$ (free base)+1]

Example 37

Disodium [2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-thienyl]methyl phosphate (disodium salt of example number 5C-48)

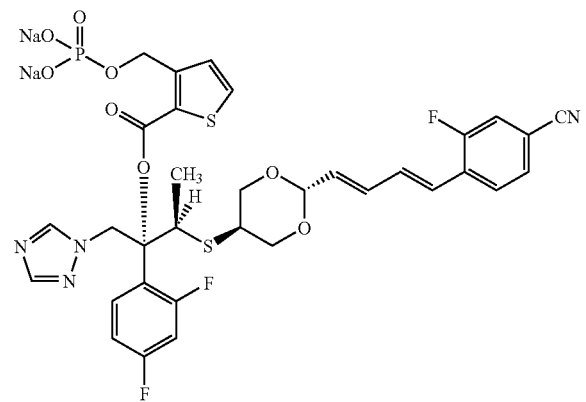

(1) Methyl 3-(acetoxymethyl)-2thenoate

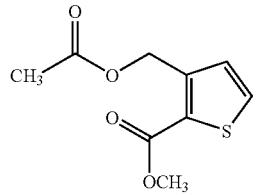

To a solution of methyl 3-(bromomethyl)-2-thenoate (described in Tetrahedron Lett., 22, 5097-5100, (1981); 6.80 g, 28.9 mmol) in N,N-dimethylformamide (80 ml) was added sodium acetate (7.12 g, 86.8 mmol). The mixture was stirred at room temperature for 24 hours, and then stirred at 40° C. for 1 hour. A phosphate buffer solution (pH 7, 100 ml) was added to the reaction mixture, and the product was extracted with ethyl acetate. The organic layer was washed three times with water, and the solvent was distilled off under reduced pressure. The residue was subjected to chromatography on a silica gel (150 g) column (eluent; ethyl acetate:hexane=1:10~1:1) to afford the title compound (4.89 g, 79% yield) as a colorless solid (mp. 42-43° C.).

NMR spectrum (400 MHz, CDCl$_3$) δ ppm: 2.13 (3H, s), 3.89 (3H, s), 5.49 (2H, s), 7.14 (1H, d, J=5 Hz), 7.48 (1H, d, J=5 Hz)

IR spectrum ν max KBr cm$^{-1}$: 1742, 1707, 1439, 1416, 1353, 1261, 1249, 1229

Mass spectrum m/z (EI): 214 (M$^+$)

Methyl 3-(hydroxymethyl)-2-thenoate

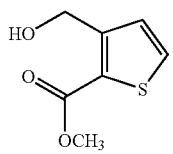

To a solution of methyl 3-(acetoxymethyl)-2-thenoate (4.89 g, 22.8 mmol) obtained from Example 37-(1) in methanol (60 ml) was added potassium carbonate (157.7 mg, 1.14 mmol), and the mixture was stirred at room temperature for 1 hour. A phosphate buffer solution (pH 7, 20 ml) was added to the reaction mixture, and the methanol was evaporated under reduced pressure. The product was extracted with ethyl acetate, and then the solvent was evaporated under reduced pressure. The obtained oily residue was subjected to chromatography on a silica gel (90 g) column (eluent; ethyl acetate:hexane=1:2) to give the title compound (3.94 g, quantitative yield) as needle crystals (mp. 35-36° C.).

NMR spectrum (400 MHz, CDCl$_3$) δ ppm: 3.78 (1H, t, J=7 Hz), 3.91 (3H, s), 4.84 (2H, d, J=7 Hz), 7.10 (1H, d, J=5 Hz), 7.47 (1H, d, J=5 Hz)

IR spectrum ν max KBr cm$^{-1}$: 1710, 1536, 1438, 1417, 1269, 1080

Mass spectrum m/z (EI): 172 (M$^+$).

(3) 4-Methoxybenzl 3[[bis(allyloxy)phosphoryl]oxymethyl]-2-thenoate

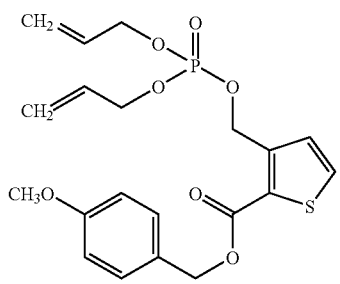

Methyl 3-(hydroxymethyl)-2-thenoate (3.03 g, 17.6 mmol) obtained from 37-(2) was dissolved in a mixed solvent of tetrahydrofuran (20 ml) and methanol (5 ml), and sodium hydroxide (1.004N aqueous solution; 16.1 ml, 16.2 mmol) was added thereto. The mixture was stirred at room temperature for 1 hour, warmed to 50° C., and stirred for another 1 hour. The solvent was evaporated under reduced pressure to give a solid residue. The residue was dissolved in N,N-dimethylformamide (30 ml), and 4-methoxybenzyl chloride (2.75 g, 17.6 mmol) was added thereto. The mixture was stirred at 70° C. for 1.5 hours, and then cooled to 0° C., and dichloromethane (30 ml) was added thereto. To the mixture were added tetrazole (3.08 g, 44.0 mmol) and bis(allyloxy)(diisopropylamino)phosphine (described in Tetrahedron Lett., 30, 4219 (1989); 6.47 g, 26.4 mmol), and the resulting mixture was stirred at the same temperature for 30 minutes, then methanol (0.5 ml) was added thereto followed by stirring for another 5 minutes. To the reaction mixture was added tert-butyl hydroperoxide (80% di-tert-butyl peroxide solution; Merck; 2.7 g, 24 mmol), and the mixture was stirred for 30 minutes, and then an aqueous solution of sodium hydrogen carbonate and an aqueous solution of sodium thiosulfate were added thereto, then the product was extracted with ethyl acetate. The organic layer was washed three times with water, and the solvent was distilled off under reduced pressure. The obtained oily residue was subjected to chromatography on a silica gel (100 g) column (eluent; ethyl acetate:hexane=1:2~3:2) to afford the title compound (2.8 g, 36% yield) as a colorless oil.

NMR spectrum (400 MHz, CDCl$_3$) δ ppm: 3.81 (3H, s), 4.55 (4H, t, J=7 Hz), 5.23-5.28 (2H, m), 5.25 (2H, s), 5.33-5.40 (2H, m), 5.47 (2H, d, J=8 Hz), 5.92 (2H, ddt, J=17, 11, 6 Hz), 6.90 (2H, d, J=9 Hz), 7.27 (1H, d, J=5 Hz), 7.37 (2H, d, J=9 Hz), 7.48 (1H, d, J=5 Hz)

IR spectrum ν max CHCl$_3$ cm$^{-1}$: 1705, 1613, 1516, 1424, 1267, 1250, 1035, 989

Mass spectrum m/z (FAB): 439 (M$^+$+1).

(4) 3-[[Bis(allyloxy)phosphoryl]oxymethyl]-2-thenoate acid

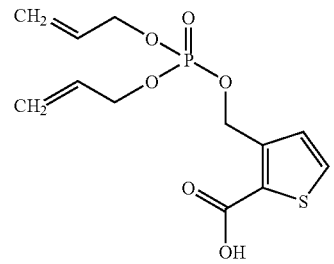

A mixture of 4-methoxybenzyl 3-[[bis(allyloxy)phosphoryl]oxymethyl]-2-thenoate (2.79 g, 6.36 mmol) obtained from 37-(3) and anisole (4 g) was cooled to 0° C., and trifluoroacetic acid (10 ml) was added thereto. The mixture was warmed to room temperature and allowed to stand for 20 minutes, then toluene was added thereto followed by evaporation of the solvent under reduced pressure. The oily residue was subjected to chromatography on a silica gel (25 g) column (eluent; ethyl acetate:dichloromethane=1:1) to give the title compound (1.57 g, 78% yield) as an oil.

NMR spectrum (400 MHz, CDCl$_3$) δ ppm: 4.59 (4H, m), 5.26 (2H, br d, J=10 Hz), 5.37 (2H, br d, J=17 Hz), 5.53 (2H, d, J=8 Hz), 5.94 (2H, ddt, J=17, 10, 6 Hz), 7.28 (1H, d, J=5 Hz), 7.54 (1H, d, J=5 Hz)

IR spectrum ν max CHCl$_3$ cm$^{-1}$: 1679, 1543, 1432, 1273, 1033, 989

Mass spectrum m/z (FAB): 319 (M$^+$+1).

(5) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 3-[[bis(allyloxy)phosphoryl]oxymethyl]-2-thenoate

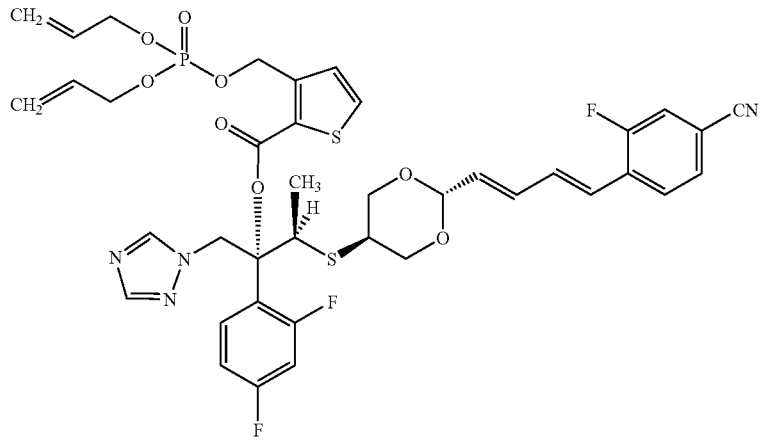

To a solution of 3-[[bis(allyloxy)phosphoryl]oxymethyl]-2-thenoic acid (533 mg, 1.68 mmol) obtained from 37-(4) in dichloromethane (10 ml), was added N,N-dimethylformamide (0.02 ml) and oxalyl chloride (0.7 g). The mixture was stirred at room temperature for 30 minutes, and after the addition of toluene, the solvent was evaporated under reduced pressure to give crude 3-[[bis(allyloxy)phosphoryl]oxymethyl]-2-thenoyl chloride.

A solution of 4-[(1E,3E)-4-[trans-5-[[(1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile (699.1 mg, 1.29 mmol) described in Reference example 1 in 1,2-dimethoxyethane (10 ml) was cooled to 0° C., and sodium hydride (55% dispersion in mineral oil; 67.5 mg, 1.55 mmol) was added thereto, and the resulting mixture was stirred at room temperature for 3 hours. To the mixture was added a solution of the crude 3-[[bis(allyloxy)phosphoryl]oxymethyl]-2-thenoyl chloride obtained above in 1,2-dimethoxyethane (2 ml), and the mixture was stirred at room temperature for 20 minutes and cooled to 0° C., then a phosphate buffer solution (pH 7) was added to the reaction mixture to stop the reaction, and the product was extracted with ethyl acetate. The crude product was subjected to chromatography on a silica gel (40 g) column (eluent; ethyl acetate:hexane=3:2~5:1) to give the title compound (520.6 mg, 48% yield) as a pale yellow amorphous solid.

NMR spectrum (400 MHz, CDCl$_3$) δ ppm: 1.45 (3H, dd, J=7, 2 Hz), 3.12 (1H, tt, J=11, 5 Hz), 3.53 (1H, t, J=11 Hz), 3.55 (1H, t, J=11 Hz), 3.92 (1H, q, J=7 Hz), 4.19-4.28 (2H, m), 4.55-4.59 (4H, m), 5.02 (1H, d, J=4 Hz), 5.25 (2H, dd, J=10, 1 Hz), 5.34-5.48 (6H, m), 5.87 (1H, dd, J=16, 4 Hz), 5.94 (2H, ddt, J=17, 11, 5 Hz), 6.59 (1H, dd, J=16, 11 Hz), 6.74 (1H, d, J=15 Hz), 6.88-6.93 (2H, m), 6.94 (1H, dd, J=15, 11 Hz), 7.33 (1H, d, J=15 Hz), 7.33-7.35 (1H, m), 7.39-7.46 (2H, m), 7.55 (1H, d, J=5 Hz), 7.57 (1H, t, J=8 Hz), 7.86 (1H, s), 7.91 (1H, s)

IR spectrum ν max CHCl$_3$ cm$^{-1}$: 2233, 1711, 1616, 1504, 1420, 1276, 1259, 1140, 1035, 991

Mass spectrum m/z (FAB): 843 (M$^+$+1).

(6) Disodium 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-3-thienyl]methyl phosphate (title target compound)

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 3-[[bis(allyloxy)phosphoryl]oxymethyl]-2-thenoate (500 mg, 0.593 mmol) obtained from 37-(5) in dichloromethane (20 ml) was cooled to 0° C., and tetrakis(triphenylphosphine)palladium (20.6 mg, 1.78×10$^{-2}$ mmol) and pyrrolidine (0.84 g, 11.9 mmol) were added thereto under an atmosphere of nitrogen gas. The mixture was stirred at room temperature for 30 minutes, and then toluene was added thereto followed by evaporation of the solvent under reduced pressure. The oily residue was subjected to reverse phase column chromatography using Cosmosil 75 C$_{18}$-PREP (Nacalai Tesque, Inc.; 35 g) (eluent; water:acetonitrile=3:1~7:3). The obtained fractions were concentrated, and the residue was subjected to a cation exchange resin (Dowex 50W-8X, Na type preparated using 1N aqueous solution of sodium hydroxide; 8 ml) (eluent; water). The collected fractions were concentrated under reduced pressure and lyophilized to afford the title target compound (335.6 mg, 70% yield) as an amorphous colorless solid.

NMR spectrum (400 MHz, CD$_3$OD) δ ppm: 1.41 (3H, dd, J=7, 2 Hz), 3.13 (1H, tt, J=12, 5 Hz), 3.52 (1H, t, J=12 Hz), 3.57 (1H, t, J=12 Hz), 3.99 (1H, q, J=7 Hz), 4.17-4.23 (2H, m), 5.05 (1H, d, J=4 Hz), 5.22 (1H, dd, J=16, 5 Hz), 5.27 (1H, dd, J=16, 6 Hz), 5.52 (1H, d, J=16 Hz), 5.56 (1H, d, J=16 Hz), 5.88 (1H, dd, J=15, 4 Hz), 6.60 (1H, dd, J=15, 11 Hz), 6.80 (1H, d, J=16 Hz), 6.96-7.06 (2H, m), 7.10 (1H, dd, J=16, 11 Hz), 7.50-7.56 (3H, m), 7.59 (1H, d, J=5 Hz), 7.62 (1H, d, J=5 Hz), 7.79 (1H, t, J=8 Hz), 7.90 (1H, s), 8.26 (1H, s)

IR spectrum ν max KBr cm$^{-1}$: 2231, 1708, 1615, 1503, 1419, 1276, 1256, 1141, 1101, 1071, 1053, 975

Mass spectrum m/z (FAB): 807 (M$^+$+1).

Example 38

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(4-methyl-1-piperazinyl)-4-oxobutyryl]oxymethyl]benzoate (example number 5A-105)

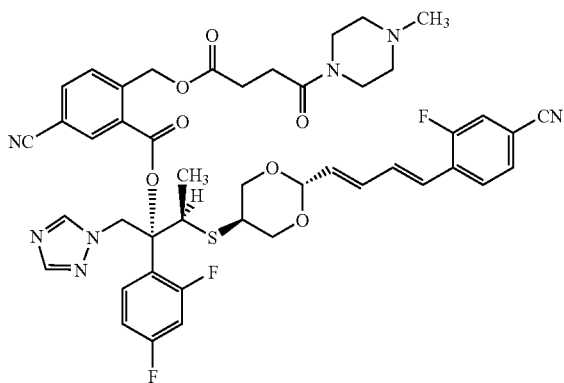

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-(hydroxymethyl)benzoate (1.38 g, 1.97 mmol) obtained from Example 33 in dichloromethane (40 ml) was cooled to 0° C., and 4-(N,N-dimethylamino)pyridine (481.3 mg, 3.94 mmol), 4-(4-methyl-1-piperazinyl)-4-oxobutanoic acid (described in Bioorg. Med. Chem., 8, 2693 (2000); 708.0 mg, 3.54 mmol), 1-ethyl-3-(3-dimethylaminopropyl)carbodiimide hydrochloride (830.8 mg, 4.33 mmol) were added thereto. The reaction mixture was stirred at the same temperature for 2 hours, and diluted with dichloromethane, then the organic layer was washed successively with water and a saturated aqueous solution of sodium chloride. The solvent was evaporated under reduced pressure, and the obtained residue was subjected to chromatography on a silica gel (30 g) column (eluent; ethyl acetate:methanol=4:1) to afford a mixture of the title compound and 4-(N,N-dimethylamino)pyridine (component ratio; 6:1, 1.33 g). A part (790.8 mg) of the mixture was separated by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title target compound (763.0 mg, 44% yield) as a colorless amorphous solid.

NMR spectrum (400 MHz, CDCl$_3$) δ ppm: 1.45 (3H, dd, J=7, 2 Hz), 2.30 (3H, s), 2.37 (2H, t, J=5 Hz), 2.30 (2H, t, J=5 Hz), 2.67-2.71 (2H, m), 2.77-2.80 (2H, m), 3.02 (1H, tt, J=12, 5 Hz), 3.50 (2H, t, J=5 Hz), 3.54 (1H, t, J=12 Hz), 3.55 (1H, t, J=12 Hz), 3.63 (2H, t, J=5 Hz), 4.02 (1H, q, J=7 Hz), 4.14-4.19 (2H, m), 5.01 (1H, d, J=4 Hz), 5.46 (1H, dd, J=15, 2 Hz), 5.51 (1H, d, J=15 Hz), 5.53 (1H, d, J=15 Hz), 5.60 (1H, d, J=15 Hz), 5.87 (1H, dd, J=15, 4 Hz), 6.58 (1H, dd, J=15, 10 Hz), 6.73 (1H, d, J=16 Hz), 6.90-6.96 (2H, m), 6.93 (1H, dd, J=16, 10 Hz), 7.32-7.37 (2H, m), 7.40 (1H, d, J=8 Hz), 7.57 (1H, t, J=8 Hz), 7.82-7.88 (2H, m), 7.89 (1H, s), 7.95 (1H, s), 8.18 (1H, d, J=1 Hz)

IR spectrum ν max KBr cm$^{-1}$: 2232, 1736, 1644, 1616, 1503, 1418, 1258, 1143

Mass spectrum m/z (FAB): 884 (M$^+$+1).

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(4-methyl-1-piperazinyl)-4-oxobutyryl]oxymethyl]benzoate (264.3 mg, 0.30 mmol) obtained above in ethyl acetate (5 ml) was cooled to 0° C., and then hydrogen chloride (4 mol/l ethyl acetate solution; 68.8 μl, 0.27 mmol) was added thereto, then the mixture was stirred at 0° C. for 5 minutes. The solvent was evaporated under reduced pressure, and the dried residue was dissolved in water (5 ml), which was lyophilized to give the mono hydrochloric acid salt (238.3 mg, 87% yield) of the title target compound as a colorless amorphous solid.

NMR spectrum (400 MHz, CD$_3$OD) δ ppm: 1.42 (3H, dd, J=7, 1 Hz), 2.79 (4H, s), 2.82 (3H, s), 3.01 (1H, tt, J=11, 4 Hz), 3.08-3.12 (2H, m), 3.16-3.20 (2H, m), 3.47 (1H, t, J=11 Hz), 3.53 (1H, t, J=11 Hz), 3.76-3.86 (4H, m), 3.95 (1H, q, J=7 Hz), 4.02 (1H, ddd, J=11, 4, 2 Hz), 4.16 (1H, ddd, J=11, 4, 2 Hz), 5.01 (1H, d, J=5 Hz), 5.47 (1H, d, J=16 Hz), 5.58 (2H, s), 5.59 (2H, d, J=16 Hz), 5.88 (1H, dd, J=15, 5 Hz), 6.57 (1H, dd, J=15, 11 Hz), 6.78 (1H, d, J=16 Hz), 7.08 (1H, dd, J=16, 11 Hz), 7.02-7.12 (2H, m), 7.49-7.54 (2H, m), 7.58 (1H, td, J=9, 6 Hz), 7.77 (1H, t, J=8 Hz), 7.84 (1H, d, J=8 Hz), 7.97-7.99 (1H, m), 7.98 (1H, s), 8.19 (1H, d, J=1 Hz), 8.44 (1H, s)

IR spectrum ν max KBr cm$^{-1}$: 2232, 1734, 1653, 1503, 1419, 1275, 1256, 1144, 1051

Mass spectrum m/z (FAB): 884 [M$^+$ (free base)+1]

Example 39

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-hydroxyacetate (example number 4A-1)

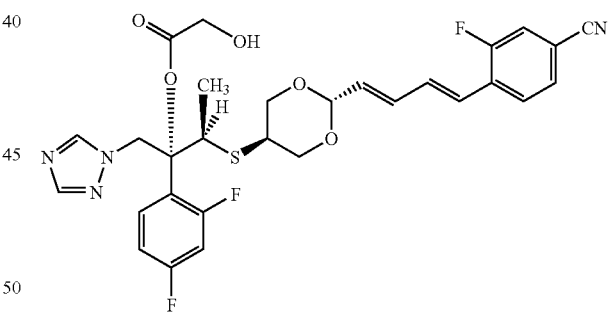

(1) 4-Methoxybenzl 2-hydroxyacetate

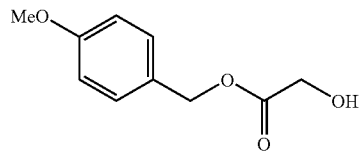

Glycolic acid (15.21 g, 0.2 mmol) was dissolved in water (20 ml), sodium hydrogen carbonate (16.8 g, 0.2 mmol) added thereto, and the resulting mixture was allowed to stand overnight. The solvent was evaporated under reduced pressure, and the residue was dried to give the crude sodium salt of glycolic acid (19.62 g). To a solution of the crude sodium glycolate (13.5 g, 0.138 mmol) in N,N-dimethylformamide (70 ml) was added 4-methoxybenzyl chloride (21.6 g, 0.138 mmol) and the mixture was stirred at 100° C. for 1 hour. After the mixture was cooled to room temperature, water was added to the mixture, and the product was extracted with ethyl acetate. The organic layer was washed with water, and the solvent was removed by distillation under reduced pressure to give an oily residue. The residue was purified by column chromatography using silica gel (200 g; eluent, ethyl acetate:hexane=2:3), to give the title compound (16.17 g, yield 60%) as a colorless oil.

NMR spectrum (400 MHz, CDCl$_3$) δ ppm: 3.82 (3H, s), 4.17 (2H, d, J=5 Hz), 5.17 (2H, s), 6.90 (2H, d, J=9 Hz), 7.31 (2H, d, J=9 Hz)

IR spectrum ν max CHCl$_3$ cm$^{-1}$: 1738, 1613, 1516, 1253, 1175, 1085, 1035

Mass spectrum m/z (EI): 196 (M$^+$)

(2) 4-Methoxybenzl 2-(allyloxycarbonyloxy)acetate

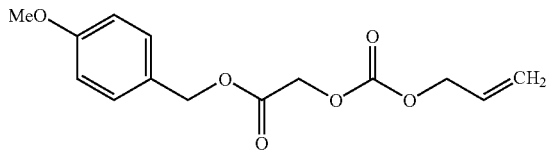

A solution of 4-methoxybenzyl hydroxyacetate (1.46 g, 7.4 mmol) obtained from Example 39-(1) in dichloromethane (20 ml) was cooled to 0° C., and to the solution were added 4-(N,N -dimethylamino)pyridine (1.00 g, 8.2 mmol) and allyl chloroformate (0.99 g, 8.2 mmol). The mixture was warmed to room temperature and stirred for 1 hour. The reaction was stopped by addition of water. The product was extracted with dichloromethane and the solvent was removed by distillation under reduced pressure to give an oily residue. The residue was purified by column chromatography using silica gel (40 g; eluent, ethyl acetate:hexane=1:5), to give the title compound (1.80 g, yield 86%) as a pale brown oil.

NMR spectrum (400 MHz, CDCl$_3$) δ ppm: 3.81 (3H, s), 4.65 (2H, s), 4.67 (2H, dd, J=5, 1 Hz), 5.15 (2H, s), 5.28 (1H, dt, J=11, 1 Hz), 5.38 (1H, dd, J=18, 1 Hz), 5.93 (1H, ddt, J=18, 11, 5 Hz), 6.89 (2H, d, J=8 Hz), 7.30 (2H, d, J=8 Hz)

IR spectrum ν max CHCl$_3$ cm$^{-1}$: 1752, 1614, 1516, 1299, 1282, 1255, 1175

Mass spectrum m/z (EI): 280 (M$^+$).

(3) 2-(Allyloxycarbonloxy)acetic acid

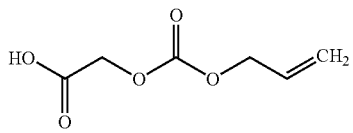

A mixture of 4-methoxybenzyl 2-(allyloxycarbonyloxy) acetate (1.77 g, 6.3 mmol) obtained from Example 39-(2) and anisole (2.0 g, 18.5 mmol) was cooled to 0° C., and to the mixture was added trifluoroacetic acid (9 ml). The resulting mixture was allowed to stand at room temperature for 20 minutes. At the end of this time, toluene (8 ml) was added to the mixture. The solvent was removed by distillation under reduced pressure to eliminate volatile components. To the mixture was added a saturated aqueous solution of sodium hydrogen carbonate. The aqueous layer was washed with hexane twice. To the solution was added an aqueous solution of 2N hydrochloric acid, and the components were back extracted with ethyl acetate. The solvent was removed by distillation under reduced pressure to give the crude title compound (1.00 g, quantitative yield) as a pale brown oil.

NMR spectrum (400 MHz, CDCl$_3$) δ ppm: 4.69 (2H, d, J=6 Hz), 4.71 (2H, s), 5.30 (1H, dd, J=10, 1 Hz), 5.40 (1H, dd, J=10, 1 Hz), 5.95 (1H, ddt, J=17, 11, 6 Hz)

IR spectrum ν max CHCl$_3$ cm$^{-1}$: 1758, 1740, 1296, 1278, 1253,

Mass spectrum m/z (FAB): 161 (M$^+$+1).

(4) 2-(Allyloxycarbonyloxy)acetyl chloride

A solution of 2-(allyloxycarbonyloxy)acetic acid (3.03 g, 18.9 mmol) obtained from Example 39-(3) in tetrahydrofuran (30 ml) was cooled to 0° C., and to the solution were added oxalyl chloride (2.64 g, 20.8 mmol) and N,N-dimethylformamide (30 μl). The mixture was warmed to room temperature. After the mixture was stirred for 30 minutes, the solvent was distilled off under reduced pressure, and the resulting residue was purified using simple distillation under reduced pressure to give the title compound (3.04 g, yield 90%) as a colorless oil.

NMR spectrum (400 MHz, CDCl$_3$) δ ppm: 4.70 (2H, d, J=6 Hz), 4.93 (2H, s), 5.32 (1H, d, J=11 Hz), 5.40 (1H, d, J=17 Hz), 5.94 (1H, ddt, J=17, 11, 6 Hz)

(5) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(allyloxycarbonyloxy)acetate To a solution of 4-[(1E,3E)-4-[trans-5-[[(1R,2R)-2-(2,4-difluorophenyl)-2-hydroxy-1-methyl-3-[(1H-1,2,4-triazol-1-yl)propyl]thio]-1,3-dioxan-2-yl]-1,3-butadienyl]-3-fluorobenzonitrile (542.6 mg, 1.00 mmol) obtained from Reference example 1 in tetrahydrofuran (13 ml) was added sodium hydride (55% dispersion in mineral oil; 104.7 mg, 2.40 mmol), and the mixture was irradiated with ultrasonic waves for 30 minutes using a commercially available ultrasonic cleaner. The mixture was taken out of the ultrasonic cleaner and cooled to 0° C., and 2-(allyloxycarbonyloxy) acetyl chloride (392.9 mg, 2.20 mmol) obtained from Example 39-(4) was added thereto. The resulting mixture was stirred at room temperature for 40 minutes, and then the reaction was stopped by addition of water. The mixture was extracted with ethyl acetate, and the solvent was removed under reduced pressure. The resulting oily residue was purified by column chromatography using silica gel (30 g; eluent, ethyl acetate:hexane=2:1), to give the title compound (109.6 mg, yield 16%) as a pale yellow amorphous solid.

NMR spectrum (400 MHz, CDCl$_3$) δ ppm: 1.37 (3H, dd, J=7, 2 Hz), 3.00 (1H, tt, J=11, 5 Hz), 3.50 (1H, t, J=11 Hz), 3.51 (1H, t, J=11 Hz), 3.83 (1H, q, J=7 Hz), 4.11-4.21 (2H, m), 4.66 (2H, d, J=2 Hz), 4.69 (2H, d, J=6 Hz), 4.99 (1H, d, J=4 Hz), 5.30 (1H, d, J=11 Hz), 5.32-5.41 (3H, m), 5.85 (1H, dd, J=15, 4 Hz), 5.94 (1H, ddt, J=17, 11, 6 Hz), 6.58 (1H, dd, J=15, 10 Hz), 6.74 (1H, d, J=16 Hz), 6.86-6.94 (2H, m), 6.93

(1H, dd, J=16, 10 Hz), 7.34 (1H, d, J=10 Hz), 7.35-7.39 (1H, m), 7.40 (1H, d, J=10 Hz), 7.57 (1H, t, J=8 Hz), 7.93 (1H, s), 8.04 (1H, s)

IR spectrum ν max KBr cm$^{-1}$: 2231, 1754, 1504, 1419, 1277, 1188, 1141, 972

Mass spectrum m/z (FAB): 685 (M$^+$+1)

(6) (1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-hydroxyacetate (Title Target Compound)

To a solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-(allyloxycarbonyloxy)acetate (250.7 mg, 0.37 mmol) obtained from Example 39-(5) in dichloromethane (5 ml) were added bis(triphenylphosphine)dichloropalladium (12.9 mg, 0.018 mmol) and tributyltin hydride (106.5 mg, 0.366 mmol), and the mixture was stirred at room temperature for 30 minutes. The resulting mixture was purified by column chromatography using silica gel (30 g; eluent, ethyl acetate:hexane=3:1), to give the title target compound (230.7 mg, quantitative yield) as a colorless amorphous solid.

NMR spectrum (400 MHz, CDCl$_3$) δ ppm: 1.36 (2H, dd, J=7, 2 Hz), 2.53 (1H, t, J=5 Hz), 3.03 (1H, tt, J=11, 5 Hz), 3.51 (2H, t, J=11 Hz), 3.90 (1H, q, J=7 Hz), 4.13-4.22 (3H, m), 4.27 (1H, dd, J=17, 5 Hz), 5.00 (1H, d, J=4 Hz) 5.35 (1H, d, J=15 Hz), 5.42 (1H, dd, J=15, 2 Hz), 5.85 (1H, dd, J=15, 4 Hz), 6.59 (1H, dd, J=15, 11 Hz), 6.74 (1H, d, J=16 Hz), 6.87-6.93 (2H, m), 6.93 (1H, dd, J=16, 11 Hz), 7.31-7.37 (2H, m), 7.40 (1H, d, J=8 Hz), 7.57 (1H, t, J=8 Hz), 7.92 (2H, s)

IR spectrum ν max KBr cm$^{-1}$: 3433, 2231, 1757, 1615, 1503, 1419, 1276, 1141, 1100, 1051, 973

Mass spectrum m/z (FAB): 601 (M$^+$+1).

Example 40

Sodium 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2-oxoethyl succinate (Sodium Salt of Example Number 4A-2)

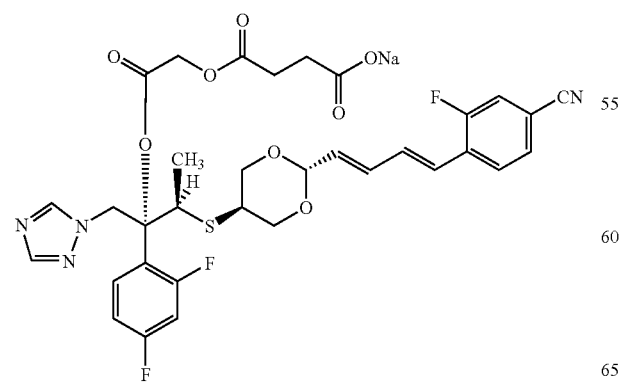

Allyl 2-](1R,2R)-2-]]trans-2-](1E,3E)-4-(4-cyano-2fluorophenyl-1,3-butadienyl]-1,3-dioxan-5-yl]thio]-1-(2,4-difluorophenyl)-1-[(1H-1,2,4-triazol-1-yl) methyl]propoxy]-2-oxoethyl succinate (Disodium Salt of Example Number 4A-2)

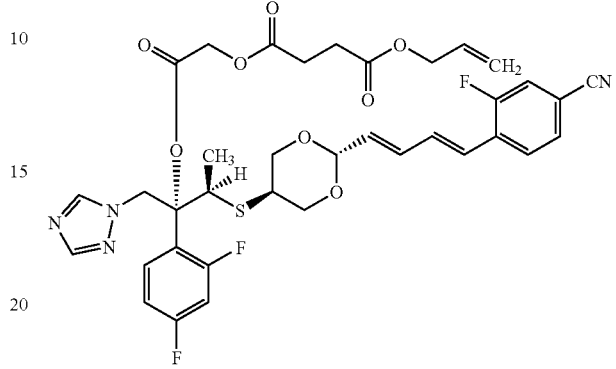

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-hydroxyacetate (327.0 mg, 0.54 mmol) obtained from Example 39 in dichloromethane (10 ml) was cooled to 0° C., and to the solution were added triethylamine (66.1 mg, 0.65 mmol) and allyl 4-chloro-4-oxobutyrate (115.4 mg, 0.65 mmol) obtained from Example 14-(1). The mixture was stirred at the same temperature for 2 hours. At the end of this time, the resulting mixture was diluted with dichloromethane and was washed with water and then with a saturated aqueous solution of sodium chloride. The solvent was removed under reduced pressure. The resulting oily residue was purified by column chromatography using silica gel (20 g; eluent, ethyl acetate:hexane=1:1), to give the title target compound (311.8 mg, yield 77%) as a pale brown oil.

NMR spectrum (400 MHz, CDCl$_3$) δ ppm: 1.36 (3H, dd, J=7, 2 Hz), 2.69-2.72 (2H, m), 2.76-2.79 (2H, m), 3.01 (1H, tt, J=11, 5 Hz), 3.50 (1H, t, J=11 Hz), 3.51 (1H, t, J=11 Hz), 3.81 (1H, q, J=7 Hz), 4.13-4.20 (2H, m), 4.60 (2H, d, J=6 Hz), 4.62 (1H, d, J=15 Hz), 4.68 (1H, d, J=15 Hz), 4.99 (1H, d, J=4 Hz), 5.24 (1H, d, J=11 Hz), 5.32 (1H, d, J=17 Hz), 5.33 (1H, d, J=15 Hz), 5.38 (1H, dd, J=15, 2 Hz), 5.85 (1H, dd, J=16, 5 Hz), 5.91 (1H, ddt, J=17, 11, 6 Hz), 6.58 (1H, dd, J=15, 11 Hz), 6.74 (1H, d, J=15 Hz), 6.85-6.95 (2H, m), 6.93 (1H, dd, J=15, 11 Hz), 7.35-7.40 (1H, m), 7.34 (1H, d, J=10 Hz), 7.40 (1H, d, J=8 Hz), 7.57 (1H, t, J=8 Hz), 7.94 (1H, s), 8.03 (1H, s)

IR spectrum ν max KBr cm$^{-1}$: 2231, 1741, 1615, 1504, 1419, 1276, 1145

Mass spectrum m/z (FAB): 741 (M$^+$+1).

(2) Sodium 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2-oxoethyl succinate (Title Target Compound)

According to a similar procedure to that described in Example 1-(13) using allyl 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl) methyl]propoxy]-2-oxoethyl succinate (297.8 mg, 0.402 mmol) obtained from (1), bis(triphenylphosphine)dichloropalladium (14.1 mg, 0.02 mmol) and tributyltin hydride (117.0 mg, 0.40 mmol), the crude title target compound was obtained as an oil.

The oil was subjected to reverse phase column chromatography using Cosmosil 75 $C_{18}$-PREP (Nacalai Tesque, Inc.; 20 g) (eluent; water:methanol=4:6~3:7). The obtained fractions were concentrated, and the residue was lyophilized to afford the title target compound (100.0 mg, yield 34%) as a colorless solid.

NMR spectrum (400 MHz, $D_2O$) δ ppm: 1.35 (3H, dd, J=7, 2 Hz), 2.51 (2H, t, J=7 Hz), 2.71 (2H, t, J=7 Hz), 3.02 (1H, tt, J=11, 5 Hz), 3.57 (1H, t, J=11 Hz), 3.58 (1H, t, J=11 Hz), 3.78 (1H, d, J=7 Hz), 4.15 (1H, ddd, J=11, 5, 2 Hz), 4.19 (1H, ddd, J=11, 5, 2 Hz), 4.77-4.78 (2H, m), 5.11 (1H, d, J=5 Hz), 5.40 (1H, d, J=15 Hz), 5.51 (1H, d, J=15 Hz), 5.89 (1H, dd, J=15, 5 Hz), 6.63 (1H, dd, J=15, 11 Hz), 6.83 (1H, d, J=16 Hz), 7.03-7.12 (2H, m), 7.11 (1H, dd, J=16, 11 Hz), 7.51-7.61 (3H, m), 7.81 (1H, t, J=8 Hz), 8.04 (1H, s), 8.40 (1H, s)

IR spectrum ν max KBr $cm^{-1}$: 2231, 1747, 1614, 1598, 1503, 1419, 1385, 1143

Mass spectrum m/z (FAB): 723 ($M^+$+1).

Example 41

Sodium hydrogen 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2-oxoethyl phosphate (Sodium Salt of Example Number 4A-2)

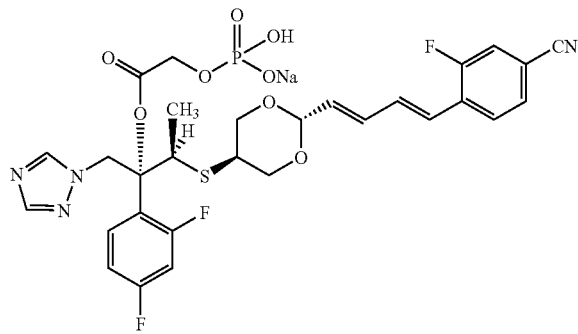

(1) Diallyl 2-](1R,2R)-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]-2-oxoethyl phosphate

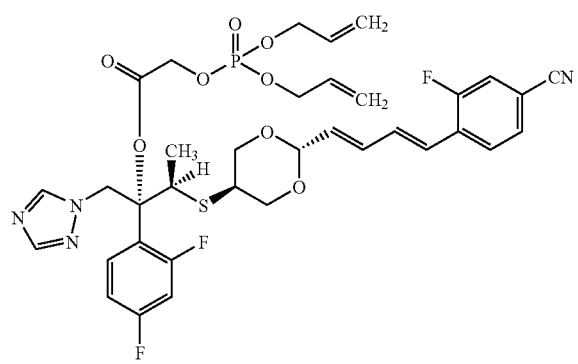

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-hydroxyacetate (343.2 mg, 0.571 mmol) obtained from Example 39 in dichloromethane (10 ml) was cooled to 0° C., and to the solution were added tetrazole (80.1 mg, 1.15 mmol) and bis(allyloxy)(diisopropylamino)phosphine (described in Tetrahedron Lett., 30, 4219, (1989); 182.1 mg, 0.742 mmol). The mixture was stirred at the same temperature for 20 minutes. To the mixture was added methanol (0.1 ml), and the mixture was stirred for 5 minutes. To the mixture was added tert-butyl hydroperoxide (80% di-tert-butyl hydroperoxide solution; 0.27 g, 2.4 mmol) at 0° C., and the mixture was stirred at room temperature for 15 minutes. To the mixture were added a saturated aqueous solution of sodium hydrogen carbonate and a solution of sodium thiosulfate, and the mixture was stirred for 10 minutes. At the end of this time, the product was extracted with ethyl acetate, and the solvent was removed under reduced pressure. The resulting oily residue was purified by column chromatography using silica gel (20 g; eluent, ethyl acetate:hexane=4:1), to give the title compound (365.4 mg, yield 84%) as a pale brown amorphous solid.

NMR spectrum (400 MHz, $CDCl_3$) δ ppm: 1.36 (3H, dd, J=7, 2 Hz), 2.99 (1H, tt, J=11, 5 Hz), 3.50 (1H, t, J=11 Hz), 3.51 (1H, t, J=11 Hz), 3.83 (1H, q, J=7 Hz), 4.11-4.20 (2H, m), 4.56-4.71 (6H, m), 4.99 (1H, d, J=4 Hz), 5.25-5.40 (6H, m), 5.84 (1H, dd, J=15, 4 Hz), 5.96 (2H, ddt, J=17, 11, 6 Hz), 6.58 (1H, dd, J=15, 11 Hz), 6.73 (1H, d, J=16 Hz), 6.86-6.93 (2H, m), 6.93 (1H, dd, J=16, 11 Hz), 7.33 (1H, d, J=10 Hz), 7.35-7.39 (1H, m), 7.40 (1H, d, J=8 Hz), 7.57 (1H, t, J=8 Hz), 7.91 (1H, s), 8.01 (1H, s)

IR spectrum ν max $CHCl_3$ $cm^{-1}$: 2233, 1772, 1616, 1504, 1277, 1259, 1140, 1041, 991

Mass spectrum m/z (FAB): 761 ($M^+$+1)

(2) Sodium hydrogen 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2-oxoethyl phosphate (Title Target compound)

According to a similar procedure to that described in Example 1-(13) using diallyl 2-[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]-2-oxoethyl phosphate (319.0 mg, 0.42 mmol) obtained from Example 41-(1), bis(triphenylphosphine)dichloropalladium (14.7 mg, 0.021 mmol) and tributyltin hydride (292.9 mg, 1.01 mmol), the crude title target compound was obtained as an oil.

The oil was subjected to reverse phase column chromatography using Cosmosil 75 $C_{18}$-PREP (Nacalai Tesque, Inc.; 25 g) (eluent; water:methanol=4:6~3:7). The obtained fractions were concentrated, and the residue was lyophilized to afford the title target compound (151.9 mg, yield 52%) as a colorless solid.

NMR spectrum (400 MHz, $D_2O$) δ ppm: 1.21 (3H, d, J=7 Hz), 2.91 (1H, tt, J=12, 5 Hz) 3.50 (1H, t, J=12 Hz), 3.53 (1H, t, J=12 Hz), 3.64 (1H, q, J=7 Hz), 4.04-4.10 (2H, m), 4.33 (1H, dd, J=17, 6 Hz), 4.42 (1H, dd, J=17, 6 Hz), 5.05 (1H, d, J=5 Hz), 5.21 (1H, d, J=15 Hz), 5.39 (1H, d, J=15 Hz), 5.73 (1H, dd, J=15, 4 Hz), 6.51 (1H, dd, J=15, 11 Hz), 6.73 (1H, d, J=16 Hz), 6.86-6.98 (3H, m), 7.37-7.41 (3H, m), 7.59 (1H, t, J=8 Hz), 7.88 (1H, s), 8.27 (1H, s)

IR spectrum ν max KBr $cm^{-1}$: 2231, 1755, 1615, 1503, 1418, 1385, 1277, 1140, 1050, 988, 976

Mass spectrum m/z (FAB): 703 ($M^+$+1).

Example 42

(1R,2R)-2-[[trans-2-[(1E,3E)-4-(4-Cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(4-methyl-1-piperazinyl)acetyl]oxymethyl]benzoate (Example Number 5A-94)

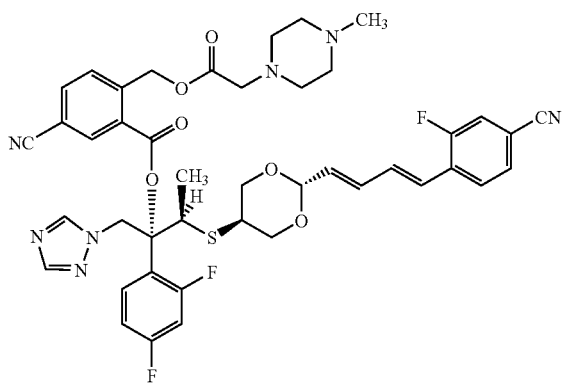

A solution of (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-(hydroxymethyl)benzoate (666.1 mg, 0.95 mmol) obtained from Example 33 in dichloromethane (20 ml) was cooled to 0° C., and to the solution were added 4-(N,N-dimethylamino)pyridine (231.9 mg, 1.90 mmol), (4-methyl-1-piperazinyl)acetic acid (J. Med. Chem., 43, 1493, (2000); 270.3 mg, 1.71 mmol) and 1-ethyl-3-(3-dimethylaminopropyl)carbodiimide hydrochloride (546.2 mg, 2.85 mmol). The mixture was stirred at room temperature for 2 hours. The mixture was diluted with dichloromethane, and the organic layer was washed with water, and then with a saturated aqueous solution of sodium chloride. The solvent was removed under reduced pressure. The resulting residue was purified by recycle preparative HPLC [LC-908; Japan Analytical Industry Co., Ltd.; GPC column JAIGEL-1H (20 mm i.d. ×600 mm) and JAIGEL-2H (20 mm i.d. ×600 mm) connected in series for use; solvent, chloroform] to afford the title target compound (306.7 mg, 38% yield) as a colorless amorphous solid.

NMR spectrum (400 MHz, CDCl$_3$) δ ppm: 1.46 (3H, dd, J=7, 2 Hz), 2.40-2.73 (11H, m), 3.02 (1H, tt, J=11, 5 Hz), 3.37 (2H, s), 3.50 (1H, t, J=11 Hz), 3.55 (1H, t, J=11 Hz), 4.02 (1H, q, J=7 Hz), 4.13-4.20 (2H, m), 5.01 (1H, d, J=4 Hz), 5.49 (2H, s), 5.54 (1H, d, J=15 Hz), 5.60 (1H, d, J=15 Hz), 5.86 (1H, dd, J=15, 4 Hz), 6.58 (1H, dd, J=15, 11 Hz), 6.73 (1H, d, J=16 Hz), 6.90-6.94 (2H, m), 6.93 (1H, dd, J=16, 11 Hz), 7.33 (1H, dd, J=10, 1 Hz), 7.36-7.41 (2H, m), 7.57 (1H, t, J=8 Hz), 7.71 (1H, d, J=9 Hz), 7.86 (1H, dd, J=8, 1 Hz), 7.89 (1H, s), 7.95 (1H, s), 8.19 (1H, d, J=1 Hz)

IR spectrum ν max KBr cm$^{-1}$: 2232, 1733, 1614, 1504, 1418, 1276, 1182, 1167, 1142

Mass spectrum m/z (FAB): 842 (M$^+$+1)

A solution of [(1R,2R)-2-[[trans-2-[(1E,3E)-4-(4-cyano-2-fluorophenyl)-1,3-butadienyl]-1,3-dioxan-5-yl]thio]1-[(2,4-difluorophenyl)-1-[(1H-1,2,4-triazol-1-yl)methyl]propyl 5-cyano-2-[[2-(4-methyl-1-piperazinyl)acetyl]oxymethyl]benzoate (260.8 mg, 0.31 mmol) obtained above in ethyl acetate (5 ml) was cooled to 0° C., and to the solution was added hydrogen chloride (4 N solution in ethyl acetate; 73.6 μl, 0.29 mmol). The mixture was stirred at 0° C. for 5 minutes, and the solvent was removed under reduced pressure to give the mono hydrochloric acid salt of the title compound (277.2 mg, quantitative yield) as a pale yellow amorphous solid.

NMR spectrum (400 MHz, CDCl$_3$) δ ppm: 1.46 (1H, dd, J=7, 1 Hz), 2.75 (3H, s), 3.0-3.1 (9H, m), 3.46 (2H, s), 3.55 (2H, t, J=12 Hz), 4.01 (1H, q, J=7 Hz), 4.13-4.20 (2H, m), 5.01 (1H, d, J=4 Hz), 5.47 (1H, d, J=15 Hz), 5.51 (1H, d, J=15 Hz), 5.53 (1H, d, J=15 Hz), 5.64 (1H, d, J=15 Hz), 5.86 (1H, dd, J=15, 4 Hz), 6.58 (1H, dd, J=15, 10 Hz), 6.74 (1H, d, J=16 Hz), 6.90-6.97 (3H, m), 7.33 (1H, dd, J=10, 1 Hz), 7.33-7.37 (1H, m), 7.40 (1H, dd, J=8, 1 Hz), 7.58 (1H, t, J=8 Hz), 7.70 (1H, d, J=8 Hz), 7.88 (1H, s), 7.89 (1H, dd, J=9, 2 Hz), 7.97 (1H, s), 8.24 (1H, d, J=1 Hz)

IR spectrum ν max KBr cm$^{-1}$: 2232, 1733, 1614, 1504, 1418, 1275, 1257, 1183, 1143

Mass spectrum m/z (FAB): 842 [M(free base)$^+$+1].

Reference Example 1

4-[1E,3E)-4-[trans-5-[[(1R,2R)-2-(2,4-Difluorophenyl)-2-hydroxy-1-methyl-3-[(1H-1,2,4-triazol-1-yl)propyl]thio]-1,3-dioxan-2-yl]-1,3-butadienyl]-3-fluorobenzonitrile

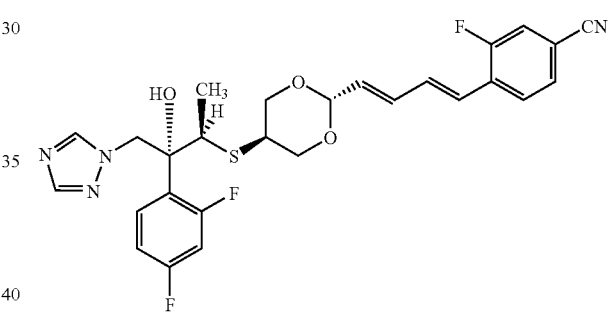

(1) Diethyl 4-cyano-2-flourobenzylphosphonate

A mixture of 4-(bromomethyl)-3-fluorobenzonitrile (1.5 g, 7.0 mmol)[J. Med. Chem., 40, 2064 (1997)] and triethyl phosphite (1.4 g, 8.4 mmol) was heated at 150° C. for 2 hours. At the end of this time, the reaction mixture was concentrated under reduced pressure. Volatile materials in the residue thus obtained were removed by heating said residue at 100° C. in vacuo for 1 hour to afford the title compound (1.97 g, quantitative yield) as an oil which solidified in the freezer. This oily product was used in the next step without further purification.

NMR spectrum (270 MHz, CDCl$_3$) δ ppm: 1.27 (6H, t, J=7.1 Hz), 3.24 (2H, d, J=22.3 Hz), 4.00-4.05 (4H, m), 7.37 (1H, d, J=9.2 Hz), 7.43 (1H, d, J=7.9 Hz), 7.51 (1H, td, J=9.2, 2.6 Hz)

IR spectrum ν max CHCl$_3$ cm$^{-1}$: 2237, 1262, 1054, 1029

Mass spectrum m/z (EI): 271 (M$^+$), 139, 109 (100%), 93.

(2) 3-Fluoro-4-[(1E,3E)-5-oxo-1,3-pentadienyl]benzonitrile

Butyllithium (hexane solution, 1.53 N, 0.5 ml, 0.77 mmol) was added dropwise to a solution of diethyl 4-cyano- 2-fluorobenzylphosphonate (209 mg, 0.77 mmol) obtained from Reference example 1-(1) in anhydrous tetrahydrofuran (4 ml) at −78° C. with stirring. The mixture was stirred at −78° C. for 30 minutes. At the end of this time, commercially available fumaraldehyde mono-dimethylacetal (100 mg, 0.77 mmol) in anhydrous tetrahydrofuran (2 ml) was added to the mixture, and the resulting mixture was stirred at −78° C. for 2 hours. The cooling bath was then removed and the mixture was stirred in an ice bath for a further 15 minutes. 0.1N hydrochloric acid (3.9 ml, 0.39 mmol) was added to the reaction mixture and the mixture was then stirred for 30 minutes in the ice bath and then for 1 hour at ambient temperature. At the end of this time, a saturated aqueous sodium hydrogen carbonate solution was added to the mixture in an ice bath. The resulting mixture was partitioned between ethyl acetate and water, the organic layer was washed with water and with aqueous sodium chloride solution, dried over anhydrous magnesium sulfate and then the solvent was distilled off under reduced pressure. The crystalline residue thus obtained was recrystallized from a mixture of ethyl acetate and hexane to afford the title compound (127 mg, 82% yield) as pale yellow crystals. m.p. 174-177° C.

NMR spectrum (270 MHz, CDCl$_3$) δ ppm: 6.36 (1H, dd, J=15, 8 Hz), 7.14 (1H, d-like, J=3 Hz), 7.16 (1H, d, J=8 Hz), 7.28 (1H, ddd, J=15, 8, 3 Hz), 7.40 (1H, dd, J=10, 1 Hz), 7.47 (1H, dd, J=8, 1 Hz), 7.67 (1H, t, J=8 Hz), 9.68 (1H, d, J=8 Hz)

IR spectrum ν max KBr cm$^{-1}$: 2230, 1681, 1672, 1621, 1421, 1159, 1124

Mass spectrum m/z (EI): 201 (M$^+$), 172 (100%), 158, 145

Elemental analysis for C$_{12}$H$_8$FNO:

Calculated: C:71.64, H:4.01, N:6.96. Found: C:71.84, H:4.27, N:6.83.

(3) 4-[(1E,3E)-4-[trans-5-[[(1R,2R)-2-(2,4-Difluorophenyl)-2-hydroxy-1-methyl-3-[(1H-1,2,4-triazol-1-yl)propyl]thio]-1,3-dioxan-2-yl]-1,3-butadienyl]-3-fluorobenzonitrile (Title Target Compound)

A mixture of 3fluoro4-[(1E,3E)-5-oxo-1,3-pentadienyl] benzonitrile (4.63 g, 23.0 mmol) obtained from Reference example 1-(2), (2R,3R)-2-(2,4-difluorophenyl)-3-[[1-(hydroxymethyl) -2-hydroxyethyl]thio]-1-(1H-1,2, 4-triazol-1-yl) -2-butanol (described in Japanese Patent Application Publication (Kokai) No. Hei 8-333350, 8.73 g, 24.3 mmol), p-toluenesulfonic acid monohydrate (5.07 g, 26.7 mmol) and anhydrous tetrahydrofuran (200 ml) was allowed to stand at ambient temperature for 30 minutes. At the end of this time, the reaction mixture was concentrated using a rotary evaporator and dried in vacuo. The resulting residue was dissolved in anhydrous tetrahydrofuran (150 ml) and the resulting mixture was then evaporated to dryness in vacuo using a rotary evaporator. This procedure was repeated twice more. A solution of the resulting residue in anhydrous tetrahydrofuran (150 ml) was poured into a saturated aqueous sodium hydrogen carbonate solution with stirring. The product was then extracted with ethyl acetate and the organic layer was washed with aqueous sodium chloride solution, dried over anhydrous magnesium sulfate and then concentrated under reduced pressure. The residual oil was purified by chromatography on a silica gel (500 g; eluent, ethyl acetate hexane =2:1), to give the title target compound (9.35 g, yield 74%) as a pale yellow amorphous solid. NMR spectrum (400 MHz, CDCl$_3$) δppm: 1.19 (3H, d, J=7 Hz), 3.33 (1H, q, J=7 Hz), 3.40 (1H, tt, J=11, 5 Hz), 3.62 (1H, t, J=11 Hz), 3.64 (1H, t, J=11 Hz), 4.30 (1H, ddd, J=11, 5, 2 Hz), 4.43 (1H, ddd, J=11, 5, 2 Hz), 4.83 (1H, d, J=14 Hz), 5.01 (1H, s), 5.03 (1H, d, J=14 Hz), 5.07 (1H, d, J=4 Hz), 5.90 (1H, dd, J=15, 4 Hz), 6.62 (1H, dd, J=15, 11 Hz), 6.7-6.8 (2H, m), 6.73 (1H, d, J=16 Hz), 6.95 (1H, dd, J=16, 11 Hz), 7.3-7.4 (1H, m), 7.34 (1H, d, J=9 Hz), 7.40 (1H, d, J=8 Hz), 7.58 (1H, t, J=8 Hz), 7.79 (2H, s)

IR spectrum ν max (KBr) cm$^{-1}$: 2232, 1616, 1499, 1418, 1140

Mass spectrum m/z (FAB): 543 (M$^+$+1)

Specific rotation [α]$_D^{25}$ −76.6°(c=1.00, CHCl$_3$)

Test Example 1

Test to Confirm Formation of Active Substance

At first, 1 mg of the test compound was weighed in a test tube, then 100 µl of distilled water was added into the test tube and the substance was macroscopically confirmed to be soluble in distilled water at concentrations of 10 mg/ml and higher.

The test compound was dissolved in a human liver microsome preparation (0.5 mg protein/ml, GENTEST Corporation) at an intial concentration of 1 µM and the mixture was incubated at 37° C.

A small aliquot of the sample was collected at certain time intervals, and the rate of persistence of the original compound and the rate of formation of compound A, the active substance with the chemical structure shown below, were determined by HPLC.

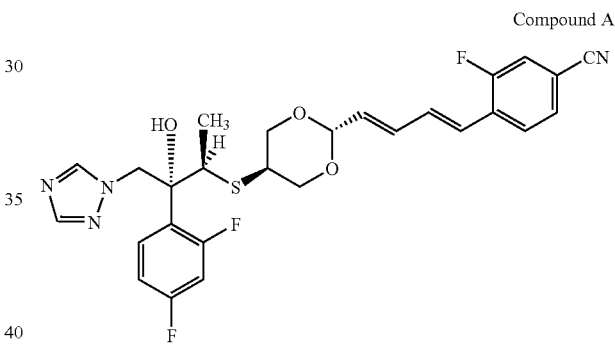

Compound A

The results of incubating the compound of Example 5 (the disodium salt of example number 5-16) with the human liver microsome preparation are shown in FIG. 1.

As clearly shown, the amount of the compound of Example 5 (disodium salt of example number 5-16) diminished immediately after the incubation started, and the compound was completely converted to compound A after incubation for 30 min. Thus the compounds of the present invention were clearly demonstrated to be water-soluble and to be converted by hydrolysis in vivo to compounds exerting antifungal activity.

Test Example 2

Determination of the Antifungal Activity of Compound A

The antifungal activities of compound A were assessed according to the minimum inhibitory concentrations (MICs) which were measured by the methods described below:

Determination of antifungal activity against *Candida*: The MICs were determined by the broth microdilution method. Test compound was dissolved in dimethyl sulfoxide (DMSO). Serial two-fold dilution of the test compound was performed with DMSO, and then the final dilution was performed with RPMI1640 medium (product of Dainippon Pharmaceutical Co., Ltd.) which was buffered to pH 7.0 with 0.165M 3-(morpholino)propanesulfonic acid (MOPS). The final concentration of DMSO did not exceed 1%. Colonies of the test fungi were suspended in physiological saline followed by adjustment to $5.0\times10^2$ to $2.5\times10^3$ cells/ml with RPMI1640 medium which was buffered to pH 7.0 with 0.165M MOPS. 100 µl of the fungal suspension and 100 µl of each diluted test compound solution were mixed in each well of microtitre plates, before incubating at 35° C. for 24-72 hours. When obvious growth was observed in the compound-free control wells, the MICs were determined for the test compound. The MICs were defined as the lowest compound concentrations causing at least 80% growth inhibition when compared with the control.

Determination of antifungal activity against *Cryptococcus neoformans*: MICs were determined by the broth microdilution method. Test compound was dissolved in DMSO. Serial two-fold dilution of the test compound was performed with DMSO, and the final dilution was performed with yeast nitrogen base medium (product of Difco Laboratories) buffered to pH 7.0 with 0.165M MOPS. The final concentration of DMSO did not exceed 1%. Colonies of the test fungi were suspended in physiological saline followed by adjustment to $5.0\times10^3$ to $2.5\times10^4$ cells/ml with yeast nitrogen base medium buffered to pH 7.0 with 0.165M MOPS. 100 µl of the fungal suspension and 100 µl of each diluted test compound solution were mixed in each well of microtitre plates, before incubating at 35° C. for 48-72 hours. When obvious growth was observed in the compound-free control wells, the MICs were determined for the test compound. The MICs were defined as the lowest compound concentrations causing at least 50% growth inhibition when compared with the control as measured by light absorbance at 485 nm.

Determination of antifungal activity against *Aspergillus*: MICs were determined by the broth microdilution method. Test compound was dissolved in DMSO. Serial two-fold dilution of the test compound was performed with DMSO, and then the final dilution was performed with RPMI1640 medium (product of Dainippon Pharmaceutical Co., Ltd.) which was buffered to pH 7.0 with 0.165M MOPS. The final concentration of DMSO did not exceed 1%. Colonies of the test fungi were suspended in physiological saline followed by adjustment to about $1.0\times10^4$ cells/ml with RPMI1640 medium which was buffered to pH 7.0 with 0.165M MOPS. 100 µl of the fungal suspension and 100 µl of each diluted test compound solution were mixed in each well of microtitre plates, before incubating at 30° C. for 24-72 hours. When obvious growth was observed in the compound-free control wells, the MICs were determined for the test compound. The MICs were defined as the lowest compound concentrations causing at least 80% growth inhibition when compared with the control.

The antifungal activities of the compounds are more potent the lower the MIC values.

The results of the antifungal activity tests of compound A are shown in Table α.

TABLE α

| | Antifungal activity | | | | |
|---|---|---|---|---|---|
| | MIC values (microgram/ml) | | | | |
| Test Compound | C.a. (1)[a] | C.a. (2)[b] | C.a. (3)[c] | C.n.[d] | A.f.[e] |
| Compound A | 0.25 | <=0.008 | 0.063 | <=0.008 | 0.031 |

[a] C.a. (1) = *Candida albicans* ATCC 64550.
[b] C.a. (2) = *Candida albicans* TIMM 3164.
[c] C.a. (3) = *Candida albicans* TIMM 3165.
[d] C.n. = *Cryptococcus neoformans* TIMM 0362.
[e] A.f. = *Aspergillus fumigatus* SANK 10569.

As shown in the above Table, compound A exhibited excellent antifungal activity.

Formulation Example 1

Preparation for Injection

The test compound 1 (500 mg) is dissolved in distilled water for injection (25 ml), passed through a sterilizing filter, and freeze-dried. Thus a freeze-dried preparation for injection is made.

Water-soluble triazole antifungal agents shown by the general formula (I), i.e. the present invention, are highly water-soluble and exert antifungal activities by rapid cleavage of the ester moiety. In addition, the compounds of the present invention are safe. Thus these agents are useful as remedies (particularly as antifungal agents for injection).

What is claimed is:

1. A triazole compound of a formula (I) or a pharmacologically acceptable salt thereof:

(I)

wherein
X represents a group of a formula (II),

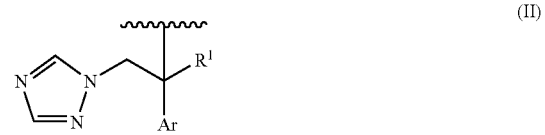

(II)

wherein
Ar represents a $C_6$-$C_{10}$ aryl group which is unsubstituted or substituted with 1 to 3 of the same or different groups selected from the group consisting of a halogen atom and a halogenated $C_1$-$C_6$ alkyl group, and
$R^1$ represents an organic residue group, provided that a compound of a formula X—OH has antifungal activity,
L represents a group of a formula —$L^a$—$L^b$—
wherein
$L^a$ represents a single bond, an oxygen atom, a $C_6$-$C_{10}$ aryl group which is unsubstituted or substituted with 1 to 3 same or different groups selected from the group consisting of a Substituent group α, a heterocyclic group which is unsubstituted or substituted with 1 to 3 of the same or different groups selected from the group consisting of the Substituent group α, and a $C_3$-$C_7$ cycloalkyl group which is unsubstituted or substituted with 1 to 3 of the same or different groups from the Substituent group α, and
$L^b$ represents a $C_1$-$C_5$ alkylene group which is unsubstituted or substituted with 1 to 3 of the same or different groups from the Substituent group α, and
R represents a hydrogen atom, a $C_1$-$C_6$ alkanoyl group which is unsubstituted or substituted with 1 to 3 of the same or different groups selected from the group consisting of a Substituent group β, a group of formula —C(O)—$NR^2R^3$, wherein $R^2$ and $R^3$ are the same or different and independently represent a hydrogen atom or a $C_1$-$C_6$ alkyl group, or $R^2$ and $R^3$, together with the nitrogen atom to which they are attached, form a 4- to 7-membered heterocyclic group containing one or more nitrogen atoms or a —P(=O) (OH)$_2$ group, Substituent group a is selected from the group consisting of a $C_1$-$C_6$ alkyl group, a $C_1$-$C_6$ alkoxy group, a halogen atom, a hydroxy group, a cyano group, an amino group, a $C_1$-$C_6$ alkylamino group, a di $C_1$-$C_6$ alkylamino group, an amino $C_1$-$C_6$ alkyl group, a $C_1$-$C_6$ alkylamino-$C_1$-$C_6$ alkyl group, a di $C_1$-$C_6$ alkylamino-$C_1$-$C_6$ alkyl group, a carboxy group, a —O—P(=O) (OH)$_2$ group, and a $C_1$-$C_6$ alkyl group substituted with one —O—P(=O) (OH)$_2$ group, and Substituent group β is selected from the group consisting of a hydroxy group; a —Q—NR$^{2'}$R$^{3'}$ group, wherein Q represents a single bond or a carbonyl group, and R$^{2'}$ and R$^{3'}$ are the same or different and independently represent a hydrogen atom or a $C_1$-$C_6$ alkyl group, or R$^{2'}$ and R$^{3'}$, together with the nitrogen atom to which they are attached, form a 4- to 7-membered heterocyclic group containing one or more nitrogen atoms, said heterocyclic group containing one or more nitrogen atoms is unsubstituted or substituted with 1 or 2 of the same or different $C_1$-$C_6$ alkyl groups; a carboxy group; an —O—P(=O) (OH)$_2$ group and a —SO$_3$H group.

2. The triazole compound or a pharmacologically acceptable salt thereof according to claim 1, wherein L$^a$ represents a $C_6$-$C_{10}$ aryl group which is unsubstituted or substituted with 1 to 3 of the same or different groups selected from the group consisting of the Substituent group α, a heterocyclic group which is unsubstituted or substituted with 1 to 3 of the same or different groups selected from the group consisting of the Substituent group α, or a $C_3$-$C_7$ cycloalkyl group which is unsubstituted or substituted with 1 to 3 of the same or different groups from the Substituent group α.

3. The triazole compound or a pharmacologically acceptable salt thereof according to claim 2, wherein the carbon atom in the group of —L$^a$— to which the group of formula X—O—C(=O)— is bonded and the carbon atom in the group of —L$^a$— to which the group of formula —L$^b$—O—R is bonded are adjacent to each other.

4. The triazole compound or a pharmacologically acceptable salt thereof according to claim 1, wherein L$^b$ represents an unsubstituted methylene group or a methylene group which is substituted with 1 or 2 of the same or different groups from the Substituent group α.

5. The triazole compound or a pharmacologically acceptable salt thereof according to claim 1, wherein L represents an unsubstituted -(o-phenylene)-CH$^2$— group or an -(o-phenylene)-CH$_2$— group which is substituted with one group from the Substituent group α.

6. The triazole compound or a pharmacologically acceptable salt thereof according to claim 5, wherein L represents an -(o-phenylene)-CH$_2$— group which is substituted with one group from the Substituent group α.

7. The triazole compound or a pharmacologically acceptable salt thereof according to claim 1, wherein R represents a hydrogen atom.

8. The triazole compound or a pharmacologically acceptable salt thereof according to claim 1, wherein R represents a $C_1$-$C_6$ alkanoyl group which is unsubstituted or substituted with 1 to 3 of the same or different groups from the Substituent group β.

9. The triazole compound or a pharmacologically acceptable salt thereof according to claim 1, wherein R represents a —P(=O) (OH)$_2$ group.

10. The triazole compound or a pharmacologically acceptable salt thereof according to claim 1, wherein the Substituent group α represents a Substituent group α1 which is selected from the group consisting of a methyl group, a methoxy group, a halogen atom, a cyano group and a —CH$_2$—O—P(=O) (OH)$_2$ group.

11. The triazole compound or a pharmacologically acceptable salt thereof according to claim 1, wherein the Substituent group β represents a Substituent group β1 which is selected from the group consisting of an amino group, a $C_1$-$C_6$ alkylamino group and a di $C_1$-$C_6$ alkylamino group.

12. The triazole compound or a pharmacologically acceptable salt thereof according to claim 11, wherein the Substituent group β represents a di $C_1$-$C_6$ alkylamino group.

13. The triazole compound or a pharmacologically acceptable salt thereof according to claim 12, wherein the Substituent group β represents an N,N-dimethylamino group.

14. The triazole compound or a pharmacologically acceptable salt thereof according to claim 1, wherein the Substituent group β represents a carboxy group.

15. The triazole compound or a pharmacologically acceptable salt thereof according to claim 1, wherein the Substituent group β represents a 4- to 7-membered heterocyclic group containing one or more nitrogen atoms, said heterocyclic group containing one or more nitrogen atoms is unsubstituted or substituted with 1 or 2 $C_1$-$C_6$ alkyl groups which are the same or different.

16. The triazole compound or a pharmacologically acceptable salt thereof according to claim 15, wherein the Substituent group β represents a 4- to 7-membered heterocyclic group containing one or more nitrogen atoms, said heterocyclic group containing one or more nitrogen atoms is substituted with 1 or 2 $C_1$-$C_6$ alkyl groups which are the same or different.

17. The triazole compound or a pharmacologically acceptable salt thereof according to claim 16, wherein Substituent group β represents a 4-methyl-1-piperazinyl group.

18. The triazole compound or a pharmacologically acceptable salt thereof according to claim 1, wherein the Substituent group β represents a group of formula —C(O)—W, wherein W represents a 4- to 7-membered heterocyclic group containing one or more nitrogen atoms, said heterocyclic group containing one or more nitrogen atoms is unsubstituted or substituted with 1 or 2 $C_1$-$C_6$ alkyl groups which are the same or different.

19. The triazole compound or a pharmacologically acceptable salt thereof according to claim 18, wherein Substituent group β represents a group of formula —C(O)—W$^1$, wherein W$^1$ represents a 4- to 7-membered heterocyclic group containing one or more nitrogen atoms, said heterocyclic group containing one or more nitrogen atoms is substituted with 1 or 2 of the same or different $C_1$-$C_6$ alkyl groups.

20. The triazole compound or a pharmacologically acceptable salt thereof according to claim 19, wherein the Substituent group β represents a (4-methyl-1-piperazinyl) carbonyl group.

21. The triazole compound or a pharmacologically acceptable salt thereof according to claim 1, wherein X represents a group of a formula (III),

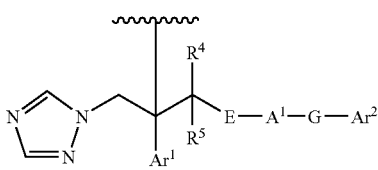

(III)

wherein Ar¹ represents a phenyl group which is unsubstituted or substituted with 1 to 3 of the same or different groups selected from the group consisting of a halogen atom and a trifluoromethyl group, Ar² represents a phenyl group which is unsubstituted or substituted with 1 to 5 of the same or different groups from the Substituent group γ; a monocyclic heteroaryl group which is unsubstituted or substituted with 1 to 5 of the same or different groups selected from the group consisting of the Substituent group γ; a naphthyl group which is unsubstituted or substituted with 1 to 5 of the same or different groups selected from the group consisting of the Substituent group γ; and a fused bicyclic heteroaryl group which is unsubstituted or substituted with 1 to 5 of the same or different groups from the Substituent group γ, E represents a methylene group or a group of formula —S(O)$_{n1}$— wherein, n1 is an integer from 0 to 2, A¹ represents a C$_4$-C$_7$ cycloalkyl group or a heterocyclyl group, R⁴ and R⁵ independently represent a hydrogen atom or a C$_1$-C$_6$ alkyl group, G represents a group of a formula (Ga)

—(CO)$_p$—(R⁶C=CR⁷)$_q$—(C≡C)$_r$—(R⁸C=CR⁹)$_s$— (Ga)

wherein R⁶, R⁷, R⁸ and R⁹ independently represent a hydrogen atom or a C$_1$-C$_6$ alkyl group which is unsubstituted or substituted with 1 to 5 of the same or different halogen atoms, p is an integer 0 or 1, q is an integer from 0 to 3, and r and s independently are an integer from 0 to 2, or G represents a group of a formula (Gb)

—Φ—CO—NR¹⁰⁴—T— (Gb)

wherein φ represents a phenylene group which is unsubstituted or substituted with 1 or 2 of the same or different groups selected from the group consisting of a fluorine atom and a chlorine atom, or a naphthylene group which is unsubstituted or substituted with 1 or 2 of the same or different groups selected from the group consisting of a fluorine atom and a chlorine atom, R¹⁰⁴ represents a hydrogen atom or a C$_1$-C$_6$ alkyl group, and T represents a single bond or a straight or branched chain C$_1$-C$_8$ alkylene group, and the Substituent group γ is selected from the group consisting of a halogen atom, a hydroxy group, a mercapto group, a nitro group, an amino group, a cyano group, a carboxy group, a C$_1$-C$_6$ alkyl group which is unsubstituted or substituted with 1 to 5 of the same or different groups selected from the group consisting of a Substituent group ζ, a C$_1$-C$_6$ alkoxy group which is unsubstituted or substituted with 1 to 5 of the same or different groups selected from the group consisting of the Substituent group ζ, a C$_1$-C$_6$ alkanoyl group which is unsubstituted or substituted with 1 to 5 of the same or different groups selected from the group consisting of the Substituent group ζ, a C$_2$-C$_6$ alkanoyloxy group which may optionally be substituted with 1 to 5 same or different groups selected from the group consisting of the Substituent group ζ, a C$_2$-C$_7$ alkoxycarbonyl group, a C$_2$-C$_5$ alkanoylamino group, a group of formula —C(O)—NR$^{2a}$R$^{3a}$, wherein, R$^{2a}$ and R$^{3a}$ independently represent a hydrogen atom or a C$_1$-C$_6$ alkyl group, or R$^{2a}$ and R$^{3a}$, together with the nitrogen atom to which they are attached, form a 4- to 7-membered heterocyclic group containing one or more nitrogen atoms, a group of formula —S(O)$_{μ1}$—R$^{ξ1}$, wherein μ1 is an integer from 0 to 2 and R$^ξ$ represents a C$_1$-C$_6$ alkyl group which is unsubstituted or substituted with 1 to 5 of the same or different groups selected from the group consisting of a Substituent group η, a group of formula —S(O)$_{μ2}$—O—R$^{ξ2}$, wherein, μ2 is an integer from 0 to 2 and R$^{ξ2}$ represents a C$_1$-C$_6$ alkyl group which is unsubstituted or substituted with 1 to 5 of the same or different groups selected from the group consisting of the Substituent group η, a group of formula —O—S(O)$_{μ3}$—R$^{ξ3}$, wherein μ3 is an integer from 0 to 2 and R$^{ξ3}$ represents a C$_1$-C$_6$ alkyl group which is unsubstituted or substituted with 1 to 5 of the same or different groups selected from the group consisting of Substituent group η, an imidazolyl group which is unsubstituted or substituted with 1 or 2 of the same or different groups selected from the group consisting of the Substituent group δ, a pyrazolyl group which is unsubstituted or substituted with 1 or 2 of the same or different groups selected from the group consisting of the Substituent group δ, a triazolyl group which is unsubstituted or substituted with 1 or 2 of the same or different groups selected from the group consisting of the Substituent group δ, a tetrazolyl group which is unsubstituted or substituted with 1 or 2 of the same or different groups selected from the group consisting of the Substituent group δ, a C$_2$-C$_6$ alkenyl group, a C$_2$-C$_6$ alkynyl group, a C$_3$-C$_6$ cycloalkyl group, and a C$_1$-C$_6$ alkyl group which is substituted with a C$_3$-C$_6$ cycloalkyl group;

Substituent group δ is selected from the group consisting of a C$_1$-C$_4$ alkyl group, a C$_1$-C$_4$ alkyl group which is substituted with 1 to 5 of the same or different halogen atoms, and a halogen atom;

Substituent group ζ is selected from the group consisting of a halogen atom, a hydroxy group, a cyano group, and a C$_1$-C$_6$ alkoxy group;

Substituent group η is selected from the group consisting of a halogen atom and a hydroxy group.

22. The triazole compound or a pharmacologically acceptable salt thereof according to claim 21, wherein Ar² represents a phenyl group which is unsubstituted or substituted with 1 to 5 of the same or different groups from the Substituent group γ, or a monocyclic heteroaryl group which is unsubstituted or substituted with 1 to 5 of the same or different groups from the Substituent group γ, E represents a formula —S(O)$_{n1}$— group, wherein n1 is an integer from 0 to 2, R⁴ represents a C$_1$-C$_4$ alkyl group, R⁵ represents a hydrogen atom or a C$_1$-C$_4$ alkyl group, G represents a group of a formula (Ga')

—(CO)$_{p'}$—(R⁶'C=CR⁷')$_{q'}$—(C≡C)$_{r'}$—(R⁸'C=CR⁹')$_{s'}$— (Ga')

wherein R⁶', R⁷', R⁸' and R⁹' independently represent a hydrogen atom or a C$_1$-C$_6$ alkyl group which is unsubstituted or substituted with 1 to 5 of the same or different halogen atoms, p' is an integer 0 or 1, and q', r' and s' independently are an integer from 0 to 2.

23. The triazole compound or a pharmacologically acceptable salt thereof according to claim 22, wherein X represents a group of a formula (IV)

(IV)

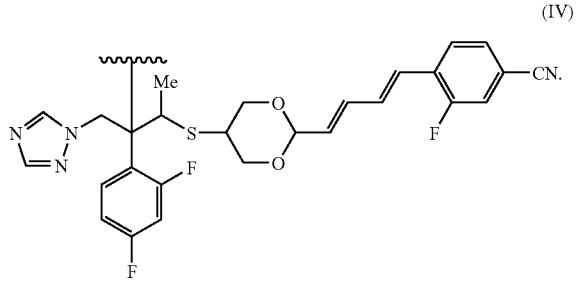

24. The triazole compound or a pharmacologically acceptable salt thereof according to claim 21, wherein
E represents a methylene group,
A' represents a group selected from the group consisting of

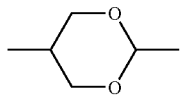 (B1)

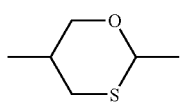 (B2)

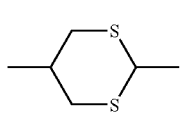 (B3)

G represents a group of a formula (Ga")

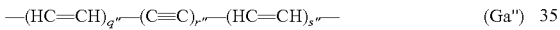
—(HC=CH)$_{q''}$—(C≡C)$_{r''}$—(HC=CH)$_{s''}$— (Ga")

wherein, q" is an integer from 0 to 3, and r" and s" independently are an integer from 0 to 2, provided that total of q", r" and s" is 3 or less.

25. The triazole compound or a pharmacologically acceptable salt thereof according to claim 24, wherein X represents a group of a formula (V)

(V)

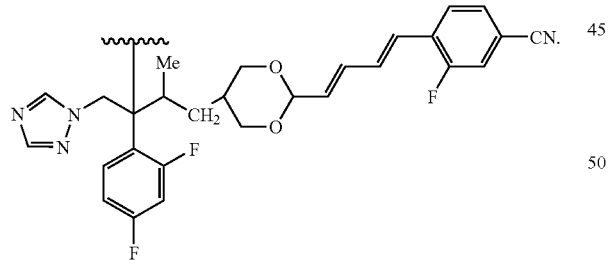

26. The triazole compound or a pharmacologically acceptable salt thereof according to claim 21, wherein
Ar$^2$ represents a naphthyl group which is unsubstituted or substituted with 1 to 5 of the same or different groups selected from the group consisting of the Substituent group γ, and a fused bicyclic heteroaryl group which is unsubtituted or substituted with 1 to 5 of the same or different groups from Substituent group γ,
E represents a formula —S(O)$_{n1}$— group, wherein n1 is an integer from 0 to 2,
R$^4$ represents a C$_1$-C$_6$ alkyl group,
R$^5$ represents a hydrogen atom,
G represents a group of a formula (Ga')

—(CO)$_{p'}$—(R$^{6'}$C=CR$^{7'}$)$_{q'}$—(C≡C)$_{r'}$—(R$^{8'}$C=CR$^{9'}$)$_{s'}$— (Ga')

wherein R$^{6'}$, R$^{7'}$, R$^{8'}$ and R$^{9'}$ independently represent a hydrogen atom or a C$_1$-C$_6$ alkyl group which is unsubstituted or substituted with 1 to 5 of the same or different halogen atoms,
p' is an integer 0 or 1, and
q', r' and s' independently are an integer from 0 to 2.

27. The triazole compound or a pharmacologically acceptable salt thereof according to claim 21, wherein
Ar$^2$ represents a phenyl group which may is unsubtituted or substituted with 1 to 5 of the same or different groups selected from the group consisting of the Substituent group γ, and a naphthyl group which is unsubstituted or substituted with 1 to 5 of the same or different groups from the Substituent group γ,
E represents a methylene group or a sulfur atom,
R$^5$ represents a hydrogen atom, and
G represents a group of a formula (Gb)

—Φ—CO—NR$^\psi$—T— (Gb)

wherein φ represents a phenylene group which is unsubtituted or substituted with 1 or 2 of the same or different groups selected from the group consisting of a fluorine atom and a chlorine atom, or a naphthylene group which is unsubtituted or substituted with 1 or 2 of the same or different groups selected from the group consisting of a fluorine atom and a chlorine atom,
R$^\psi$ represents a hydrogen atom or a C$_1$-C$_6$ alkyl group, and
T represents a single bond or a straight or branched chain C$_1$-C$_8$ alkylene group.

28. The triazole compound or a pharmacologically acceptable salt thereof according to claim 1, wherein X represents a group of a formula (VI)

(VI)

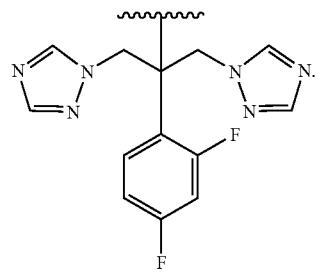

29. The triazole compound or a pharmacologically acceptable salt thereof according to claim 1, wherein X represents a group of a formula (VII)

(VII)

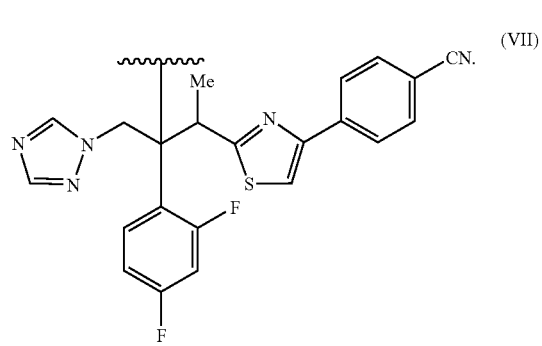

30. The triazole compound or a pharmacologically acceptable salt thereof according to claim 1, wherein X represents a group of a formula (VIII)

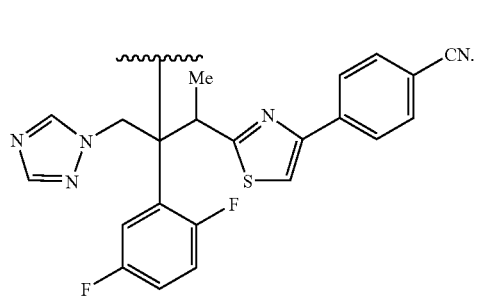
(VIII)

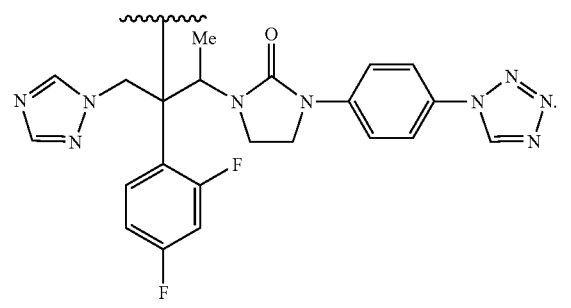
(X)

31. The triazole compound or a pharmacologically acceptable salt thereof according to claim 1, wherein X represents a group of a formula (IX)

33. The triazole compound or a pharmacologically acceptable salt thereof according to claim 1, wherein X represents a group of a formula (XI)

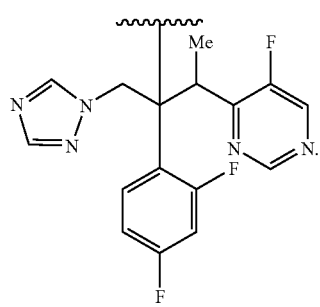
(IX)

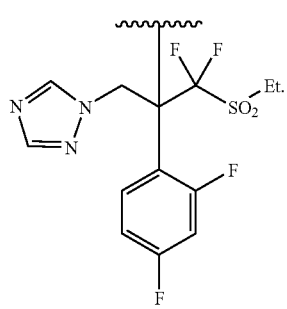
(XI)

32. The triazole compound or a pharmacologically acceptable salt thereof according to claim 1, wherein X represents a group of a formula (X)

34. The triazole compound or a pharmacologically acceptable salt thereof according to claim 1, wherein X represents a group of a formula (XII)

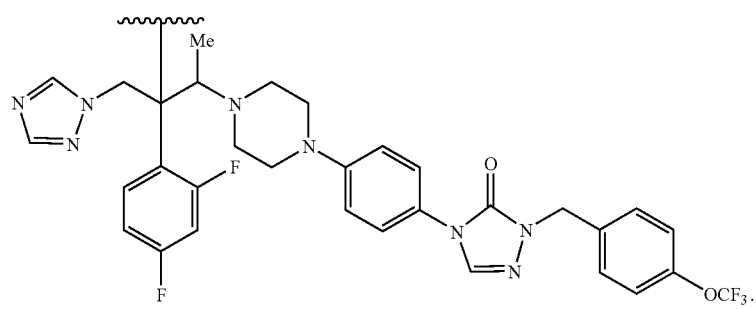
(XII)

35. The triazole compound or a pharmacologically acceptable salt thereof according to claim 1, wherein X represents a group of a formula (XIII)

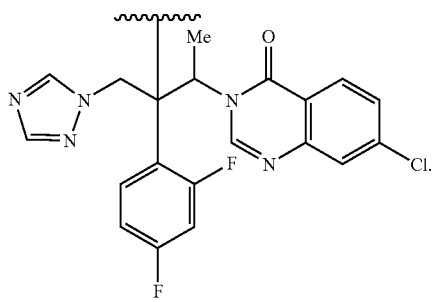
(XIII)

36. The triazole compound or a pharmacologically acceptable salt thereof according to claim 1, wherein the compound is dihydrogen 4-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate.

37. The triazole compound or a pharmacologically acceptable salt thereof according to claim 1, wherein the compound is (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-(hydroxymethyl)benzoate.

38. The triazole compound or a pharmaceutically acceptable salt according to thereof according to claim 23, wherein L is

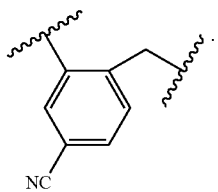

39. The triazole compound or a pharmaceutically acceptable salt thereof according to claim 23, wherein R is a —P(=O) (OH)$_2$ group.

40. The triazole compound or a pharmaceutically acceptable salt thereof according to claim 38, wherein R is a —P(=O) (OH)$_2$ group.

41. The triazole compound or a pharmaceutically acceptable salt thereof according to claim 23, wherein R is a hydrogen atom.

42. The triazole compound or a pharmaceutically acceptable salt thereof according to claim 38, wherein R is a hydrogen atom.

43. The triazole compound or a pharmacologically acceptable salt thereof according to claim 38, wherein R represents a $C_1$-$C_6$ alkanoyl group which is unsubstituted or substituted with 1 to 3 of the same or different groups from the substituent group β.

44. The triazole compound or a pharmacologically acceptable salt thereof according to claim 23, wherein R represents a $C_1$-$C_6$ alkanoyl group which is unsubstituted or substituted with 1 to 3 of the same or different groups from the substituent group β.

45. The triazole compound or a pharmacologically acceptable salt thereof according to claim 22, wherein L is an (o-phenylene)-CH$_2$— group which is substituted with one group from the Substituent group a.

46. The triazole compound or a pharmacologically acceptable salt thereof according to claim 45, wherein R represents a hydrogen atom.

47. The triazole compound or a pharmacologically acceptable salt thereof according to claim 45, wherein R represents a $C_1$-$C_6$ alkanoyl group which is unsubstituted or substituted with 1 to 3 of the same or different groups from the substituent group β.

48. The triazole compound or a pharmacologically acceptable salt thereof according to claim 45, wherein R represents a —P(=O) (OH)$_2$ group.

49. The triazole compound or a pharmacologically acceptable salt thereof according to claim 21, wherein L represents an unsubstituted -(o-phenylene)-CH$_2$— group which is substituted with one group from the substituent group a.

50. The triazole compound or a pharmacologically acceptable salt thereof according to claim 49, wherein R represents a hydrogen atom.

51. The triazole compound or a pharmacologically acceptable salt thereof according to claim 49, wherein R represents a $C_1$-$C_6$ alkanoyl group which is unsubstituted or substituted with 1 to 3 of the same or different groups from the substituent group β.

52. The triazole compound or a pharmacologically acceptable salt thereof according to claim 49, wherein R represents a —P(=O) (OH)$_2$ group.

53. A triazole compound of a formula (I) or a pharmacologically acceptable salt thereof:

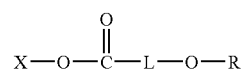
(I)

wherein
X represents a group of formula (II)

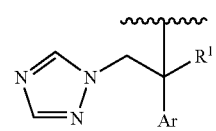
(II)

wherein,
Ar represents a $C_6$-$C_{10}$ aryl group which is unsubstituted or substituted with one or more groups selected from the group consisting of a halogen atom and a halogenated $C_1$-$C_6$ alkyl group, and $R^1$ represents an organic residue group, provided that a compound of a formula X—OH has antifungal activity, L represents a $C_3$-$C_4$ alkylene group which is unsubstituted or substituted with 1 to 3 groups selected from the group consisting of a Substituent group α; an —O— ($C_2$-$C_3$ alkylene) group which is unsubstituted or substituted with 1 to 3 groups from a Substituent group α; an (adjacently substituted $C_6$-$C_{10}$ aryl)CH$_2$— group which is unsubstituted or substituted with 1 to 3 groups from the Substituent group α; and an—(adjacently substituted $C_3$-$C_7$ cycloalkyl)$CH_2$— group which is unsubstituted or substituted with 1 to 3 group from the Substituent group α;

R represents a hydrogen atom, a $C_1$-$C_6$ alkanoyl group, a $C_1$-$C_6$ alkanoyl group which is substituted with 1 to 3 groups from a Substituent group β, and a —P(=O)(OH)$_2$ group Substituent group α represents a group selected from the group consisting of a $C_1$-$C_6$ alkyl group; a $C_1$-$C_6$ alkoxy group; a halogen atom; a cyano group; a hydroxy group; an —NR$^2$R$^3$ group, wherein, R$^2$ and R$^3$ each independently represent a hydrogen atom or a $C_1$-$C_6$ alkyl group; a —($C_1$-$C_6$ alkyl)NR$^2$R$^3$ group, wherein, R$^2$ and R$^3$ have the same meanings as defined above; a carboxyl group; an —O—P(=O) (OH)$_2$ group and a —($C_1$-$C_6$ alkyl)O—P(=O) (OH)$_2$ group;

Substituent group β represents a group selected from the group consisting of a hydroxyl group, an amino group, a carboxyl group, a —O—P(=O) (OH)$_2$ group and an —SO$_3$H group.

54. A composition for treating or preventing a fungal infection comprising a pharmaceutically effective amount of the triazole compound or a pharmacologically acceptable salt thereof according to any one of claims 1 to 53 in combination with a pharmaceutically acceptable carrier.

55. A method for treating or preventing a fungal infection in a warm-blooded animal comprising administering to the warm-blooded animal an effective antifungal amount of the triazole compound or pharmaceutically acceptable salt thereof according to claim 1.

56. A method for treating or preventing a fungal infection in a human comprising administering to the human an effective antifungal amount of the triazole compound or pharmaceutically acceptable salt according to any one of claims 1 to 53.

57. A method according to claim 56, wherein the method is for treating a fungal infection; the administering is by intravenous administration, intramuscular administration or subcutaneous administration; and the fungal infection is caused by a fungus of a genus selected from the group consisting of *Candida, Aspergillus, Cryptococcus, Mucor, Histoplasma, Blastomyces, Coccidioides, Paracoccidioides, Trichophyton, Epidermophyton, Microsporum, Malassezia, Pseudallescheria, Sporothrix, Rhinosporidium, Fonsecaea, wangiella, Phialophora, Exophiala, Cladosporium, Alternaria, Aureobasidium, Chaetomium, Curvularia, Drechslera, Mycocentrospora, Phoma, Hendersonula, Scytalidium, Corynespora, Leptosphaeria, Madurella, Neotestudina, Sedosporium, Pyrenochaeta, Geotrichum, Trichosporon, Chrysosporium, Coprinus, Schizophyllum, Pneumocystis, Conidiobolus, Basidiobolus, Paecilomyces, Penicilliun, Acremonium, Fusarium, Scopulariopsis, Saccharomyces, Cephalosporium, Loboa, Rhizopus, Rhizomucor* and *Absidia*.

58. The method according to claim 57, wherein the injection is intravenous.

59. The triazole compound according to claim 1, wherein the compound is selected from the group consisting of dihydrogen 4-[(1R,2R)-2-trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl}propoxy}-4-oxobutyl phosphate, dihydrogen 4-[(1R,2R)-2-trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl}propoxy]-2,2-dimethyl-4-oxobutyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl}propoxy]carbonyl]benzyl phosphate, dihydrogen 4-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-fluorobenzyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxyl]carbonyl]-5-fluorobenzyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-fluorobenzyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methylbenzyl phosphate, dihydrogen 2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-6-methoxybenzyl phosphate, dihydrogen [8-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-1-naphthyl]methyl phosphate, dihydrogen 6-chloro-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[2-(4-methyl-1-piperazinyl) acetoxylbutyrate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 4-[[4-(4-methyl-1-piperazinyl)-4-oxobutyryl]oxy]butyrate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N-methylamino)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(N,N-dimethylamino)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[2-(4-methyl-1-piperaziriyl)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[3-N-methylamino)propanoyl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[3-(N,N-dimethylamino)propionyl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[3-(4-methyl-1-piperazinyl)propionyl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(4-methyl-1-piperazinyl)-4-oxobutyryl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(N-methylamino)butyryl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 2-[[4-(N,N-dimethylamino)butyryl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-ditluorophenyl)-1-[(1H-1,2,4-triazol-1-yl)methyl]propyl 5-cyano-2-[[2-(N-methylamino)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(N,N-dimethylamino)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[2-(4-methyl-1-piperazinyl)acetoxy]methyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(N-methylamino)propanoyl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(N,N-dimethylamino)propanoyl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[3-(4-methyl-1-piperazinyl)propanoyl]oxymethyl]benzoate, (1R,2R)-2-[[trans-2-[[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(4-methyl-1-piperazinyl)-4-oxobutyryl]oxymethyl]benzoate, (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(N-methylamino)butyryl]oxymethyl]benzoate, and (1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propyl 5-cyano-2-[[4-(N,N-dimethylamino)butyryl]oxymethyl]benzoate, or a pharmacologically acceptable salt thereof.

60. The triazole compound according to claim 1, wherein the compound is dihydrogen 4-cyano-2-[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate or a pharmacologically acceptable salt thereof.

61. The triazole compound according to claim 1, wherein the compound is dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]benzyl phosphate or a pharmacologically acceptable salt thereof.

62. The triazole compound according to claim 1, wherein the compound is dihydrogen 2-([[[(1R,2R)-2-[[trans-2-[[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-4-fluorobenzyl phosphate or a pharmacologically acceptable salt thereof.

63. The triazole compound according to claim 1, wherein the compound is dihydrogen 2-[[[(1R,2R)-2-[[trans-2-[(1E,3E)-4-(4-cyano-2-fluorophenyl)-1,3-butadienyl]-1,3-dioxan-5-yl]thio]-1-(2,4-difluorophenyl)-1-[(1H-1,2,4-triazol-1-yl)methyl]propoxy]carbonyl]-5-fluorobenzyl phosphate or a pharmacologically acceptable salt thereof.

* * * * *